(12) United States Patent
Nagarajan et al.

(10) Patent No.: US 12,234,463 B2
(45) Date of Patent: Feb. 25, 2025

(54) ENGINEERED MICROORGANISMS WITH G3P → 3PG ENZYME AND/OR FRUCTOSE-1,6-BISPHOSPHATASE INCLUDING THOSE HAVING SYNTHETIC OR ENHANCED METHYLOTROPHY

(71) Applicant: Genomatica, Inc., San Diego, CA (US)

(72) Inventors: Harish Nagarajan, San Diego, CA (US); Tae Hoon Yang, San Diego, CA (US); Ali Khodayari, San Diego, CA (US)

(73) Assignee: Genomatica, Inc., San Diego, CA (US)

(*) Notice: Subject to any disclaimer, the term of this patent is extended or adjusted under 35 U.S.C. 154(b) by 217 days.

(21) Appl. No.: 17/255,352

(22) PCT Filed: Jun. 26, 2019

(86) PCT No.: PCT/US2019/039207
§ 371 (c)(1),
(2) Date: Dec. 22, 2020

(87) PCT Pub. No.: WO2020/006058
PCT Pub. Date: Jan. 2, 2020

(65) Prior Publication Data
US 2022/0177895 A1 Jun. 9, 2022

Related U.S. Application Data

(60) Provisional application No. 62/690,209, filed on Jun. 26, 2018.

(51) Int. Cl.
| | | |
|---|---|---|
| *C12N 9/16* | (2006.01) |
| *C12N 9/02* | (2006.01) |
| *C12N 9/88* | (2006.01) |
| *C12N 9/90* | (2006.01) |
| *C12N 15/52* | (2006.01) |
| *C12P 5/00* | (2006.01) |
| *C12P 5/02* | (2006.01) |
| *C12P 7/16* | (2006.01) |
| *C12P 7/18* | (2006.01) |
| *C12P 7/24* | (2006.01) |
| *C12P 7/42* | (2006.01) |
| *C12P 7/46* | (2006.01) |
| *C12P 7/6409* | (2022.01) |
| *C12P 13/00* | (2006.01) |

(52) U.S. Cl.
CPC ........... *C12N 15/52* (2013.01); *C12N 9/0008* (2013.01); *C12N 9/16* (2013.01); *C12N 9/88* (2013.01); *C12N 9/90* (2013.01); *C12P 5/007* (2013.01); *C12P 5/026* (2013.01); *C12P 7/16* (2013.01); *C12P 7/18* (2013.01); *C12P 7/24* (2013.01); *C12P 7/42* (2013.01); *C12P 7/46* (2013.01); *C12P 7/6409* (2013.01); *C12P 13/001* (2013.01); *C12P 13/005* (2013.01); *C12Y 102/01012* (2013.01); *C12Y 301/03011* (2013.01); *C12Y 401/02009* (2013.01); *C12Y 401/02043* (2013.01); *C12Y 503/01027* (2013.01)

(58) Field of Classification Search
CPC ..... C12Y 102/01009; C12Y 102/01013; C12P 13/08; C12N 2310/315; C12N 9/0008; C12N 9/0071; C12N 9/18
USPC .................................... 435/254.11, 196, 189
See application file for complete search history.

(56) References Cited

U.S. PATENT DOCUMENTS

| | | |
|---|---|---|
| 10,563,180 B2 | 2/2020 | Andrae et al. |
| 11,384,340 B2 | 7/2022 | Andrae et al. |
| 11,441,128 B2 | 9/2022 | Barton et al. |
| 2011/0201089 A1 | 8/2011 | Burgard et al. |

(Continued)

FOREIGN PATENT DOCUMENTS

| | | |
|---|---|---|
| EP | 1 937 821 A2 | 7/2008 |
| JP | 2017504330 A | 2/2017 |

(Continued)

OTHER PUBLICATIONS

Devos et al., Proteins: Structure, Function and Genetics, 2000, vol. 41: 98-107.*

(Continued)

*Primary Examiner* — Robert B Mondesi
*Assistant Examiner* — Mohammad Y Meah
(74) *Attorney, Agent, or Firm* — Kagan Binder, PLLC

(57) ABSTRACT

Described herein are engineered cells including ones having synthetic methylotrophy which include an NADH-dependent enzyme capable of converting G3P to 3PG (e.g., *B. methanolicus* gapN) and/or fructose-1,6-bisphosphatase, along with hexulose-6-phosphate synthase, 6-phospho-3-hexuloisomerase, a phosphoketolase, or a combination thereof. Engineered cells of the disclosure beneficially maintain adequate pool sizes of phosphorylated C3 and/or C4 compounds, and/or provide increased levels of NADPH. As such, the modifications allow for the generation of C6 compounds from C1 (e.g., a methanol feedstod) and C5 compounds, the regeneration of C5 compounds from C6 compounds by carbon rearrangement, and an improved balance between regeneration of C5 compounds and lower glycolysis. In turn, this allows the engineered microorganism to generate sufficient quantities of metabolic precursors (e.g., acetyl-CoA) which can be used in a bioproduct pathway, and the engineered cells can include further modifications to those pathway enzymes allowing for production of a desired bioproduct.

12 Claims, 11 Drawing Sheets
Specification includes a Sequence Listing.

(56) References Cited

U.S. PATENT DOCUMENTS

| | | | |
|---|---|---|---|
| 2014/0058056 | A1 | 2/2014 | Burgard et al. |
| 2014/0288254 | A1 | 9/2014 | Burgard et al. |
| 2014/0302575 | A1 | 10/2014 | Burgard et al. |
| 2014/0329916 | A1 | 11/2014 | Burgard et al. |
| 2015/0050708 | A1 | 2/2015 | Burgard et al. |

FOREIGN PATENT DOCUMENTS

| | | | |
|---|---|---|---|
| WO | WO 2007/030830 A2 | 3/2007 | |
| WO | WO 2008/115840 A2 | 9/2008 | |
| WO | WO 2009/023493 A1 | 2/2009 | |
| WO | WO 2009/094485 A1 | 7/2009 | |
| WO | WO 2009/111672 A1 | 9/2009 | |
| WO | WO 2009/135074 A2 | 11/2009 | |
| WO | WO 2010/030711 A2 | 3/2010 | |
| WO | WO 2010/071697 A1 | 6/2010 | |
| WO | WO 2010/127319 A2 | 11/2010 | |
| WO | WO 2010/129936 A1 | 11/2010 | |
| WO | WO 2010/141780 A1 | 12/2010 | |
| WO | WO 2010/141920 A2 | 12/2010 | |
| WO | WO 2011/031897 A1 | 3/2011 | |
| WO | WO 2011/071682 A1 | 6/2011 | |
| WO | WO 2011/140171 A2 | 11/2011 | |
| WO | WO 2012/018624 A2 | 2/2012 | |
| WO | WO 2012/099621 A1 | 7/2012 | |
| WO | WO 2012/106516 A1 | 8/2012 | |
| WO | WO 2012/135789 A2 | 10/2012 | |
| WO | WO 2012/177599 A2 | 12/2012 | |
| WO | WO 2012/177619 A2 | 12/2012 | |
| WO | WO 2012/177710 A1 | 12/2012 | |
| WO | WO 2012/177721 A1 | 12/2012 | |
| WO | WO 2013/012975 A1 | 1/2013 | |
| WO | WO 2013/028519 A1 | 2/2013 | |
| WO | WO 2013/036764 A1 | 3/2013 | |
| WO | WO 2013/040383 A1 | 3/2013 | |
| WO | WO 2013/071226 A1 | 5/2013 | |
| WO | WO 2013/110797 A1 | 8/2013 | |
| WO | WO 2014/035925 A1 | 3/2014 | |
| WO | 2014153036 A1 | 9/2014 | |
| WO | WO 2014/153207 A2 | 9/2014 | |
| WO | WO 2015/051298 A2 | 4/2015 | |
| WO | 2015108777 A1 | 7/2015 | |
| WO | WO 2017/075208 A1 | 5/2017 | |

OTHER PUBLICATIONS

Whisstock et al., Quarterly Reviews of Biophysics 2003, vol. 36 (3): 307-340.*

Witkowski et al., Biochemistry 38:11643-11650, 1999.*

Kisselev L., Structure, 2002, vol. 10: 8-9.*

Kocharin, K., et al. (2013) "Improved Polyhydroxybutyrate Production by *Saccharomyces cerevisiae* Through the Use of the Phosphoketolase Pathway", Biotechnology and Bioengineering, 110(8):2216-2224.

Database UniProt, accession No. I3EBG2, "Full=NADP-dependent glyceraldehyde-3-phosphate dehydrogenase, EC=I.2.1.9", Feb. 28, 2018, 1 pg.

Takeno, S., et al. (2010) "Engineering of C01ynebacterium glutamicum with an NADP1I-Genera6ng Glycolytic Pathway forL-Lysine Production", Applied and Environmental Microbiology, 76:21:7154-7160.

Ding, J et al. (2015) "Overexpression of acetyl-CoA synthetase in *Saccharomyces cerevisiae* increases acetic acid tolerance", FEMS Microbiology Letters, 362:1-7.

Yurimoto, Hiro, et al. (2013) Seibutsu-kogaku Kaishi, vol. 91, No. 7, pp. 384-387, Print ISSN: 0919-3758, Online ISSN: 2435-8630 (Non-English version available only).

Angov, E., "Condon usage: Nature's roadmap to expression and folding of proteins," Biotechnology Journal, vol. 6, No. 6, May 2011, pp. 650-659.

Anthony, C., "Part II: Growth and Metabolism, Chapter 4—Assimilation of Carbon by Methylotrophs," in Biology of Methylotrophs, Biotechnology Series, Edited by Israel Goldberg and J. Stefan Rokem, 1991 Elsevier Ltd., pp. 79-109.

Araujo et al., "Before It Gets Started: Regulating Translation at the 5' UTR," Comparative and Functional Genomics, vol. 4, May 2012, Article ID 475731, 8 pp.

Arraiano et al., "The critical role of RNA processing and degradation in the control of gene expression," FEMS Microbiology Reviews, vol. 34, No. 5, Jul. 2010, pp. 883-932.

Bleykasten-Grosshans et al., "Transposable elements in yeasts Les éléments transposables chez les levures," Comptes Rendus Biologies, vol. 334, Nos. 8-9, Aug.-Sep. 2011, pp. 679-686.

Bock et al., "Purification and Characterization of Two Extremely thermostable Enzymes, Phosphate Acetyltransferase and acetate Kinase, from the Hyperthermophilic Eubacterium *Thermotoga maritima*," Journal of Bacteriology, vol. 181, No. 6, Mar. 1999, pp. 1861-1867.

Bräsen et al., "Unusual ADP-forming acetyl-coenzyme A synthetases from the mesophilic halophilic euryarhaeon *Haloarcula marismortui* and from the hyperthermophilic crenarchaeon *Pyrobaculum aerophilum*," Archives of Microbiology, vol. 182, No. 4, Aug. 2004, pp. 277-287.

Brautaset et al., "Plasmid-Dependent Methylotrophy in Thermotolerant *Bacillus methanolicus*," Journal of Bacteriology, vol. 186, No. 5, Mar. 2004, pp. 1229-1238.

Brown et al., "The Enzymic Interconversion of Acetate and Acetyl-coenzyme A in *Escherichia coli*," Journal of General Microbiology, vol. 102, No. 2, Oct. 1977, pp. 327-336.

Buck et al., "Primary Structure of the Succinyl-CoA Synthetase of *Escherichia coli*," Biochemistry, vol. 24, No. 22, Oct. 1985, pp. 6245-6252.

Castel et al., "RNA interference in the nucleus: roles for small RNAs in transcription, epigenetics and beyond," Nature Reviews Genetics, No. 14, No. 2, Jan. 2013, pp. 100-112.

Castillo et al., "A Mutant D-Fructose-6-Phosphate Aldolase (Ala129Ser) with Improved Affinity towards Dihydroxyacetone for the Synthesis of Polyhydroxylated Compounds," Advanced Synthesis & Catalysis, vol. 352, No. 6, Apr. 2010, pp. 1039-1046.

Daigaku et al., "Loss of heterozygosity in yeast can occur by ultraviolet irradiation during the S phase of the cell cycle," Mutation Research—Fundamental and Molecular Mechanisms of Mutagenesis, vol. 600, Nos. 1-2, Jun. 2006, pp. 177-183. (Abstract Only).

Dietrich et al., "High throughput Metabolic Engineering: Advances in Small-Molecular Screening and Selection," Annual Review of Biochemistry, vol. 79, Apr. 2010, pp. 563-590.

Donovan et al., "Review: Optimizing inducer and culture conditions for expression of foreign proteins under the control of the lac promoter," Journal of Industrial Microbiology and Biotechnology, vol. 16, No. 3, Mar. 1996, pp. 145-154.

Essenberg et al., "Two Ribose-5-Phosphate Isomerases from *Escherichia coli* K12: Partial Characterization of the Enzymes and Consideration of Their Possible Physiological Roles," European Journal of Biochemistry, vol. 55, No. 2, Jul. 1975, pp. 323-332.

Fernández-Valverde et al., "Purification of *Pseudomonas putida* Acyl Coenzyme A Ligase Active with a Range of Aliphatic and Aromatic Substrates," Applied and Environmental Microbiology, vol. 59, No. 4, Apr. 1993, pp. 1149-1154.

Grill et al., "Characterization of fructose 6 phosphate phosphoketolases purified from *Bifidobacterium* species," Current Microbiology, vol. 31, No. 1, Jul. 1995, pp. 49-54. (Abstract Only (1 pp.)).

Gulick et al., "The 1.75 Å Crystal Structure of Acetyl-CoA Synthetase Bound to Adenosine-5'-propylphosphate and Coenzyme A," Biochemistry, vol. 42, No. 10, Feb. 2003, pp. 2866-2873.

Gutierrez et al., "Structure-guided redesign of D-fructose-6-phosphate aldolase from *E. coli*: remarkable activity and selectivity towards acceptor substrates by two-point mutation," Chemical Communications, vol. 47, No. 20, Apr. 2011, pp. 5762-5764.

Hansen et al., "The effect of the lacY gene on the induction of IPTG inducible promoters, studied in *Escherichia coli* and *Pseudomonas fluorescens*," Current Microbiology, vol. 36, No. 6, Jun. 1998, pp. 341-347.

Hayes, F., "Transposon-Based Strategies for Microbial Functional Genomics and Proteomics," Annual Review of Genetics, vol. 37, Sep. 2003, pp. 3-29.

(56) References Cited

OTHER PUBLICATIONS

Hesslinger et al., "Novel keto acid formate-lyase and propionate kinase enzymes are components of an anaerobic pathway in *Escherichia coli* that degrades L-threonine to propionate," Molecular Microbiology, vol. 27, No. 2, Jan. 1998, pp. 477-492.
Hochstrasser, M., "Ubiquitin-Dependent Protein Degradation," Annual Review of Genetics, vol. 30, Dec. 1996, pp. 405-439. (Abstract Only).
Hoffmeister et al., "Mitochondrial trans-2-Enoyl-CoA Reductase of Wax Ester Fermentation from *Euglena gracilis* Defines a New Family of Enzymes Involved in Lipid Synthesis," Journal of Biological Chemistry, vol. 280, No. 6, Feb. 2005, pp. 4329-4338.
Houseley et al., "The Many Pathways of RNA Degradation," Cell, vol. 136, No. 4, Feb. 2009, pp. 763-776.
Ingram-Smith et al., "AMP-forming acetyl-CoA synthetases in Archaea show unexpected diversity in substrate utilization," Archaea, vol. 2, No. 2, May 2007, pp. 95-107.
Jeong et al., "Cloning and Characterization of a Gene Encoding Phosphoketolase in a *Lactobacillus paraplantarum* Isolated from Kimchi," Journal of Microbiology and Biotechnology, vol. 17, No. 5, May 2007, pp. 822-829.
Jogl et al., "Crystal Structure of Yeast Acetyl-Coenzyme A Synthetase in Complex with AMP," Biochemistry, vol. 43, No. 6, Jan. 2004, pp. 1425-1431.
Kawasaki et al., "Transcriptional gene silencing by short interfering RNAs," Current Opinion in Molecular Therapeutics, vol. 7, No. 2, Apr. 2005, pp. 125-131. (Abstract Only).
Kloosterman et al., "Molecular, Biochemical, and Functional Characterization of a Nudix Hydrolase Protein That Stimulates the Activity of a Nicotinoprotein Alcohol Dehydrogenase," The Journal of Biological Chemistry, vol. 277, No. 38, Jun. 2002, pp. 334785-34792.
Krog et al., "Methylotrophic *Bacillus methanolicus* Encodes Two Chromosomal and One Plasmid Born NAD Dependent Methanol Dehydrogenase Paralogs with Different Catalytic and Biochemical Properties," PLoS ONE, vol. 8, No. 3, Mar. 2013, pp. e59188 (11 pp).
Kurdistani et al., "Histone acetylation and deacetylation in yeast," Nature reviews. Molecular Cell Biology, vol. 4, No. 4, Apr. 2003, pp. 276-284. (Abstract Only).
Lee et al., "Antisense technology in molecular and cellular bioengineering," Current Opinion in Biotechnology, vol. 14, No. 5, Oct. 2003, pp. 505-511. (Abstract Only).
Lee et al., "Cloning and characterization of the gene encoding phosphoketolase in *Leuconostoc mesenteroides* isolated from kimchi," Biotechnology Letters, vol. 27, No. 12, May 2005, pp. 853-858. (Abstract Only (1 pp.)).
Lin et al., "Fed-Batch Culture of a Metabolically Engineered *Escherichia coli* Strain Designed for High-Level Succinate Production and Yield Under Aerobic Conditions," Biotechnology and Bioengineering, vol. 90, No. 6, Mar. 2005, pp. 775-779.
Louis et al., "Restricted Distribution of the Butyrate Kinase Pathway among Butyrate-Producing Bacteria from the Human Colon," Journal of Bacteriology, vol. 186, No. 7, Apr. 2004, pp. 2099-2106.
Mann et al., "Proteomic analysis of post-translational modifications," Nature Biotechnology, vol. 21, No. 3, Mar. 2003, pp. 255-261.
Markert et al., "Characterization of two transketolases encoded on the chromosome and the plasmid pBM19 of the facultative ribulose monophosphate cycle methylotroph *Bacillus methanolicus*," BMC Microbiology, vol. 14, No. 7, Jan. 2014, pp. 11.
McCue et al., "Gene Expression and Stress Response Mediated by the Epigenetic Regulation of a Transposable Element Small RNA," PLoS Genetics, vol. 8, No. 2, Feb. 2012, pp. e1002474. (18 pp.).
Meile et al., "Characterization of the D-Xylulose 5-Phosphate/D-Fructose 6-Phosphate Phosphoketolase Gene (xfp) from *Bifidobacterium lactis*," Journal of Bacteriology, vol. 183, No. 9, May 2001, pp. 2929-2936.
Miko, I., "Gregor Mendel and the Principles of Inheritance," Nature Education, vol. 1, No. 1, 2008, pp. 134 (5 pp.).

Musfeldt et al., "Novel Type of ADP-Forming Acetyl Coenzyme A Synthetase in Hyperthermophilic *Archaea*: Heterologous Expression and Characterization of Isoenzymes from the Sulfate Reduces *Archaeoglobus fulgidus* and the Methanogen *Methanococcus jannaschii*," Journal of Bacteriology, vol. 184, No. 3, Feb. 2002, pp. 636-644.
Nakai et al., "A knowledge base for predicting protein localization sites in eukaryotic cells," Genomics, vol. 14, No. 4, Dec. 1992, pp. 897-911.
Nishizawa et al., "Regulation of inducible gene expression by natural antisense transcripts," Frontiers in Bioscience (Landmark Edition), vol. 17, No. 3, Jan. 2012, pp. 938-958.
O'Sullivan, C.K., "Aptasensors—the future of biosensing?", Analytical and Bioanalytical Chemistry, vol. 372, No. 1, Dec. 2001, pp. 44-48. (Abstract Only).
Papini et al., "Physiological characterization of recombinant *Saccharomyces cerevisiae* expressing the *Aspergillus nidulans* phosphoketolase pathway: validation of activity through $^{13}$C-based metabolic flux analysis," Applied Microbiology and Biotechnology, vol. 95, No. 4, Feb. 2012, pp. 1001-1010.
Park et al., "Growth of Mycobacteria on Carbon Monoxide and Methanol," Journal of Bacteriology, vol. 185, No. 1, Jan. 2003, pp. 142-147.
Pasquinelli, A. E., "MicroRNAs and their targets: recognition, regulation and an emerging reciprocal relationship," Nature Reviews Genetics, vol. 13, No. 4, Mar. 2012, pp. 271-282. (Abstract Only).
Priefert et al., "Identification and molecular characterization of the acetyle coenzyme A synthetase gene (acoE) of *Alcaligenes eutrophus*," Journal of Bacteriology, vol. 174, No. 20, Oct. 1992, pp. 6590-6599.
Rado et al., "Phosphotransacetylase from *Bacillus subtilis*: Purification and Physiological Studies," Biochimica et Biophysica Acta (BBA)—Enzymology, vol. 321, No. 1, Sep. 1973, pp. 114-125.
Ringnér et al., "Folding Free Energies of 5'-UTRs Impact Post-Transcriptional Regulation on a Genomic Scale in Yeast," PLoS Computational Biology, vol. 1, No. 7, Nov. 2005, pp. e72, 0585-0592 (8 pp.).
Ro et al., "Dihydroxyacetone Synthase from a Methanol-Utilizing Carboxydobacterium, *Acinetobacter* sp.," Journal of Bacteriology, vol. 179, No. 19, Oct. 1997, pp. 6041-6047.
Russell et al., "Peptide Signals Encode Protein Localization," Journal of Bacteriology, vol. 189, No. 21, Aug. 2007, pp. 7581-7585.
Sambrook et al., "Molecular Cloning—A Laboratory Manual," vols. 1-3, Third Edition, Cold Spring Harbor Laboratory Press, Cold Spring Harbor, New York, 2001, 2231 pp. (Filed in 7 parts).
Schurmann et al., "Fructose-6-phosphate Aldolase Is a Novel Class I Aldolase from *Escherichia coli* and Is Related to a Novel Group of Bacterial Transaldolases," The Journal of Biological Chemistry, vol. 276, No. 14, Dec. 2000, pp. 11055-11061.
Servinsky et al., "Arabinose is metabolized via a phosphoketolase pathway in *Clostridium acetobutylicum* ATCC 824," Journal of Industrial Microbiology Biotechnology, vol. 39, No. 12, Aug. 2012, pp. 1859-1867.
Sgorbati et al., "Purification and properties of two fructose-6-phosphate phosphoketolases in *Bifidobacterium*," Antonie van Leeuwenhoek, vol. 42, Mar. 1976, pp. 49-57. (Abstract Only (1 pp.)).
Simicevic et al., "DNA-centered approaches to characterize regulatory protein-DNA interaction complexes," Molecular BioSystems, vol. 6, No. 3, Dec. 2009, pp. 462-468.
Skarstedt et al., "*Escherichia coli* Acetate Kinase Mechanism Studied by Net Initial Rate, Equilibrium, and Independent Isotopic Exchange Kinetics," The Journal of Biological Chemistry, vol. 251, No. 21, Nov. 1976, pp. 6775-6783.
Sprenger et al., "Transketolase A of *Escherichia coli* K12, Purification and properties of the enzyme from recombinant strains," European Journal of Biochemistry, vol. 230, No. 2, Jun. 1995, pp. 525-532.
Stradtman, E.R., "[98] Phosphotransacetylase from *Clostridium kluyveri*: Ae~P+CoA⇌Ac~SCoA+Pi," Methods in Enzymology, vol. 1, 1955, pp. 596-599. (First Page Only).

(56) References Cited

OTHER PUBLICATIONS

Sunohara et al., "Nascent-peptide-mediated ribosome stalling at a stop codon induces mRNA cleavage resulting in nonstop mRNA that is recognized by tmRNA," RNA, vol. 10, No. 3, Mar. 2004, pp. 378-386.
Sunohara et al., "Ribosome Stalling during Translation Elongation Induces Cleavage of mRNA Being Translated in *Escherichia coli*," Journal of Biological Chemistry, vol. 279, No. 15, Apr. 2004, pp. 15368-15374.
Suzuki et al., "Overexpression, crystallization and preliminary X-ray analysis of xylulose-t-phosphate/fructose-6-phosphae phosphoketolase from *Bifidobacterium breve*," Acta Crystallographica Section F—Structural Biology and Crystallization Communications, vol. 66, Part 8, Jul. 2010, pp. 941-943.
Suzuki, T., "Phosphotransacetylase of *Escherichia coli* B, Activation by Pyruvate and Inhibition by NADH and Certain Nucleotides," Biochimica et Biophyisica Acta (BBA)—Enzymology, vol. 191, No. 3, Dec. 1969, pp. 559-569.
Vazquez et al., "Phosphotransbutyrylase Expression in *Bacillus megaterium*," Current Microbiology, vol. 42, No. 5, May 2001, pp. 345-349.
Walter et al., "Sequence and arrangement of two genes of the butyrate-synthesis pathway of *Clostridium acetobutylicum* ATCC 824," Gene, vol. 134, No. 1, Nov. 1993, pp. 107-111.
Wang et al., "Activation of Silent Genes by transposons Tn5 and Tn10," Genetics, vol. 120, No. 4, Dec. 1988, pp. 875-885.
Wang et al., "Overview of Regulatory Strategies and Molecular Elements in Metabolic Engineering of Bacteria," Molecular Biotechnology, vol. 52, No. Feb. 3, 2012, pp. 300-308. (Abstract Only (1 pp.)).
Wieland et al., "Engineering of ribozyme-based riboswitches for mammalian cells," Methods, vol. 56, No. 3, Jan. 2012, pp. 351-357. (Abstract Only).
Wiesenborn et al., "Phosphotransbutyrylase from *Clostridium acetobutylicum* ATCC 824 and Its Role in Acidogenesis," Applied and Environmental Microbiology, vol. 55, No. 2, Feb. 1989, pp. 317-322.
Yang et al., "Collaborative spirit of histone deacetylases in regulating chromatin structure and gene expression," Current Opinion in Genetics & Development, vol. 13, No. 2, Apr. 2003, pp. 143-153. (Abstract Only).
Yin et al., "The gene encoding xylulose-t-phosphate/fructose-6-phosphate phosphoketolase (xfp) is conserved among *Bifidobacterium* species within a more variable region of the genome and both are useful for strain identification," FEMS Microbiology Letters, vol. 246, No. 2, Apr. 2005, pp. 251-257.
Yuan et al., "Prokaryotic Ubiquitin-Like ThiS Fusion Enhances the Heterologous Protein Overexpression and Aggregation in *Escherichia coli*," PLoS One, vol. 8, No. 4, Apr. 2013, pp. e62529. (10 pp.).
NCBI GenBank Accession No. AAR39392.1, "3-hexulose-6-phosphate synthase [Bacillus methanolicus MGA3]," 211aa, Feb. 19, 2004, 2 pp.
NCBI GenBank Accession No. AAR39393.1, "6-phospho-3-hexuloisomerase [Bacillus methanolicus MGA3]," 184aa, Feb. 19, 2004, 2 pp.
NCBI GenBank Accession No. EIJ77593.1, "fructose-bisphosphate aldolase (plasmid) [Bacillus methanolicus MGA3]," 284aa, May 14, 2012, 2 pp.
NCBI GenBank Accession No. EIJ77615., "transketolase (plasmid) [Bacillus methanolicus PB1]," 667aa, May 14, 2012, 2 pp.
NCBI GenBank Accession No. EIJ77616.1, "fructose-bisphosphate aldolase (plasmid) [Bacillus methanolicus PB1]," 284aa, May 14, 2012, 2 pp.
NCBI GenBank Accession No. EIJ80286.1, "fructose-bisphosphate aldolase [Bacillus methanolicus PB1]," 296aa, May 14, 2012, 2 pp.
NCBI GenBank Accession No. EIJ81375.1, "3-hexulose-6-phosphate synthase [Bacillus methanolicus PB1]," 211aa, May 14, 2012, 2 pp.
NCBI GenBank Accession No. EIJ81376.1, "6-phospho 3-hexuloisomerase [Bacillus methanolicus PB1]," 184aa, May 14, 2012, 2 pp.
NCBI GenBank Accession No. P0A9B2.2, "Glyceraldehyde-3-phosphate dehydrogenase A," 331aa, Feb. 22, 2023, 7 pp.
NCBI GenBank Accession No. P0A799.2, "Phosphoglycerate kinase," 387aa, Feb. 22, 2023, 4 pp.
NCBI GenBank Accession No. WP_003351798.1, "NADP-dependent glyceraldyehyde-3-phosphate dehydrogenase [Bacillus methanolicus]," 481aa, Jan. 11, 2018, 2 pp.
NCBI GenBank Accession No. WP_003352248.1, "class II fructose-bisphosphatase [Bacillus methanolicus]," 320aa, Dec. 26, 2019, 2 pp.
NCBI GenBank Accession No. WP_012298822.1, "SIS domain-containing protein [Clavibacter michiganensis]," 203aa, Jul. 28, 2019, 1 pp.
NCBI GenBank Accession No. WP_054009748.1, 3-hexulose-6-phosphate synthase [*Arthrobacter* sp. ERGS1:01], 207aa, Jun. 3, 2019, 2 pp.
NCBI GenBank Accession No. WP_003346738.1, "NADP-dependent glyceraldehyde-3-phosphate dehydrogenase [Bacillus methanolicus]," 481aa, Jul. 28, 2019, 2 pp.
NCBI GenBank Accession No. ZP_11548894, "fructose bisphosphatase (plasmid) [Bacillus methanolicus MGA3]," 320aa, Nov. 15, 2012, 2 pp.
U.S. Appl. No. 17/861,036, filed Jul. 8, 2022, naming inventors Stefan Andrae et al.
U.S. Appl. No. 17/943,482, filed Sep. 13, 2022, naming inventors Nelson R. Barton et al.
NCBI GenBank Accession No. ABK84147.1, "nonphosphorylating glyceraldehyde-3-phosphate dehydrogenase [Bacillus thuringiensis str. Al Hakam]," 504 aa, Jan. 28, 2014, 2 pp.
NCBI GenBank Accession No. AIE81030.1, "Non-phosphorylating glyceraldehyde-3-phosphate dehydrogenase [Bacillus cereus]," 478 aa, May 13, 2015, 2 pp.
NCBI GenBank Accession No. EEL51944.1, NADP-dependent glyceraldehyde-3-phosphate dehydrogenase [Bacillus cereus Rock3-44], Apr. 30, 2009, 2 pp.
NCBI GenBank Accession No. EEM06723.1, "NADP-dependent glyceraldehyde-3-phosphate dehydrogenase [Bacillus pseudomycoides]," 504 aa, Jun. 25, 2018, 2 pp.
NCBI GenBank Accession No. WP_000213645.1, "NADP-dependent-glyceraldehyde-3-phosphate dehydrogenase] Bacillus toyonensis]," 479 aa, Mar. 14, 2022, 1 pp.
NCBI GenBank Accession No. WP_000213646.1, "NADP-dependent-glyceraldehyde-3-phosphate dehydrogenase] Bacillus toyonensis]," 479 aa, May 6, 2023, 2 pp.
NCBI GenBank Accession No. WP_011983786.1, "Multispecies: NADP-dependent glyceraldehyde-3-phosphate dehydrogenase [Bacillus cereus group]," 479 aa, Mar. 26, 2022, 2 pp.
NCBI GenBank Accession No. WP_026964094.1, "NADP-dependent glyceraldehyde-3-phosphate dehydrogenase [Alicyclobacillus pomorum]," 482 aa, Jul. 28, 2019, 2 pp.
NCBI GenBank Accession No. WP_068447188.1, "NADP-dependent glyceraldehyde-3-phosphate dehydrogenase [Lentibacillus amyloliquefaciens]," 484 aa, May 13, 2017, 2 pp.
NCBI GenBank Accession No. WP_077328816.1, "NADP-dependent glyceraldehyde-3-phosphate dehydrogenase [Virgibacillus siamensis]," 484 aa, Feb. 20, 2017, 2 pp.
NCBI GenBank Accession No. WP_085964931.1, "NADP-dependent glyceraldehyde-3-phosphate dehydrogenase [Bacillus pacificus]," 479 aa, Dec. 15, 2023, 2 pp.
NCBI GenBank Accession No. WP_087097851.1, "NADP-dependent glyceraldehyde-3-phosphate dehydrogenase [Bacillus cytotoxicus]," 479 aa, Jul. 10, 2019, 2 pp.
NCBI GenBank Accession No. WP_089533800.1, "NADP-dependent glyceraldehyde-3-phosphate dehydrogenase [Virgibacillus necropolis]," 482 aa, Jul. 28, 2017, 2 pp.
NCBI GenBank Accession No. WP_098359346.1, "NADP-dependent glyceraldehyde-3-phosphate dehydrogenase [Bacillus cereus]," 481 aa, Oct. 19, 2017, 2 pp.

(56) References Cited

OTHER PUBLICATIONS

NCBI GenBank Accession No. WP_098814110.1, "NADP-dependent glyceraldehyde-3-phosphate dehydrogenase [Bacillus pseudomycoides]," 479 aa, Oct. 20, 2017, 2 pp.

NCBI GenBank Accession No. WP_003351798.1, "NADP-dependent glyceraldehyde-3-phosphate dehydrogenase [Bacillus methanolicus]", 481 aa, Jan. 11, 2018, 2 pp.

GenBank Protein Accession No. WP_014697802: phosphoketolase [Bifidobacterium animalis] (825 aa), Oct. 11, 2019, 1 page.

GenBank Protein Accession No. AAV66077: phosphoketolase [Leuconostoc mesenteroides] (813 aa), Oct. 14, 2009, 2 pages.

GenBank Protein Accession No. AAR98788: xylulose-5-phosphate/fructose-6-phosphate phosphoketolase [*Bifidobacterium pseudolongum* subsp. *globosum*] (825 aa), May 18, 2005, 2 pages.

GenBank Protein Accession No. WP_022857642: phosphoketolase [Bifidobacterium pseudolongum] (825 aa), Aug. 20, 2018, 2 pages.

GenBank Protein Accession No. ADF97524: xylulose 5-phosphate/fructose 6-phosphate phosphoketolase [Bifidobacterium breve] (825 aa), Jun. 25, 2014, 2 pages.

GenBank Protein Accession No. AAQ64626: xylulose 5-phosphate phosphoketolase [Lactiplantibacillus paraplantarum] (788 aa), Oct. 5, 2005, 2 pages.

GenBank Protein Accession No. WP_010964652: Multispecies: phosphoketolase [Clostridium] (796 aa), Jul. 15, 2024, 1 page.

GenBank Protein Accession No. CBF76492: TPA: phosphoketolase, putative (AFU_orthologue; AFUA_3G10760) [Aspergillus nidulans FGSC A4] (780 aa), Feb. 27, 2015, 2 pages.

\* cited by examiner

Fig. 9

| Protein | SEQ ID NO | Accession/GI Number | Organism |
|---|---|---|---|
| GapN | SEQ ID NO:1 | WP_003346738 | Bacillus methanolicus MGA3 |
| HPS | SEQ ID NO:2 | AAR39392.1 | Bacillus methanolicus MGA |
| PHI | SEQ ID NO:3 | AAR39393.1 | Bacillus methanolicus MGA3 |
| Medh | SEQ ID NO:4 | EIJ77596.1 | Bacillus methanolicus MGA3 |
| pfk2 | SEQ ID NO:5 | WP_003347446.1 | Bacillus methanolicus MGA3 |
| rpe | SEQ ID NO:6 | WP_003349832.1 | Bacillus methanolicus MGA3 |
| rpiB | SEQ ID NO:7 | WP_003346829.1 | Bacillus methanolicus MGA3 |
| Tkt2 | SEQ ID NO:8 | WP_003350079.1 | Bacillus methanolicus PB1 |
| Fba | SEQ ID NO:9 | EIJ77593.1 | Bacillus methanolicus MGA3 |
| Zwf2 | SEQ ID NO:10 | WP_003349278.1 | Bacillus methanolicus MGA3 |

SEQUENCE LISTING

<160> NUMBER OF SEQ ID NOS: 34

<210> SEQ ID NO 1
<211> LENGTH: 481
<212> TYPE: PRT
<213> ORGANISM: Bacillus methanolicus

<400> SEQUENCE: 1

```
Met Gln Val Leu Glu Lys Asp Phe Lys Phe Leu Leu Asn Gly Glu Trp
1               5                   10                  15

Ser Phe Ser Ser Asn Gln Phe Ile Asn Ile Tyr Ser Pro Ser Thr
            20                  25                  30

Gly Glu Val Val Gly Arg Val Pro Ala Met Thr Lys Asp Glu Ile Asp
            35                  40                  45

Lys Ala Val Ala Gly Ala Arg Gln Ala Gln Lys Lys Trp Glu Lys Leu
    50                  55                  60

Ala Val Ser Glu Arg Ala Lys Ile Leu His Ala Trp Ala Asp Glu Leu
65                  70                  75                  80

Val Lys Met Ile Asp Val Ile Ala Pro Met Ile Met Asn Glu Val Gly
                85                  90                  95

Lys Asn Ile Ser Thr Ala Arg Lys Glu Val Thr Arg Thr Ala Glu Ile
                100                 105                 110

Ile Arg Tyr Thr Ala Glu Glu Gly Val Arg Ile His Gly Glu Phe Ile
            115                 120                 125

Asn Gly Gly Ser Leu Asp Ala Asp Ser Ser Ile Lys Thr Ala Ile Val
130                 135                 140

Glu Lys Lys Pro Leu Gly Val Ile Leu Ala Ile Ser Pro Phe Asn Tyr
145                 150                 155                 160

Pro Ile Asn Leu Ala Ala Thr Lys Ile Ala Pro Ala Leu Ile Ala Gly
                165                 170                 175

Asn Ala Val Val Phe Lys Pro Ala Thr Gln Gly Ala Ile Ser Gly Leu
                180                 185                 190

Leu Met Ile Gln Ala Leu Glu Asn Ala Gly Leu Pro Lys Gly Leu Val
            195                 200                 205

Asn Thr Val Thr Gly Lys Gly Ser Glu Ile Gly Asp Tyr Ile Ile Thr
210                 215                 220

His Pro Phe Ile Asp Met Ile Ser Phe Thr Gly Thr Gly Thr Gly
225                 230                 235                 240

Gln Asn Ile Ala Arg Lys Ala Ser Met Ile Pro Leu Val Leu Glu Leu
                245                 250                 255

Gly Gly Lys Asp Pro Ala Ile Val Leu Glu Asp Ala Asp Leu Glu Leu
                260                 265                 270

Ala Ala Thr Glu Ile Val Ser Gly Ala Phe Ser Tyr Ser Gly Gln Arg
            275                 280                 285

Cys Thr Ala Ile Lys Arg Val Leu Val Leu Lys Asp Val Ala Ala Pro
        290                 295                 300

Leu Ile Glu Lys Ile Lys Glu Lys Val Glu Lys Leu Thr Val Gly Arg
305                 310                 315                 320

Pro Glu Asp Asp Ala Asp Ile Thr Pro Leu Ile Asp Glu Ser Ser Ala
                325                 330                 335

Asp Phe Val Gln Gly Leu Ile Asp Asp Ala Leu Ala Lys Gly Ala Ser
                340                 345                 350

Leu Ile Thr Gly Asn Lys Arg Glu Lys Asn Leu Ile Tyr Pro Thr Val
            355                 360                 365
```

```
Leu Ser Asn Val Thr Lys Asp Met Lys Val Ala Trp Glu Glu Pro Phe
    370             375                 380
Gly Pro Val Leu Pro Cys Ile Ile Val Asp Ser Val Glu Glu Ala Ile
385                 390                 395                 400
Glu Ile Ala Asn Glu Ser Glu Phe Gly Leu Gln Ala Ser Val Phe Thr
                405                 410                 415
Ser Asn Ile Glu Lys Ala Phe Thr Ile Ala Ser Ser Leu Asp Val Gly
                420                 425                 430
Ser Val Gln Ile Asn Gly Arg Thr Glu Arg Gly Pro Asp His Phe Pro
                435                 440                 445
Phe Ser Ala Val Lys Asn Ser Gly Leu Gly Ser Gln Gly Ile Arg Gln
450                 455                 460
Ser Ile Ile Ser Met Met Arg Asp Lys Val Thr Val Ile Asn Leu Lys
465                 470                 475                 480
Lys

<210> SEQ ID NO 2
<211> LENGTH: 211
<212> TYPE: PRT
<213> ORGANISM: Bacillus methanolicus

<400> SEQUENCE: 2

Met Glu Leu Gln Leu Ala Leu Asp Leu Val Asn Ile Glu Ala Lys
1               5                   10                  15

Gln Val Val Ala Glu Val Gln Glu Tyr Val Asp Ile Val Glu Ile Gly
                20                  25                  30

Thr Pro Val Ile Lys Ile Trp Gly Leu Gln Ala Val Lys Ala Val Lys
            35                  40                  45

Asp Ala Phe Pro His Leu Gln Val Leu Ala Asp Met Lys Thr Met Asp
        50                  55                  60

Ala Ala Ala Tyr Glu Val Ala Lys Ala Ala Glu His Gly Ala Asp Ile
65                  70                  75                  80

Val Thr Ile Leu Ala Ala Ala Glu Asp Val Ser Ile Lys Gly Ala Val
                85                  90                  95

Glu Glu Ala Lys Lys Leu Gly Lys Lys Ile Leu Val Asp Met Ile Ala
                100                 105                 110

Val Lys Asn Leu Glu Glu Arg Ala Lys Gln Val Asp Glu Met Gly Val
            115                 120                 125

Asp Tyr Ile Cys Val His Ala Gly Tyr Asp Leu Gln Ala Val Gly Lys
130                 135                 140

Asn Pro Leu Asp Asp Leu Lys Arg Ile Lys Ala Val Val Lys Asn Ala
145                 150                 155                 160

Lys Thr Ala Ile Ala Gly Gly Ile Lys Leu Glu Thr Leu Pro Glu Val
                165                 170                 175

Ile Lys Ala Glu Pro Asp Leu Val Ile Val Gly Gly Gly Ile Ala Asn
            180                 185                 190

Gln Thr Asp Lys Lys Ala Ala Ala Glu Lys Ile Asn Lys Leu Val Lys
            195                 200                 205

Gln Gly Leu
    210

<210> SEQ ID NO 3
<211> LENGTH: 184
<212> TYPE: PRT
<213> ORGANISM: Bacillus methanolicus
```

<400> SEQUENCE: 3

```
Met Leu Thr Thr Glu Phe Leu Ala Glu Ile Val Lys Glu Leu Asn Ser
1               5                   10                  15

Ser Val Asn Gln Ile Ala Asp Glu Glu Ala Glu Ala Leu Val Asn Gly
            20                  25                  30

Ile Leu Gln Ser Lys Lys Val Phe Val Ala Gly Ala Gly Arg Ser Gly
        35                  40                  45

Phe Met Ala Lys Ser Phe Ala Met Arg Met Met His Met Gly Ile Asp
    50                  55                  60

Ala Tyr Val Val Gly Glu Thr Val Thr Pro Asn Tyr Glu Lys Glu Asp
65                  70                  75                  80

Ile Leu Ile Ile Gly Ser Gly Ser Gly Glu Thr Lys Ser Leu Val Ser
                85                  90                  95

Met Ala Gln Lys Ala Lys Ser Ile Gly Gly Thr Ile Ala Ala Val Thr
            100                 105                 110

Ile Asn Pro Glu Ser Thr Ile Gly Gln Leu Ala Asp Ile Val Ile Lys
        115                 120                 125

Met Pro Gly Ser Pro Lys Asp Lys Ser Glu Ala Arg Glu Thr Ile Gln
    130                 135                 140

Pro Met Gly Ser Leu Phe Glu Gln Thr Leu Leu Leu Phe Tyr Asp Ala
145                 150                 155                 160

Val Ile Leu Arg Phe Met Glu Lys Lys Gly Leu Asp Thr Lys Thr Met
                165                 170                 175

Tyr Gly Arg His Ala Asn Leu Glu
            180
```

<210> SEQ ID NO 4
<211> LENGTH: 382
<212> TYPE: PRT
<213> ORGANISM: Bacillus methanolicus

<400> SEQUENCE: 4

```
Met Thr Thr Asn Phe Phe Ile Pro Pro Ala Ser Val Ile Gly Arg Gly
1               5                   10                  15

Ala Val Lys Glu Val Gly Thr Arg Leu Lys Gln Ile Gly Ala Lys Lys
            20                  25                  30

Ala Leu Ile Val Thr Asp Ala Phe Leu His Ser Thr Gly Leu Ser Glu
        35                  40                  45

Glu Val Ala Lys Asn Ile Arg Glu Ala Gly Val Asp Val Ala Ile Phe
    50                  55                  60

Pro Lys Ala Gln Pro Asp Pro Ala Asp Thr Gln Val His Glu Gly Val
65                  70                  75                  80

Asp Val Phe Lys Gln Glu Asn Cys Asp Ser Leu Val Ser Ile Gly Gly
                85                  90                  95

Gly Ser Ser His Asp Thr Ala Lys Ala Ile Gly Leu Val Ala Ala Asn
            100                 105                 110

Gly Gly Arg Ile Asn Asp Tyr Gln Gly Val Asn Ser Val Glu Lys Pro
        115                 120                 125

Val Val Pro Val Val Ala Ile Thr Thr Thr Ala Gly Thr Gly Ser Glu
    130                 135                 140

Thr Thr Ser Leu Ala Val Ile Thr Asp Ser Ala Arg Lys Val Lys Met
145                 150                 155                 160

Pro Val Ile Asp Glu Lys Ile Thr Pro Thr Val Ala Ile Val Asp Pro
                165                 170                 175
```

```
Glu Leu Met Val Lys Lys Pro Ala Gly Leu Thr Ile Ala Thr Gly Met
            180                 185                 190

Asp Ala Leu Ser His Ala Ile Glu Ala Tyr Val Ala Lys Gly Ala Thr
            195                 200                 205

Pro Val Thr Asp Ala Phe Ala Ile Gln Ala Met Lys Leu Ile Asn Glu
    210                 215                 220

Tyr Leu Pro Lys Ala Val Ala Asn Gly Glu Asp Ile Glu Ala Arg Glu
225                 230                 235                 240

Lys Met Ala Tyr Ala Gln Tyr Met Ala Gly Val Ala Phe Asn Asn Gly
                245                 250                 255

Gly Leu Gly Leu Val His Ser Ile Ser His Gln Val Gly Gly Val Tyr
            260                 265                 270

Lys Leu Gln His Gly Ile Cys Asn Ser Val Asn Met Pro His Val Cys
        275                 280                 285

Ala Phe Asn Leu Ile Ala Lys Thr Glu Arg Phe Ala His Ile Ala Glu
    290                 295                 300

Leu Leu Gly Glu Asn Val Ala Gly Leu Ser Thr Ala Ala Ala Ala Glu
305                 310                 315                 320

Arg Ala Ile Val Ala Leu Glu Arg Ile Asn Lys Ser Phe Gly Ile Pro
                325                 330                 335

Ser Gly Tyr Ala Glu Met Gly Val Lys Glu Glu Asp Ile Glu Leu Leu
            340                 345                 350

Ala Lys Asn Ala Tyr Glu Asp Val Cys Thr Gln Ser Asn Pro Arg Val
        355                 360                 365

Pro Thr Val Gln Asp Ile Ala Gln Ile Ile Lys Asn Ala Met
    370                 375                 380

<210> SEQ ID NO 5
<211> LENGTH: 319
<212> TYPE: PRT
<213> ORGANISM: Bacillus methanolicus

<400> SEQUENCE: 5

Met Lys Lys Ile Gly Val Leu Thr Ser Gly Gly Asp Ser Pro Gly Met
1               5                   10                  15

Asn Ala Ala Ile Arg Ala Val Val Arg Lys Ala Ile Tyr His Asn Leu
            20                  25                  30

Glu Val Tyr Gly Val Tyr Gly Gly Tyr Leu Gly Leu Ile Asn Gly Asn
        35                  40                  45

Ile Lys Lys Leu Glu Leu Gly Ser Val Gly Asp Ile Ile His Arg Gly
    50                  55                  60

Gly Thr Met Leu Tyr Ser Ala Arg Cys Glu Glu Phe Lys Thr Lys Glu
65                  70                  75                  80

Gly Gln Leu Lys Gly Val Glu Gln Leu Lys Lys His Gly Ile Asp Gly
                85                  90                  95

Leu Val Val Ile Gly Gly Asp Gly Ser Tyr Arg Gly Ala Lys Ala Leu
            100                 105                 110

Thr Glu Leu Gly Phe Pro Cys Val Gly Val Pro Gly Thr Ile Asp Asn
        115                 120                 125

Asp Ile Pro Gly Thr Glu His Thr Ile Gly Phe Asp Thr Ala Leu Asn
    130                 135                 140

Thr Val Ile Asp Ala Ile Asp Lys Ile Arg Asp Thr Ala Ser Ser His
145                 150                 155                 160

Glu Arg Thr Phe Val Val Glu Val Met Gly Arg Asn Ala Gly Asp Ile
                165                 170                 175
```

```
Ala Leu Trp Ala Gly Leu Ala Gly Gly Ala Glu Ala Ile Val Ile Pro
            180                 185                 190

Glu Glu Asn Tyr Asp Ile Asn Glu Ile Ala Asp Arg Leu Lys Arg Ser
            195                 200                 205

His Glu Arg Gly Lys Arg His Ser Ile Ile Val Ala Glu Gly Val
210             215                 220

Cys Arg Gly Glu Glu Leu Ser Lys Gln Ile Thr Glu Ala Thr Gly Phe
225             230                 235                 240

Ala Thr Trp Val Thr Val Leu Gly His Val Gln Arg Gly Gly Ser Pro
            245                 250                 255

Ser Ala Phe Asp Arg Val Leu Ala Ser Arg Leu Gly Ala Arg Ala Val
            260                 265                 270

Glu Leu Leu Ile Glu Gly Lys Gly Arg Ala Val Gly Ile Arg Lys
            275                 280                 285

Asn Gln Val Val Asp Tyr Asp Phe Asp Glu Val Phe Ser Asn Glu His
            290                 295                 300

Thr Leu Asp Leu Glu Leu Cys Lys Leu Ser Lys Glu Leu Ser Ile
305                 310                 315

<210> SEQ ID NO 6
<211> LENGTH: 214
<212> TYPE: PRT
<213> ORGANISM: Bacillus methanolicus

<400> SEQUENCE: 6

Met Ile Lys Ile Ala Pro Ser Ile Leu Ser Ala Asn Phe Ala Arg Leu
1               5                   10                  15

Glu Glu Glu Ile Lys Asp Val Glu Arg Gly Gly Ala Asp Tyr Ile His
            20                  25                  30

Val Asp Val Met Asp Gly His Phe Val Pro Asn Ile Thr Ile Gly Pro
        35                  40                  45

Leu Ile Val Glu Ala Ile Arg Pro Val Thr Asn Leu Pro Leu Asp Val
    50                  55                  60

His Leu Met Ile Glu Asn Pro Asp Gln Tyr Ile Gly Thr Phe Ala Lys
65                  70                  75                  80

Ala Gly Ala Asp Ile Leu Ser Val His Val Glu Ala Cys Thr His Leu
                85                  90                  95

His Arg Thr Ile Gln Tyr Ile Lys Ser Glu Gly Ile Lys Ala Gly Val
            100                 105                 110

Val Leu Asn Pro His Thr Pro Val Ser Met Ile Glu His Val Ile Glu
        115                 120                 125

Asp Val Asp Leu Val Leu Leu Met Thr Val Asn Pro Gly Phe Gly Gly
    130                 135                 140

Gln Ser Phe Ile His Ser Val Leu Pro Lys Ile Lys Gln Val Ala Asn
145                 150                 155                 160

Ile Val Lys Glu Lys Asn Leu Gln Val Glu Ile Glu Val Asp Gly Gly
                165                 170                 175

Val Asn Pro Glu Thr Ala Lys Leu Cys Val Glu Ala Gly Ala Asn Val
            180                 185                 190

Leu Val Ala Gly Ser Ala Ile Tyr Asn Gln Glu Asp Arg Ser Gln Ala
        195                 200                 205

Ile Ala Lys Ile Arg Asn
    210
```

-continued

```
<210> SEQ ID NO 7
<211> LENGTH: 148
<212> TYPE: PRT
<213> ORGANISM: Bacillus methanolicus

<400> SEQUENCE: 7

Met Lys Val Ala Ile Ala Ser Asp His Gly Gly Val Asn Ile Arg Gln
1               5                   10                  15

Glu Ile Ile Asn Leu Leu Glu Glu Met Gly Ile Glu Tyr Glu Asp Phe
            20                  25                  30

Gly Cys Glu Cys Thr Thr Ser Val Asp Tyr Pro Asp Tyr Ala Leu Pro
        35                  40                  45

Val Ala Glu Lys Val Ala Asn Gly Glu Phe Asp Arg Gly Ile Leu Ile
    50                  55                  60

Cys Gly Thr Gly Ile Gly Met Ser Ile Ala Ala Asn Lys Val Lys Gly
65                  70                  75                  80

Ile Arg Cys Ala Leu Val His Asp Val Phe Ser Ala Lys Ala Thr Arg
                85                  90                  95

Glu His Asn Asp Ser Asn Ile Leu Ala Met Gly Glu Arg Val Ile Gly
            100                 105                 110

Pro Gly Leu Ala Arg Glu Ile Ala Lys Thr Trp Leu Thr Thr Glu Phe
        115                 120                 125

Gln Gly Gly Arg His Ser Asn Arg Ile Glu Lys Ile Cys Lys Tyr Glu
    130                 135                 140

Ser Val Asn Leu
145

<210> SEQ ID NO 8
<211> LENGTH: 668
<212> TYPE: PRT
<213> ORGANISM: Bacillus methanolicus

<400> SEQUENCE: 8

Met Phe Asp Lys Ile Asp Gln Leu Ser Ile Thr Ser Ile Arg Thr Leu
1               5                   10                  15

Ser Ile Asp Ala Ile Glu Lys Ala Asn Ser Gly His Pro Gly Met Pro
            20                  25                  30

Met Gly Ala Ala Pro Met Ala Tyr Thr Leu Trp Thr Arg Tyr Met Asn
        35                  40                  45

His Asn Pro Lys Asn Pro Asn Trp Phe Asn Arg Asp Arg Phe Val Leu
    50                  55                  60

Ser Ala Gly His Gly Ser Met Leu Leu Tyr Ser Leu Leu His Leu Ser
65                  70                  75                  80

Gly Tyr Asp Val Thr Met Asp Asp Ile Lys Glu Phe Arg Gln Trp Gly
                85                  90                  95

Ser Lys Thr Pro Gly His Pro Glu Tyr Gly His Thr Pro Gly Val Glu
            100                 105                 110

Ala Thr Thr Gly Pro Leu Gly Gln Gly Ile Ala Met Ala Val Gly Ile
        115                 120                 125

Gly Met Ala Glu Arg His Leu Ala Ala Val Tyr Asn Lys Asp Asn Tyr
    130                 135                 140

Gln Ile Ile Asn His Tyr Thr Tyr Ser Ile Cys Gly Asp Gly Asp Leu
145                 150                 155                 160

Met Glu Gly Val Ser Ala Glu Ala Ala Ser Leu Ala Gly His Leu Arg
                165                 170                 175

Leu Gly Arg Leu Ile Val Leu Tyr Asp Ser Asn Asp Ile Ser Leu Asp
```

```
            180                 185                 190
Gly Glu Leu Asn Arg Ser Phe Ser Glu Ser Val Glu Met Arg Phe Lys
            195                 200                 205
Ser Tyr Gly Trp Gln Tyr Ile Arg Val Glu Asp Gly Asn Asp Leu Glu
            210                 215                 220
Ala Ile Ala Lys Ala Ile Glu Glu Ala Lys Gln Asp Glu Thr Arg Pro
225                 230                 235                 240
Thr Leu Ile Glu Val Lys Thr Ile Ile Gly Tyr Gly Ser Pro Asn Arg
                245                 250                 255
Ala Gly Thr Ser Asp Ile His Gly Ser Pro Leu Gly Ala Glu Glu Arg
                260                 265                 270
Lys Leu Thr Lys Glu Ala Tyr Lys Trp Thr Phe Glu Glu Asp Phe Tyr
                275                 280                 285
Val Pro Gln Glu Val Tyr Asp His Phe Lys Gln Asn Val Ile Glu Arg
            290                 295                 300
Gly Glu Ala Lys Glu Gln Glu Trp Asn Glu Leu Phe Ala Gln Tyr Lys
305                 310                 315                 320
Lys Glu Tyr Pro Glu Leu Gly Lys Gln Leu Glu Gln Ala Ile Asn Gly
                325                 330                 335
Glu Leu Pro Glu Gly Trp Asp Lys Asp Ile Pro Val Tyr Glu Val Gly
                340                 345                 350
Lys Ser Ile Ala Ser Arg Ala Ser Ser Gly Glu Val Leu Asn Ala Ile
                355                 360                 365
Ala Lys Asn Leu Pro Ser Phe Ile Gly Gly Ser Ala Asp Leu Ala Ser
            370                 375                 380
Ser Asn Lys Thr Thr Ile Lys Gly Ala Gly Asp Tyr Ser Pro Glu Ser
385                 390                 395                 400
Phe Glu Gly Lys Asn Ile Trp Phe Gly Val Arg Glu Phe Ala Met Gly
                405                 410                 415
Ala Ala Leu Asn Gly Met Ala Leu His Gly Gly Leu Lys Val Phe Gly
                420                 425                 430
Gly Thr Phe Phe Val Phe Ser Asp Tyr Leu Arg Pro Ala Ile Arg Leu
            435                 440                 445
Ala Ala Leu Met Lys Leu Pro Val Ile Tyr Val Phe Thr His Asp Ser
450                 455                 460
Ile Ala Val Gly Glu Asp Gly Pro Thr His Glu Pro Val Glu Gln Leu
465                 470                 475                 480
Ala Ser Leu Arg Ala Met Pro Asn Leu Ser Val Ile Arg Pro Ala Asp
                485                 490                 495
Gly Asn Glu Thr Ala Ala Ala Trp Arg Leu Ala Val Glu Ser Lys Asp
            500                 505                 510
Lys Pro Thr Ala Leu Val Leu Ser Arg Gln Asn Leu Pro Thr Leu Lys
            515                 520                 525
Gly Thr Ala Glu Thr Ala Tyr Asp Gly Val Ser Lys Gly Ala Tyr Val
            530                 535                 540
Val Ser Pro Ala Asp Lys Asp Thr Pro Asp Ala Leu Leu Leu Ala Ser
545                 550                 555                 560
Gly Ser Glu Val Gly Leu Ala Val Glu Ala Gln Val Arg Leu Ala Glu
                565                 570                 575
Glu Gly Ile His Val Ser Val Ile Ser Met Pro Ser Phe Asp Arg Phe
            580                 585                 590
Glu Ala Gln Ser Lys Glu Tyr Lys Glu Ser Val Ile Pro Lys Asn Val
            595                 600                 605
```

```
Lys Lys Arg Leu Val Ile Glu Met Ala Ser Ser Leu Gly Leu His Arg
            610                 615                 620

Tyr Ala Gly Asp Glu Gly Asp Val Leu Ala Ile Asp Gln Phe Gly Ala
625                 630                 635                 640

Ser Ala Pro Gly Glu Ile Ile Met Glu Glu Tyr Gly Phe Asn Val Asp
                645                 650                 655

Asn Val Val Ala Lys Val Lys Ala Leu Leu Glu Lys
            660                 665

<210> SEQ ID NO 9
<211> LENGTH: 284
<212> TYPE: PRT
<213> ORGANISM: Bacillus methanolicus

<400> SEQUENCE: 9

Met Pro Leu Val Ser Met Lys Asp Met Leu Asn His Gly Lys Glu Asn
1               5                   10                  15

Gly Tyr Ala Val Gly Gln Phe Asn Ile Asn Leu Glu Phe Gly Gln
            20                  25                  30

Ala Ile Leu Gln Ala Ala Glu Glu Lys Ser Pro Val Ile Ile Gly
            35                  40                  45

Val Ser Val Gly Ala Ala Asn Tyr Met Gly Gly Phe Lys Leu Ile Val
50                  55                  60

Asp Met Val Lys Ser Ser Met Asp Ser Tyr Asn Val Thr Val Pro Val
65                  70                  75                  80

Ala Ile His Leu Asp His Gly Pro Ser Leu Glu Lys Cys Val Gln Ala
                85                  90                  95

Ile His Ala Gly Phe Thr Ser Val Met Ile Asp Gly Ser His Leu Pro
            100                 105                 110

Leu Glu Glu Asn Ile Glu Leu Thr Lys Arg Val Val Glu Ile Ala His
            115                 120                 125

Ser Val Gly Val Ser Val Glu Ala Glu Leu Gly Arg Ile Gly Gly Gln
            130                 135                 140

Glu Asp Asp Val Val Ala Glu Ser Phe Tyr Ala Ile Pro Ser Glu Cys
145                 150                 155                 160

Glu Gln Leu Val Arg Glu Thr Gly Val Asp Cys Phe Ala Pro Ala Leu
                165                 170                 175

Gly Ser Val His Gly Pro Tyr Lys Gly Glu Pro Lys Leu Gly Phe Asp
            180                 185                 190

Arg Met Glu Glu Ile Met Lys Leu Thr Gly Val Pro Leu Val Leu His
            195                 200                 205

Gly Gly Thr Gly Ile Pro Thr Lys Asp Ile Gln Lys Ala Ile Ser Leu
            210                 215                 220

Gly Thr Ala Lys Ile Asn Val Asn Thr Glu Ser Gln Ile Ala Ala Thr
225                 230                 235                 240

Lys Ala Val Arg Glu Val Leu Asn Asn Asp Ala Lys Leu Phe Asp Pro
                245                 250                 255

Arg Lys Phe Leu Ala Pro Ala Arg Glu Ala Ile Lys Glu Thr Ile Lys
            260                 265                 270

Gly Lys Met Arg Glu Phe Gly Ser Ser Gly Lys Ala
            275                 280

<210> SEQ ID NO 10
<211> LENGTH: 484
<212> TYPE: PRT
```

<213> ORGANISM: Bacillus methanolicus

<400> SEQUENCE: 10

```
Met Asp Ser Met Thr Phe Val Leu Phe Gly Ala Ser Gly Asp Leu Ala
 1               5                  10                  15

Lys Arg Lys Ile Tyr Pro Ala Leu Tyr Asn Leu Phe Leu Asp Gln Lys
            20                  25                  30

Met Pro Gln Ser Phe Ser Val Ile Gly Leu Gly Arg Arg Asp Trp Ser
        35                  40                  45

Asp Asn Glu Tyr Gln Met Arg Val Glu Gln Ser Leu Lys Thr Phe Ser
    50                  55                  60

Arg Arg Phe Val Ile Asp Ser Ile Lys Met Lys Glu Phe Leu Ser Ala
65                  70                  75                  80

Phe Arg Phe Phe Arg Leu Asp Val Asn Asn Glu Glu Gly Phe Arg Asp
                85                  90                  95

Leu Phe Glu Phe Val Lys Lys Arg Glu Glu Leu Asn Ile Pro Glu
            100                 105                 110

Asn Arg Met Phe Tyr Leu Ser Val Ala Pro Glu Phe Ile Gly Val Ile
            115                 120                 125

Ala Ser Asn Ile Lys Lys Ser Gly Leu Gly Thr Thr Lys Gly Trp Lys
130                 135                 140

Arg Leu Val Ile Glu Lys Pro Phe Gly Asn Asp Leu Lys Ser Ala Gln
145                 150                 155                 160

Glu Leu Asn Glu Ser Leu Arg Asn Val Phe Glu Glu Asp Glu Ile Tyr
                165                 170                 175

Arg Ile Asp His Tyr Leu Gly Lys Pro Met Val Gln Asn Leu Glu Ala
            180                 185                 190

Leu Glu Phe Ala Asn Pro Val Leu Gln Ala Ile Trp Asn Asn Gln Tyr
            195                 200                 205

Ile Ala Asn Val Gln Ile Thr Ala Ser Glu Thr Val Gly Val Glu Glu
210                 215                 220

Arg Ala Gly Tyr Tyr Asp Gln Ala Gly Ala Ile Arg Asp Met Phe Gln
225                 230                 235                 240

Asn His Met Leu Gln Leu Leu Met Met Thr Ala Met Lys Met Pro Glu
                245                 250                 255

Arg Ile Ser Ser Lys Asp Ile Arg Asn Glu Lys Ile Lys Val Met Glu
            260                 265                 270

Tyr Leu Arg Pro Leu Leu Lys Glu Asp Val Ala Lys His Val Val Arg
            275                 280                 285

Gly Gln Tyr Gly Pro Gly Glu Ile Asn Gly Glu Pro Val Val Gly Tyr
290                 295                 300

Arg Glu Glu Pro Gly Val Asp Ala Ser Ser Thr Thr Asp Thr Phe Val
305                 310                 315                 320

Ala Ala Arg Leu Trp Ile Asp Val Pro Phe Trp Ser Gly Val Pro Phe
                325                 330                 335

Tyr Ile Arg Thr Gly Lys Arg Met Arg Glu Lys Cys Thr Lys Ile Val
            340                 345                 350

Ile Glu Phe Lys Asn Pro Leu Lys Asp Leu Tyr Ile Thr Asp Asn Met
            355                 360                 365

Lys Thr Val Pro Asn Leu Leu Val Ile Glu Ile Asn Pro Asn Glu Arg
        370                 375                 380

Val Ser Phe Gln Leu Asn Ser Asn Pro Ile Asp Gly Lys Ile Glu
385                 390                 395                 400
```

Pro Val His Val Asn Phe Ser Ala Ser Gln Lys Asp Ala Pro Glu Ala
            405                 410                 415

Tyr Glu Ile Leu Leu Tyr Asp Ala Leu Arg Gly Asp Ser Thr Tyr Phe
            420                 425                 430

Ala His Trp Lys Glu Val Glu Leu Ser Trp Lys Trp Val Gln Pro Ile
            435                 440                 445

Leu Glu Ala Phe Glu Glu Asn Ile Leu Pro Leu His His Tyr Thr Ser
450                 455                 460

Gly Ser Met Gly Pro Glu Ala Ser His Lys Leu Leu Glu Glu Asp Gly
465                 470                 475                 480

Phe Asn Trp Trp

<210> SEQ ID NO 11
<211> LENGTH: 481
<212> TYPE: PRT
<213> ORGANISM: Bacillus methanolicus

<400> SEQUENCE: 11

Met Gln Val Leu Glu Lys Asp His Lys Phe Leu Leu Asn Gly Lys Trp
1               5                   10                  15

Cys Tyr Ser Ser Asn Glu Phe Ile Asn Ile Tyr Ser Pro Ser Thr
            20                  25                  30

Gly Glu Ile Val Gly Arg Val Pro Ala Met Thr Lys Asp Glu Ile Asp
            35                  40                  45

Lys Ala Val Ala Gly Ala Cys Gln Ala Gln Lys Asn Trp Glu Lys Leu
50                  55                  60

Ala Val Ser Asp Arg Ala Lys Ile Leu His Ala Trp Ala Asp Glu Leu
65                  70                  75                  80

Val Lys Met Ile Asp Val Ile Ala Pro Met Ile Met Asn Glu Val Gly
            85                  90                  95

Lys Asn Ile Ser Thr Ala Lys Arg Glu Val Ile Arg Thr Ala Asp Ile
            100                 105                 110

Ile Arg Tyr Thr Ala Glu Glu Gly Val Arg Ile His Gly Glu Phe Ile
            115                 120                 125

Asn Gly Gly Ser Leu Asp Ala Asp Ser Ser Lys Lys Thr Ala Ile Val
            130                 135                 140

Glu Lys Lys Pro Leu Gly Val Ile Leu Ala Ile Ser Pro Phe Asn Tyr
145                 150                 155                 160

Pro Ile Asn Leu Ala Ala Thr Lys Ile Ala Pro Ala Leu Ile Ala Gly
            165                 170                 175

Asn Ala Val Val Phe Lys Pro Ala Thr Gln Gly Ala Ile Ser Gly Leu
            180                 185                 190

Leu Met Ile Gln Ala Leu Glu Asn Ala Gly Leu Pro Glu Gly Leu Val
            195                 200                 205

Asn Thr Val Thr Gly Lys Gly Ser Glu Ile Gly Asp Tyr Ile Ile Thr
210                 215                 220

His Pro Phe Ile Asp Met Ile Ser Phe Thr Gly Gly Thr Gly Thr Gly
225                 230                 235                 240

Gln Asn Ile Ala Arg Lys Ala Ser Met Ile Pro Leu Val Leu Glu Leu
            245                 250                 255

Gly Gly Lys Asp Pro Ala Ile Val Leu Glu Asp Ala Asp Leu Glu Leu
            260                 265                 270

Ala Ala Ala Glu Ile Val Ser Gly Ala Phe Ser Tyr Ser Gly Gln Arg
            275                 280                 285

```
Cys Thr Ala Ile Lys Arg Val Ile Val Leu Lys Asp Ala Ala Ala Pro
    290                 295                 300

Leu Ile Glu Lys Ile Lys Glu Lys Val Glu Lys Leu Thr Val Gly Lys
305                 310                 315                 320

Pro Glu Asp Asp Ala Asp Ile Thr Pro Leu Ile Asp Glu Ser Ser Ala
                    325                 330                 335

Asp Phe Val Gln Gly Leu Ile Asp Asp Ala Leu Ala Lys Gly Ala Thr
                340                 345                 350

Leu Ile Thr Gly Asn Lys Arg Glu Lys Asn Leu Ile Tyr Pro Thr Val
            355                 360                 365

Leu Ser Asn Val Thr Lys Asp Met Lys Val Ala Trp Glu Glu Pro Phe
370                 375                 380

Gly Pro Val Leu Pro Cys Ile Ile Val Asp Ser Ala Glu Glu Ala Ile
385                 390                 395                 400

Glu Ile Ala Asn Glu Ser Glu Phe Gly Leu Gln Ala Ser Val Phe Thr
                405                 410                 415

Thr Asn Ile Glu Lys Ala Phe Ser Ile Ala Ser Ser Leu Asp Val Gly
                420                 425                 430

Ser Val Gln Ile Asn Gly Arg Thr Glu Arg Gly Pro Asp His Phe Pro
            435                 440                 445

Phe Ser Ala Val Lys Asn Ser Gly Leu Gly Ser Gln Gly Ile Arg Gln
450                 455                 460

Ser Ile Ile Ser Met Met Arg Asp Lys Val Thr Val Ile Asn Leu Lys
465                 470                 475                 480

Arg

<210> SEQ ID NO 12
<211> LENGTH: 482
<212> TYPE: PRT
<213> ORGANISM: Alicyclobacillus pomorum

<400> SEQUENCE: 12

Met Gln Gln Val Leu Asp Gly Val Ile Asp Tyr His Phe Leu Leu Asn
1               5                   10                  15

Gly Asn Trp Gly Gln Ser Ala Ser Asn Arg Phe Ile Asp Val Val Ser
                20                  25                  30

Pro Asn Asp Gly Cys Val Ala Gly Arg Ile Pro Ala Met Thr Lys Glu
            35                  40                  45

Glu Val Asp Leu Ala Val Gln Gly Ala Val Gln Ala Lys Gln Gln Trp
        50                  55                  60

Gly Leu Leu Pro Val His Glu Arg Gly Gln Leu Leu Asn Trp Ala
65                  70                  75                  80

Asp Glu Leu Ala Met Met Ser Asp Glu Ile Ala Glu Met Ile Met Lys
                85                  90                  95

Glu Val Gly Lys Thr Tyr Ser Ala Ala Lys Asn Glu Val Leu Arg Thr
            100                 105                 110

Ser Asp Leu Ile Arg Tyr Thr Val Glu Glu Gly Lys Arg Ile His Gly
        115                 120                 125

Glu Val Met Thr Gly Asp Ser Phe Gln Gly Ser Asn Ala Asn Lys Val
    130                 135                 140

Ala Ile Val Arg Lys Glu Pro Leu Gly Val Ile Leu Ala Ile Ser Pro
145                 150                 155                 160

Phe Asn Tyr Pro Val Asn Leu Ser Ala Ala Lys Ile Ala Pro Ala Leu
                165                 170                 175
```

```
Ile Ser Gly Asn Thr Val Ile Leu Lys Pro Ala Thr Gln Gly Ser Ile
            180                 185                 190

Ser Ala Leu Leu Met Ala Lys Ala Leu Asp Lys Val Gly Leu Pro Lys
        195                 200                 205

Gly Val Leu Asn Val Val Thr Gly Lys Gly Ser Glu Ile Gly Asp Tyr
    210                 215                 220

Leu Val Thr His Pro Ser Ile Arg Met Ile Ser Phe Thr Gly Gly Thr
225                 230                 235                 240

Lys Thr Gly Arg Asp Ile Ala Lys Lys Ala Thr Met Ile Pro Leu Val
                245                 250                 255

Leu Glu Leu Gly Gly Lys Asp Pro Ala Ile Val Leu Glu Asp Ala Asn
            260                 265                 270

Leu Asp Lys Ala Ala Arg His Ile Val Ser Gly Ala Phe Ser Tyr Ser
        275                 280                 285

Gly Gln Arg Cys Thr Ala Ile Lys Arg Val Leu Val Met Asp Ser Val
    290                 295                 300

Ala Asp Ser Leu Ile Glu Lys Val Lys Gln Val Glu Lys Leu Thr
305                 310                 315                 320

Val Gly Met Pro Glu Gln Asp Ala Ala Ile Thr Pro Leu Ile Asp Ala
                325                 330                 335

Ser Ser Ala Asp Phe Val Asn Asp Leu Ile Leu Asp Ala Leu Asn Lys
            340                 345                 350

Gly Ala Ile Pro Ile Thr Glu Tyr Arg Arg Val Gly Asn Leu Ile Tyr
        355                 360                 365

Pro Leu Val Leu Asp His Val Thr Gln Asp Met Lys Val Ala Trp Glu
370                 375                 380

Glu Pro Phe Gly Pro Val Leu Pro Ile Ile Arg Val Lys Asn Glu Gln
385                 390                 395                 400

Glu Ala Val Glu Ile Ala Asn Ala Ser Glu Tyr Gly Leu Gln Ala Ser
                405                 410                 415

Ile Phe Thr Gln Asp Ile Asp Lys Ala Phe His Leu Ala Ser Lys Leu
            420                 425                 430

Glu Val Gly Ser Val Gln Ile Asn Gly Arg Thr Glu Arg Gly Pro Asp
        435                 440                 445

His Phe Pro Phe Leu Gly Val Lys Asn Ser Gly Met Gly Val Gln Gly
    450                 455                 460

Val Arg Lys Ser Ile Glu Ser Met Thr Arg Asp Lys Val Leu Val Leu
465                 470                 475                 480

Asn Leu

<210> SEQ ID NO 13
<211> LENGTH: 482
<212> TYPE: PRT
<213> ORGANISM: Virgibacillus necropolis

<400> SEQUENCE: 13

Met Lys Ala Glu Met Ile Ala Asn Thr Tyr Gln Phe Leu Leu Asn Gly
1               5                   10                  15

Glu Trp Arg Glu Ser Leu Ser Gly Lys Thr Ile Glu Asn Gln Ser Pro
            20                  25                  30

Ser Asp Asn Thr Pro Val Gly Ser Val Gln Ala Met Thr Glu Asn Glu
        35                  40                  45

Val Asn Leu Ala Val Thr Gly Ala Lys Ala Ala Gln Lys Asp Trp Ala
    50                  55                  60
```

```
Asn Leu Ser Phe Ser Glu Arg Ala Glu Leu Tyr Ala Trp Ala Asp
 65                  70                  75                  80

Gln Leu Leu Glu Met Lys Glu Glu Ile Ala Glu Thr Ile Met Lys Glu
                 85                  90                  95

Val Gly Lys Gly Tyr Ser Ser Ala Glu Lys Glu Val Val Arg Thr Ala
            100                 105                 110

Asp Phe Ile Lys Tyr Thr Ala Glu Glu Gly Lys Arg Ile His Gly Glu
        115                 120                 125

Leu Ile Asn Gly Gly Ser Phe Asn Ala Gly Ser Ala Asn Lys Leu Ala
    130                 135                 140

Met Val Gln Arg Glu Pro Leu Gly Val Ile Leu Ala Ile Ser Pro Phe
145                 150                 155                 160

Asn Tyr Pro Val Asn Leu Ser Ala Ala Lys Ile Ala Pro Ala Leu Ile
                165                 170                 175

Ala Gly Asn Ala Val Val Phe Lys Pro Ala Thr Gln Gly Ala Ile Ser
            180                 185                 190

Gly Thr Leu Met Val Arg Ala Leu Asp Lys Ala Gly Leu Pro Ser Gly
        195                 200                 205

Leu Val Asn Leu Val Thr Gly Lys Gly Ser Glu Ile Gly Asp Tyr Leu
    210                 215                 220

Thr Thr His Pro Ser Ile Asp Leu Ile Asn Phe Thr Gly Gly Ser Glu
225                 230                 235                 240

Thr Gly Glu Tyr Ile Ser Lys Lys Ala Ser Met Ile Pro Val Ile Leu
                245                 250                 255

Glu Leu Gly Gly Lys Asp Pro Ala Ile Val Leu Asn Asp Ala Asp Leu
            260                 265                 270

Glu Lys Ala Ala Gly Asp Ile Val Gly Gly Phe Ser Tyr Ser Gly
        275                 280                 285

Gln Arg Cys Thr Ala Ile Lys Arg Val Leu Val Leu Asp Glu Val Ala
    290                 295                 300

Asp Ala Leu Val Asp Lys Leu Lys Asp Lys Ile Lys Ala Leu Glu Val
305                 310                 315                 320

Gly Met Pro Glu Asp Asn Ala Thr Val Thr Pro Leu Ile Asn Glu Lys
                325                 330                 335

Ala Ala Asp Phe Val Gln Gln Leu Val Asp Asp Ala Val Gly Lys Gly
            340                 345                 350

Ala Thr Pro Leu Thr Asp Ile Arg Arg Glu Gly Asn Leu Val Tyr Pro
        355                 360                 365

Val Leu Leu Asp Asn Val Thr Val Asp Met Thr Val Ala Trp Glu Glu
    370                 375                 380

Pro Phe Gly Pro Val Leu Pro Ile Ile Arg Val Gln Asn Ile Glu Glu
385                 390                 395                 400

Ala Val Ile Ile Ala Asn Glu Ser Glu Tyr Gly Leu Gln Ala Ser Val
                405                 410                 415

Phe Thr Lys Asn Val Glu Gln Ala Ile Arg Ile Gly Ser Glu Leu Glu
            420                 425                 430

Val Gly Ser Val Gln Ile Asn Gly Lys Thr Glu Arg Gly Pro Asp His
        435                 440                 445

Phe Pro Phe Leu Gly Val Lys Asn Ser Gly Leu Gly Ala Gln Gly Ile
    450                 455                 460

Arg Lys Ser Ile Glu Ser Val Thr Arg Glu Lys Val Thr Val Leu Asn
465                 470                 475                 480

Met Ser
```

<210> SEQ ID NO 14
<211> LENGTH: 479
<212> TYPE: PRT
<213> ORGANISM: Bacillus cytotoxicus

<400> SEQUENCE: 14

Met Thr Thr Ser Asn Thr Tyr Lys Phe Tyr Leu Asn Gly Glu Trp Arg
1               5                   10                  15

Glu Ser Ser Ser Gly Gln Thr Ile Asp Ile Val Ser Pro Tyr Leu His
            20                  25                  30

Glu Val Ile Gly Lys Val Gln Ala Ile Thr Arg Asp Glu Val Asp Glu
        35                  40                  45

Ala Ile Ala Ser Ala Lys Glu Ala Gln Lys Asp Trp Ala Ala Ala Ser
    50                  55                  60

Leu Gln Asp Arg Ala Lys Phe Leu Tyr Lys Trp Ala Asp Glu Leu Val
65                  70                  75                  80

Asn Met Gln Asp Glu Ile Ala Asp Ile Val Met Lys Glu Val Gly Lys
                85                  90                  95

Gly His Lys Asp Ala Lys Lys Glu Val Val Arg Thr Ala Asp Leu Ile
            100                 105                 110

Arg Tyr Thr Val Asp Glu Ala Leu His Met His Gly Asp Ser Met Met
        115                 120                 125

Gly Asp Ser Phe Pro Gly Gly Ser Lys Ser Lys Leu Ala Ile Ile Gln
    130                 135                 140

Arg Ala Pro Leu Gly Val Val Leu Ala Ile Ser Pro Phe Asn Tyr Pro
145                 150                 155                 160

Val Asn Leu Ala Ala Ala Lys Val Ala Pro Ala Leu Ile Met Gly Asn
                165                 170                 175

Ala Val Ile Phe Lys Pro Ala Thr Gln Gly Ala Ile Ser Gly Ile Lys
            180                 185                 190

Met Val Glu Ala Leu His Lys Ala Gly Leu Pro Lys Gly Leu Val Asn
        195                 200                 205

Val Val Thr Gly Arg Gly Ser Val Ile Gly Asp Tyr Leu Val Glu His
    210                 215                 220

Pro Gly Ile Asn Met Val Ser Phe Thr Gly Gly Thr Asn Thr Gly Ala
225                 230                 235                 240

His Leu Ala Lys Lys Ala Ala Met Ile Pro Leu Val Leu Glu Leu Gly
                245                 250                 255

Gly Lys Asp Pro Gly Ile Val Cys Glu Asp Ala Asp Leu Thr Glu Ala
            260                 265                 270

Ala Lys His Ile Val Ser Gly Ala Phe Ser Tyr Ser Gly Gln Arg Cys
        275                 280                 285

Thr Ala Ile Lys Arg Val Leu Val His Glu Asn Val Ala Asp Glu Leu
    290                 295                 300

Val Ser Leu Leu Lys Glu Gln Val Ala Ala Leu Ser Val Gly Ser Pro
305                 310                 315                 320

Glu Gln Asp Ser Thr Ile Val Pro Leu Ile Asp Asp Lys Ser Ala Asp
                325                 330                 335

Phe Val Gln Gly Leu Val Asp Asp Ala Val Glu Asn Gly Ala Thr Ile
            340                 345                 350

Ile Ile Gly Asn Lys Arg Glu Arg Asn Leu Ile Tyr Pro Thr Ile Ile
        355                 360                 365

Asp Asn Val Thr Glu Glu Met Lys Val Ala Trp Glu Glu Pro Phe Gly

```
                370             375             380
Pro Ile Leu Pro Ile Ile Arg Val Ser Ser Asp Glu Glu Ala Ile Glu
385                 390                 395                 400

Ile Ala Asn Lys Ser Glu Phe Gly Leu Gln Ala Ser Val Phe Thr Lys
            405                 410                 415

Asp Ile Asn Lys Ala Phe Ala Ile Ala Asn Lys Ile Asp Thr Gly Ser
            420                 425                 430

Val Gln Ile Asn Gly Arg Thr Glu Arg Gly Pro Asp His Phe Pro Phe
        435                 440                 445

Ile Gly Val Lys Gly Ser Gly Met Gly Ala Gln Gly Ile Arg Lys Ser
    450                 455                 460

Leu Glu Ser Met Thr Arg Glu Lys Val Thr Val Leu Asn Leu Val
465                 470                 475

<210> SEQ ID NO 15
<211> LENGTH: 479
<212> TYPE: PRT
<213> ORGANISM: Bacillus cytotoxicus

<400> SEQUENCE: 15

Met Thr Thr Ser Asn Thr Tyr Lys Phe Tyr Leu Asn Gly Glu Trp Arg
1               5                   10                  15

Glu Ser Ser Ser Gly Gln Thr Ile Asp Ile Leu Ser Pro Tyr Leu His
            20                  25                  30

Glu Val Ile Gly Lys Val Gln Ala Ile Thr Arg Asp Glu Val Asp Glu
        35                  40                  45

Ala Ile Ala Ala Ala Lys Glu Ala Gln Lys Asp Trp Ala Glu Ala Ser
    50                  55                  60

Leu Gln Asp Arg Ala Lys Phe Leu Tyr Lys Trp Ala Asp Glu Leu Val
65                  70                  75                  80

Asn Met Gln Asp Glu Ile Ala Asp Ile Met Lys Glu Val Gly Lys
                85                  90                  95

Gly Tyr Lys Asp Ala Lys Lys Glu Val Val Arg Thr Ala Asp Phe Ile
            100                 105                 110

Arg Tyr Thr Val Asp Glu Ala Leu His Met His Gly Glu Ser Met Met
        115                 120                 125

Gly Asp Ser Phe Pro Gly Gly Thr Lys Ser Lys Leu Ala Ile Ile Gln
130                 135                 140

Arg Ala Pro Leu Gly Val Val Leu Ala Ile Ala Pro Phe Asn Tyr Pro
145                 150                 155                 160

Val Asn Leu Ser Ala Ala Lys Leu Ala Pro Ala Leu Ile Met Gly Asn
                165                 170                 175

Ala Val Ile Phe Lys Pro Ala Thr Gln Gly Ala Ile Ser Gly Ile Lys
            180                 185                 190

Met Val Glu Ala Ile His Lys Ala Gly Leu Pro Lys Gly Leu Val Asn
        195                 200                 205

Val Val Thr Gly Arg Gly Ser Val Ile Gly Asp Tyr Leu Val Glu His
    210                 215                 220

Glu Asp Ile Asn Met Val Ser Phe Thr Gly Gly Thr Asn Thr Gly Lys
225                 230                 235                 240

His Leu Ala Lys Lys Ala Ala Met Ile Pro Leu Val Leu Glu Leu Gly
                245                 250                 255

Gly Lys Asp Pro Gly Ile Val Arg Glu Asp Ala Asp Leu Gln Asp Ala
            260                 265                 270
```

```
Ala Asn His Ile Val Ser Gly Ala Phe Ser Tyr Ser Gly Gln Arg Cys
            275                 280                 285

Thr Ala Ile Lys Arg Val Leu Val His Glu Asn Val Ala Asp Glu Leu
290                 295                 300

Val Ser Leu Leu Lys Glu Lys Val Ala Ala Leu Ser Val Gly Ser Pro
305                 310                 315                 320

Glu Gln Asp Ser Thr Ile Val Pro Leu Ile Asp Asp Lys Ser Ala Asp
                325                 330                 335

Phe Val Gln Gly Leu Val Asp Asp Ala Val Lys Gly Ala Thr Ile
                340                 345                 350

Ile Ile Gly Asn Lys Arg Glu Arg Asn Leu Ile Tyr Pro Thr Ile Ile
            355                 360                 365

Asp Asn Val Thr Glu Glu Met Lys Val Ala Trp Glu Pro Phe Gly
370                 375                 380

Pro Ile Leu Pro Ile Ile Arg Val Ser Ser Asp Glu Glu Ala Ile Glu
385                 390                 395                 400

Ile Ala Asn Lys Ser Glu Phe Gly Leu Gln Ala Ser Val Phe Thr Lys
                405                 410                 415

Asp Ile Asn Lys Ala Phe Ala Ile Ala Asn Lys Ile Asp Thr Gly Ser
                420                 425                 430

Val Gln Ile Asn Gly Arg Thr Glu Arg Gly Pro Asp His Phe Pro Phe
            435                 440                 445

Ile Gly Val Lys Gly Ser Gly Met Gly Ala Gln Gly Ile Arg Lys Ser
            450                 455                 460

Leu Glu Ser Met Thr Arg Glu Lys Val Thr Val Leu Asn Leu Val
465                 470                 475

<210> SEQ ID NO 16
<211> LENGTH: 484
<212> TYPE: PRT
<213> ORGANISM: Lentibacillus amyloliquefaciens

<400> SEQUENCE: 16

Met Ser Glu Val Glu Thr Ile Lys Ala Tyr Pro Phe Leu Leu Asn Gly
1               5                   10                  15

Glu Trp Gln Asn Thr Thr Ser Glu Arg Thr Ile Glu Ile Glu Ser Pro
                20                  25                  30

Ser Gly Ala Glu Thr Pro Gly Ala Val Gln Ala Met Thr Glu Ser Glu
            35                  40                  45

Val Asn Ala Ala Ile Ser Gly Ala Asn Glu Ala Gln Lys Asn Trp Ala
50                  55                  60

Arg Lys Ser Phe Asp Glu Arg Ala Gln Val Leu His Ser Trp Ala Asp
65                  70                  75                  80

Gln Leu Leu Leu Met Lys Asp Glu Ile Ala Glu Ala Ile Met Lys Glu
                85                  90                  95

Ala Gly Lys Gly Leu Ser Ser Ala Glu Lys Glu Val Val Arg Thr Ala
            100                 105                 110

Asp Phe Ile Lys Tyr Thr Ala Glu Glu Gly Lys Arg Leu His Gly Glu
            115                 120                 125

Leu Ile Asn Gly Gly Ser Phe Asn Ala Gly Ser Ala Asn Lys Phe Ala
            130                 135                 140

Leu Val Asn Arg Asn Pro Ile Gly Val Val Leu Ala Ile Ser Pro Phe
145                 150                 155                 160

Asn Tyr Pro Val Asn Leu Ser Ala Ala Lys Ile Ala Pro Ala Leu Ile
                165                 170                 175
```

```
Gly Gly Asn Ala Val Val Phe Lys Pro Ala Thr Gln Gly Ala Ile Ser
            180                 185                 190

Gly Thr Leu Met Ile Glu Ala Leu Asp Lys Ala Gly Leu Pro Ser Gly
        195                 200                 205

Leu Val Asn Leu Val Thr Gly Lys Gly Ala Glu Ile Gly Asp His Leu
    210                 215                 220

Ile Thr His Pro Leu Ile Asp Leu Ile Asn Phe Thr Gly Gly Ser Gln
225                 230                 235                 240

Thr Gly Lys Ser Ile Ser Gln Lys Ala Ser Met Val Pro Leu Ile Leu
                245                 250                 255

Glu Leu Gly Gly Lys Asp Pro Ala Ile Val Leu Glu Asp Ala Asp Leu
            260                 265                 270

Asp Lys Ala Ala Ala Asp Ile Ala Ser Gly Gly Phe Ser Tyr Ser Gly
        275                 280                 285

Gln Arg Cys Thr Ala Ile Lys Arg Val Leu Val Gln Asp Glu Lys Ala
    290                 295                 300

Asp Glu Leu Val Ala Lys Ile Lys Glu Lys Met Asn Gly Leu Lys Val
305                 310                 315                 320

Gly Ala Pro Glu Asp Ser Ala Asp Val Thr Pro Leu Ile Asn Ser Lys
                325                 330                 335

Ala Ala Asp Tyr Val Thr Gly Leu Ile Asp Asp Ala Val Glu Lys Gly
            340                 345                 350

Ala Glu Val Ala Ser Gly Asn Gln Arg Glu Gly Asn Leu Ile Tyr Pro
        355                 360                 365

Thr Leu Leu Asp Ser Val Thr Lys Asp Met Gln Ile Ala Trp Glu Glu
    370                 375                 380

Pro Phe Gly Pro Val Ile Pro Val Ile Arg Val Glu Ser Val Asp Glu
385                 390                 395                 400

Ala Ile Asn Ile Ala Asn Glu Ser Glu Tyr Gly Leu Gln Ala Ser Ile
                405                 410                 415

Phe Thr Lys Asn Met Glu Gln Ala Ile Gln Ile Gly Asn Glu Leu Glu
            420                 425                 430

Val Gly Ser Val Gln Ile Asn Gly Lys Thr Glu Arg Gly Pro Asp His
        435                 440                 445

Phe Pro Phe Leu Gly Val Lys Ser Ser Gly Val Gly Gly Gln Gly Ile
    450                 455                 460

Arg Lys Ser Ile Glu Ser Met Thr Arg Glu Lys Val Thr Val Leu Asn
465                 470                 475                 480

Met Thr Gln Gly

<210> SEQ ID NO 17
<211> LENGTH: 481
<212> TYPE: PRT
<213> ORGANISM: Bacillus cereus
<400> SEQUENCE: 17

Met Thr Thr Ile Thr Ser Asn Thr Tyr Lys Phe Tyr Val Asn Gly Glu
1               5                   10                  15

Trp Arg Glu Ser Ser Ser Gly Gln Thr Ile Asp Ile Pro Ser Pro Tyr
            20                  25                  30

Leu His Glu Val Ile Gly Gln Val Gln Ala Ile Thr Arg Glu Glu Val
        35                  40                  45

Asp Glu Ala Ile Ala Ser Ala Lys Glu Ala Gln Lys Glu Trp Ala Glu
    50                  55                  60
```

```
Ala Ser Leu Gln Asp Arg Ala Lys Tyr Leu Tyr Lys Trp Ala Asp Glu
 65                  70                  75                  80

Leu Val Asn Met Gln Asp Glu Ile Ala Asp Ile Val Met Lys Glu Val
             85                  90                  95

Gly Lys Gly Tyr Lys Asp Ala Lys Lys Glu Val Val Arg Thr Ala Asp
            100                 105                 110

Leu Ile Arg Tyr Thr Val Asp Glu Ala Leu His Met His Gly Glu Ser
            115                 120                 125

Met Met Gly Asp Ser Phe Pro Gly Gly Ser Lys Ser Lys Leu Ala Ile
130                 135                 140

Val Gln Arg Ala Pro Arg Gly Val Ile Leu Ala Ile Ala Pro Phe Asn
145                 150                 155                 160

Tyr Pro Val Asn Leu Ser Ala Ala Lys Leu Ala Pro Ala Leu Ile Met
                165                 170                 175

Gly Asn Ala Val Ile Phe Lys Pro Ala Thr Gln Gly Ala Ile Ser Gly
                180                 185                 190

Ile Lys Met Ile Glu Ala Leu His Lys Ala Gly Leu Pro Lys Gly Leu
        195                 200                 205

Val Asn Val Ala Thr Gly Arg Gly Ser Val Ile Gly Asp Tyr Leu Val
210                 215                 220

Glu His Pro Gly Val Asn Met Val Ser Phe Thr Gly Gly Thr Asn Thr
225                 230                 235                 240

Gly Ala His Leu Ala Lys Lys Ala Ala Met Ile Pro Leu Val Leu Glu
                245                 250                 255

Leu Gly Gly Lys Asp Pro Gly Ile Val Arg Glu Asp Ala Asp Leu Gln
                260                 265                 270

Glu Ala Ala Asn His Ile Val Ser Gly Ala Phe Ser Tyr Ser Gly Gln
                275                 280                 285

Arg Cys Thr Ala Ile Lys Arg Val Leu Val His Glu Asn Val Ala Asp
        290                 295                 300

Glu Leu Ile Ser Leu Leu Lys Glu Gln Val Ala Ala Leu Thr Val Gly
305                 310                 315                 320

Ser Pro Glu Gln Asp Ser Thr Ile Val Pro Leu Ile Asp Asp Lys Ser
                325                 330                 335

Ala Asp Phe Val Gln Gly Leu Val Asp Asp Ala Val Glu Lys Gly Ala
            340                 345                 350

Thr Ile Val Ile Gly Asn Lys Arg Glu Arg Asn Leu Ile Tyr Pro Thr
            355                 360                 365

Leu Ile Asp Asn Val Thr Glu Asp Met Lys Val Ala Trp Glu Glu Pro
370                 375                 380

Phe Gly Pro Ile Leu Pro Ile Ile Arg Val Ser Ser Asp Glu Gln Ala
385                 390                 395                 400

Ile Glu Ile Ala Asn Lys Ser Asp Phe Gly Leu Gln Ala Ser Val Phe
            405                 410                 415

Thr Lys Asp Ile Asn Lys Ala Phe Ala Ile Ala Asn Lys Ile Asp Thr
                420                 425                 430

Gly Ser Val Gln Ile Asn Gly Arg Thr Glu Arg Gly Pro Asp His Phe
            435                 440                 445

Pro Phe Ile Gly Val Lys Gly Ser Gly Met Gly Ala Gln Gly Ile Arg
            450                 455                 460

Lys Ser Leu Glu Ser Met Thr Arg Glu Lys Val Thr Val Leu Asn Leu
465                 470                 475                 480
```

Val

<210> SEQ ID NO 18
<211> LENGTH: 506
<212> TYPE: PRT
<213> ORGANISM: Bacillus cereus Rock3-44

<400> SEQUENCE: 18

```
Met Lys Asn Ile Leu Ile Pro Pro Thr Ile Thr Ile Tyr Ser Leu Leu
1               5                   10                  15

Gln Val Ala Ile Leu Gly Gly Gln Ile Met Thr Thr Ile Thr Ser Asn
            20                  25                  30

Thr Tyr Lys Phe Tyr Val Asn Gly Glu Trp Arg Glu Ser Ser Gly
        35                  40                  45

Gln Thr Ile Asp Ile Pro Ser Pro Tyr Leu His Glu Val Ile Gly Gln
    50                  55                  60

Val Gln Ala Ile Thr Arg Glu Glu Val Asp Glu Ala Ile Ala Ser Ala
65                  70                  75                  80

Lys Glu Ala Gln Lys Glu Trp Ala Glu Ala Ser Leu Gln Asp Arg Ala
                85                  90                  95

Lys Tyr Leu Tyr Lys Trp Ala Asp Glu Leu Val Asn Met Gln Asp Glu
            100                 105                 110

Ile Ala Asp Ile Val Met Lys Glu Val Gly Lys Gly Tyr Lys Asp Ala
        115                 120                 125

Lys Lys Glu Val Val Arg Thr Ala Asp Leu Ile Arg Tyr Thr Val Asp
130                 135                 140

Glu Ala Leu His Met His Gly Glu Ser Met Met Gly Asp Ser Phe Pro
145                 150                 155                 160

Gly Gly Ser Lys Ser Lys Leu Ala Ile Val Gln Arg Ala Pro Arg Gly
                165                 170                 175

Val Ile Leu Ala Ile Ala Pro Phe Asn Tyr Pro Val Asn Leu Ser Ala
            180                 185                 190

Ala Lys Leu Ala Pro Ala Leu Ile Met Gly Asn Ala Val Ile Phe Lys
        195                 200                 205

Pro Ala Thr Gln Gly Ala Ile Ser Gly Ile Lys Met Ile Glu Ala Leu
    210                 215                 220

His Lys Ala Gly Leu Pro Lys Gly Leu Val Asn Val Ala Thr Gly Arg
225                 230                 235                 240

Gly Ser Val Ile Gly Asp Tyr Leu Val Glu His Pro Gly Val Asn Met
                245                 250                 255

Val Ser Phe Thr Gly Gly Thr Asn Thr Gly Ala His Leu Ala Lys Lys
            260                 265                 270

Ala Ala Met Ile Pro Leu Val Leu Glu Leu Gly Gly Lys Asp Pro Gly
        275                 280                 285

Ile Val Arg Glu Asp Ala Asp Leu Gln Glu Ala Asn His Ile Val
    290                 295                 300

Ser Gly Ala Phe Ser Tyr Ser Gly Gln Arg Cys Thr Ala Ile Lys Arg
305                 310                 315                 320

Val Leu Val His Glu Asn Val Thr Asp Glu Leu Ile Ser Leu Leu Lys
                325                 330                 335

Glu Gln Val Ala Ala Leu Thr Val Gly Ser Pro Glu Gln Asp Ser Thr
            340                 345                 350

Ile Val Pro Leu Ile Asp Asp Lys Ser Ala Asp Phe Val Gln Gly Leu
        355                 360                 365
```

-continued

Val Asp Asp Ala Val Glu Lys Gly Ala Thr Ile Val Ile Gly Asn Lys
370 375 380

Arg Glu Arg Asn Leu Ile Tyr Pro Thr Leu Ile Asp Asn Val Thr Glu
385 390 395 400

Asp Met Lys Val Ala Trp Glu Glu Pro Phe Gly Pro Ile Leu Pro Ile
405 410 415

Ile Arg Val Ser Ser Asp Glu Gln Ala Ile Glu Ile Ala Asn Lys Ser
420 425 430

Asp Phe Gly Leu Gln Ala Ser Val Phe Thr Lys Asp Ile Asn Lys Ala
435 440 445

Phe Ala Ile Ala Asn Lys Ile Asp Thr Gly Ser Val Gln Ile Asn Gly
450 455 460

Arg Thr Glu Arg Gly Pro Asp His Phe Pro Phe Ile Gly Val Lys Gly
465 470 475 480

Ser Gly Met Gly Ala Gln Gly Ile Arg Lys Ser Leu Glu Ser Met Thr
485 490 495

Arg Glu Lys Val Thr Val Leu Asn Leu Val
500 505

<210> SEQ ID NO 19
<211> LENGTH: 479
<212> TYPE: PRT
<213> ORGANISM: Bacillus cereus group

<400> SEQUENCE: 19

Met Thr Thr Ser Asn Thr Tyr Lys Phe Tyr Leu Asn Gly Glu Trp Arg
1 5 10 15

Glu Ser Ser Ser Gly Gln Thr Ile Asp Ile Pro Ser Pro Tyr Leu His
20 25 30

Glu Val Ile Gly Gln Val Gln Ala Ile Thr Arg Gly Glu Val Asp Glu
35 40 45

Ala Ile Ala Ser Ala Lys Glu Ala Gln Lys Ser Trp Ala Glu Ala Ser
50 55 60

Leu Gln Asp Arg Ala Lys Tyr Leu Tyr Lys Trp Ala Asp Glu Leu Val
65 70 75 80

Asn Met Gln Asp Glu Ile Ala Asp Ile Ile Met Lys Glu Val Gly Lys
85 90 95

Gly Tyr Lys Asp Ala Lys Lys Glu Val Val Arg Thr Ala Asp Phe Ile
100 105 110

Arg Tyr Thr Ile Glu Glu Ala Leu His Met His Gly Glu Ser Met Met
115 120 125

Gly Asp Ser Phe Pro Gly Gly Thr Lys Ser Lys Leu Ala Ile Ile Gln
130 135 140

Arg Ala Pro Leu Gly Val Val Leu Ala Ile Ala Pro Phe Asn Tyr Pro
145 150 155 160

Val Asn Leu Ser Ala Ala Lys Leu Ala Pro Ala Leu Ile Met Gly Asn
165 170 175

Ala Val Ile Phe Lys Pro Ala Thr Gln Gly Ala Ile Ser Gly Ile Lys
180 185 190

Met Val Glu Ala Leu His Lys Ala Gly Leu Pro Lys Gly Leu Val Asn
195 200 205

Val Ala Thr Gly Arg Gly Ser Val Ile Gly Asp Tyr Leu Val Glu His
210 215 220

Glu Gly Ile His Met Val Ser Phe Thr Gly Gly Thr Asn Thr Gly Lys
225 230 235 240

-continued

```
His Leu Ala Lys Lys Ala Ser Met Ile Pro Leu Val Leu Glu Leu Gly
            245                 250                 255

Gly Lys Asp Pro Gly Ile Val Arg Glu Asp Ala Asp Leu Gln Asp Ala
        260                 265                 270

Ala Asn His Ile Val Ser Gly Ala Phe Ser Tyr Ser Gly Gln Arg Cys
            275                 280                 285

Thr Ala Ile Lys Arg Val Leu Val His Glu Asn Val Ala Asp Glu Leu
    290                 295                 300

Val Glu Leu Val Lys Ala Gln Val Ala Lys Leu Ser Val Gly Ser Pro
305                 310                 315                 320

Glu Gln Asp Ser Thr Ile Val Pro Leu Ile Asp Lys Ser Ala Asp
                325                 330                 335

Phe Val Gln Gly Leu Val Asp Asp Ala Val Glu Lys Gly Ala Thr Ile
                340                 345                 350

Val Ile Gly Asn Lys Arg Glu Arg Asn Leu Ile Tyr Pro Thr Leu Ile
            355                 360                 365

Asp His Val Thr Glu Glu Met Lys Val Ala Trp Glu Glu Pro Phe Gly
        370                 375                 380

Pro Ile Leu Pro Ile Ile Arg Val Ser Ser Asp Glu Gln Ala Ile Glu
385                 390                 395                 400

Ile Ala Asn Lys Ser Glu Phe Gly Leu Gln Ala Ser Val Phe Thr Lys
                405                 410                 415

Asp Ile Asn Lys Ala Phe Ala Ile Ala Asn Lys Ile Glu Thr Gly Ser
            420                 425                 430

Val Gln Ile Asn Gly Arg Thr Glu Arg Gly Pro Asp His Phe Pro Phe
        435                 440                 445

Ile Gly Val Lys Gly Ser Gly Met Gly Ala Gln Gly Ile Arg Lys Ser
    450                 455                 460

Leu Glu Ser Met Thr Arg Glu Lys Val Thr Val Leu Asn Leu Val
465                 470                 475
```

<210> SEQ ID NO 20
<211> LENGTH: 484
<212> TYPE: PRT
<213> ORGANISM: Virgibacillus siamensis

<400> SEQUENCE: 20

```
Met Asn Lys Val Glu Ser Ile Lys Ala Tyr Pro Phe Leu Leu Asn Gly
1               5                   10                  15

Glu Trp Lys Ser Ser Thr Ser Glu Arg Thr Ile Glu Met Gln Ser Pro
            20                  25                  30

Ser Gly Ala Gly Ile Pro Gly Lys Val Gln Ala Met Thr Glu Ser Glu
        35                  40                  45

Val Asn Thr Ala Leu Thr Gly Ala Lys Asp Ala Gln Lys Glu Trp Gly
    50                  55                  60

Arg Lys Ser Phe Asp Glu Arg Ala Arg Leu Leu Tyr Ser Trp Ala Asp
65                  70                  75                  80

Gln Leu Leu Leu Met Lys Asp Glu Ile Ala Glu Thr Ile Met Lys Glu
                85                  90                  95

Val Gly Lys Gly Leu Ala Ser Ala Glu Lys Glu Val Ile Arg Thr Ala
            100                 105                 110

Asp Phe Ile Lys Tyr Thr Ala Glu Glu Gly Lys Arg Leu His Gly Glu
        115                 120                 125

Leu Ile Asn Gly Gly Ser Phe Asn Ser Gly Ser Ala Asn Lys Phe Ala
```

```
                    130                 135                 140
Leu Val Asn Arg Asn Pro Val Gly Val Val Leu Ala Ile Ser Pro Phe
145                 150                 155                 160

Asn Tyr Pro Val Asn Leu Ala Ala Ala Lys Ile Ala Pro Ala Leu Ile
                    165                 170                 175

Ala Gly Asn Ala Val Val Phe Lys Pro Ala Thr Gln Gly Ala Ile Ser
                180                 185                 190

Gly Thr Arg Met Ile Glu Ala Leu Asp Lys Ala Gly Leu Pro Ser Gly
                195                 200                 205

Leu Val Asn Leu Val Thr Gly Lys Gly Ser Glu Ile Gly Asp Tyr Leu
            210                 215                 220

Ile Thr His Pro Leu Val Asp Leu Ile Asn Phe Thr Gly Gly Ser Asp
225                 230                 235                 240

Thr Gly Lys Ser Ile Ser Glu Lys Ala Ser Met Val Pro Val Ile Leu
                245                 250                 255

Glu Leu Gly Gly Lys Asp Pro Ala Ile Val Leu Glu Asp Ala Asp Leu
                260                 265                 270

Asp Lys Ala Ala Ser Asp Ile Val Ser Gly Gly Phe Ser Tyr Ser Gly
            275                 280                 285

Gln Arg Cys Thr Ala Ile Lys Arg Val Leu Val Ile Asp Asn Lys Ala
        290                 295                 300

Asp Lys Leu Val Glu Asn Ile Lys Glu Lys Met Glu Ser Leu Lys Val
305                 310                 315                 320

Gly Ala Pro Glu Asp Asn Ala Asp Val Thr Pro Leu Ile Asn Arg Lys
                325                 330                 335

Ala Thr Asp Phe Val Thr Gly Leu Ile Glu Asp Ala Ile Glu Lys Gly
                340                 345                 350

Ala Arg Val Val Ser Gly Asn His Arg Glu Gly Asn Leu Ile Tyr Pro
            355                 360                 365

Thr Leu Leu Asp Cys Val Thr Lys Asn Met Ala Ile Ala Trp Glu Glu
        370                 375                 380

Pro Phe Gly Pro Val Ile Pro Val Ile Arg Val Glu Ser Val Asp Glu
385                 390                 395                 400

Ala Ile Asp Ile Ala Asn Glu Ser Gln Tyr Gly Leu Gln Ala Ser Ile
                405                 410                 415

Phe Thr Lys Asn Met Glu Gln Ala Ile Arg Ile Gly Asn Glu Leu Glu
                420                 425                 430

Val Gly Ser Val Gln Ile Asn Gly Lys Thr Glu Arg Gly Pro Asp His
            435                 440                 445

Phe Pro Phe Leu Gly Val Lys Ser Ser Gly Val Gly Val Gln Gly Ile
        450                 455                 460

Arg Lys Ser Ile Glu Ser Met Thr Arg Glu Lys Val Thr Val Leu Asn
465                 470                 475                 480

Met Ser Gln Gly

<210> SEQ ID NO 21
<211> LENGTH: 504
<212> TYPE: PRT
<213> ORGANISM: Bacillus thuringiensis str. Al Hakam

<400> SEQUENCE: 21

Met Lys Asn Val Ile Lys Pro His Thr Ile Thr Leu Tyr Ser Leu Leu
1               5                   10                  15

Gln Val Ala Ile Leu Gly Gly Leu Ile Met Thr Thr Ser Asn Thr Tyr
```

```
              20                  25                  30
Lys Phe Tyr Leu Asn Gly Glu Trp Arg Glu Ser Ser Gly Glu Thr
             35                  40                  45
Ile Glu Ile Pro Ser Pro Tyr Leu His Glu Val Ile Gly Gln Val Gln
 50                  55                  60
Ala Ile Thr Arg Gly Glu Val Asp Glu Ala Ile Ala Ser Ala Lys Glu
 65                  70                  75                  80
Ala Gln Lys Ser Trp Ala Glu Ala Ser Leu Gln Asp Arg Ala Lys Tyr
                 85                  90                  95
Leu Tyr Lys Trp Ala Asp Glu Leu Val Asn Met Gln Asp Glu Ile Ala
                100                 105                 110
Asp Ile Ile Met Lys Glu Val Gly Lys Gly Tyr Lys Asp Ala Lys Lys
            115                 120                 125
Glu Val Val Arg Thr Ala Asp Phe Ile Arg Tyr Thr Ile Glu Glu Ala
            130                 135                 140
Leu His Met His Gly Glu Ser Met Met Gly Asp Ser Phe Pro Gly Gly
145                 150                 155                 160
Thr Lys Ser Lys Leu Ala Ile Ile Gln Arg Ala Pro Leu Gly Val Val
            165                 170                 175
Leu Ala Ile Ala Pro Phe Asn Tyr Pro Val Asn Leu Ser Ala Ala Lys
            180                 185                 190
Leu Ala Pro Ala Leu Ile Met Gly Asn Ala Val Ile Phe Lys Pro Ala
            195                 200                 205
Thr Gln Gly Ala Ile Ser Gly Ile Lys Met Val Glu Ala Leu His Lys
            210                 215                 220
Ala Gly Leu Pro Lys Gly Leu Val Asn Val Ala Thr Gly Arg Gly Ser
225                 230                 235                 240
Val Ile Gly Asp Tyr Leu Val Glu His Glu Gly Ile Asn Met Val Ser
            245                 250                 255
Phe Thr Gly Gly Thr Asn Thr Gly Lys His Leu Ala Lys Lys Ala Ser
            260                 265                 270
Met Ile Pro Leu Val Leu Glu Leu Gly Gly Lys Asp Pro Gly Ile Val
            275                 280                 285
Arg Glu Asp Ala Asp Leu Gln Asp Ala Ala Asn His Ile Val Ser Gly
            290                 295                 300
Ala Phe Ser Tyr Ser Gly Gln Arg Cys Thr Ala Ile Lys Arg Val Leu
305                 310                 315                 320
Val His Glu Asn Val Ala Asp Glu Leu Val Ser Leu Val Lys Glu Gln
            325                 330                 335
Val Ala Lys Leu Ser Val Gly Ser Pro Glu Gln Asp Ser Thr Ile Val
            340                 345                 350
Pro Leu Ile Asp Asp Lys Ser Ala Asp Phe Val Gln Gly Leu Val Asp
            355                 360                 365
Asp Ala Val Glu Lys Gly Ala Thr Ile Val Ile Gly Asn Lys Arg Glu
            370                 375                 380
Arg Asn Leu Ile Tyr Pro Thr Leu Ile Asp His Val Thr Glu Glu Met
385                 390                 395                 400
Lys Val Ala Trp Glu Glu Pro Phe Gly Pro Ile Leu Pro Ile Ile Arg
            405                 410                 415
Val Ser Ser Asp Glu Gln Ala Ile Glu Ile Ala Asn Lys Ser Glu Phe
            420                 425                 430
Gly Leu Gln Ala Ser Val Phe Thr Lys Asp Ile Asn Lys Ala Phe Ala
            435                 440                 445
```

```
Ile Ala Asn Lys Ile Glu Thr Gly Ser Val Gln Ile Asn Gly Arg Thr
            450                 455                 460

Glu Arg Gly Pro Asp His Phe Pro Phe Ile Gly Val Lys Gly Ser Gly
465                 470                 475                 480

Met Gly Ala Gln Gly Ile Arg Lys Ser Leu Glu Ser Met Thr Arg Glu
                485                 490                 495

Lys Val Thr Val Leu Asn Leu Val
                500

<210> SEQ ID NO 22
<211> LENGTH: 504
<212> TYPE: PRT
<213> ORGANISM: Bacillus mycoides Rock1-4

<400> SEQUENCE: 22

Met Lys Asn Val Leu Lys Pro Pro Thr Ile Thr Ile Tyr Ser Leu Leu
1               5                   10                  15

Gln Val Ala Ile Leu Gly Gly Gln Ile Met Thr Thr Ser Asn Thr Tyr
            20                  25                  30

Lys Phe Tyr Leu Asn Gly Glu Trp Arg Glu Ser Ser Gly Gln Thr
        35                  40                  45

Ile Asp Ile Pro Ser Pro Tyr Leu His Glu Val Ile Gly Lys Val Gln
50                  55                  60

Ala Ile Thr Arg Glu Glu Val Asp Glu Ala Ile Lys Ser Ala Gln Gln
65                  70                  75                  80

Ala Gln Lys Glu Trp Ala Glu Ala Ser Leu Gln Asp Arg Ala Lys Tyr
                85                  90                  95

Leu Tyr Lys Trp Ala Asp Glu Leu Val Asn Met Gln Asp Glu Ile Ala
            100                 105                 110

Asp Ile Val Met Lys Glu Val Gly Lys Gly Tyr Lys Asp Ala Lys Lys
            115                 120                 125

Glu Val Val Arg Thr Ala Asp Leu Ile Arg Tyr Thr Val Asp Glu Ala
        130                 135                 140

Leu His Met His Gly Glu Ser Met Met Gly Asp Ser Phe Pro Gly Gly
145                 150                 155                 160

Ser Lys Ser Lys Leu Ala Ile Ile Gln Arg Ala Pro Arg Gly Val Val
                165                 170                 175

Leu Ala Ile Ala Pro Phe Asn Tyr Pro Val Asn Leu Ser Ala Ala Lys
            180                 185                 190

Leu Ala Pro Ala Leu Ile Met Gly Asn Ala Val Ile Phe Lys Pro Ala
        195                 200                 205

Thr Gln Gly Ala Ile Ser Gly Ile Lys Met Val Glu Ala Leu His Lys
210                 215                 220

Ala Gly Leu Pro Lys Gly Leu Val Asn Val Ala Thr Gly Arg Gly Ser
225                 230                 235                 240

Val Ile Gly Asp Tyr Leu Val Glu His Pro Gly Val Asn Met Val Ser
                245                 250                 255

Phe Thr Gly Gly Thr Asn Thr Gly Ala His Leu Ala Lys Lys Ala Ala
            260                 265                 270

Met Ile Pro Leu Val Leu Glu Leu Gly Gly Lys Asp Pro Gly Ile Val
        275                 280                 285

Arg Glu Asp Ala Asp Leu Gly Glu Ala Ala Lys His Ile Val Ser Gly
290                 295                 300

Ala Phe Ser Tyr Ser Gly Gln Arg Cys Thr Ala Ile Lys Arg Val Leu
```

```
               305                 310                 315                 320
       Val His Glu Asn Val Ala Asp Glu Leu Val Ser Leu Leu Lys Asp Gln
                       325                 330                 335

Val Ala Glu Leu Thr Val Gly Ser Pro Glu Gln Asp Ser Thr Ile Val
                       340                 345                 350

Pro Leu Ile Asp Asp Lys Ser Ala Asp Phe Val Gln Gly Leu Val Asp
                       355                 360                 365

Asp Ala Val Glu Lys Gly Ala Thr Ile Val Ile Gly Asn Lys Arg Glu
       370                 375                 380

Arg Asn Leu Ile Tyr Pro Thr Leu Ile Asp Asn Val Thr Glu Asp Met
       385                 390                 395                 400

Lys Val Ala Trp Glu Glu Pro Phe Gly Pro Ile Leu Pro Ile Ile Arg
                       405                 410                 415

Val Ser Ser Asp Glu Gln Ala Ile Glu Ile Ala Asn Lys Ser Asp Phe
                       420                 425                 430

Gly Leu Gln Ala Ser Val Phe Thr Lys Asp Ile Asn Lys Ala Phe Ala
                       435                 440                 445

Ile Ala Asn Lys Ile Asp Thr Gly Ser Val Gln Ile Asn Gly Arg Thr
       450                 455                 460

Glu Arg Gly Pro Asp His Phe Pro Phe Ile Gly Val Lys Gly Ser Gly
       465                 470                 475                 480

Met Gly Ala Gln Gly Ile Arg Lys Ser Leu Glu Ser Met Thr Arg Glu
                       485                 490                 495

Lys Val Thr Val Leu Asn Leu Val
                       500

<210> SEQ ID NO 23
<211> LENGTH: 478
<212> TYPE: PRT
<213> ORGANISM: Bacillus cereus

<400> SEQUENCE: 23

Met Met Ala Ser Ile Tyr Lys Phe Tyr Leu Asn Gly Glu Trp Arg Glu
1               5                   10                  15

Ser Ser Ser Gly Glu Thr Ile Glu Ile Leu Ser Pro Tyr Leu His Glu
                20                  25                  30

Val Ile Gly Gln Val Gln Ala Ile Thr Arg Gly Glu Val Asp Glu Ala
            35                  40                  45

Ile Ala Ser Ala Lys Glu Ala Gln Lys Ser Trp Ala Glu Ala Ser Leu
        50                  55                  60

Gln Asp Arg Ala Lys Tyr Leu Tyr Lys Trp Ala Asp Glu Leu Val Asn
65                  70                  75                  80

Met Gln Asp Glu Ile Ala Asp Ile Ile Met Lys Glu Val Gly Lys Gly
                85                  90                  95

Tyr Lys Asp Ala Lys Lys Glu Val Val Arg Thr Ala Asp Phe Ile Arg
            100                 105                 110

Tyr Thr Ile Glu Glu Ala Leu His Met His Gly Glu Ser Met Met Gly
        115                 120                 125

Asp Ser Phe Pro Gly Gly Thr Lys Ser Lys Leu Ala Ile Ile Gln Arg
    130                 135                 140

Ala Pro Leu Gly Val Val Leu Ala Ile Ala Pro Phe Asn Tyr Pro Val
145                 150                 155                 160

Asn Leu Ser Ala Ala Lys Leu Ala Pro Ala Leu Ile Met Gly Asn Ala
                165                 170                 175
```

Val Ile Phe Lys Pro Ala Thr Gln Gly Ala Ile Ser Gly Ile Lys Met
                180                 185                 190

Val Glu Ala Leu His Lys Ala Gly Leu Pro Lys Gly Leu Val Asn Val
            195                 200                 205

Ala Thr Gly Arg Gly Ser Val Ile Gly Asp Tyr Leu Val Glu His Glu
        210                 215                 220

Gly Ile Asn Met Val Ser Phe Thr Gly Gly Thr Asn Thr Gly Lys His
225                 230                 235                 240

Leu Ala Lys Lys Ala Ser Met Ile Pro Leu Val Glu Leu Gly Gly
                245                 250                 255

Lys Asp Pro Gly Ile Val Arg Glu Asp Ala Asp Leu Gln Asp Ala Ala
                260                 265                 270

Asn His Ile Val Ser Gly Ala Phe Ser Tyr Ser Gly Gln Arg Cys Thr
            275                 280                 285

Ala Ile Lys Arg Val Leu Val His Glu Asn Val Ala Asp Glu Leu Val
        290                 295                 300

Gly Leu Leu Lys Ala Gln Val Ala Lys Leu Ser Val Gly Ser Pro Glu
305                 310                 315                 320

Gln Asp Ser Thr Ile Val Pro Leu Ile Asp Asp Lys Ser Ala Asp Phe
                325                 330                 335

Val Gln Gly Leu Val Asp Asp Ala Val Glu Lys Gly Ala Thr Ile Val
            340                 345                 350

Ile Gly Asn Lys Arg Glu Arg Asn Leu Ile Tyr Pro Thr Leu Ile Asp
        355                 360                 365

His Val Thr Glu Asp Met Thr Val Ala Trp Glu Glu Pro Phe Gly Pro
370                 375                 380

Ile Leu Pro Ile Ile Arg Val Ser Ser Asp Glu Gln Ala Ile Glu Ile
385                 390                 395                 400

Ala Asn Lys Ser Glu Phe Gly Leu Gln Ala Ser Val Phe Thr Lys Asp
                405                 410                 415

Ile Asn Lys Ala Phe Ala Ile Ala Asn Lys Ile Glu Thr Gly Ser Val
            420                 425                 430

Gln Ile Asn Gly Arg Thr Glu Arg Gly Pro Asp His Phe Pro Phe Ile
        435                 440                 445

Gly Val Lys Gly Ser Gly Met Gly Ala Gln Gly Ile Arg Lys Ser Leu
    450                 455                 460

Glu Ser Met Thr Arg Glu Lys Val Thr Val Val Asn Phe Lys
465                 470                 475

<210> SEQ ID NO 24
<211> LENGTH: 479
<212> TYPE: PRT
<213> ORGANISM: Bacillus cereus

<400> SEQUENCE: 24

Met Thr Thr Ser Asn Thr Tyr Lys Phe Tyr Leu Asn Gly Glu Trp Arg
1               5                   10                  15

Glu Ser Ser Ser Gly Gln Ile Ile Asp Ile Pro Ser Pro Tyr Leu His
                20                  25                  30

Glu Val Ile Gly Gln Val Gln Ala Ile Thr Arg Gly Glu Val Asp Glu
            35                  40                  45

Ala Ile Ala Ser Ala Lys Glu Ala Gln Lys Ser Trp Ala Glu Ala Ser
50                  55                  60

Leu Gln Asp Arg Ala Lys Tyr Leu Tyr Lys Trp Ala Asp Glu Leu Val
65                  70                  75                  80

```
Asn Met Gln Asp Glu Ile Ala Asp Ile Ile Met Lys Glu Val Gly Lys
                85                  90                  95

Gly Tyr Lys Asp Ala Lys Lys Glu Val Val Arg Thr Ala Asp Phe Ile
            100                 105                 110

Arg Tyr Thr Ile Glu Glu Ala Leu His Met His Gly Ser Met Met
        115                 120                 125

Gly Asp Ser Phe Pro Gly Gly Thr Lys Ser Lys Leu Ala Ile Ile Gln
130                 135                 140

Arg Ala Pro Leu Gly Val Val Leu Ala Ile Ala Pro Phe Asn Tyr Pro
145                 150                 155                 160

Val Asn Leu Ser Ala Ala Lys Leu Ala Pro Ala Leu Ile Met Gly Asn
                165                 170                 175

Ala Val Ile Phe Lys Pro Ala Thr Gln Gly Ala Ile Ser Gly Ile Lys
                180                 185                 190

Met Val Glu Ala Leu His Lys Ala Gly Leu Pro Lys Gly Leu Val Asn
            195                 200                 205

Val Ala Thr Gly Arg Gly Ser Val Ile Gly Asp Tyr Leu Val Glu His
        210                 215                 220

Glu Gly Ile Asn Met Val Ser Phe Thr Gly Gly Thr Asn Thr Gly Lys
225                 230                 235                 240

His Leu Ala Lys Lys Ala Ala Met Ile Pro Leu Val Leu Glu Leu Gly
                245                 250                 255

Gly Lys Asp Pro Gly Ile Val Arg Glu Asp Ala Asp Leu Gln Asp Ala
            260                 265                 270

Ala Asn His Ile Val Ser Gly Ala Phe Ser Tyr Ser Gly Gln Arg Cys
        275                 280                 285

Thr Ala Ile Lys Arg Val Leu Val His Glu Asn Val Ala Asp Glu Leu
290                 295                 300

Val Asp Leu Val Lys Ala Gln Val Ala Glu Leu Ser Val Gly Ser Pro
305                 310                 315                 320

Glu Gln Asp Ser Thr Ile Val Pro Leu Ile Asp Asp Lys Ser Ala Asp
                325                 330                 335

Phe Val Gln Gly Leu Val Asp Asp Ala Val Glu Lys Gly Ala Thr Ile
                340                 345                 350

Val Ile Gly Asn Lys Arg Glu Arg Asn Leu Ile Tyr Pro Thr Leu Ile
            355                 360                 365

Asp His Val Thr Glu Glu Met Lys Val Ala Trp Glu Glu Pro Phe Gly
        370                 375                 380

Pro Ile Leu Pro Ile Ile Arg Val Ser Ser Asp Gln Ala Ile Glu
385                 390                 395                 400

Ile Ala Asn Lys Ser Glu Phe Gly Leu Gln Ala Ser Val Phe Thr Lys
                405                 410                 415

Asp Ile Asn Lys Ala Phe Ala Ile Ala Asn Lys Ile Glu Thr Gly Ser
                420                 425                 430

Val Gln Ile Asn Gly Arg Thr Glu Arg Gly Pro Asp His Phe Pro Phe
            435                 440                 445

Ile Gly Val Lys Gly Ser Gly Met Gly Ala Gln Gly Ile Arg Lys Ser
            450                 455                 460

Leu Glu Ser Met Thr Arg Glu Lys Val Thr Val Leu Asn Leu Val
465                 470                 475

<210> SEQ ID NO 25
<211> LENGTH: 479
```

```
<212> TYPE: PRT
<213> ORGANISM: Bacillus cereus

<400> SEQUENCE: 25
```

Met Met Met Ala Ser Ile Tyr Lys Phe Tyr Leu Asn Gly Glu Trp Arg
1               5                   10                  15

Glu Ser Ser Ser Gly Glu Thr Ile Glu Ile Leu Ser Pro Tyr Leu His
            20                  25                  30

Glu Val Ile Gly Gln Val Gln Ala Ile Thr Arg Gly Glu Val Asp Glu
        35                  40                  45

Ala Ile Ala Ser Ala Lys Glu Ala Gln Lys Ser Trp Ala Glu Ala Ser
    50                  55                  60

Leu Gln Asp Arg Ala Lys Tyr Leu Tyr Lys Trp Ala Asp Glu Leu Val
65                  70                  75                  80

Asn Met Gln Asp Glu Ile Ala Asp Ile Ile Met Lys Glu Val Gly Lys
                85                  90                  95

Gly Tyr Lys Asp Ala Lys Lys Glu Val Val Arg Thr Ala Asp Phe Ile
            100                 105                 110

Arg Tyr Thr Ile Glu Glu Ala Leu His Met His Gly Glu Ser Met Met
        115                 120                 125

Gly Asp Ser Phe Pro Gly Gly Thr Lys Ser Lys Leu Ala Ile Ile Gln
130                 135                 140

Arg Ala Pro Leu Gly Val Val Leu Ala Ile Ala Pro Phe Asn Tyr Pro
145                 150                 155                 160

Val Asn Leu Ser Ala Ala Lys Leu Ala Pro Ala Leu Ile Met Gly Asn
                165                 170                 175

Ala Val Ile Phe Lys Pro Ala Thr Gln Gly Ala Ile Ser Gly Ile Lys
            180                 185                 190

Met Val Glu Ala Leu His Lys Ala Gly Leu Pro Lys Gly Leu Val Asn
        195                 200                 205

Val Ala Thr Gly Arg Gly Ser Val Ile Gly Asp Tyr Leu Val Glu His
    210                 215                 220

Glu Gly Ile Asp Met Val Ser Phe Thr Gly Gly Thr Asn Thr Gly Lys
225                 230                 235                 240

His Leu Ala Lys Lys Ala Ala Met Ile Thr Leu Val Leu Glu Leu Gly
                245                 250                 255

Gly Lys Asp Pro Gly Ile Val Arg Glu Asp Ala Asp Leu Gln Asp Ala
            260                 265                 270

Ala Asn His Ile Val Ser Gly Ala Phe Ser Tyr Ser Gly Gln Arg Cys
        275                 280                 285

Thr Ala Ile Lys Arg Val Leu Val His Glu Asn Val Ala Asp Glu Leu
    290                 295                 300

Val Ser Leu Leu Gln Glu Gln Val Ala Lys Leu Ser Val Gly Ser Pro
305                 310                 315                 320

Glu Gln Asp Ser Thr Ile Val Pro Leu Ile Asp Asp Lys Ser Ala Asp
                325                 330                 335

Phe Val Gln Gly Leu Val Asp Asp Ala Val Glu Lys Gly Ala Thr Ile
            340                 345                 350

Val Ile Gly Asn Lys Arg Glu Arg Asn Leu Ile Tyr Pro Thr Leu Ile
        355                 360                 365

Asp His Val Thr Glu Asp Met Thr Val Ala Trp Glu Pro Phe Gly
370                 375                 380

Pro Ile Leu Pro Ile Ile Arg Val Ser Ser Asp Glu Gln Ala Ile Glu
385                 390                 395                 400

```
Ile Ala Asn Lys Ser Glu Phe Gly Leu Gln Ala Ser Val Phe Thr Lys
            405                 410                 415

Asp Ile Asn Lys Ala Phe Ala Ile Ala Asn Lys Ile Glu Thr Gly Ser
            420                 425                 430

Val Gln Ile Asn Gly Arg Thr Glu Arg Gly Pro Asp His Phe Pro Phe
            435                 440                 445

Ile Gly Val Lys Gly Ser Gly Met Gly Ala Gln Gly Ile Arg Lys Ser
            450                 455                 460

Leu Glu Ser Met Thr Arg Glu Lys Val Thr Val Val Asn Phe Lys
465                 470                 475

<210> SEQ ID NO 26
<211> LENGTH: 479
<212> TYPE: PRT
<213> ORGANISM: Bacillus pseudomycoides

<400> SEQUENCE: 26

Met Thr Thr Ser Asn Thr Tyr Lys Phe Tyr Leu Asp Gly Glu Trp Arg
1               5                   10                  15

Glu Ser Ser Gly Gln Thr Ile Asp Ile Pro Ser Pro Tyr Leu His
            20                  25                  30

Glu Val Ile Gly Lys Val Gln Ala Ile Thr Arg Glu Val Asp Glu
            35                  40                  45

Ala Ile Lys Ser Ala Gln Gln Ala Gln Lys Glu Trp Ala Glu Ala Ser
            50                  55                  60

Leu Gln Asp Arg Ala Lys Tyr Leu Tyr Lys Trp Ala Asp Glu Leu Val
65                  70                  75                  80

Asn Met Gln Asp Glu Ile Ala Asp Ile Val Met Lys Glu Val Gly Lys
            85                  90                  95

Gly Tyr Lys Asp Ala Lys Lys Glu Val Val Arg Thr Ala Asp Leu Ile
            100                 105                 110

Arg Tyr Thr Val Asp Glu Ala Leu His Met His Gly Glu Ser Met Met
            115                 120                 125

Gly Asp Ser Phe Pro Gly Gly Ser Lys Ser Lys Leu Ala Ile Ile Gln
            130                 135                 140

Arg Ala Pro Arg Gly Val Val Leu Ala Ile Ala Pro Phe Asn Tyr Pro
145                 150                 155                 160

Val Asn Leu Ser Ala Ala Lys Leu Ala Pro Ala Leu Ile Met Gly Asn
            165                 170                 175

Ala Val Ile Phe Lys Pro Ala Thr Gln Gly Val Ile Ser Gly Ile Lys
            180                 185                 190

Met Val Glu Ala Leu His Lys Ala Gly Leu Pro Lys Gly Leu Val Asn
            195                 200                 205

Val Ala Thr Gly Arg Gly Ser Val Ile Gly Asp Tyr Leu Val Glu His
            210                 215                 220

Pro Gly Val Asn Met Val Ser Phe Thr Gly Gly Thr His Thr Gly Ala
225                 230                 235                 240

His Leu Ala Lys Lys Ala Ala Met Ile Pro Leu Val Leu Glu Leu Gly
            245                 250                 255

Gly Lys Asp Pro Gly Ile Val Arg Glu Asp Ala Asp Leu Gly Glu Ala
            260                 265                 270

Ala Lys His Ile Val Ser Gly Ala Phe Ser Tyr Ser Gly Gln Arg Cys
            275                 280                 285

Thr Ala Ile Lys Arg Val Leu Val His Glu Asn Val Ala Asp Glu Leu
```

```
            290                 295                 300
Val Ser Leu Leu Lys Asp Gln Val Ala Glu Leu Thr Val Gly Ser Pro
305                 310                 315                 320

Glu Gln Asp Ser Thr Ile Val Pro Leu Ile Asp Asp Lys Ser Ala Asp
                325                 330                 335

Phe Val Gln Gly Leu Val Asp Ala Val Glu Lys Gly Ala Thr Ile
                340                 345                 350

Val Ile Gly Asn Lys Arg Glu Arg Asn Leu Ile Tyr Pro Thr Leu Ile
                355                 360                 365

Asp Asn Val Thr Glu Asp Met Lys Val Ala Trp Glu Glu Pro Phe Gly
                370                 375                 380

Pro Ile Leu Pro Ile Ile Arg Val Ser Ser Asp Gln Ala Ile Glu
385                 390                 395                 400

Ile Ala Asn Lys Ser Asp Phe Gly Leu Gln Ala Ser Val Phe Thr Lys
                405                 410                 415

Asp Ile Asn Lys Ala Phe Ala Ile Ala Asn Lys Ile Asp Thr Gly Ser
                420                 425                 430

Val Gln Ile Asn Gly Arg Thr Glu Arg Gly Pro Asp His Phe Pro Phe
                435                 440                 445

Ile Gly Val Lys Gly Ser Gly Met Gly Ala Gln Gly Ile Arg Lys Ser
                450                 455                 460

Leu Glu Ser Met Thr Arg Glu Lys Val Thr Val Leu Asn Leu Val
465                 470                 475

<210> SEQ ID NO 27
<211> LENGTH: 825
<212> TYPE: PRT
<213> ORGANISM: Bifidobacterium animalis

<400> SEQUENCE: 27

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
                20                  25                  30

Asn Tyr Met Ser Ile Gly Gln Ile Tyr Leu Arg Ser Asn Pro Leu Met
                35                  40                  45

Lys Glu Pro Phe Thr Arg Asp Asp Val Lys His Arg Leu Val Gly His
50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Ile Asp Gly Thr Tyr
                100                 105                 110

Thr Glu Tyr Tyr Pro Asn Ile Thr Lys Asp Glu Ala Gly Leu Gln Lys
                115                 120                 125

Phe Phe Arg Gln Phe Ser Tyr Pro Gly Gly Ile Pro Ser His Phe Ala
                130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asn Asn Pro Ser Leu Phe Val
                165                 170                 175

Pro Cys Ile Ile Gly Asp Gly Glu Ala Glu Thr Gly Pro Leu Ala Thr
                180                 185                 190
```

```
Gly Trp Gln Ser Asn Lys Leu Val Asn Pro Arg Thr Asp Gly Ile Val
            195                 200                 205

Leu Pro Ile Leu His Leu Asn Gly Tyr Lys Ile Ala Asn Pro Thr Leu
210                 215                 220

Leu Ala Arg Ile Ser Asp Glu Glu Leu His Asp Phe Arg Gly Met
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
                260                 265                 270

Glu Ile Cys Asp Ile Lys Ala Ala Ala Gln Thr Asp Asp Met Thr Arg
                275                 280                 285

Pro Phe Tyr Pro Met Leu Ile Phe Arg Thr Pro Lys Gly Trp Thr Cys
290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Gly Trp Met Glu Ser Tyr Lys Pro Glu Glu Leu Phe Asn Ala
                340                 345                 350

Asp Gly Ser Ile Lys Asp Val Thr Ala Phe Met Pro Lys Gly Glu
                355                 360                 365

Leu Arg Ile Gly Ala Asn Pro Asn Ala Asn Gly Gly Arg Ile Arg Glu
                370                 375                 380

Asp Leu Lys Leu Pro Glu Leu Asp Gln Tyr Glu Ile Thr Gly Val Lys
385                 390                 395                 400

Glu Tyr Gly His Gly Trp Gly Gln Val Glu Ala Pro Arg Ser Leu Gly
                405                 410                 415

Ala Tyr Cys Arg Asp Ile Ile Lys Asn Asn Pro Asp Ser Phe Arg Ile
                420                 425                 430

Phe Gly Pro Asp Glu Thr Ala Ser Asn Arg Leu Asn Ala Thr Tyr Glu
                435                 440                 445

Val Thr Lys Lys Gln Trp Asp Asn Gly Tyr Leu Ser Ala Leu Val Asp
450                 455                 460

Glu Asn Met Ala Val Thr Gly Gln Val Val Glu Gln Leu Ser Glu His
465                 470                 475                 480

Gln Cys Glu Gly Phe Leu Glu Ala Tyr Leu Leu Thr Gly Arg His Gly
                485                 490                 495

Met Trp Ser Thr Tyr Glu Ser Phe Ala His Val Ile Asp Ser Met Leu
                500                 505                 510

Asn Gln His Ala Lys Trp Leu Glu Ala Thr Val Arg Glu Ile Pro Trp
            515                 520                 525

Arg Lys Pro Ile Ser Ser Val Asn Leu Leu Val Ser Ser His Val Trp
530                 535                 540

Arg Gln Asp His Asn Gly Phe Ser His Gln Asp Pro Gly Val Thr Ser
545                 550                 555                 560

Val Leu Ile Asn Lys Thr Phe Asn Asn Asp His Val Thr Asn Ile Tyr
                565                 570                 575

Phe Ala Thr Asp Ala Asn Met Leu Leu Ala Ile Ala Glu Lys Cys Phe
                580                 585                 590

Lys Ser Thr Asn Lys Ile Asn Ala Ile Phe Ser Gly Lys Gln Pro Ala
                595                 600                 605

Pro Thr Trp Ile Thr Leu Asp Glu Ala Arg Ala Glu Leu Glu Ala Gly
```

```
                    610                 615                 620
Ala Ala Glu Trp Lys Trp Ala Ser Asn Ala Lys Ser Asn Asp Glu Val
625                 630                 635                 640

Gln Ile Val Leu Ala Ala Gly Asp Val Pro Thr Gln Glu Ile Met
            645                 650                 655

Ala Ala Ser Asp Ala Leu Asn Lys Asp Gly Ile Lys Phe Lys Val Val
            660                 665                 670

Asn Val Val Asp Leu Leu Lys Leu Gln Ser Pro Glu Asn Asn Asp Glu
            675                 680                 685

Ala Met Ser Asn Glu Asp Phe Thr Glu Leu Phe Thr Ala Asp Lys Pro
        690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe Asn Val Val Gly Tyr Lys Glu
                725                 730                 735

Gln Gly Ser Thr Thr Thr Pro Phe Asp Met Val Arg Val Asn Asp Met
            740                 745                 750

Asp Arg Tyr Ala Leu Glu Ala Gln Ala Leu Glu Leu Ile Asp Ala Asp
            755                 760                 765

Lys Tyr Ala Asp Lys Ile Asp Glu Leu Asn Ala Phe Arg Lys Thr Ala
            770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Gln Met Leu Ser Ala
                805                 810                 815

Thr Ala Ala Thr Ala Gly Asp Asn Glu
                820                 825

<210> SEQ ID NO 28
<211> LENGTH: 813
<212> TYPE: PRT
<213> ORGANISM: Leuconostoc mesenteroides

<400> SEQUENCE: 28

Met Ala Asp Phe Asp Ser Lys Glu Tyr Leu Glu Leu Val Asp Lys Trp
1               5                   10                  15

Trp Arg Ala Thr Asn Tyr Leu Ser Ala Gly Met Ile Phe Leu Lys Ser
            20                  25                  30

Asn Pro Leu Phe Ser Val Thr Asn Thr Pro Ile Lys Ala Glu Asp Val
        35                  40                  45

Lys Val Lys Pro Ile Gly His Trp Gly Thr Ile Ser Gly Gln Thr Phe
50                  55                  60

Leu Tyr Ala His Ala Asn Arg Leu Ile Asn Lys Tyr Gly Leu Asn Met
65                  70                  75                  80

Phe Tyr Val Gly Gly Pro Gly His Gly Gln Val Met Val Thr Asn
            85                  90                  95

Ala Tyr Leu Asp Gly Ala Tyr Thr Glu Asp Tyr Pro Glu Ile Thr Gln
            100                 105                 110

Asp Ile Glu Gly Met Ser His Leu Phe Lys Arg Phe Ser Phe Pro Gly
        115                 120                 125

Gly Ile Gly Ser His Met Thr Ala Gln Thr Pro Gly Ser Leu His Glu
    130                 135                 140

Gly Gly Glu Leu Gly Tyr Ser Leu Ser His Ala Phe Gly Ala Val Leu
145                 150                 155                 160
```

-continued

```
Asp Asn Pro Asp Gln Val Ala Phe Ala Val Gly Asp Gly Glu Ala
            165                 170                 175
Glu Thr Gly Pro Ser Met Ala Ser Trp His Ser Ile Lys Phe Leu Asn
        180                 185                 190
Ala Lys Asn Asp Gly Ala Val Leu Pro Val Leu Asp Leu Asn Gly Phe
        195                 200                 205
Lys Ile Ser Asn Pro Thr Ile Phe Ser Arg Met Ser Asp Glu Ile
        210                 215                 220
Thr Lys Phe Phe Glu Gly Leu Gly Tyr Ser Pro Arg Phe Ile Glu Asn
225                 230                 235                 240
Asp Asp Ile His Asp Tyr Ala Thr Tyr His Gln Leu Ala Ala Asn Ile
            245                 250                 255
Leu Asp Gln Ala Ile Glu Asp Ile Gln Ala Ile Gln Asn Asp Ala Arg
        260                 265                 270
Glu Asn Gly Lys Tyr Gln Asp Gly Glu Ile Pro Ala Trp Pro Val Ile
        275                 280                 285
Ile Ala Arg Leu Pro Lys Gly Trp Gly Pro Thr His Asp Ala Ser
        290                 295                 300
Asn Asn Pro Ile Glu Asn Ser Phe Arg Ala His Gln Val Pro Leu Pro
305                 310                 315                 320
Leu Glu Gln His Asp Leu Ala Thr Leu Pro Glu Phe Glu Asp Trp Met
            325                 330                 335
Asn Ser Tyr Lys Pro Glu Glu Leu Phe Asn Ala Asp Gly Ser Leu Lys
        340                 345                 350
Asp Glu Leu Lys Ala Ile Ala Pro Lys Gly Asp Lys Arg Met Ser Ala
        355                 360                 365
Asn Pro Ile Thr Asn Gly Gly Ala Asp Arg Ser Asp Leu Lys Leu Pro
        370                 375                 380
Asn Trp Arg Glu Phe Ala Asn Asp Ile Asn Asp Asp Thr Arg Gly Lys
385                 390                 395                 400
Glu Phe Ala Asp Ser Lys Arg Asn Met Asp Met Ala Thr Leu Ser Asn
            405                 410                 415
Tyr Leu Gly Ala Val Ser Gln Leu Asn Pro Thr Arg Phe Arg Phe Phe
        420                 425                 430
Gly Pro Asp Glu Thr Met Ser Asn Arg Leu Trp Gly Leu Phe Asn Val
        435                 440                 445
Thr Pro Arg Gln Trp Met Glu Glu Ile Lys Glu Pro Gln Asp Gln Leu
        450                 455                 460
Leu Ser Pro Thr Gly Arg Ile Ile Asp Ser Gln Leu Ser Glu His Gln
465                 470                 475                 480
Ala Glu Gly Trp Leu Glu Gly Tyr Thr Leu Thr Gly Arg Val Gly Ile
            485                 490                 495
Phe Ala Ser Tyr Glu Ser Phe Leu Arg Val Val Asp Thr Met Val Thr
        500                 505                 510
Gln His Phe Lys Trp Leu Arg His Ala Ser Glu Gln Ala Trp Arg Asn
        515                 520                 525
Asp Tyr Pro Ser Leu Asn Leu Ile Ala Thr Ser Thr Ala Phe Gln Gln
        530                 535                 540
Asp His Asn Gly Tyr Thr His Gln Asp Pro Gly Met Leu Thr His Leu
545                 550                 555                 560
Ala Glu Lys Lys Ser Asn Phe Ile Arg Glu Tyr Leu Pro Ala Asp Gly
            565                 570                 575
Asn Ser Leu Leu Ala Val Gln Glu Arg Ala Phe Ser Glu Arg His Lys
```

```
                580              585              590
Val Asn Leu Leu Ile Ala Ser Lys Gln Pro Arg Gln Gln Trp Phe Thr
            595              600              605

Val Glu Glu Ala Glu Val Leu Ala Asn Glu Gly Leu Lys Ile Ile Asp
            610              615              620

Trp Ala Ser Thr Ala Pro Ser Ser Asp Val Asp Ile Thr Phe Ala Ser
625              630              635              640

Ala Gly Thr Glu Pro Thr Ile Glu Thr Leu Ala Ala Leu Trp Leu Ile
            645              650              655

Asn Gln Ala Phe Pro Asp Val Lys Phe Arg Tyr Val Asn Val Val Glu
            660              665              670

Leu Leu Arg Leu Gln Lys Lys Ser Glu Pro Asn Met Asn Asp Glu Arg
            675              680              685

Glu Leu Ser Ala Glu Glu Phe Asn Lys Tyr Phe Gln Ala Asp Thr Pro
            690              695              700

Val Ile Phe Gly Phe His Ala Tyr Glu Asn Leu Ile Glu Ser Phe Phe
705              710              715              720

Phe Glu Arg Lys Phe Thr Gly Asp Val Tyr Val His Gly Tyr Arg Glu
            725              730              735

Asp Gly Asp Ile Thr Thr Thr Tyr Asp Met Arg Val Tyr Ser His Leu
            740              745              750

Asp Arg Phe His Gln Ala Lys Glu Ala Glu Ile Leu Ser Ala Asn
            755              760              765

Gly Lys Ile Asp Gln Ala Ala Ala Asp Thr Phe Ile Ala Lys Met Asp
            770              775              780

Asp Thr Leu Ala Lys His Phe Gln Val Thr Arg Asn Glu Gly Arg Asp
785              790              795              800

Ile Glu Glu Phe Thr Asp Trp Thr Trp Ser Pro Leu Lys
            805              810

<210> SEQ ID NO 29
<211> LENGTH: 796
<212> TYPE: PRT
<213> ORGANISM: Clostridium acetobutylicum ATCC 824

<400> SEQUENCE: 29

Met Gln Ser Ile Ile Gly Lys His Lys Asp Glu Gly Lys Ile Thr Pro
1               5               10              15

Glu Tyr Leu Lys Lys Ile Asp Ala Tyr Trp Arg Ala Ala Asn Phe Ile
            20              25              30

Ser Val Gly Gln Leu Tyr Leu Leu Asp Asn Pro Leu Leu Arg Glu Pro
            35              40              45

Leu Lys Pro Glu His Leu Lys Arg Lys Val Val Gly His Trp Gly Thr
        50              55              60

Ile Pro Gly Gln Asn Phe Ile Tyr Ala His Leu Asn Arg Val Ile Lys
65              70              75              80

Lys Tyr Asp Leu Asp Met Ile Tyr Val Ser Gly Pro Gly His Gly Gly
            85              90              95

Gln Val Met Val Ser Asn Ser Tyr Leu Asp Gly Thr Tyr Ser Glu Val
            100             105             110

Tyr Pro Asn Val Ser Arg Asp Leu Asn Gly Leu Lys Lys Leu Cys Lys
            115             120             125

Gln Phe Ser Phe Pro Gly Gly Ile Ser Ser His Met Ala Pro Glu Thr
        130             135             140
```

```
Pro Gly Ser Ile Asn Glu Gly Gly Glu Leu Gly Tyr Ser Leu Ala His
145                 150                 155                 160

Ser Phe Gly Ala Val Phe Asp Asn Pro Asp Leu Ile Thr Ala Cys Val
            165                 170                 175

Val Gly Asp Gly Glu Ala Glu Thr Gly Pro Leu Ala Thr Ser Trp Gln
        180                 185                 190

Ala Asn Lys Phe Leu Asn Pro Val Thr Asp Gly Ala Val Leu Pro Ile
    195                 200                 205

Leu His Leu Asn Gly Tyr Lys Ile Ser Asn Pro Thr Val Leu Ser Arg
210                 215                 220

Ile Pro Lys Asp Glu Leu Glu Lys Phe Phe Glu Gly Asn Gly Trp Lys
225                 230                 235                 240

Pro Tyr Phe Val Glu Gly Glu Asp Pro Glu Thr Met His Lys Leu Met
            245                 250                 255

Ala Glu Thr Leu Asp Ile Val Thr Glu Glu Ile Leu Asn Ile Gln Lys
        260                 265                 270

Asn Ala Arg Glu Asn Asn Asp Cys Ser Arg Pro Lys Trp Pro Met Ile
    275                 280                 285

Val Leu Arg Thr Pro Lys Gly Trp Thr Gly Pro Lys Phe Val Asp Gly
290                 295                 300

Val Pro Asn Glu Gly Ser Phe Arg Ala His Gln Val Pro Leu Ala Val
305                 310                 315                 320

Asp Arg Tyr His Thr Glu Asn Leu Asp Gln Leu Glu Glu Trp Leu Lys
            325                 330                 335

Ser Tyr Lys Pro Glu Glu Leu Phe Asp Glu Asn Tyr Arg Leu Ile Pro
        340                 345                 350

Glu Leu Glu Glu Leu Thr Pro Lys Gly Asn Lys Arg Met Ala Ala Asn
    355                 360                 365

Leu His Ala Asn Gly Gly Leu Leu Leu Arg Glu Leu Arg Thr Pro Asp
370                 375                 380

Phe Arg Asp Tyr Ala Val Asp Val Pro Thr Pro Gly Ser Thr Val Lys
385                 390                 395                 400

Gln Asp Met Ile Glu Leu Gly Lys Tyr Val Arg Asp Val Val Lys Leu
            405                 410                 415

Asn Glu Asp Thr Arg Asn Phe Arg Ile Phe Gly Pro Asp Glu Thr Met
        420                 425                 430

Ser Asn Arg Leu Trp Ala Val Phe Glu Gly Thr Lys Arg Gln Trp Leu
    435                 440                 445

Ser Glu Ile Lys Glu Pro Asn Asp Glu Phe Leu Ser Asn Asp Gly Arg
450                 455                 460

Ile Val Asp Ser Met Leu Ser Glu His Leu Cys Glu Gly Trp Leu Glu
465                 470                 475                 480

Gly Tyr Leu Leu Thr Gly Arg His Gly Phe Phe Ala Ser Tyr Glu Ala
            485                 490                 495

Phe Leu Arg Ile Val Asp Ser Met Ile Thr Gln His Gly Lys Trp Leu
        500                 505                 510

Lys Val Thr Ser Gln Leu Pro Trp Arg Lys Asp Ile Ala Ser Leu Asn
    515                 520                 525

Leu Ile Ala Thr Ser Asn Val Trp Gln Gln Asp His Asn Gly Tyr Thr
530                 535                 540

His Gln Asp Pro Gly Leu Leu Gly His Ile Val Asp Lys Lys Pro Glu
545                 550                 555                 560

Ile Val Arg Ala Tyr Leu Pro Ala Asp Ala Asn Thr Leu Leu Ala Val
```

```
                    565                 570                 575
Phe Asp Lys Cys Leu His Thr Lys His Lys Ile Asn Leu Leu Val Thr
                580                 585                 590

Ser Lys His Pro Arg Gln Gln Trp Leu Thr Met Asp Gln Ala Val Lys
                595                 600                 605

His Val Glu Gln Gly Ile Ser Ile Trp Asp Trp Ala Ser Asn Asp Lys
            610                 615                 620

Gly Gln Glu Pro Asp Val Val Ile Ala Ser Cys Gly Asp Thr Pro Thr
625                 630                 635                 640

Leu Glu Ala Leu Ala Ala Val Thr Ile Leu His Glu His Leu Pro Glu
                645                 650                 655

Leu Lys Val Arg Phe Val Asn Val Val Asp Met Met Lys Leu Leu Pro
                660                 665                 670

Glu Asn Glu His Pro His Gly Leu Ser Asp Lys Asp Tyr Asn Ala Leu
            675                 680                 685

Phe Thr Thr Asp Lys Pro Val Ile Phe Ala Phe His Gly Phe Ala His
            690                 695                 700

Leu Ile Asn Gln Leu Thr Tyr His Arg Glu Asn Arg Asn Leu His Val
705                 710                 715                 720

His Gly Tyr Met Glu Glu Gly Thr Ile Thr Thr Pro Phe Asp Met Arg
                725                 730                 735

Val Gln Asn Lys Leu Asp Arg Phe Asn Leu Val Lys Asp Val Val Glu
                740                 745                 750

Asn Leu Pro Gln Leu Gly Asn Arg Gly Ala His Leu Val Gln Leu Met
                755                 760                 765

Asn Asp Lys Leu Val Glu His Asn Gln Tyr Ile Arg Glu Val Gly Glu
                770                 775                 780

Asp Leu Pro Glu Ile Thr Asn Trp Gln Trp His Val
785                 790                 795

<210> SEQ ID NO 30
<211> LENGTH: 780
<212> TYPE: PRT
<213> ORGANISM: Aspergillus nidulans

<400> SEQUENCE: 30

Met Pro Gly Glu Val Ile Glu Arg Pro Asn Pro Ala Pro Lys Pro Ser
1               5                   10                  15

His Val Pro Asp Leu Val Glu Lys Leu Ile Ile Pro Ala Gln Lys Thr
                20                  25                  30

Lys Leu Glu Lys Ser Asp Cys Asp Ala Leu His Lys Tyr Arg Arg Ala
            35                  40                  45

Ala Ala Tyr Ile Ala Ala Gly His Trp Gly Thr Cys Pro Gly Leu Ile
        50                  55                  60

Leu Val Tyr Ser His Leu Asn Tyr Leu Ile Lys Lys Gln Asn Leu Asp
65                  70                  75                  80

Met Leu Tyr Val Val Gly Pro Gly His Gly Ala Pro Gly Leu Leu Ala
                85                  90                  95

Ser Leu Trp Leu Glu Gly Ser Leu Gly Lys Phe Tyr Pro Gln Tyr Thr
                100                 105                 110

Lys Asp Lys Glu Gly Leu His Asn Leu Ile Ser Thr Phe Ser Thr Ser
            115                 120                 125

Ala Gly Leu Pro Ser His Ile Asn Ala Glu Thr Pro Gly Ala Ile His
        130                 135                 140
```

-continued

| | | | | | | | | | | | |
|---|---|---|---|---|---|---|---|---|---|---|---|
| Glu | Gly | Gly | Glu | Leu | Gly | Tyr | Ala | Leu | Ser | Val | Ser | Phe | Gly | Ala | Val |
| 145 | | | | | 150 | | | | | 155 | | | | | 160 |

Met Asp Asn Pro Asp Leu Ile Val Thr Cys Val Val Gly Asp Gly Glu
               165             170             175

Ala Glu Thr Gly Pro Thr Ala Thr Ser Trp His Ala Ile Lys Tyr Ile
        180             185             190

Asp Pro Ala Glu Ser Gly Ala Val Leu Pro Ile Leu His Val Asn Gly
    195             200             205

Phe Lys Ile Ser Glu Arg Thr Ile Phe Gly Cys Met Asp Asn Arg Glu
    210             215             220

Ile Val Cys Leu Phe Thr Gly Tyr Gly Tyr Gln Val Arg Ile Val Glu
225             230             235             240

Asp Leu Glu Asp Ile Asp Asn Asp Leu His Ser Ala Met Ser Trp Ala
            245             250             255

Val Glu Glu Ile Arg Asn Ile Gln Lys Ala Ala Arg Ser Gly Lys Pro
        260             265             270

Ile Met Lys Pro Gln Trp Pro Met Ile Val Leu Arg Thr Pro Lys Gly
    275             280             285

Trp Ser Gly Pro Lys Glu Leu His Gly Gln Phe Ile Glu Gly Ser Phe
290             295             300

His Ser His Gln Val Pro Leu Pro Asn Ala Lys Lys Asp Asp Glu Glu
305             310             315             320

Leu Gln Ala Leu Gln Lys Trp Leu Ser Tyr Lys Pro Asp Glu Leu
            325             330             335

Phe Thr Glu Ser Gly Asp Val Ile Asp Glu Ile Leu Ser Ile Ile Pro
        340             345             350

Ser Asp Asp Lys Lys Leu Gly Met Arg Pro Glu Ala Tyr Lys Thr His
            355             360             365

Leu Pro Pro Asp Leu Pro Asp Trp Arg Gln Phe Cys Val Lys Lys Gly
    370             375             380

Asp Gln Phe Ser Ala Met Lys Ala Ile Gly Ser Phe Ile Asp Gln Val
385             390             395             400

Phe Val Lys Asn Pro His Thr Val Arg Leu Phe Ser Pro Asp Glu Leu
            405             410             415

Glu Ser Asn Lys Leu Ser Ala Ala Leu Ser His Thr Gly Arg Asn Phe
        420             425             430

Gln Trp Asp Glu Phe Ser Asn Ala Lys Gly Gly Arg Val Ile Glu Val
    435             440             445

Leu Ser Glu His Leu Cys Gln Gly Phe Met Gln Gly Tyr Thr Leu Thr
450             455             460

Gly Arg Thr Gly Ile Phe Pro Ser Tyr Glu Ser Phe Leu Gly Ile Ile
465             470             475             480

His Thr Met Met Val Gln Tyr Ala Lys Phe Ala Lys Met Ala Lys Glu
            485             490             495

Thr Ala Trp His His Asp Val Ser Ser Ile Asn Tyr Ile Glu Thr Ser
        500             505             510

Thr Trp Ala Arg Gln Glu His Asn Gly Phe Ser His Gln Asn Pro Ser
    515             520             525

Phe Ile Gly Ala Val Leu Lys Leu Lys Pro Tyr Ala Ala Arg Val Tyr
    530             535             540

Leu Pro Pro Asp Ala Asn Thr Phe Leu Thr Thr Leu His His Cys Leu
545             550             555             560

Lys Ser Lys Asn Tyr Ile Asn Leu Met Val Gly Ser Lys Gln Pro Thr

```
                       565                 570                 575
Pro Val Tyr Leu Ser Pro Glu Ala Glu Ser His Cys Arg Ala Gly
            580                 585                 590

Ala Ser Ile Phe Lys Phe Cys Ser Thr Asp Gly Gly Leu Arg Pro Asp
            595                 600                 605

Val Val Leu Val Gly Ile Gly Val Glu Val Met Phe Glu Val Ile Lys
            610                 615                 620

Ala Ala Ala Ile Leu Arg Glu Arg Cys Pro Glu Leu Arg Val Arg Val
625                 630                 635                 640

Val Asn Val Thr Asp Leu Phe Ile Leu Glu Asn Glu Gly Ala His Pro
            645                 650                 655

His Ala Leu Lys His Glu Ala Phe Asp Asn Leu Phe Thr Glu Asp Arg
            660                 665                 670

Ser Ile His Phe Asn Tyr His Gly Tyr Val Asn Glu Leu Gln Gly Leu
            675                 680                 685

Leu Phe Gly Arg Pro Arg Leu Asp Arg Ala Thr Ile Lys Gly Tyr Lys
            690                 695                 700

Glu Glu Gly Ser Thr Thr Thr Pro Phe Asp Met Met Leu Val Asn Glu
705                 710                 715                 720

Val Ser Arg Tyr His Val Ala Lys Ala Ala Val Thr Gly Gly Ala Arg
            725                 730                 735

Phe Asn Glu Lys Val Lys Leu Arg His Gln Glu Leu Cys Ser Glu Phe
            740                 745                 750

Asp His Asn Ile Ala Glu Thr Arg Lys Tyr Ile Met Asn Asn His Gln
            755                 760                 765

Asp Pro Glu Asp Thr Tyr Asn Met Pro Ser Phe Asn
            770                 775                 780

<210> SEQ ID NO 31
<211> LENGTH: 825
<212> TYPE: PRT
<213> ORGANISM: Bifidobacterium pseudolongum subsp. globosum

<400> SEQUENCE: 31

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Thr
            20                  25                  30

Asn Tyr Met Ser Ile Gly Gln Ile Tyr Leu Arg Ser Asn Pro Leu Met
            35                  40                  45

Lys Glu Pro Phe Thr Arg Asp Asp Val Lys His Arg Leu Val Gly His
            50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
            85                  90                  95

His Gly Gly Pro Ala Gly Thr Ser Gln Ser Tyr Val Asp Gly Thr Tyr
            100                 105                 110

Thr Glu Tyr Tyr Pro Asn Ile Thr Lys Asp Glu Ala Gly Leu Gln Lys
            115                 120                 125

Phe Phe Arg Gln Phe Ser Tyr Pro Gly Gly Ile Pro Ser His Phe Ala
            130                 135                 140

Pro Glu Thr Pro Gly Ser Ile His Glu Gly Gly Glu Leu Gly Tyr Ala
145                 150                 155                 160
```

```
Leu Ser His Ala Tyr Gly Ala Val Met Asn Pro Ser Leu Phe Val
            165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
        210                 215                 220

Leu Ala Arg Ile Ser Asp Glu Leu His Asp Phe Phe Arg Gly Met
225             230                 235                 240

Gly Tyr His Pro Tyr Glu Phe Val Ala Gly Phe Asp Asn Glu Asp His
            245                 250                 255

Met Ser Ile His Arg Arg Phe Ala Glu Leu Phe Glu Thr Ile Phe Asp
            260                 265                 270

Glu Ile Cys Asp Ile Lys Ala Ala Ala Gln Thr Asp Asp Met Thr Arg
            275                 280                 285

Pro Phe Tyr Pro Met Leu Ile Phe Arg Thr Pro Lys Gly Trp Thr Cys
            290                 295                 300

Pro Lys Phe Ile Asp Gly Lys Lys Thr Glu Gly Ser Trp Arg Ala His
305             310                 315                 320

Gln Val Pro Leu Ala Ser Ala Arg Asp Thr Glu Glu His Phe Glu Val
            325                 330                 335

Leu Lys Gly Trp Leu Glu Ser Tyr Lys Pro Glu Glu Leu Phe Asn Ala
            340                 345                 350

Asp Gly Ser Ile Lys Asp Val Thr Ala Phe Met Pro Lys Gly Asp
            355                 360                 365

Leu Arg Ile Gly Ala Asn Pro Asn Ala Asn Gly Gly Val Ile Arg Glu
    370                 375                 380

Asp Leu Lys Leu Pro Glu Leu Asp Gln Tyr Glu Val Thr Gly Val Lys
385             390                 395                 400

Glu Tyr Gly His Gly Trp Gly Gln Val Glu Ala Pro Arg Ser Leu Gly
            405                 410                 415

Ala Tyr Cys Arg Asp Ile Ile Lys Asn Asn Pro Asp Ser Phe Arg Ile
            420                 425                 430

Phe Gly Pro Asp Glu Thr Ala Ser Asn Arg Leu Asn Ala Thr Tyr Glu
            435                 440                 445

Val Thr Asp Lys Gln Trp Asp Asn Gly Tyr Leu Ser Ser Leu Val Asp
            450                 455                 460

Glu His Met Ala Val Thr Gly Gln Val Thr Glu Gln Leu Ser Glu His
465             470                 475                 480

Gln Cys Glu Gly Phe Leu Glu Ala Tyr Leu Leu Thr Gly Arg His Gly
            485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
            515                 520                 525

Arg Lys Pro Ile Ser Ser Val Asn Leu Leu Val Ser Ser His Val Trp
            530                 535                 540

Arg Gln Asp His Asn Gly Phe Ser His Gln Asp Pro Gly Val Thr Ser
545             550                 555                 560

Val Leu Ile Asn Lys Thr Phe Asn Asn Asp His Val Thr Asn Ile Tyr
            565                 570                 575

Phe Ala Thr Asp Ala Asn Met Leu Leu Ala Ile Ser Glu Lys Cys Phe
```

```
                580             585             590
Lys Ser Thr Asn Lys Ile Asn Ala Ile Phe Ala Gly Lys Gln Pro Ala
        595                 600                 605

Pro Thr Trp Ile Thr Leu Asp Glu Ala Arg Ala Glu Leu Glu Ala Gly
    610                 615                 620

Ala Ala Glu Trp Lys Trp Ala Ser Asn Ala Glu Asn Asn Asp Glu Val
625                 630                 635                 640

Gln Val Val Leu Ala Ala Gly Asp Val Pro Thr Gln Glu Ile Met
                645                 650                 655

Ala Ala Ser Asp Ala Leu Asn Lys Met Gly Ile Lys Phe Lys Val Val
        660                 665                 670

Asn Val Val Asp Leu Leu Lys Leu Gln Ser Arg Glu Asn Asn Asp Glu
    675                 680                 685

Ala Leu Thr Asp Glu Glu Phe Thr Asp Leu Phe Thr Ala Asp Lys Pro
        690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe Asn Val Val Gly Tyr Lys Glu
            725                 730                 735

Gln Gly Ser Thr Thr Pro Phe Asp Met Val Arg Val Asn Asp Met
                740                 745                 750

Asp Arg Tyr Ala Leu Gln Ala Ala Ala Leu Lys Met Ile Asp Ala Asp
            755                 760                 765

Lys Tyr Ala Asp Lys Ile Asp Glu Leu Asn Ala Phe Arg Gln Lys Ala
        770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Gln Met Leu Ser Ala
                805                 810                 815

Thr Ala Thr Ala Gly Asp Asn Glu
            820                 825

<210> SEQ ID NO 32
<211> LENGTH: 825
<212> TYPE: PRT
<213> ORGANISM: Bifidobacterium pseudolongum subsp. globosum

<400> SEQUENCE: 32

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Thr
                20                  25                  30

Asn Tyr Met Ser Ile Gly Gln Ile Tyr Leu Arg Ser Asn Pro Leu Met
            35                  40                  45

Lys Glu Pro Phe Thr Arg Asp Asp Val Lys His Arg Leu Val Gly His
        50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Val Asp Gly Thr Tyr
                100                 105                 110

Thr Glu Tyr Tyr Pro Asn Ile Thr Lys Asp Glu Ala Gly Leu Gln Lys
            115                 120                 125
```

```
Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
210                 215                 220

Leu Ala Arg Ile Ser Asp Glu Glu Leu His Asp Phe Arg Gly Met
225                 230                 235                 240

Gly Tyr His Pro Tyr Glu Phe Val Ala Gly Phe Asn Glu Asp His
                245                 250                 255

Met Ser Ile His Arg Arg Phe Ala Glu Leu Phe Glu Thr Ile Phe Asp
            260                 265                 270

Glu Ile Cys Asp Ile Lys Ala Ala Ala Gln Thr Asp Asp Met Thr Arg
        275                 280                 285

Pro Phe Tyr Pro Met Leu Ile Phe Arg Thr Pro Lys Gly Trp Thr Cys
290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Glu His Phe Glu Val
                325                 330                 335

Leu Lys Gly Trp Met Glu Ser Tyr Lys Pro Glu Glu Leu Phe Asn Ala
            340                 345                 350

Asp Gly Ser Ile Lys Asp Val Thr Glu Phe Met Pro Lys Gly Glu
        355                 360                 365

Leu Arg Ile Gly Ala Asn Pro Asn Ala Asn Gly Gly Arg Ile Arg Glu
370                 375                 380

Asp Leu Lys Leu Pro Glu Leu Asp Gln Tyr Glu Val Thr Gly Val Lys
385                 390                 395                 400

Glu Tyr Gly His Gly Trp Gln Val Glu Ala Pro Arg Ser Leu Gly
                405                 410                 415

Ala Tyr Ser Arg Asp Ile Ile Lys Asn Asn Pro Asp Ser Phe Arg Ile
            420                 425                 430

Phe Gly Pro Asp Glu Thr Ala Ser Asn Arg Leu Asn Ala Thr Tyr Glu
        435                 440                 445

Val Thr Lys Lys Gln Trp Asp Asn Gly Tyr Leu Ser Ala Leu Val Asp
450                 455                 460

Glu Asn Met Ala Val Thr Gly Gln Val Val Glu Gln Leu Ser Glu His
465                 470                 475                 480

Gln Cys Glu Gly Trp Leu Glu Gly Tyr Ile Leu Thr Gly Arg His Gly
                485                 490                 495

Met Trp Ser Thr Tyr Glu Ser Phe Ala His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Val Asn Leu Leu Ile Ser Ser His Val Trp
530                 535                 540

Arg Gln Asp His Asn Gly Phe Ser His Gln Asp Pro Gly Val Thr Ser
```

```
                    545                 550                 555                 560
Val Leu Ile Asn Lys Thr Phe Asn Asn Asp His Val Thr Asn Ile Tyr
                565                 570                 575

Phe Ala Thr Asp Ala Asn Met Leu Leu Ala Ile Ala Glu Lys Cys Phe
                580                 585                 590

Lys Ser Thr Asn Lys Ile Asn Ala Ile Phe Ser Gly Lys Gln Pro Ala
                595                 600                 605

Pro Thr Trp Ile Thr Leu Asp Glu Ala Arg Ala Glu Leu Glu Ala Gly
                610                 615                 620

Ala Ala Glu Trp Lys Trp Ala Ser Asn Ala Lys Ser Asn Asp Glu Val
625                 630                 635                 640

Gln Ile Val Leu Ala Ala Gly Asp Val Pro Thr Gln Glu Ile Met
                645                 650                 655

Ala Ala Ser Asp Ala Leu Asn Lys Glu Gly Ile Lys Phe Lys Val Val
                660                 665                 670

Asn Val Val Asp Leu Leu Lys Leu Gln Ser Pro Glu Asn Asn Asp Glu
                675                 680                 685

Ala Met Ser Asn Glu Asp Phe Ala Glu Leu Phe Thr Ala Asp Lys Pro
690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe His Val Val Gly Tyr Lys Glu
                725                 730                 735

Gln Gly Ser Thr Thr Thr Pro Phe Asp Met Val Arg Val Asn Asp Met
                740                 745                 750

Asp Arg Tyr Ala Leu Glu Ala Gln Ala Leu Glu Leu Ile Asp Ala Asp
                755                 760                 765

Lys Tyr Ala Asp Lys Ile Asn Glu Leu Asn Glu Phe Arg Lys Lys Ala
                770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Gln Met Leu Ser Ala
                805                 810                 815

Thr Ala Thr Ala Gly Asp Asn Glu
                820                 825

<210> SEQ ID NO 33
<211> LENGTH: 825
<212> TYPE: PRT
<213> ORGANISM: Bifidobacterium breve

<400> SEQUENCE: 33

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Thr
                20                  25                  30

Asn Tyr Met Ser Ile Gly Gln Ile Tyr Leu Arg Ser Asn Pro Leu Met
                35                  40                  45

Lys Glu Pro Phe Thr Arg Asp Asp Val Lys His Arg Leu Val Gly His
                50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95
```

His Gly Gly Pro Ala Gly Thr Ser Gln Ser Tyr Val Asp Gly Thr Tyr
                100                 105                 110

Thr Glu Tyr Tyr Pro Asn Ile Thr Lys Asp Glu Ala Gly Leu Gln Lys
            115                 120                 125

Phe Phe Arg Gln Phe Ser Tyr Pro Gly Gly Ile Pro Ser His Phe Ala
        130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
210                 215                 220

Leu Ala Arg Ile Ser Asp Glu Glu Leu His Asp Phe Phe Arg Gly Met
225                 230                 235                 240

Gly Tyr His Pro Tyr Glu Phe Val Ala Gly Phe Asp Asn Glu Asp His
                245                 250                 255

Met Ser Ile His Arg Arg Phe Ala Glu Leu Phe Glu Thr Ile Phe Asp
            260                 265                 270

Glu Ile Cys Asp Ile Lys Ala Ala Ala Gln Thr Asp Asp Met Thr Arg
        275                 280                 285

Pro Phe Tyr Pro Met Leu Ile Phe Arg Thr Pro Lys Gly Trp Thr Cys
290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu His Phe Glu Val
                325                 330                 335

Leu Lys Gly Trp Met Glu Ser Tyr Lys Pro Glu Glu Leu Phe Asn Ala
            340                 345                 350

Asp Gly Ser Ile Lys Asp Val Thr Ala Phe Met Pro Lys Gly Glu
        355                 360                 365

Leu Arg Ile Gly Ala Asn Pro Asn Ala Asn Gly Gly Val Ile Arg Glu
370                 375                 380

Asp Leu Lys Leu Pro Glu Leu Asp Gln Tyr Glu Val Thr Gly Val Lys
385                 390                 395                 400

Glu Tyr Gly His Gly Trp Gly Gln Val Glu Ala Pro Arg Ala Leu Gly
                405                 410                 415

Ala Tyr Cys Arg Asp Ile Ile Lys Asn Asn Pro Asp Ser Phe Arg Ile
            420                 425                 430

Phe Gly Pro Asp Glu Thr Ala Ser Asn Arg Leu Asn Ala Thr Tyr Glu
        435                 440                 445

Val Thr Asp Lys Gln Trp Asp Asn Gly Tyr Leu Ser Gly Leu Val Asp
450                 455                 460

Glu His Met Ala Val Thr Gly Gln Val Thr Glu Gln Leu Ser Glu His
465                 470                 475                 480

Gln Cys Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp

```
            515                 520                 525
Arg Lys Pro Ile Ser Ser Val Asn Leu Leu Val Ser Ser His Val Trp
530                 535                 540

Arg Gln Asp His Asn Gly Phe Ser His Gln Asp Pro Gly Val Thr Ser
545                 550                 555                 560

Leu Leu Ile Asn Lys Thr Phe Asn Asn Asp His Val Thr Asn Ile Tyr
                565                 570                 575

Phe Ala Thr Asp Ala Asn Met Leu Leu Ala Ile Ser Glu Lys Cys Phe
            580                 585                 590

Lys Ser Thr Asn Lys Ile Asn Ala Ile Phe Ala Gly Lys Gln Pro Ala
        595                 600                 605

Pro Thr Trp Val Thr Leu Asp Glu Ala Arg Ala Glu Leu Glu Ala Gly
    610                 615                 620

Ala Ala Glu Trp Lys Trp Ala Ser Asn Ala Glu Asn Asn Asp Glu Val
625                 630                 635                 640

Gln Val Val Leu Ala Ser Ala Gly Asp Val Pro Thr Gln Glu Leu Met
                645                 650                 655

Ala Ala Ser Asp Ala Leu Asn Lys Met Gly Ile Lys Phe Lys Val Val
            660                 665                 670

Asn Val Val Asp Leu Leu Lys Leu Gln Ser Arg Glu Asn Asn Asp Glu
        675                 680                 685

Ala Leu Thr Asp Glu Glu Phe Thr Glu Leu Phe Thr Ala Asp Lys Pro
    690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe His Val Val Gly Tyr Lys Glu
                725                 730                 735

Gln Gly Ser Thr Thr Thr Pro Phe Asp Met Val Arg Val Asn Asp Met
            740                 745                 750

Asp Arg Tyr Ala Leu Gln Ala Ala Ala Leu Lys Leu Ile Asp Ala Asp
        755                 760                 765

Lys Tyr Ala Asp Lys Ile Asp Glu Leu Asn Ala Phe Arg Lys Lys Ala
    770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Gln Met Leu Ser Ala
                805                 810                 815

Thr Ala Thr Ala Gly Asp Asn Glu
            820                 825

<210> SEQ ID NO 34
<211> LENGTH: 788
<212> TYPE: PRT
<213> ORGANISM: Lactobacillus paraplantarum

<400> SEQUENCE: 34

Met Thr Thr Asp Tyr Ser Ser Pro Ala Tyr Leu Gln Lys Val Asp Lys
1               5                   10                  15

Tyr Trp Arg Ala Ala Asn Tyr Leu Ser Val Gly Gln Leu Tyr Leu Lys
            20                  25                  30

Asp Tyr Pro Leu Leu Gln Gln Pro Leu Lys Ala Ser Asp Val Lys Val
        35                  40                  45

His Pro Ile Cys His Trp Gly Thr Ile Ala Gly Gln Asn Ser Ile Tyr
    50                  55                  60
```

Ala His Leu Asn Arg Val Ile Asn Lys Tyr Gly Leu Lys Met Phe Tyr
65                  70                  75                  80

Val Glu Gly Pro Gly His Gly Gly Gln Val Met Val Ser Asn Ser Tyr
            85                  90                  95

Leu Asp Gly Thr Tyr Thr Asp Ile Tyr Pro Glu Ile Thr Gln Asp Val
            100                 105                 110

Glu Gly Met Gln Lys Leu Phe Lys Gln Phe Ser Phe Pro Gly Gly Val
            115                 120                 125

Ala Ser His Ala Ala Pro Glu Thr Pro Gly Ser Ile His Glu Gly Gly
130                 135                 140

Glu Leu Gly Tyr Ser Ile Ser His Gly Val Gly Ala Ile Leu Asp Asn
145                 150                 155                 160

Pro Asp Glu Ile Ala Ala Val Val Gly Asp Gly Glu Ser Glu Thr
                165                 170                 175

Gly Pro Leu Ala Thr Ser Trp Gln Ser Thr Lys Phe Ile Asn Pro Ile
                180                 185                 190

Asn Asp Gly Ala Val Leu Pro Ile Leu Asn Leu Asn Gly Phe Lys Ile
            195                 200                 205

Ser Asn Pro Thr Ile Phe Gly Arg Thr Ser Asp Ala Lys Ile Lys Glu
210                 215                 220

Tyr Phe Glu Ser Met Ser Trp Glu Pro Ile Phe Val Glu Gly Asp Asp
225                 230                 235                 240

Pro Glu Lys Val His Pro Val Leu Ala Lys Ala Met Asp Glu Ala Val
                245                 250                 255

Glu Lys Ile Lys Ala Ile Gln Lys His Ala Arg Glu Asn Asp Asp Ala
            260                 265                 270

Thr Leu Pro Val Trp Pro Met Ile Val Phe Arg Ala Pro Lys Gly Trp
            275                 280                 285

Thr Gly Pro Lys Ser Trp Asp Gly Asp Lys Ile Glu Gly Ser Phe Arg
            290                 295                 300

Ala His Gln Ile Pro Ile Pro Val Asp Gln Asn Asp Met Glu His Ala
305                 310                 315                 320

Asp Ala Leu Val Asp Trp Leu Glu Ser Tyr Gln Pro Lys Glu Leu Phe
                325                 330                 335

Asn Glu Asp Gly Ser Leu Lys Asp Ile Lys Glu Ile Ile Pro Thr
            340                 345                 350

Gly Asp Ser Arg Met Ala Ala Asn Pro Ile Thr Asn Gly Gly Val Asp
            355                 360                 365

Pro Lys Ala Leu Asn Leu Pro Asn Phe Arg Asp Tyr Ala Val Asp Thr
370                 375                 380

Ser Lys Glu Gly Ala Asn Val Lys Gln Asp Met Leu Val Trp Ser Asp
385                 390                 395                 400

Tyr Leu Arg Asp Val Ile Lys Lys Asn Pro Asp Asn Phe Arg Leu Phe
                405                 410                 415

Gly Pro Asp Glu Thr Met Ser Asn Arg Leu Tyr Gly Val Phe Glu Thr
            420                 425                 430

Thr Asn Arg Gln Trp Met Glu Asp Ile His Pro Asp Ser Asp Gln Tyr
            435                 440                 445

Glu Ala Ala Gly Arg Val Leu Asp Ala Gln Leu Ser Glu His Gln
        450                 455                 460

Ala Glu Gly Trp Leu Glu Gly Tyr Val Leu Thr Gly Arg His Gly Leu
465                 470                 475                 480

Phe Ala Ser Tyr Glu Ala Phe Leu Arg Val Val Asp Ser Met Leu Thr

-continued

```
                        485                 490                 495
Gln His Phe Lys Trp Leu Arg Lys Ala Asn Glu Leu Asp Trp Arg Lys
                500                 505                 510

Lys Tyr Pro Ser Leu Asn Ile Ile Ala Ala Ser Thr Val Phe Gln Gln
                515                 520                 525

Asp His Asn Gly Tyr Thr His Gln Asp Pro Gly Ala Leu Thr His Leu
        530                 535                 540

Ala Glu Lys Lys Pro Glu Tyr Ile Arg Glu Tyr Leu Pro Ala Asp Ala
545                 550                 555                 560

Asn Thr Leu Leu Ala Val Gly Asp Val Ile Phe Arg Ser Gln Glu Lys
                565                 570                 575

Ile Asn Tyr Val Val Thr Ser Lys His Pro Arg Gln Gln Trp Phe Ser
                580                 585                 590

Ile Glu Glu Ala Lys Gln Leu Val Asp Asn Gly Leu Gly Ile Ile Asp
        595                 600                 605

Trp Ala Ser Thr Asp Gln Gly Ser Glu Pro Asp Ile Val Phe Ala Ala
        610                 615                 620

Ala Gly Thr Glu Pro Thr Leu Glu Thr Leu Ala Ala Ile Gln Leu Leu
625                 630                 635                 640

His Asp Ser Phe Pro Glu Met Lys Ile Arg Phe Val Asn Val Val Asp
                645                 650                 655

Ile Leu Lys Leu Arg Ser Pro Gly Lys Asp Pro Arg Gly Leu Ser Asp
                660                 665                 670

Ala Glu Phe Asp His Tyr Phe Thr Lys Asp Lys Pro Val Val Phe Ala
        675                 680                 685

Phe His Gly Tyr Glu Asp Leu Val Arg Asp Ile Phe Phe Asp Arg His
        690                 695                 700

Asn His Asn Leu Tyr Val His Gly Tyr Arg Glu Asn Gly Asp Ile Thr
705                 710                 715                 720

Thr Pro Phe Asp Val Arg Val Met Asn Gln Met Asp Arg Phe Asp Leu
                725                 730                 735

Ala Lys Thr Ala Ile Ala Ala Gln Pro Ala Met Glu Asn Thr Gly Ala
                740                 745                 750

Ala Phe Val Gln Ser Met Asp Asn Met Leu Ala Lys His Asn Ala Tyr
        755                 760                 765

Ile Arg Asp Ala Gly Thr Asp Leu Pro Glu Val Asn Asp Trp Gln Trp
        770                 775                 780

Lys Gly Leu Lys
785
```

ENGINEERED MICROORGANISMS WITH G3P → 3PG ENZYME AND/OR FRUCTOSE-1,6-BISPHOSPHATASE INCLUDING THOSE HAVING SYNTHETIC OR ENHANCED METHYLOTROPHY

PRIORITY CLAIM

This application claims the benefit of priority to International Application No. PCT/US2019/039207, filed Jun. 26, 2019, which claims priority to U.S. Provisional Patent Application Ser. No. 62/690,209 filed Jun. 26, 2018, entitled Engineered Microorganisms with G3P→3PG Enzyme and/or Fructose-1,6-Bisphosphatase Including those Having Synthetic or Enhanced Methylotrophy, the disclosure of which is incorporated herein by reference.

REFERENCE TO SEQUENCE LISTING

This application contains a Sequence Listing in a computer readable form, submitted via USPTO Patent Center. The entire contents of the ASCII text file entitled "GNO0088US_Sequence_Listing V2.txt" created on Jul. 21, 2024, and having a size of 153,131 bytes, is incorporated herein by reference.

FIELD OF INVENTION

The disclosure is directed to engineered microorganisms having synthetic or enhanced methylotrophy as well as engineered microorganisms that utilize a NADP-dependent glyceraldehyde-3-phosphate dehydrogenase and/or a fructose-1,6-bisphosphatase.

BACKGROUND

Methylotrophy relates to the ability of a microorganism to use single carbon (C1) compounds, such as methanol and methane, as energy and carbon sources. Carbon feedstocks that include methane, which is available from natural gas, and it oxidation product, methanol, have become widely available and are now relatively inexpensive. Therefore, using C1 feedstocks has become attractive for fermentation technologies for the production of bioproducts, as compared to traditional feedstocks which typically use C6 or C5 sugars, which can be more costly.

Methylotrophic microorganisms are generally not favored for industrial processes as many have strict aerobic requirements, generate relatively few metabolic intermediates, and are thus far unsuitable for facile genetic engineering. Therefore, the development of synthetic methylotrophy in industrially useful microorganisms is challenging.

SUMMARY

In some embodiments, the current invention provides engineered microorganisms having synthetic or improved methylotrophy, methods for producing a bioproduct using the engineered microorganisms, compositions that include the microorganisms, and also bioproduct-containing compositions prepared using the microorganisms. Engineered microorganisms of the invention include at least one modification relating to an enzyme(s) leading into the lower glycolysis (EMP) pathway (a NADP-dependent glyceraldehyde-3-phosphate dehydrogenase), and an enzyme(s) of the ribulose monophosphate (RuMP) cycle.

It has been found that native organisms, such as *E. coli*, which are incapable of performing methylotrophy, typically have a relatively high-flux through the EMP pathway. To achieve synthetic methylotrophy, engineered microorganisms of the disclosure utilize one or more enzyme(s) of the RuMP cycle and are also engineered to beneficially maintain an adequate pool size of one or more phosphorylated 3 and/or 4 carbon species (e.g., glyceraldehyde 3-phosphate (G3P), dihydroxyacetone phohsphate (DHAP), and erythrose 4-phosphate (E4P)). In one aspect of the disclosure, it has been discovered that this can be achieved in engineered organisms using an enzyme that converts glyceraldehyde 3-phosphate (G3P) to 3-phosphoglycerate (3PG), wherein the enzyme reduces NADP to NADPH (and also may be referred to as a non-phosphorylating enzyme as discussed herein), such as *B. methanolicus* GapN, or a functional equivalent thereof. In another aspect of the disclosure, this can be achieved in engineered organisms using a fructose-1,6-bisphosphatase, such as *B. methanolicus* GlpN, or a functional equivalent thereof.

Accordingly, an embodiment of the invention provides an engineered microorganism having synthetic or enhanced methylotrophy, the engineered microorganism including: (a) exogenous enzyme A that (ai) is capable of converting glyceraldehyde 3-phosphate (G3P) to 3-phosphoglycerate (3PG), that (aii) has at least 50% sequence identity to SEQ ID NO:1 (*B. methanolicus* gapN), wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii).

The modifications to the microorganism allows for the generation of C6 compounds from C1 and C5 compounds, the regeneration of C5 compounds from C6 compounds by carbon rearrangement, and an improved balance between regeneration of C5 compounds and lower glycolysis. In turn, this allows the engineered microorganism to generate sufficient quantities of metabolic precursors (e.g., acetyl-CoA) which can be used in a bioproduct pathway to produce a target compound, while at the same time providing good cell health for growth during fermentation methods.

In embodiments, the engineered microorganism can optionally include one or more modifications to native gene(s) of the organism's lower glycolysis pathway. For example, the modification can be one that attenuates or eliminates the organism's native NAD-dependent glyceraldehyde-3-phosphate dehydrogenase activity (GapA), native phosphoglycerate kinase activity (pgk). Along with the gapN modification, such deletions can enhance the pool size of the one or more phosphorylated 3 and/or 4 carbon species to provide cellular benefits as described herein.

In embodiments, the engineered microorganism can optionally include a $NAD^+$-dependent methanol dehydrogenase (MDH), such as an exogenous MDH. The organism can have high MDH activity made possible by enhanced enzymatic activity, e.g., using a MDH variant, enhanced expression, or both. The MDH activity can provide an increased pool of C1 compound (formaldehyde), and the cell modifications can provide for generation of C5 compounds, for increased flux to the C6 compounds using the RuMP enzymes.

In embodiments, the engineered microorganism can optionally include one or more modifications to provide: (a) expression or increased activity of a transketolase(s) to increase the pool size of erythrose 4-phosphate, (b) expression or increased activity of sedoheptulose 1,7 bisphosphatase (SBPase or GlpX) to operate the SBPase variant of the RuMP cycle in the engineered organism; attenuates or eliminates the organism's native transaldolase activity (e.g., talB, talA, talC).

In embodiments, the disclosure provides an engineered microorganism comprising the following modifications:

I. (1) exogenous enzyme A (e.g., GapN), (2) exogenous Hps, (3) exogenous Phi, (4) exogenous MeDH, (5) exogenous GlpX, and (6) optionally exogenous phosphoketolase (PK);

II. optional modification causing deletion or attenuation of one or more of the following endogenous enzymes: (7) ATP-dependent 6-phosphofructokinase (Pfk), (8) ribulose-phosphate 3-epimerase (Rpe), (9) ribose-5-phosphate isomerase (Rpi), (10) transketolase (Tkt), (11) fructose-bisphosphate aldolase (Fba), (12) glucose-6-phosphate 1-dehydrogenase (Zwf), and optionally replacement of any of (7)-(11) with an exogenous counterpart enzyme, such as from *Bacillus*; and III. optional modification causing deletion or attenuation of one or more of the following endogenous enzymes: (12) NAD-dependent glyceraldehyde-3-phosphate dehydrogenase (GapA), (13) transaldolase (e.g., TalB, TalA, and/or TalC), (14) phosphoglycerate kinase (Pgk), (15) phosphoglycerate mutase (Gpm), (16) enolase (Eno), (17) deoxyribose phosphate aldolase (DeoC), (18) methyl glyoxal synthase (MgsA), and (19) ATP-dependent 6-phosphofructokinase (pfkA and pfkB).

In other embodiments, the current invention provides engineered microorganisms (where synthetic or improved methylotrophy is not necessarily required) that include exogenous enzyme A that (ai) is capable of converting glyceraldehyde 3-phosphate (G3P) to 3-phosphoglycerate (3PG) or (aii) has at least 50% sequence identity to SEQ ID NO:1 (*B. methanolicus* GapN), wherein enzyme A is capable of reducing NADP to NADPH. Such a modification is useful in a metabolically engineered organism when a pathway to a desired chemical product utilizes NADPH as a redox source. In embodiments, the generation of NADPH can provide an advantage as a redox source in that fewer cellular reactions utilize NADPH, and in turn these electrons can be directed to the product pathway rather than other cellular reactions. Further, cellular ratios of NADPH to NADP+ can be higher than NADH to NAD+ ratios, which can provide an additional thermodynamic driving force for the product pathway. For example, an engineered microorganism that includes enzyme A (e.g., GapN or a functional equivalent thereof) can include a product pathway that utilizes increased cellular amounts of NADPH, such as amino acid pathways, particularly pathways to aromatic amino acids that require high levels of C3 and C4-phosphates such as G3P and E4P. Additionally the use of GapN with attenuated or deleted GapA can be used to improve the production of NADPH intensive products, such as 1,3 BDO.

In embodiments, the engineered microorganism can optionally include one or more transgene(s) encoding a protein of a metabolic pathway that promotes production of a target product or intermediate thereof, wherein the metabolic pathway uses a compound resulting from methanol consumption by the cell. In some embodiments, the one or more transgenes can be part of a pathway that forms an alcohol such as 1-butanol, isobutanol, 1,4-butanediol, or 1,3-butanediol. In some embodiments, the one or more transgenes can be part of a pathway that forms an acid or an acid ester such as methacrylic acid (MAA) or methyl methacrylate (MMA).

Other embodiments are directed to compositions including an engineered microorganism of the disclosure, such as cell culture compositions, and also compositions including one or more product(s) produced from the engineered microorganism. For example, a composition can include a target product produced by the engineered microorganisms, where the composition has been purified to remove cells or other components useful for cell culturing. The composition may be treated to enrich or purify the target product or intermediate thereof.

Other embodiments of the disclosure are directed to products made from the target product obtained from methods using the engineered microorganism.

DESCRIPTION OF THE DRAWINGS

FIG. 9 is a table listing SEQ ID NOs of corresponding proteins.

DETAILED DESCRIPTION

Figure 1:
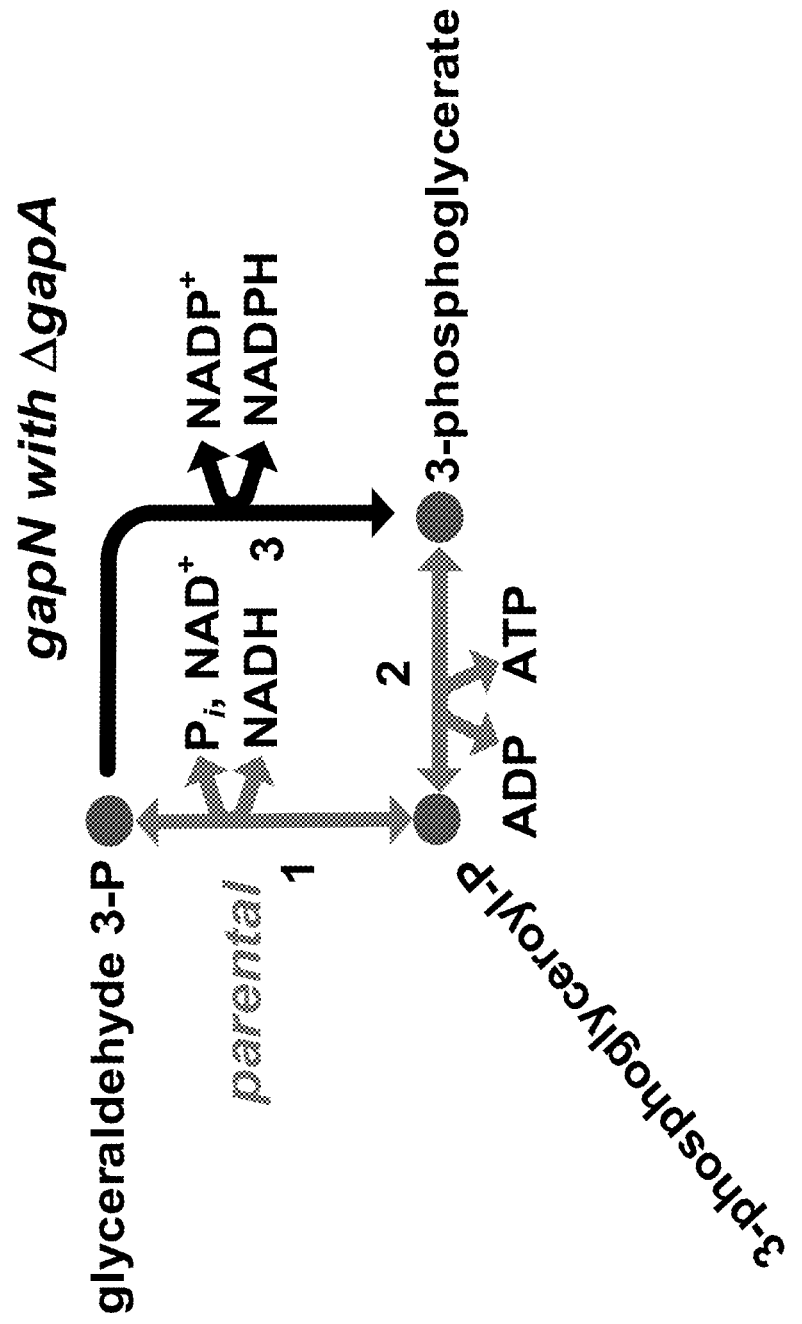
FIG. 1 illustrates the conversion of G3P to 3PG through 1,3-BPG (also referred to as 3-phosphoglyceroyl-P) using gapA and pgk (in a native/parental cell), as compared to the direct conversion of G3P to 3PG using gapN and NADP$^+$ in a cell modified with exogenous gapN and having a gapA deletion. Reactions 1 and 2, native to *E. coli*, are marked as "parental". Reaction 3, the GapN by-pass of the present invention where gapN is expressed with a deleted or otherwise attenuated gapA, is marked as "gapN with delta gapA".

The embodiments of the description described herein are not intended to be exhaustive or to limit the disclosure to the precise forms disclosed in the following detailed description. Rather, the embodiments are chosen and described so that others skilled in the art can appreciate and understand the principles and practices of the description.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The term "synthetic methylotrophy" refers to the engineering in a microbial cell that allows it to utilize a C1 carbon (such as methanol or methane) as an energy source. A host cell in which the synthetic methylotrophy is engineered into otherwise is not able to grow on a C1 carbon source. Engineering a microorganism to provide synthetic methylotrophy will generally involve the expression of least one exogenous (i.e., "non-native") enzyme in the cell, and more typically two or more, or three or more exogenous, enzymes in the cell. Other modifications can involve deletion of native genes or modification(s) that otherwise cause attenuation of native gene activity. The exogenous enzyme (s) can be incorporated into a natural metabolite pathway in the cell with one or more endogenous (i.e., "native") enzymes, wherein exogenous enzyme(s) can convert a metabolite derived from 1C carbon into one that can be utilized by the cell's native enzymes, such as for cell growth or bioproduct production. Microorganisms that are non-methylotrophic and that can be engineered with exogenous enzyme(s) of the disclosure include E. coli and other prokaryotic and eukaryotic organisms as described herein.

The term "enhanced methylotrophy" refers to engineering a methylotrophic microbial cell that improves utilization of a 1C carbon (such as methanol or methane) as an energy source. A cell with "enhanced methylotrophy" can demonstrate enhanced cell growth or bioproduct production over the native methylotropic microbial cell. Microorganisms that are non-methylotropic and that can be engineered with exogenous enzyme(s) of the disclosure include E. coli and other prokaryotic and eukaryotic organisms as described herein.

Aspects of the current disclosure are directed to engineered microorganisms having at least one modification (i.e., "Enzyme A") that affects the products leading into lower glycolysis (EMP) cycle. In one embodiment, Enzyme A is an enzyme that converts glyceraldehyde 3-phosphate to 3-phosphoglicerate (3PG), or is an enzyme that has at least 50% sequence identity to SEQ ID NO:1 (B. methanolicus gapN), wherein enzyme A is capable of reducing NADP to NADPH. In another embodiment, Enzyme A is a fructose-1,6-bisphosphatase, such as B. methanolicus GlpN, or a functional equivalent thereof.

The engineered microorganism can also have one or more exogenous enzyme(s) of the ribulose monophosphate (RuMP) cycle, (i.e., "Enzyme B"). The one or more RUMP cycle enzymes include, but is not limited to a hexulose-6-phosphate synthase, a 6-phospho-3-hexuloisomerase, a phosphoketolase, or any combination of these enzymes.

In preferred embodiments, the engineered microorganism also includes an exogenous methanol dehydrogenase, such as a methanol dehydrogenase that has one or more variant amino acids as compared to a wild type sequence.

In some embodiments, the engineered microorganism includes an enzyme ("enzyme A") that is capable of irreversibly converting glyceraldehyde 3-phosphate (G3P) to 3-phosphoglycerate (3PG) using the reduction of NADP+ to NADPH, or an enzyme that has at least 50% sequence identity to SEQ ID NO:1 (B. methanolicus gapN). Unlike E. coli gapA (glyceraldehyde-3-phosphate dehydrogenase A; P0A9B2) which uses the cofactor NAD to catalyze the oxidative phosphorylation of G3P to 13BPG, enzyme A of the current disclosure uses NADP to catalyze the conversion of G3P to 3PG (shown below). The conversion of G3P to 3PG, which utilizes NADP, appears to require no detectable amounts of phosphate for the conversion, and therefore may be referred to as a "non-phosphorylating" enzyme, which further distinguishes its enzymatic activity from E. coli gapA, which otherwise carriers out oxidative phosphorylation. Further, Enzyme A (e.g., GapN) converts G3P at a slower rate, based on comparing the conversion of G3P to 3PG by GapN, as compared to the conversion of G3P to 13BPG by *E. coli* GapA. FIG. 1 illustrates the conversion of G3P to 3PG through 1,3-BPG using gapA and pgk, as compared to the direct conversion of G3P to 3PG using gapN and $NADP^+$.

For example, the enzyme kinetics of gapN are:

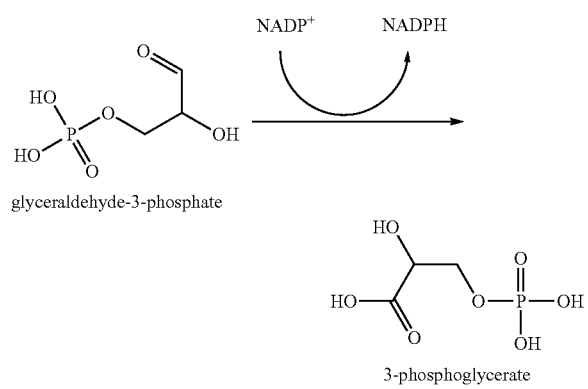

One exemplary Enzyme A sequence is based on the *Bacillus methanolicus* NADP-dependent glyceraldehyde-3-phosphate dehydrogenase gapN (Genbank Accession number WP_003346738, 481 amino acids long; SEQ ID NO:1). The engineered microorganism of the disclosure can express an Enzyme A that has a sequence that is related *Bacillus methanolicus* gapN, such as a *Bacillus methanolicus* gapN homolog. For example, Enzyme A can have a sequence that has 50% or greater, 60% or greater, 70% or greater, 80% or greater, 85% or greater, 90% or greater, or 95% or greater, identity to SEQ ID NO: 1. Homologs of SEQ ID NO: 1 can be identified by sequence identity searching (e.g., algorithms well known to those skilled in the art, such as Align, BLAST, Clustal W, as described herein).

Exemplary Enzyme A sequences include those found in Table 1 below, which include many sequences from various *Bacillus* species.

TABLE 1

| Accession | Organism | % ID to *B. methanolicus* MGA3 |
|---|---|---|
| WP_003346738 | *Bacillus methanolicus* | 100 |
| WP_003351798 | *Bacillus methanolicus* | 95.01 |
| WP_026964094 | *Alicyclobacillus pomorum* | 68.75 |
| SEQ ID NO: 12 | | |
| WP_089533800 | *Virgibacillus necropolis* | 66.527 |
| SEQ ID NO: 13 | | |
| WP_011983786 | *Bacillus cytotoxicus* | 65.89 |
| SEQ ID NO: 14 | | |
| WP_097894576 | *Bacillus* | 65.89 |
| WP_087097851 | *Bacillus cytotoxicus* | 65.678 |
| SEQ ID NO: 15 | | |
| WP_068447188 | *Lentibacillus amyloliquefaciens* | 65.546 |
| SEQ ID NO: 16 | | |
| WP_098359346 | *Bacillus cereus* | 65.466 |
| SEQ ID NO: 17 | | |
| WP_098558080 | *Bacillus cereus* | 65.466 |
| EEL51944 | *Bacillus cereus* Rock3-44 | 65.254 |
| SEQ ID NO: 18 | | |
| WP_000208150 | *Bacillus cereus* | 65.254 |
| WP_088038585 | *Bacillus mycoides* | 65.254 |

TABLE 1-continued

| Accession | Organism | % ID to *B. methanolicus* MGA3 |
|---|---|---|
| WP_000213646 | *Bacillus cereus* group | 65.042 |
| SEQ ID NO: 19 | | |
| WP_000213650 | *Bacillus cereus* group | 65.042 |
| WP_002010835 | *Bacillus* | 65.042 |
| WP_002125495 | *Bacillus cereus* group | 65.042 |
| WP_002134606 | *Bacillus cereus* | 65.042 |
| WP_002140513 | *Bacillus cereus* | 65.042 |
| WP_016093244 | *Bacillus cereus* | 65.042 |
| WP_017153122 | *Bacillus bingmayongensis* | 65.042 |
| WP_025150283 | *Bacillus* sp. H1a | 65.042 |
| WP_070141032 | *Bacillus cereus* group | 65.042 |
| WP_078178206 | *Bacillus mycoides* | 65.042 |
| WP_088035237 | *Bacillus thuringiensis* | 65.042 |
| WP_088106515 | *Bacillus cereus* | 65.042 |
| WP_088292461 | *Bacillus mycoides* | 65.042 |
| WP_105585763 | *Bacillus* sp. MYb209 | 65.042 |
| WP_105989975 | *Bacillus* sp. M21 | 65.042 |
| WP_077328816 | *Virgibacillus siamensis* | 64.916 |
| SEQ ID NO: 20 | | |
| ABK84147 | *Bacillus thuringiensis* str. Al Hakam | 64.831 |
| SEQ ID NO: 21 | | |
| WP_000213613 | *Bacillus* | 64.831 |
| WP_000213620 | *Bacillus cereus* | 64.831 |
| WP_000213631 | *Bacillus* | 64.831 |
| WP_000213637 | *Bacillus* | 64.831 |
| WP_000213642 | *Bacillus cereus* | 64.831 |
| WP_000213643 | *Bacillus thuringiensis* | 64.831 |
| WP_002063972 | *Bacillus cereus* | 64.831 |
| WP_002087376 | *Bacillus cereus* | 64.831 |
| WP_003205982 | *Bacillus cereus* group | 64.831 |
| WP_016113266 | *Bacillus cereus* group | 64.831 |
| WP_018783531 | *Bacillus* | 64.831 |
| WP_048373546 | *Bacillus* sp. LK2 | 64.831 |
| WP_052943462 | *Bacillus thuringiensis* | 64.831 |
| WP_070169862 | *Bacillus mycoides* | 64.831 |
| WP_074615306 | *Bacillus cereus* | 64.831 |
| WP_076869997 | *Bacillus cereus* | 64.831 |
| WP_078985830 | *Bacillus anthracis* | 64.831 |
| WP_086388821 | *Bacillus thuringiensis* | 64.831 |
| WP_097786660 | *Bacillus pseudomycoides* | 64.831 |
| WP_097793698 | *Bacillus pseudomycoides* | 64.831 |
| WP_097955132 | *Bacillus toyonensis* | 64.831 |
| WP_098116852 | *Bacillus pseudomycoides* | 64.831 |
| WP_098162831 | *Bacillus toyonensis* | 64.831 |
| WP_098335345 | *Bacillus cereus* | 64.831 |
| WP_098492658 | *Bacillus cereus* | 64.831 |
| WP_098925877 | *Bacillus anthracis* | 64.831 |
| WP_101195307 | *Bacillus* sp. HBCD-sjtu | 64.831 |
| WP_101218479 | *Bacillus cereus* | 64.831 |
| EEM06723 | *Bacillus mycoides* Rock1-4 | 64.619 |
| SEQ ID NO: 22 | | |
| WP_000213623 | *Bacillus cereus* | 64.619 |
| WP_000213628 | *Bacillus thuringiensis* | 64.619 |
| WP_000213640 | *Bacillus anthracis* | 64.619 |
| WP_002114874 | *Bacillus cereus* | 64.619 |
| WP_002201632 | *Bacillus cereus* group | 64.619 |
| WP_018767657 | *Bacillus* | 64.619 |
| WP_033798237 | *Bacillus mycoides* | 64.619 |
| WP_040119176 | *Bacillus mycoides* | 64.619 |
| WP_041488274 | *Bacillus cereus* group | 64.619 |
| WP_042982143 | *Bacillus mycoides* | 64.619 |
| WP_062821571 | *Bacillus cereus* | 64.619 |
| WP_070172070 | *Bacillus cereus* group | 64.619 |
| WP_071771128 | *Bacillus* sp. NH11B | 64.619 |
| WP_088077715 | *Bacillus mycoides* | 64.619 |
| WP_088312506 | *Bacillus cereus* | 64.619 |
| WP_097831246 | *Bacillus cereus* | 64.619 |
| WP_097926598 | *Bacillus toyonensis* | 64.619 |
| WP_097988492 | *Bacillus pseudomycoides* | 64.619 |
| WP_098017785 | *Bacillus pseudomycoides* | 64.619 |
| WP_098040080 | *Bacillus pseudomycoides* | 64.619 |
| WP_098101492 | *Bacillus pseudomycoides* | 64.619 |
| WP_098135232 | *Bacillus pseudomycoides* | 64.619 |
| WP_098187957 | *Bacillus pseudomycoides* | 64.619 |
| WP_098226164 | *Bacillus toyonensis* | 64.619 |
| WP_098362014 | *Bacillus cereus* | 64.619 |

TABLE 1-continued

| Accession | Organism | % ID to B. methanolicus MGA3 |
|---|---|---|
| WP_098610496 | Bacillus pseudomycoides | 64.619 |
| WP_098639221 | Bacillus anthracis | 64.619 |
| WP_098716171 | Bacillus pseudomycoides | 64.619 |
| WP_101168380 | Bacillus sp. SN10 | 64.619 |
| AIE81030 SEQ ID NO: 23 | Bacillus cereus | 64.482 |
| WP_000213645 SEQ ID NO: 24 | Bacillus cereus | 64.407 |
| WP_002116502 | Bacillus cereus | 64.407 |
| WP_002159137 | Bacillus cereus group | 64.407 |
| WP_006093663 | Bacillus | 64.407 |
| WP_097834495 | Bacillus pseudomycoides | 64.407 |
| WP_097849866 | Bacillus pseudomycoides | 64.407 |
| WP_098160819 | Bacillus pseudomycoides | 64.407 |
| WP_085965931 SEQ ID NO: 25 | Bacillus cereus | 64.271 |
| WP_098814110 SEQ ID NO: 26 | Bacillus pseudomycoides | 64.195 |
| WP_098929011 | Bacillus pseudomycoides | 64.195 |

The disclosure also contemplates the use of variants of Enzyme A in the engineered microorganisms of the disclosure, which include one or more amino acid substitutions, deletions, or additions. Variants can be generated either randomly, or by targeted substitution by using sequence alignments of Enzyme A sequences, such as those described in Table 1. Regions that are conserved and/or important for enzymatic functioning of the Enzyme A can be determined, with variants engineered based on this information. Therefore, Enzyme A can have one or more amino acid substitutions, deletions, or additions which cause the sequence to vary from a native sequence, such as SEQ ID NO: 1.

Optionally, the engineered microorganism includes one or more modifications of genes of the host cell's lower glycolysis pathway. The cell's glycolysis pathway (known as the Embden-Meyerhof-Pamas (EMP) Pathway) has upper and lower portions. In the upper portion glucose (a hexose sugar) is "activated" by phosphorylation with two molecules of adenosine triphosphate (ATP). It is then rearranged in preparation for cleavage into two three carbon (triose) phosphate molecules using fructose bisphosphate aldolase (FBA). In the lower portion, the three carbon (triose) phosphate molecules are phosphorylated and oxidized (via NAD+) in a reaction that is catalyzed by glyceraldehyde dehydrogenase (GAPDH). Subsequently, further phosphorylation provides 4 ATP and 2 pyruvate molecules.

In addition to the introduction of exogenous gapN, the engineered microorganism can include a modification to a native gene of the cell that encodes a NAD-dependent glyceraldehyde-3-phosphate dehydrogenase. See FIG. 2. The modification can attenuate or eliminate the activity of the NAD-dependent glyceraldehyde-3-phosphate dehydrogenase. An example of such a gene that can be modified or deleted to attenuate or eliminate activity is the E. coli gapA gene (encodes glyceraldehyde-3-phosphate dehydrogenase A; P0A9B2) which uses the cofactor NAD and phosphate to catalyze the oxidative phosphorylation of G3P to 13BPG. An engineered E. coli wherein gapA is deleted or otherwise its expression reduced can be referred to as ΔgapA, or any modification which reduces enzymatic activity may be notated as such.

The deletion, reduced expression, or reduced enzymatic activity of GapA, can allow the exogenous GapN to more effectively compete for glyceraldehyde-3-phosphate (G3P) as a substrate. Since GapN displays slower conversion of G3P to 3-PG as compared to E. coli GapA conversion of G3P to 1,3-BPG, this can provide a way to enhance the pool size of the one or more phosphorylated 3 and/or 4 carbon species. In turn, this improves the balance between regeneration of C5 compounds and lower glycolysis, and enables or enhances synthetic methylotrophy in the cells having these modifications.

In one aspect of the disclosure synthetic methylotrophy is promoted by engineering the cell to provide a desired balance between lower glycolysis through glyceraldehyde-3-phosphate dehydrogenase (GapA or GapN) and C5 regeneration through the RuMP cycle (Fba, GlpX). See FIGS. 5 and 6. The genetic modifications set forth in the disclosure that provide the desired balance can be made in native E. coli, which is regulated by NADH levels, and take into account the use of exogenous methanol dehydrogenase which generates NADH (and which otherwise presents additional challenges to attain this balance). In embodiments, the use of GapN therefore not only facilitates synthetic methylotrophy by its kinetic activity, but also by its unique property to reduce NADP to NADPH. One or more genes that are part of the lower glycolysis pathway, and that are "downstream" of GapA, can also be modified to attenuate or eliminate their activity. For example, the engineered microorganism can have one or more modification(s) that (a) attenuates or eliminates an enzyme in a pathway leading from glyceraldehyde-3-phosphate to phosphoenolpyruvate (PEP).

Figure 2:
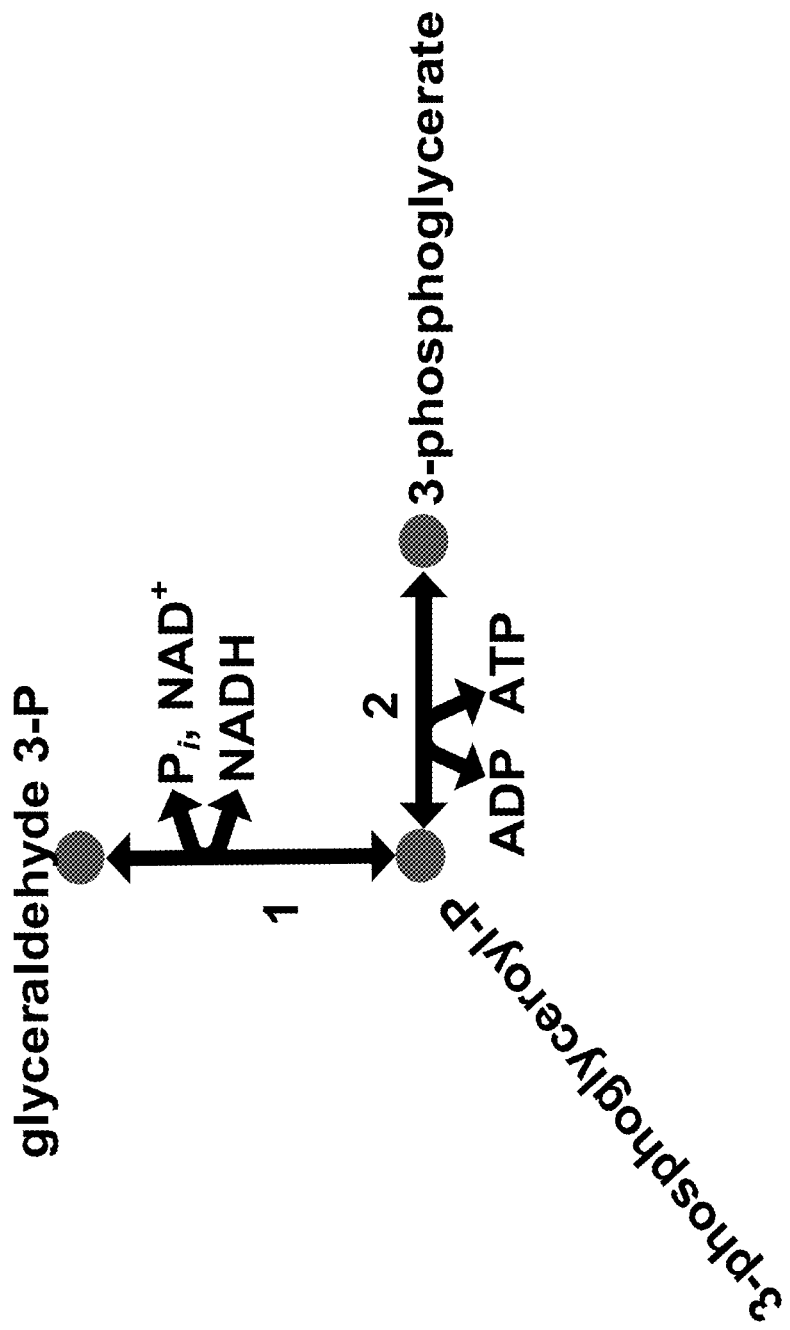
FIG. 2 illustrates a metabolic pathway leading from glyceraldehyde 3-phosphate (G3P) in a cell having gapA and pgk. Reaction 1 is catalyzed by a glyceraldehyde-3-phosphate dehydrogenase (GapA); Reaction 2 by a phosphoglycerate kinase (Pgk).

With reference to FIG. 2, in some embodiments, the engineered microorganism can have one or more modification(s) that (a) attenuates or eliminates a phosphoglycerate kinase activity (e.g., E. coli pgk, Uniprot P0A799). Pgk converts 3-phospho-D-glyceroyl phosphate to 3-phospho-D-glycerate, while generating an ATP from ADP via substrate level phosphorylation. In some embodiments, the engineered microorganism can have one or more modification(s) that (a) attenuates or eliminates a phosphoglycerate mutase activity.

In aspects, engineered cells of the disclosure also include exogenous enzyme B which is (bi) a hexulose-6-phosphate synthase, (bii) a 6-phospho-3-hexuloisomerase, (biii) a phosphoketolase, or any combination of (bi), (bii) and (biii).

In methanotrophic bacteria, formaldehyde made from methane and methanol oxidation is used to form metabolic intermediates in pathways leading to the formation of cellular products (Anthony, C. (1991) Biotechnology 18:79-109). The serine and D-ribulose 5-phosphate (RuMP) pathways use formaldehyde to produce carbon-containing intermediate compounds which are subsequently converted into other downstream products.

Figure 3:
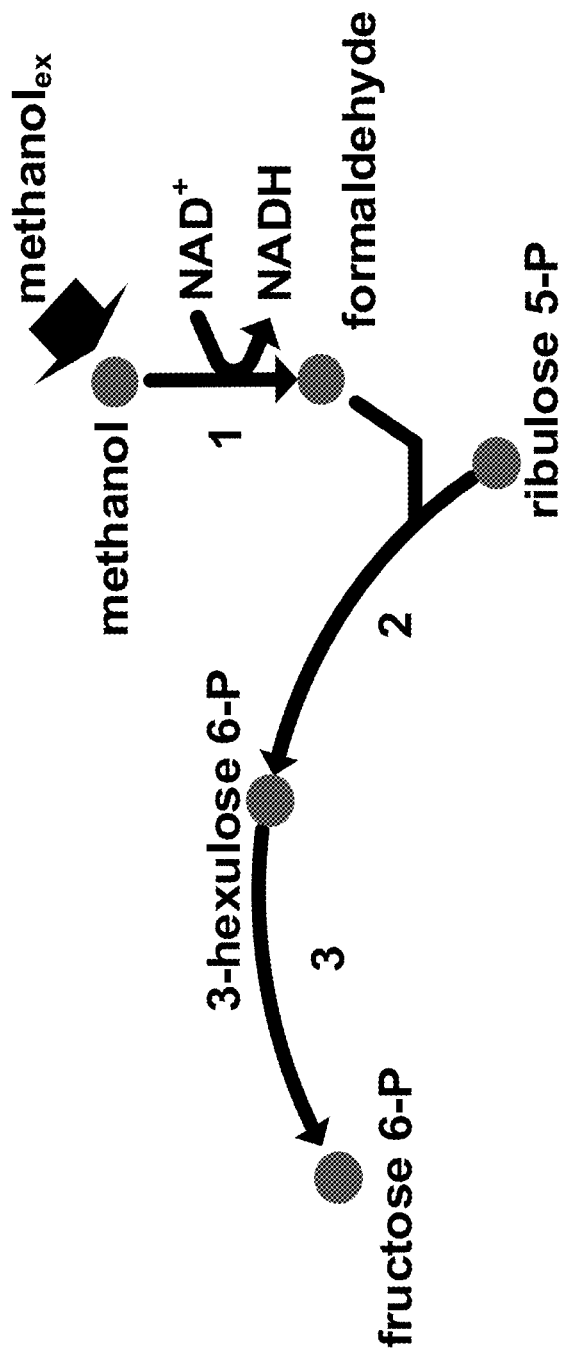
FIG. 3 illustrates a metabolic pathway leading from methanol to fructose-6-phosphate using MeDH, HPS, and PHI, in a cell having synthetic methylotrophy. Methanolex is external methanol, added as a carbon feed. Reaction 1 is catalyzed by a methanol dehydrogenase (mdh); Reaction 2 by a hexulose-6-phosphate synthase (hps); Reaction 3 by a phospho-3-hexuloisomerase.

With reference to FIG. 3, the RuMP pathway hexulose-6-phosphate synthase (HPS) enzymatically condenses formaldehyde and D-ribulose 5-phosphate (RuMP) to form hexulose 6-phosphate (HuMP). 6-phospho-3-hexuloisomerase (PHI) enzymatically converts HuMP to β-D-fructofuranose 6-phosphate (F6P). HPS and PHI are unique to natural organisms that have the RuMP pathway. For every one molecule of formaldehyde assimilated, one molecule of F6P is created. F6P can then be cleaved to 3-carbon compounds by either of two routes. Enzymes of these other routes are not exclusive to those methanotrophic bacteria expressing HPS and HPI.

In one route 6-phosphofructokinase (EC 2.7.1.11) phosphorylates F6P to fructose 1,6-bisphosphate (FDP). Fructose-bisphosphate aldolase (EC 4.1.2.13) then cleaves FDP into dihydroxy acetone phosphate (DHAP) and glyceraldehyde 3-phosphate (G3P).

In another route glucose-6-phosphate isomerase (EC 5.3.1.9) isomerizes FMP to glucose 6-phosphate (G6P). Glucose-6-phosphate 1-dehydrogenase (EC 1.1.1.49) then dehydrogenates G6P to D-glucono-1,5-lactone 6-phosphate which is further dehydrogenated to 6-phospho-gluconate by 6-phosphogluconolactonase (EC 3.1.1.31). Phosphogluconate dehydratase (EC 4.2.1.12) then converts 6-phosphogluconate to 2-keto-3-deoxy-6-phospho-D-gluconate (KDPG). Subsequently, KDPG aldolase (EC 4.1.2.14) cleaves KDPG into glyceraldehyde 3-phosphate (G3P) and pyruvate. Pyruvate and DHAP formed through this pathway can be used in cellular pathways for the synthesis of biomolecules.

3-hexulose-6-phosphate synthases are of the enzyme class (EC) 4.1.2.43. The enzyme 3-hexulose-6-phosphate synthase (HPS) can carry out the fixation of formaldehyde with ribulose 5-phosphate (Ru5P) to form d-arabino-3-hexulose-6-phosphate (Hu6P). See FIG. 2.

One exemplary HPS sequence is based on *Bacillus methanolicus* MGA HPS (Genbank Accession number AAR39392.1; 211 amino acids long; SEQ ID NO: 2). The engineered microorganism can express a HPS sequence that is related to *Bacillus methanolicus* MGA HPS, such as a *Bacillus methanolicus* MGA HPS homolog. For example, the HPS sequence can have 25% or greater, 30% or greater, 40% or greater, 50% or greater, 60% or greater, 70% or greater, 80% or greater, 85% or greater, 90% or greater, or 95% or greater identity to SEQ ID NO: 2. Homologs of SEQ ID NO: 2 can be identified by sequence identity searching (e.g., algorithms well known to those skilled in the art, such as Align, BLAST, Clustal W, as described herein).

Exemplary HPS sequences include those found in Table 2A and 2B below. For example, 3-hexulose-6-phosphate synthase include, but are not limited to, *Bacillus methanolicus* PB1 HPS (EIJ81375.1); *Methylobacillus flagellatus* HPS (YP 544362.1); *Methylobacillus flagellatus* HPS (YP 544363.1); *Bacillus subtilis* HPS (NP_388228.1); *Methylophilus methylotrophus* HPS (WP_018986666.1); *Methylophilus methylotrophus* ATCC 53528 HPS (WP_018985298.1); *Aminomonas aminovorus* HPS (AAG29505.1), *Amycolatopsis methanolica* 239 HPS (AIJ24611.1); *Geobacillus* sp. GHH01 HPS (YP_007402409.1); *Geobacillus* sp. M10EXG HPS (AAR91478.1); *Geobacillus* sp. Y4.1MC1 HPS (YP_003990382.1); *Geobacillus thermodenitrificans* NG80-2 HPS (WP 008879217.1); *Methylomonas aminofaciens* HPS (BAA83096.1); *Methylovorus glucosetrophus* SIP3-4 HPS (YP_003050044.1); *Methylovorus* sp. MP688 HPS (YP_004038706.1); and *Mycobacterium gastri* HPS (BAA90546.1).

TABLE 2A

Pairwise alignment (% ID)

| HPS | *Geobacillus thermodenitrificans* NG80-2 | *Bacillus Methanolicus* MGA3 | *Bacillus Methanolicus* PB1 | *Geobacillus* sp. GHH01 | *Geobacillus* sp. M10EXG | *Geobacillus* sp. Y4.1MC1 | *Methylophilus methylotrophus* |
|---|---|---|---|---|---|---|---|
| *Geobacillus thermodenitrificans* NG80-2 | 100 | 30.8 | 30.8 | 30.3 | 29.9 | 29.9 | 31.8 |
| *Bacillus methanolicus* MGA3 | 30.8 | 100 | 98.1 | 76.8 | 76.8 | 77.3 | 31.8 |
| *Bacillus methanolicus* PB1 | 30.8 | 98.1 | 100 | 76.3 | 76.3 | 76.8 | 37.9 |
| *Geobacillus* sp. GHH01 | 30.3 | 76.8 | 76.3 | 100 | 97.6 | 98.1 | 38.9 |
| *Geobacillus* sp M10EXG | 29.9 | 76.8 | 76.3 | 97.6 | 100 | 99.5 | 38.4 |
| *Geobacillus* sp. Y4.1MC1 | 29.9 | 77.3 | 76.8 | 98.1 | 99.5 | 100 | 38.4 |
| *Methylophilus methylotrophus* | 31.8 | 38.4 | 37.9 | 38.9 | 38.4 | 38.4 | 100 |
| *Methylophilus methylotrophus* ATCC 53528 | 32.1 | 34.4 | 34 | 38.3 | 37.8 | 37.8 | 81.9 |
| *Methylobacillus flagellatus* | 33.2 | 37.5 | 37 | 40.9 | 40.4 | 40.4 | 83.7 |
| *Methylomonas aminofaciens* | 32.7 | 36.5 | 36.1 | 39.9 | 39.4 | 39.4 | 84.7 |
| *Methylovorous glucosetrophus* SIP3-4 | 31.5 | 37.2 | 36.7 | 38.2 | 37.7 | 37.7 | 80.4 |
| *Aminomonas aminovorus* | 31.3 | 37 | 36.5 | 37.9 | 37.4 | 37.4 | 76.1 |
| *Methylobacillus flagellatus* | 31.3 | 37 | 36.5 | 37.9 | 37.4 | 37.4 | 76.5 |
| *Amycolatopsis methanolica* 239 | 33.8 | 40 | 38.6 | 37.6 | 38.1 | 38.1 | 46.2 |
| *Mycobacterium gastri* | 32.7 | 39.4 | 39.9 | 39.4 | 38.9 | 38.9 | 46.6 |

TABLE 2B

| HPS | Pairwise alignment (% ID) | | | | | | | |
|---|---|---|---|---|---|---|---|---|
| | Methylophilus methylotrophus ATCC 53528 | Methylobacillus flagellatus | Methylomonas aminofaciens | Methylovorous glucosetrophus SIP3-4 | Aminomonas aminovorus | Methylobacillus flagellatus | Amycolatopsis methanolica 239 | Mycobacterium gastri |
| Geobacillus thermodenitrificans NG80-2 | 32.1 | 33.2 | 32.7 | 31.5 | 31.3 | 31.3 | 33.8 | 32.7 |
| Bacillus methanolicus MGA3 | 34.4 | 37.5 | 36.5 | 37.2 | 37 | 37 | 40 | 39.4 |
| Bacillus methanolicus PB1 | 34 | 37 | 36.1 | 36.7 | 36.5 | 36.5 | 38.6 | 39.9 |
| Geobacillus sp. GHH01 | 38.3 | 40.9 | 39.9 | 38.2 | 37.9 | 37.9 | 37.6 | 39.4 |
| Geobacillus sp. M10EXG | 37.8 | 40.4 | 39.4 | 37.7 | 37.4 | 37.4 | 38.1 | 38.9 |
| Geobacillus sp. Y4.1MC1 | 37.8 | 40.4 | 39.4 | 37.7 | 37.4 | 37.4 | 38.1 | 38.9 |
| Methylophilus methylotrophus | 81.9 | 83.7 | 84.7 | 80.4 | 76.1 | 76.5 | 46.2 | 46.6 |
| Methylophilus methylotrophus ATCC 53528 | 100 | 87.1 | 87.6 | 82 | 83.3 | 83.8 | 47.1 | 47.1 |
| Methylobacillus flagellatus | 87.1 | 100 | 97.1 | 88.2 | 87.6 | 86.6 | 47.4 | 47.1 |
| Methylomonas aminofaciens | 87.6 | 97.1 | 100 | 89.2 | 86.1 | 86.1 | 46.9 | 45.7 |
| Methylovorous glucosetrophus SIP3-4 | 82 | 88.2 | 89.2 | 100 | 90.5 | 90.5 | 46.6 | 45.6 |
| Aminomonas aminovorus | 83.3 | 87.6 | 86.1 | 90.5 | 100 | 97.4 | 47.6 | 47.1 |
| Methylobacillus flagellatus | 83.8 | 86.6 | 86.1 | 90.5 | 97.4 | 100 | 47.6 | 46.2 |
| Amycolatopsis methanolica 239 | 47.1 | 47.4 | 46.9 | 46.6 | 47.6 | 47.6 | 100 | 60.1 |
| Mycobacterium gastri | 47.1 | 47.1 | 45.7 | 45.6 | 47.1 | 46.2 | 60.1 | 100 |

The disclosure also contemplates the use of variants of HPS enzymes in the engineered microorganisms of the disclosure, which include one or more amino acid substitutions, deletions, or additions. Variants can be generated either randomly, or by targeted substitution by using sequence alignments of HPS sequences, such as those described in Tables 2A and 2B. Regions that are conserved and/or important for enzymatic functioning of the HPS enzymes can be determined, with variants engineered based on this information. Therefore, the HPS enzymes can have one or more amino acid substitutions, deletions, or additions which cause the sequence to vary from a native sequence, such as SEQ ID NO: 2.

6-phospho-3-hexuloisomerases are of the enzyme class (EC) 5.3.1.27. 6-phospho-3-hexuloisomerases are of the enzyme class (EC) 5.3.1.27, 6-phospho-3-hexuloisomerase activity (PHI), can carry out the isomerization of d-arabino-3-hexulose-6-phosphate (Hu6P) to fructose 6-phosphate (F6P). One exemplary PHI sequence is based on Bacillus methanolicus MGA3 PHI (Genbank Accession number AAR39393.1, 184 amino acids long; SEQ ID NO: 3). The engineered microorganism can express a PHI sequence that is related to Bacillus methanolicus MGA3 PHI, such as a Bacillus methanolicus MGA PHI homolog. For example, the PHI sequence can be 30% or greater, 40% or greater, 50% or greater, 60% or greater, 70% or greater, 80% or greater, 85% or greater, 90% or greater, or 95% or greater identity to SEQ ID NO: 3. Homologs of SEQ ID NO: 3 can be identified by sequence identity searching (e.g., algorithms well known to those skilled in the art, such as Align, BLAST, Clustal W, as described herein).

Exemplary PHI sequences include those found in Table 3A and 3B below. For example, 6-phospho-3-hexuloisomerase sequences include, but are not limited to Bacillus methanolicus PB1 PHI (EIJ81376.1); Mycobacterium gastri PB1 PHI (BAA90545.1); Methylobacillus flagellatus KT PHI (YP 545762.1); Bacillus subtilis PHI (NP_388227.1); Methylophilus methylotrophus ATCC 53528 HPS (WP_018985297.1); Amycolatopsis methanolica 239 PHI (AIJ24609.1); Geobacillus sp. GHH01 PHI (YP_007402408.1); Geobacillus sp. Y4.1MC1 PHI (YP_003990383.1); Geobacillus thermodenitrificans NG80-2 PHI (WP_011887353.1); Methylomonas aminofaciens PHI (BAA83098.1); Methylovorus glucosetrophus SIP3-4 PHI (YP_003051269.1); and Methylovorus sp. MP688 PHI (ADQ84715.1).

TABLE 3A

Pairwise alignment (% ID)

| PHI | Methylobacillus flagellatus KT | Methylomonas aminofaciens | Methylophilus methylotrophus ATCC 53528 | Methylovorous glucosetrophus SIP3-4 | Geobacillus thermodenitrificans NG80-2 |
|---|---|---|---|---|---|
| Methylobacillus flagellatus KT | 100 | 95.6 | 58.9 | 64.4 | 31.1 |
| Methylomonas aminofaciens | 95.6 | 100 | 59.4 | 65 | 30.6 |
| Methylophilus methylotrophus ATCC 53528 | 58.9 | 59.4 | 100 | 86.5 | 28 |
| Methylovorous glucosetrophus SIP3-4 | 64.4 | 65 | 86.5 | 100 | 29.7 |
| Geobacillus thermodenitrificans NG80-2 | 31.1 | 30.6 | 28 | 29.7 | 100 |
| Bacillus methanolicus MGA3 | 32.4 | 33 | 32 | 33.1 | 37.2 |
| Bacillus methanolicus PB1 | 32.4 | 33 | 32 | 33.1 | 37.2 |
| Geobacillus sp. GHH01 | 35 | 34.4 | 32.4 | 32.4 | 41.5 |
| Geobacillus sp. Y4.1MC1 | 33.9 | 34.4 | 33 | 33.5 | 39.9 |
| Amycolatopsis methanolica 239 | 31.3 | 31.9 | 27.1 | 27.6 | 36.6 |
| Mycobacterium gastri | 33 | 33 | 31.5 | 33.1 | 37.7 |

TABLE 3B

Pairwise alignment (% ID)

| PHI | Bacillus methanolicus MGA3 | Bacillus methanolicus PB1 | Geobacillus sp. GHH01 | Geobacillus sp. Y4.1MC1 | Amycolatopsis methanolica 239 | Mycobacterium gastri |
|---|---|---|---|---|---|---|
| Methylobacillus flagellatus KT | 32.4 | 32.4 | 35 | 33.9 | 31.3 | 33 |
| Methylomonas aminofaciens | 33 | 33 | 34.4 | 34.4 | 31.9 | 33 |
| Methylophilus methylotrophus ATCC 53528 | 32 | 32 | 32.4 | 33 | 27.1 | 31.5 |
| Methylovorous glucosetrophus SIP3-4 | 33.1 | 33.1 | 32.4 | 33.5 | 27.6 | 33.1 |
| Geobacillus thermodenitrificans NG80-2 | 37.2 | 37.2 | 41.5 | 39.9 | 36.6 | 37.7 |
| Bacillus methanolicus MGA3 | 100 | 98.9 | 75.1 | 76.8 | 32.6 | 37.5 |
| Bacillus methanolicus PB1 | 98.9 | 100 | 74.6 | 76.2 | 32.6 | 38.6 |
| Geobacillus sp. GHH01 | 75.1 | 74.6 | 100 | 93 | 33 | 36.2 |
| Geobacillus sp. Y4.1MC1 | 76.8 | 76.2 | 93 | 100 | 32.6 | 38 |
| Amycolatopsis methanolica 239 | 32.6 | 32.6 | 33 | 32.6 | 100 | 47.7 |
| Mycobacterium gastri | 37.5 | 38.6 | 36.2 | 38 | 47.7 | 100 |

The disclosure also contemplates the use of variants of PHI enzymes in the engineered microorganisms of the disclosure, which include one or more amino acid substitutions, deletions, or additions. Variants can be generated either randomly, or by targeted substitution by using sequence alignments of PHI sequences, such as those described in Tables 3A and 3B. Regions that are conserved and/or important for enzymatic functioning of the PHI enzymes can be determined, with variants engineered based on this information. Therefore, the PHI enzymes can have one or more amino acid substitutions, deletions, or additions which cause the sequence to vary from a native sequence, such as SEQ ID NO: 3.

Engineered cells of the disclosure can also express HPS-PHI fusion protein, or variants thereof. The engineered fusion protein can include a polypeptide sequence based on natural HPS-PHI fusions, such as, a fusion from *Methylococcus capsulatas* (YP_115138.1); *Methylomicrobium album* BG8 (EIC30826.1); *Pyrococcus abyssi* (NP_127388.1); *Pyrococcus furiosus* (NP 577949.1); *Pyrococcus horikoshii* OT3 (NP_143767.1), or *Thermococcus*

*kodakaraensis* (YP_182888.1). Exemplary fusion proteins including HPS-PHI sequences are described in WO2017/075208 (Barton et al.) the disclosure of which is incorporated herein by reference.

The engineered microorganism can include an exogenous enzyme ("enzyme B") that is a phosphoketolase, such as fructose-6-phosphate phosphoketolase or xylulose-5-phosphate phosphoketolase.

Conversion of fructose-6-phosphate and phosphate to acetyl-phosphate and erythrose-4-phosphate (E4P) can be carried out by fructose-6-phosphate phosphoketolase (EC 4.1.2.22) Conversion of fructose-6-phosphate and phosphate to acetyl-phosphate and erythrose-4-phosphate is one of the key reactions in the *Bifidobacterium* shunt. There is evidence for the existence of two distinct phosphoketolase enzymes in bifidobacteria (Sgorbati et al, 1976, Antonie Van Leeuwenhoek, 42(1-2) 49-57; Grill et al, 1995, Curr Microbiol, 31(1); 49-54). The enzyme from *Bifidobacterium dentium* appeared to be specific solely for fructose-6-phosphate (EC: 4.1.2.22) while the enzyme from *Bifidobacterium pseudolongum* subsp. *globosum* is able to utilize both fructose-6-phosphate and D-xylulose 5-phosphate (EC: 4.1.2.9) (Sgorbati et al, 1976, Antonie Van Leeuwenhoek, 42(1-2) 49-57). The enzyme encoded by the xfp gene, originally discovered in *Bifidobacterium animalis lactis*, is the dual-specificity enzyme (Meile et al., 2001, J Bacteriol, 183, 2929-2936; Yin et al, 2005, FEMS Microbiol Lett, 246(2); 251-257). Additional phosphoketolase enzymes can be found in *Leuconostoc mesenteroides* (Lee et al, Biotechnol Lett. 2005 June; 27(12):853-8), *Clostridium acetobutylicum* ATCC 824 (Servinsky et al, Journal of Industrial Microbiology & Biotechnology, 2012, 39, 1859-1867), *Aspergillus nidulans* (Kocharin et al, 2013, Biotechnol Bioeng, 110(8), 2216-2224; Papini, 2012, Appl Microbiol Biotechnol, 95 (4), 1001-1010), *Bifidobacterium breve* (Suziki et al, 2010, Acta Crystallogr Sect F Struct Biol Cryst Commun., 66(Pt 8):941-3), *Lactobacillus paraplantarum* (Jeong et al, 2007, J Microbiol Biotechnol, 17(5), 822-9).

Conversion of xylulose-5-phosphate and phosphate to acetyl-phosphate and glyceraldehyde-3-phosphate can be carried out by xylulose-5-phosphate phosphoketolase (EC 4.1.2.9). There is evidence for the existence of two distinct phosphoketolase enzymes in bifidobacteria (Sgorbati et al, 1976, Antonie Van Leeuwenhoek, 42(1-2) 49-57; Grill et al, 1995, Curr Microbiol, 31(1); 49-54). The enzyme from *Bifidobacterium dentium* appeared to be specific solely for fructose-6-phosphate (EC: 4.1.2.22) while the enzyme from *Bifidobacterium pseudolongum* subsp. *globosum* is able to utilize both fructose-6-phosphate and D-xylulose 5-phosphate (EC: 4.1.2.9) (Sgorbati et al, 1976, Antonie Van Leeuwenhoek, 42(1-2) 49-57). Many characterized enzymes have dual-specificity for xylulose-5-phosphate and fructose-6-phosphate. The enzyme encoded by the xfp gene, originally discovered in *Bifidobacterium animalis lactis*, is the dual-specificity enzyme (Meile et al., 2001, J Bacteriol, 183, 2929-2936; Yin et al, 2005, FEMS Microbiol Lett, 246(2); 251-257). Additional phosphoketolase enzymes can be found in *Leuconostoc mesenteroides* (Lee et al, Biotechnol Lett. 2005 June; 27(12):853-8), *Clostridium acetobutylicum* ATCC 824 (Servinsky et al, Journal of Industrial Microbiology & Biotechnology, 2012, 39, 1859-1867), *Aspergillus nidulans* (Kocharin et al, 2013, Biotechnol Bioeng, 110(8), 2216-2224; Papini, 2012, Appl Microbiol Biotechnol, 95 (4), 1001-1010), *Bifidobacterium breve* (Suziki et al, 2010, Acta Crystallogr Sect F Struct Biol Cryst Commun., 66(Pt 8):941-3), and *Lactobacillus paraplantarum* (Jeong et al, 2007, J Microbiol Biotechnol, 17(5), 822-9).

Exemplary phosphoketolase enzymes include those found in Table 4 below.

TABLE 4

| Protein | GENBANK ID | GI NUMBER | ORGANISM |
| --- | --- | --- | --- |
| Xfp | YP_006280131.1 (WP_014697802.1) SEQ ID NO: 27 | 386867137 | *Bifidobacterium animalis lactis* |
| Xfp | AAV66077.1 SEQ ID NO: 28 | 55818565 | *Leuconostoc mesenteroides* |
| CAC1343 | NP 347971.1 (WP_010964652.1) SEQ ID NO: 29 | 15894622 | *Clostridium acetobutylicum* ATCC 824 |
| XpkA | CBF76492.1 SEQ ID NO: 30 | 259482219 | *Aspergillus nidulans* |
| Xfp | AAR98788.1 SEQ ID NO: 31 | 41056827 | *Bifidobacterium pseudolongum* subsp. *globosum* |
| Xfp | WP_022857642.1 SEQ ID NO: 32 | 551237197 | *Bifidobacterium pseudolongum* subsp. *globosum* |
| Xfp | ADF97524.1 SEQ ID NO: 33 | 295314695 | *Bifidobacterium breve* |
| Xfp | AAQ64626.1 SEQ ID NO: 34 | 34333987 | *Lactobacillus paraplantarum* |

In some embodiments, the engineered organism includes a fructose-6-phosphate phosphoketolase and optionally a phosphotransacetylase. In some embodiments, the engineered organism includes a fructose-6-phosphate phosphoketolase and optionally an acetyl-CoA tranferase, an acetyl-CoA synthetase, or an acetyl-CoA ligase.

The formation of acetyl-CoA from acetyl-phosphate can be catalyzed by phosphotransacetylase (EC 2.3.1.8). The pta gene from *E. coli* encodes an enzyme that reversibly converts acetyl-CoA into acetyl-phosphate (Suzuki, T., Biochim. Biophys. Acta 191:559-569 (969)). Additional acetyltranferase enzymes have been characterized in *Bacillus subtilis* (Rado and Hoch, Biochim. Biophys. Acta 321: 114-125 (1973), *Clostridium kluyveri* (Stadtman, E., Methods Enzymol. 1:5896-599 (1955), and *Thermotoga maritima* (Bock et al., J. Bacteriol. 181:1861-1867 (1999)). This reaction can also be catalyzed by some phosphotransbutyrylase enzymes (EC 2.3.1.19), including the ptb gene products from *Clostridium acetobutylicum* (Wiesenbom et al., App. Environ. Microbiol. 55:317-322 (1989); Walter et al., Gene 134:107-111(1993)). Additional ptb genes are found in butyrate-producing bacterium L2-50 (Louis et al., J. Bacteriol. 186:2099-2106 (2004) and *Bacillus megaterium* (Vazquez et al., Curr. Microbiol. 42:345-349 (2001). Homologs to the *E. coli* pta gene exist in several other organisms including *Salmonella enterica* and *Chlamydomonas reinhardtii*.

Exemplary phosphotransacetylase enzymes include those found in Table below.

TABLE 5

| Protein | GenBank ID | GI Number | Organism |
| --- | --- | --- | --- |
| Pta | NP_416800.1 | 71152910 | *Escherichia coli* |
| Pta | P39646 | 730415 | *Bacillus subtilis* |

TABLE 5-continued

| Protein | GenBank ID | GI Number | Organism |
|---|---|---|---|
| Pta | A5N801 | 146346896 | *Clostridium kluyveri* |
| Pta | Q9X0L4 | 6685776 | *Thermotoga maritime* |
| Ptb | NP_349676 | 34540484 | *Clostridium acetobutylicum* |
| Ptb | AAR19757.1 | 38425288 | butyrate-producing bacterium L2-50 |
| Ptb | CAC07932.1 | 10046659 | *Bacillus megaterium* |
| Pta | NP_461280.1 | 16765665 | *Salmonella enterica* subsp. *enterica* serovar Typhimurium str. LT2 |
| PAT2 | XP_001694504.1 | 159472743 | *Chlamydomonas reinhardtii* |
| PAT1 | XP_001691787.1 | 159467202 | *Chlamydomonas reinhardtii* |

The acylation of acetate to acetyl-CoA can be catalyzed by enzymes with acetyl-CoA synthetase, ligase or transferase activity. Two enzymes that can catalyze this reaction are ligase from *Pseudomonas putida* (Fernandez-Valverde et al., Appl. Environ. Microbiol. 59:1149-1154 (1993)). The aforementioned proteins are shown in Table 6 below.

TABLE 6

| Protein | GenBank ID | GI Number | Organism |
|---|---|---|---|
| Acs | AAC77039.1 | 1790505 | *Escherichia coli* |
| AcoE | AAA21945.1 | 141890 | *Ralstonia eutropha* |
| Acs1 | ABC87079.1 | 86169671 | *Methanothermobacter thermautotrophicus* |
| Acs1 | AAL23099.1 | 16422835 | *Salmonella enterica* |
| ACS1 | Q01574.2 | 257050994 | *Saccharomyces cerevisiae* |
| AF1211 | NP_070039.1 | 11498810 | *Archaeoglobus fulgidus* |
| AF1983 | NP_070807.1 | 11499565 | *Archaeoglobus fulgidus* |
| Scs | YP_135572.1 | 55377722 | *Haloarcula marismortui* |
| PAE3250 | NP_560604.1 | 18313937 | *Pyrobaculum aerophilum* str. IM2 |
| SucC | NP_415256.1 | 16128703 | *Escherichia coli* |
| SucD | AAC73823.1 | 1786949 | *Escherichia coli* |
| PaaF | AAC24333.2 | 22711873 | *Pseudomonas putida* |

AMP-forming acetyl-CoA synthetase or ligase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., J. Gen. Microbiol. 102:327-336 (1977)), *Ralstonia eutropha* (Priefert and Steinbuchel, J. Bacteriol. 174:6590-6599 (1992)), *Methanothermobacter thermautotrophicus* (Ingram-Smith and Smith, Archaea 2:95-107 (2007)), *Salmonella enterica* (Gulick et al., Biochemistry 42:2866-2873 (2003)) and *Saccharomyces cerevisiae* (Jogl and Tong, Biochemistry 43:1425-1431 (2004)). ADP-forming acetyl-CoA synthetases are reversible enzymes with a generally broad substrate range (Musfeldt and Schonheit, J. Bacteriol. 184: 636-644 (2002)). Two isozymes of ADP-forming acetyl-CoA synthetases are encoded in the *Archaeoglobus fulgidus* genome by are encoded by AF1211 and AF1983 (Musfeldt and Schonheit, supra (2002)). The enzyme from *Haloarcula marismortui* (annotated as a succinyl-CoA synthetase) also accepts acetate as a substrate and reversibility of the enzyme was demonstrated (Brasen and Schonheit, Arch. Microbiol. 182:277-287 (2004)). The ACD encoded by PAE3250 from hyperthermophilic crenarchaeon *Pyrobaculum aerophilum* showed the broadest substrate range of all characterized ACDs, reacting with acetate, isobutyryl-CoA (preferred substrate) and phenylacetyl-CoA (Brasen and Schonheit, supra (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra (2004); Musfeldt and Schonheit, supra (2002)). Additional candidates include the succinyl-CoA synthetase encoded by sucCD in *E. coli* (Buck et al., Biochemistry 24:6245-6252 (1985)) and the acyl-CoA In some embodiments, the engineered organism includes an exogenous alcohol dehydrogenase, such as an exogenous methanol dehydrogenase.

Alcohol dehydrogenases (ADHs; EC 1.1.1.1) promote the conversion of alcohols to and aldehydes or ketones, typically along with the reduction of nicotinamide adenine dinucleotide (NAD$^+$ to NADH). ADHs are instrumental in the generation of important compounds having aldehyde, ketone, and alcohol groups during biosynthesis of various metabolites.

One class of alcohol dehydrogenase is methanol dehydrogenases (MDHs). MDHs, converts methanol (MeOH) to formaldehyde (Fald), may be used in an enzymatic pathway engineered into microorganisms of the disclosure to enable MeOH as a sole carbon source or as a co-carbon source with other feed stocks. See FIG. 3. Engineered cells of the disclosure can include a natural or a non-natural NAD$^+$-dependent methanol dehydrogenases (MDHs), in particular enzymes of the class EC 1.1.1.244.

One exemplary MDH sequence is an NAD(P)+-dependent methanol dehydrogenase from *Bacillus methanolicus* MGA3 (Genbank Accession number EIJ77596.1, GI number: 387585261; designated herein as MDH 2315, 382 amino acids long; SEQ ID NO: 4). MDH 2315 is reported in the literature as an NAD(P)-dependent methanol dehydrogenase from *Bacillus methanolicus* MGA3 and its sequence was described in Brautaset et al., "Plasmid-Dependent Methylotrophy in Thermotolerant *Bacillus* methnolicus", Journal of Bacteriology, vol. 186, pp 1229-1238 (2004). It is also referred to as MDH MGA3 in WO2013/110797 to Brautaset and MDH "M" in Krog et al., "Methylotrophic *Bacillus methanolicus* Encodes Two Chromosomal and One Plasmid Born NAD+ Dependent Methanol Dehydrogenase Paralogs with Different Catalytic and Biochemical Properties", PLOS ONE, pp. 1-11, (2013), which report additional wild-type *Bacillus* MDHs.

The engineered microorganism can express a MDH sequence that is related to *Bacillus methanolicus* MGA3 MDH, such as a *Bacillus methanolicus* MGA MDH homolog. For example, the PHI sequence can be 20% or greater, 30 or greater, 40 or greater, 50 or greater, 60% or greater, 70% or greater, 80% or greater, or 90% or greater identity to SEQ ID NO: 4. Homologs of SEQ ID NO: 4 can be identified by sequence identity searching (e.g., algorithms well known to those skilled in the art, such as Align, BLAST, Clustal W, as described herein).

Exemplary MDH enzymes include those found in Table 7 below.

identity of SEQ ID NO:4 can be generated by sequence alignment of SEQ ID NO:4 with other known methanol dehydrogenases or alcohol dehydrogenases to identify regions that are conserved and/or important for enzymatic functioning of the protein. Once these regions are identified, the methanol dehydrogenase can be modified at one or more amino acid locations outside of these conserved regions. Therefore, the methanol dehydrogenase can have one or more amino acid substitutions, deletions, or additions which cause the sequence to vary from a native methanol dehydrogenase while retaining certain sequence features. Table 8 is a table of pairwise sequence identity of various methanol

TABLE 7

| GenBankID | GI No. | Organism | AA length | % Identity (global) |
|---|---|---|---|---|
| EIJ77596.1 | 387585261 | *Bacillus methanolicus* MGA3 | 382 | 100 |
| AAA22593.1 | 143175 | *Bacillus methanolicus* C1 | 381 | 97 |
| EIJ77618.1 | 387585284 | *Bacillus methanolicus* PB1 | 383 | 93 |
| EIJ78790.1 | 387586466 | *Bacillus methanolicus* PB1 | 383 | 90 |
| EIJ80770.1 | 387588449 | *Bacillus methanolicus* MGA3 | 385 | 62 |
| EIJ78397.1 | 387586073 | *Bacillus methanolicus* PB1 | 385 | 61 |
| EIJ83020.1 | 387590701 | *Bacillus methanolicus* MGA3 | 385 | 61 |
| EFI69743.1 | 298729190 | *Lysinibacillus fusiformis* | 401 | 56 |
| YP_004860127.1 | 347752562 | *Bacillus coagulans* 36D1 | 386 | 56 |
| YP_001699778.1 | 169829620 | *Lysinibacillus sphaericus* | 402 | 54 |
| ZP_11313277.1 | 410459529 | *Bacillus azotoformans* LMG 9581 | 386 | 54 |
| ZP_05587334.1 | 257139072 | *Burkholderia thailandensis* E264 | 390 | 54 |
| YP_004681552.1 | 339322658 | *Cupriavidus necator* N-1 | 390 | 53 |
| AGF87161 | 451936849 | uncultured organism | 393 | 53 |
| YP_002138168.1 | 197117741 | *Geobacter bemidjiensis* Bem | 387 | 52 |
| YP_359772.1 | 78043360 | *Carboxydothermus hydrogenoformans* Z-2901 | 383 | 52 |
| YP_001343716.1 | 152978087 | *Actinobacillus succinogenes* 130Z | 385 | 51 |
| ZP_16224338.1 | 421788018 | *Acinetobacter baumannii* Naval-82 | 390 | 51 |
| AAC45651.1 | 2393887 | *Clostridium pasteurianum* DSM 525 | 385 | 51 |
| YP_007491369.1 | 452211255 | *Alethanosarcina mazei* Tuc01 | 386 | 51 |
| YP_002434746 | 218885425 | *Desulfovibrio vulgaris* str. 'Miyazaki F' | 393 | 50 |
| YP_005052855 | 374301216 | *Desulfovibrio africanus* str. Walvis Bay | 393 | 49 |
| NP_561852.1 | 18309918 | *Clostridium perfringens* str. 13 | 385 | 49 |
| YP_001447544 | 156976638 | *Vibrio campbellii* ATCC BAA-1116 | 382 | 49 |
| YP_001113612.1 | 134300116 | *Desulfotomaculum reducens* MI-1 | 388 | 49 |
| YP_011618 | 46580810 | *Desulfovibrio vulgaris* str. Hildenborough | 393 | 49 |
| ZP_01220157.1 | 90412151 | *Photobacterium profundum* 3TCK | 382 | 48 |
| YP_003990729.1 | 312112413 | *Geobacillus* sp. Y4.1MC1 | 384 | 48 |
| ZP_07335453.1 | 303249216 | *Desulfovibrio fructosovorans* JJ | 393 | 48 |
| NP_717107 | 24373064 | *Shewanella oneidensis* MR-1 | 382 | 48 |
| YP_003310546.1 | 269122369 | *Sebaldella termitidis* ATCC 33386 | 384 | 48 |
| ZP_10241531.1 | 390456003 | *Paenibacillus peoriae* KCTC 3763 | 384 | 47 |
| YP_001337153.1 | 152972007 | *Klebsiella pneumoniae* subsp. *pneumoniae* MGH 78578 | 387 | 47 |
| YP_026233.1 | 49176377 | *Escherichia coli* | 383 | 46 |
| YP_694908 | 110799824 | *Clostridium perfringens* ATCC 13124 | 382 | 46 |
| YP_725376.1 | 113866887 | *Ralstonia eutropha* H16 | 366 | 46 |
| YP_001663549 | 167040564 | *Thermoanaerobacter* sp. X514 | 389 | 45 |
| EKC54576 | 406526935 | human gut metagenome | 384 | 37 |
| YP_001126968.1 | 138896515 | *Geobacillus themodenitrificans* NG80-2 | 387 | 27 |

Engineered cells of the disclosure can also express MDH variants. In some cases, variants having less than 100 dehydrogenases including *Bacillus methanolicus* MGA3 MeDH (SEQ ID NO: 4).

TABLE 8

| | Pairwise alignment (% ID) | | | | |
|---|---|---|---|---|---|
| MeDH | *Bacillus methanolicus* MGA3 | *Bacillus methanolicus* MGA3 | *Bacillus methanolicus* PB1 | *Lysinibacillus fusiformis* | *Clostridium perfringens* str. 13 |
| *Bacillus methanolicus* MGA3 | 100 | 62 | 60.7 | 58.4 | 48.7 |
| *Bacillus methanolicus* MGA3 | 62 | 100 | 92.7 | 72.2 | 53.2 |

TABLE 8-continued

| | Pairwise alignment (% ID) | | | | |
|---|---|---|---|---|---|
| MeDH | Bacillus methanolicus MGA3 | Bacillus methanolicus MGA3 | Bacillus methanolicus PB1 | Lysinibacillus fusiformis | Clostridium perfringens str. 13 |
| Bacillus methanolicus PB1 | 60.7 | 92.7 | 100 | 72.2 | 53.5 |
| Lysinibacillus fusiformis | 58.4 | 72.2 | 72.2 | 100 | 51.2 |
| Clostridium perfringens str. 13 | 48.7 | 53.2 | 53.5 | 51.2 | 100 |

Such variants may provide increased catalytic activity, such as increased conversion of methanol to formaldehyde. Exemplary variants of Bacillus methanolicus MGA3 MeDH (SEQ ID NO: 1) are described in International Patent Application No. PCT/US2014/059135, the disclosure of which is incorporated herein. Exemplary amino acid substitutions of SEQ ID NO: 4 include, but are not limited to, those as follows: S11T, D38N, H42Q, E48D, N53I, E56K, D60E, V61A, I63F, P65Q, D70N, P71I, P71T, P71V, T74S, D81G, K84R, E86K, N87K, I94V, S99P, S99T, A103V, I106L, G107S, L108V, L108W, V109Y, N112K, N112R, R115H, I116F, N117D, N117Q, N117Y, Q120H, Q120R, G121A, G121D, G121E, G121L, G121M, G121R, G121S, G121T, G121V, G121W, G121Y, V122A, V122P, N123D, N123I, N123L, N123R, N123Y, S124I, S124L, S124R, V125C, V125G, V125W, E126G, E126V, K127C, K127R, P128A, P128R, P128S, V129A, V129M, V129P, V129S, V130F, V130I, V130Y, A134T, S143T, T145M, T146N, S147R, L148A, L148F, L148G, L148I, L148T, L148V, L148W, A149L, A149M, A149T, A149V, V150A, V150I, T152M, A155V, K157N, V158E, V158H, V158K, V158W, P161A, P161G, P161Q, P161S, P161V, I163F, I163N, I163Q, I163T, D164G, D164N, E165G, K181R, A184T, L186M, T190A, T190S, I199V, Q217K, L226M, G256C, Q267H, G269S, G270M, G270S, G270Y, T296S, R298H, A300T, I302V, G312V, A316V, I323M, F333L, P336L, S337C, G343D, V344A, V344G, K345E, E350K, K354M, N355D, N355I, N355K, E358G, V360A, V360G, V360K, V360R, V360S, C361N, C361R, Q363K, and K379M.

Other exemplary amino acid substitutions of SEQ ID NO: 1 include: D38N, D60E, P71I, P71V, N87K, S99T, A103V, G107S, L108V, L108W, V109Y, R115H, I116F, N117D, N117Q, G121D, G121E, G121L, G121M, G121R, G121S, G121T, G121V, G121W, G121Y, V122P, N123D, N123I, N123L, N123R, N123Y, S124I, S124L, V125C, V125G, V125W, E126G, K127C, K127R, P128A, P128R, P128S, V129A, V129M, V129P, V129S, V130F, V130I, V130Y, A134T, S143T, T146N, A149L, A149M, A149T, A149V, V150A, K157N, V158E, V158H, V158K, V158W, I163Q, D164N, Q267H, G270M, G270S, G270Y, K345E, N355D, V360G, V360K, V360R, V360S, C361R.

Engineered cells of the disclosure can also express a MeDH activator protein. A MeDH activator protein can activate a MeDH enzyme by providing hydrolytic removal of a nicotinamide mononucleotide (NMN) moiety of the NAD cofactor. MeDH activator is active in the presence of magnesium ions and is also able to use ADP-ribose. (Kloosterman, H., et al. (2002) J Biol Chem. 277:34785-34792).

The engineered fusion protein can include a polypeptide sequence based on MeDH activator proteins, such as, activators of Bacillus methanolicus MGA3 (WP_004435441.1) and Bacillus methanolicus PB1 (WP_004437560.1).

Engineered cells of the disclosure can also express a fusion protein that includes methanol dehydrogenase activity and at least one other activity that promotes formaldehyde fixation. For example, the fusion can include activities which promote the conversion of methanol to formaldehyde and then from formaldehyde to a ketose phosphate such as hexulose 6-phosphate, or fructose-6-phosphate. Alternatively, for example, the fusion can include activities which promote the conversion of methanol to formaldehyde and then from formaldehyde to dihydroxyacetone (DHA) and glycerladehyde-3-phosphate (G3P), and then to fructose-6-phosphate. MeDH-containing fusion protein that includes one or more of the following sequences: a HPS sequence, a PHI sequence, and/or an MeDH activator sequence (ACT). Use of such fusions can promote methanol uptake, such as by increased efficiency of fixation of formaldehyde into ketose phosphate compounds as a result of the fusion.

Exemplary fusion proteins include those designated MeDH-ACT-PHI, MeDH-ACT-HPS, HPS-MeDH-ACT, ACT-MeDH-PHI-HPS, ACT-MeDH-HPS-PHI, HPS-PHI-MeDH-ACT, PHI-HPS-MeDH-ACT, and ACT-MeDH(P1)-HPS-MeDH(P2). Such fusion proteins are described in WO2017/075208 (Barton et al.) the disclosure of which is incorporated herein by reference.

Figure 4:
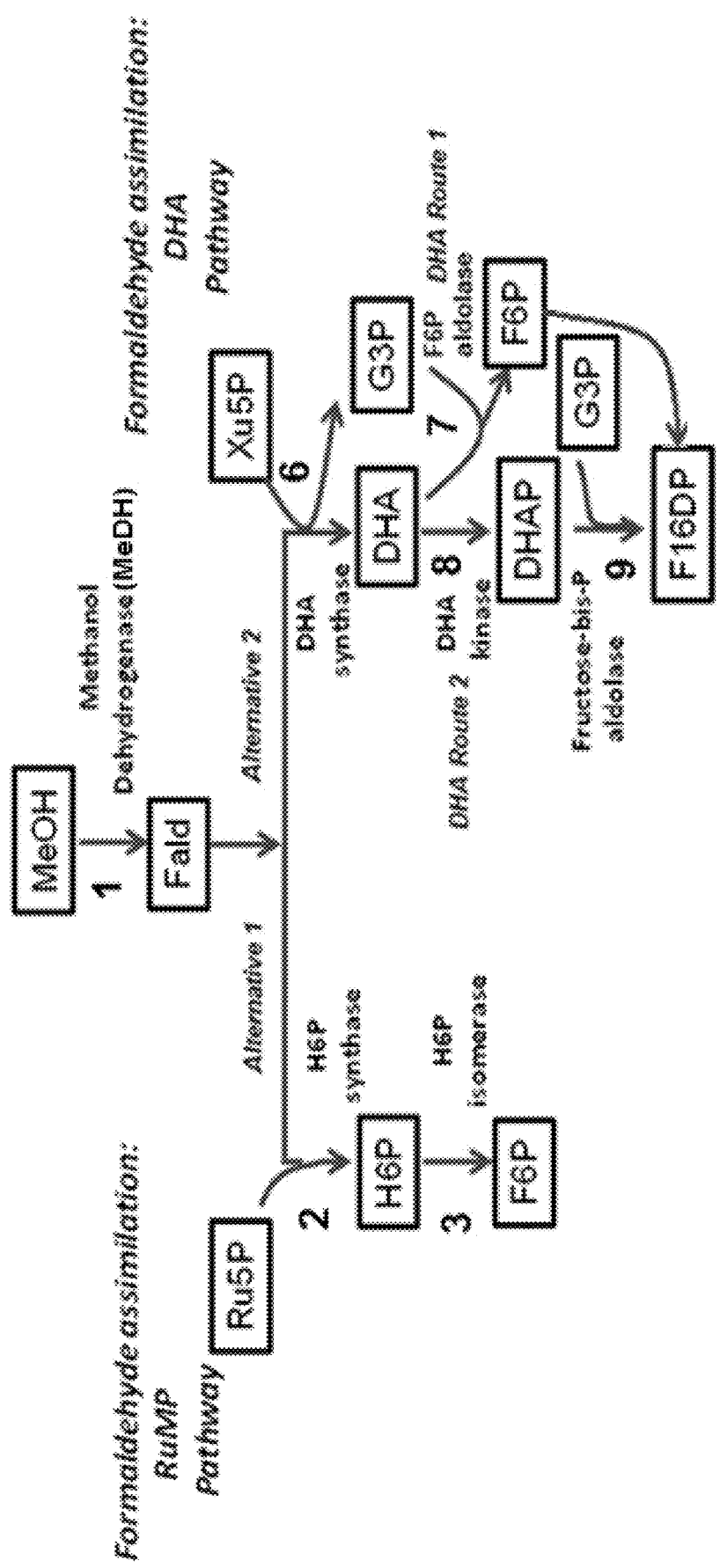
FIG. 4 illustrates alternative formaldehyde assimilation pathways (RuMP and DHA) and metabolic intermediates from each that can be used in a product pathway. Enzymes catalyzing the reactions are (1) methanol dehydrogenase, e.g. EC 1.1.1, (2) hexulose-6-phosphate synthase, e.g. EC 4.1.2.43, (3) 6-phospho-3-hexuloisomerase, e.g. EC 5.3.1.27, (6) DHA (dihydroxyacetone) synthase, e.g. EC 2.2.1.3, (7) F6P (fructose-6-phosphate) aldolase, e.g. EC 4.1.2, (8) DHA kinase, e.g. EC 2.7.1.121, (9) fructose-bisphosphate aldolase, e.g. EC 4.1.2.13. The fusions described herein can catalyze two or more of the reactions.

With reference to FIG. 4, another exemplary pathway that involves the detoxification and assimilation of formaldehyde produced from the oxidation of methanol proceeds through dihydroxyacetone. Dihydroxyacetone synthase is a transketolase that first transfers a glycoaldehyde group from xylulose-5-phosphate to formaldehyde, resulting in the formation of dihydroxyacetone (DHA) and glyceraldehyde-3-phosphate (G3P), which is an intermediate in glycolysis. The DHA obtained from DHA synthase can be then further phosphorylated to form DHA phosphate by a DHA kinase. DHAP can be assimilated into glycolysis, e.g. via isomerization to G3P, and several other pathways. Alternatively, DHA and G3P can be converted by fructose-6-phosphate aldolase to form fructose-6-phosphate (F6P)

The dihydroxyacetone synthase enzyme in Candida boidinii uses thiamine pyrophosphate and $Mg^{2+}$ as cofactors and is localized in the peroxisome. The enzyme from the methanol-growing carboxydobacterium, Mycobacter sp. strain JC1 DSM 3803, was also found to have DHA synthase and kinase activities (Ro et al., 1997, J Bac 179(19):6041-7). DHA synthase from this organism also has similar cofactor requirements as the enzyme from C. boidinii. The $K_m$s for formaldehyde and xylulose 5-phosphate were reported to be 1.86 mM and 33.3 microM, respectively. Several other mycobacteria, excluding only Mycobacterium tuberculosis, can use methanol as the sole source of carbon and energy and are reported to use dihydroxyacetone synthase (Part et al., 2003, J Bac 185(1):142-7.

TABLE 9

| Protein | GenBank ID | GI number | Organism |
| --- | --- | --- | --- |
| DAS1 | AAC83349.1 | 3978466 | *Candida boidinii* |
| HPODL_2613 | EFW95760.1 | 320581540 | *Ogataea parapolymorpha* DL-1 (*Hansenula polymorpha* DL-1) |
| | AAG12171.2 | 18497328 | *Mycobacter* sp. strain JC1 DSM 3803 |

Fructose-6-phosphate aldolase (F6P aldolase) can catalyze the combination of dihydroxyacetone (DHA) and glyceraldehyde-3-phosphate (G3P) to form fructose-6-phosphate. This activity was recently discovered in *E. coli* and the corresponding gene candidate has been termed fsa (Schurmann and Sprenger, *J Biol. Chem.*, 2001, 276(14), 11055-11061). The enzyme has narrow substrate specificity and cannot utilize fructose, fructose 1-phosphate, fructose 1,6-bisphosphate, or dihydroxyacetone phosphate. It can however use hydroxybutanone and acetol instead of DHA. The purified enzyme displayed a $V_{max}$ of 7 units/mg of protein for fructose 6-phosphate cleavage (at 30 degrees C., pH 8.5 in 50 mm glycylglycine buffer). For the aldolization reaction a $V_{max}$ of 45 units/mg of protein was found; $K_m$ values for the substrates were 9 mM for fructose 6-phosphate, 35 mM for dihydroxyacetone, and 0.8 mM for glyceraldehyde 3-phosphate. The enzyme prefers the aldol formation over the cleavage reaction.

The selectivity of the *E. coli* enzyme towards DHA can be improved by introducing point mutations. For example, the mutation A129S improved reactivity towards DHA by over 17 fold in terms of Kcat/Km (Gutierrez et al., Chem Commun (Camb), 2011, 47(20), 5762-5764). The same mutation reduced the catalytic efficiency on hydroxyacetone by more than 3 fold and reduced the affinity for glycoaldehyde by more than 3 fold compared to that of the wild type enzyme (Castillo et al., Advanced Synthesis & Catalysis, 352(6), 1039-1046). Genes similar to fsa have been found in other genomes by sequence homology. Some exemplary gene candidates have been listed in Table 10 below.

TABLE 10

| Gene | Protein accession no. | GI number | Organism |
| --- | --- | --- | --- |
| fsa | AAC73912.2 | 87081788 | *Escherichia coli* K12 |
| talC | AAC76928.1 | 1790382 | *Escherichia coli* K12 |
| fsa | WP_017209835.1 | 515777235 | *Clostridium beijerinckii* |
| DR_1337 | AAF10909.1 | 6459090 | *Deinococcus radiodurans* R1 |
| talC | NP_213080.1 | 15605703 | *Aquifex aeolicus* VF5 |
| MJ_0960 | NP_247955.1 | 15669150 | *Methanocaldococcus janaschii* |
| mipB | NP_993370.2 | 161511381 | *Yersinia pestis* |

As described below, there is an energetic advantage to using F6P aldolase in the DHA pathway. The assimilation of formaldehyde formed by the oxidation of methanol can proceed either via the dihydroxyacetone (DHA) pathway or the Ribulose monophosphate (RuMP) pathway. In the RuMP pathway, formaldehyde combines with ribulose-5-phosphate to form F6P. F6P is then either metabolized via glycolysis or used for regeneration of ribulose-5-phosphate to enable further formaldehyde assimilation. Notably, ATP hydrolysis is not required to form F6P from formaldehyde and ribulose-5-phosphate via the RuMP pathway.

In contrast, in the DHA pathway, formaldehyde combines with xylulose-5-phosphate (X5P) to form dihydroxyacetone (DHA) and glyceraldehyde-3-phosphate (G3P). Some of the DHA and G3P must be metabolized to F6P to enable regeneration of xylulose-5-phosphate. In the standard DHA pathway, DHA and G3P are converted to F6P by three enzymes: DHA kinase, fructose bisphosphate aldolase, and fructose bisphosphatase. The net conversion of DHA and G3P to F6P requires ATP hydrolysis as described below. First, DHA is phosphorylated to form DHA phosphate (DHAP) by DHA kinase at the expense of an ATP. DHAP and G3P are then combined by fructose bisphosphate aldolase to form fructose-1,6-diphosphate (FDP). FDP is converted to F6P by fructose bisphosphatase, thus wasting a high energy phosphate bond.

A more ATP efficient sequence of reactions is enabled if DHA synthase functions in combination with F6P aldolase as opposed to in combination with DHA kinase, fructose bisphosphate aldolase, and fructose bisphosphatase. F6P aldolase enables direct conversion of DHA and G3P to F6P, bypassing the need for ATP hydrolysis. Overall, DHA synthase when combined with F6P aldolase is identical in energy demand to the RuMP pathway. Both of these formaldehyde assimilation options (i.e., RuMP pathway, DHA synthase+F6P aldolase) are superior to DHA synthase combined with DHA kinase, fructose bisphosphate aldolase, and fructose bisphosphatase (exogenous glpX) in terms of ATP demand.

Transaldolase (EC 2.2.1.2) plays a role in the balance of metabolites in the pentose-phosphate pathway. There are two closely related transaldolase genes in *E. coli*, encoded by talA and talB. In *E. coli*, TalB (Transaldolase B; Uniprot P0A867) catalyzes the interconversion of sedoheptulose 7-phosphate and D-glyceraldehyde 3-phosphate to D-erythrose 4-phosphate+D-fructose 6-phosphate. Homologues of these genes can be found in other microbes including *C. glutamicum, S. cerevisiae, Pseudomonas putida, Bacillus subtilis*.

In embodiments of the disclosure, a component of autocatalytic RUMP cycle for synthetic methylotrophy includes regeneration of C5 from C7 in the form of sedoheptulose-7-phosphate (S7P) and C3 glyceraldehyde-3-phosphate (G3P). There can be variants of the RuMP cycle based on how the C7 compound S7P is generated. One is a transaldolase variant of the RuMP cycle where the transaldoalse genes talA, talB, and/or talC is used to generate S7P. Another variant is the sedoheptulose bisphosphatase (SBPase) variant where a fructose bisphosphate aldolase (fba) is used to condense DHAP and E4P into sedoheptulose-1,7-bisphosphate (SBP) which is then dephosphorylated to S7P using the SBPase enzyme encoded by the gene glpX See FIGS. 5 and 6. While the transaldolase variant of the RuMP cycle provides an energetic advantage over the SBPase variant of the RuMP cycle, the SBPase variant provides a substantial thermodynamic advantage with the glpX reaction being highly thermodynamically favourable. Exemplary candidates for the SBPase variant of the RuMP cycle include the fba (EIJ77593.1, EIJ77616.1) and glpX genes (ZP_11548894, WP_003352248.1) from *Bacillus methanolicus*.

Due to this thermodynamic advantage, and in preferred aspects of the disclosure, an engineered microorganism includes the SBPase variant of the RuMP cycle wherein exogenous fba and glpX genes are overexpressed and the native transalodolase genes (talA, talB, talC) are attenuated or eliminated. See FIGS. 5 and 6. This can also be combined with the introduction and activity of the exogenous gapN expressed in the cells, and optionally the deletion or attenuation of GapA activity. In such engineered cells, the introduction of gapN can improve pool sizes of the RuMP cycle metabolites and the SBPase variant of the RuMP cycle in the form of exogenous fba and glpX with the deletion or attenuation of ta/A, talB, talC provides the thermodynamic driving force to achieve an autocatalytic RuMP cycle.

In embodiments, the engineered microorganism can include a modification that attenuates or eliminates an endogenous activity of a fructose-bisphosphate aldolase combined with the overexpression of exogenous fructose-bisphosphate aldolase (fba2).

The enzyme fructose-bisphosphate aldolase catalyzes the conversion of fructose 1,6-bisphosphate to two C3 phosphate compounds which are dihydroxyacetone phosphate (DHAP or glycerone-phosphate) and glyceraldehyde 3-phosphate (G3P). In *E. coli*, this activity is catalyzed by either one of the two genes fbaA or fbaB. The *E. coli* fbaA and fbaB are known to be inhibited by high levels of its C3 products G3P and DHAP. However, according to the disclosure, high pool sizes of G3P and DHAP are desirably maintained for synthetic methylotrophy. In order to achieve this balance, embodiments of engineered microorganisms can include modifications to delete or attenuate native fructose-bisphosphate aldolase activity and introduction of an exogenous fructose-bisphosphate aldolase, such as one from *Bacillus*.

For example, the fructose-bisphosphate aldolase fba2 from *Bacillus methanolicus* PB1, or a homolog or variant thereof, can be introduced into the engineered microorganism. The engineered microorganism can express a fba sequence that is related to *Bacillus methanolicus* PB31 fba2, such as a *Bacillus methanolicus* PB31 fba2 homolog or variant. For example, the fba sequence can be 50% or greater, 60% or greater, 70% or greater, 80% or greater, 85% or greater, 90% or greater, or 95% or greater identity to *Bacillus methanolicus* PB1 fba2 (SEQ ID NO: 9). This can be combined with a microorganism with exogenous GapN and attenuated/deleted GapA activity.

Other exemplary fructose-bisphosphate aldolase genes that can be introduced into the engineered microorganism are listed in Table 11 below:

TABLE 11

| | | | |
|---|---|---|---|
| WP_003346852.1 | WP_066310121.1 | WP_042354391.1 | WP_098260191.1 |
| WP_003351726.1 | WP_095243208.1 | WP_019153989.1 | WP_045515920.1 |
| WP_101661177.1 | WP_079506262.1 | WP_101178886.1 | WP_076759363.1 |
| WP_038537846.1 | WP_066205853.1 | WP_098571546.1 | WP_063254575.1 |
| WP_057772794.1 | WP_053433445.1 | WP_070877989.1 | WP_044392746.1 |
| WP_053368407.1 | WP_101548883.1 | WP_066073012.1 | WP_088090227.1 |
| WP_026585103.1 | WP_102264606.1 | WP_090634787.1 | WP_016202508.1 |
| WP_102273593.1 | WP_063389040.1 | WP_029283302.1 | WP_098932372.1 |
| WP_101665800.1 | WP_053403739.1 | WP_066056862.1 | WP_098795425.1 |
| WP_066367433.1 | WP_066389558.1 | WP_071393265.1 | WP_046130283.1 |
| WP_101579374.1 | WP_009792955.1 | WP_069938500.1 | WP_075983208.1 |
| WP_077215087.1 | WP_066234213.1 | WP_047940761.1 | WP_078432014.1 |
| WP_053478524.1 | WP_053597680.1 | WP_107920563.1 | WP_071461009.1 |
| WP_027323492.1 | WP_009332285.1 | WP_098527749.1 | WP_031538951.1 |
| WP_066398310.1 | WP_101581996.1 | WP_066235121.1 | WP_026563084.1 |
| WP_075686757.1 | WP_090832678.1 | WP_059352025.1 | WP_006639440.1 |
| WP_024031049.1 | WP_046588513.1 | WP_046179059.1 | WP_006837435.1 |
| WP_080843816.1 | WP_043930083.1 | WP_102230461.1 | WP_050183379.1 |
| WP_057760136.1 | WP_015596100.1 | WP_066267408.1 | WP_046174604.1 |
| WP_066296675.1 | SHP69806.1 | WP_044894355.1 | |

TABLE 11-continued

| | | |
|---|---|---|
| WP_095312127.1 | WP_058005248.1 | WP_101567317.1 |
| WP_048827259.1 | WP_095371563.1 | WP_101356082.1 |
| WP_059171825.1 | WP_072578145.1 | WP_066248707.1 |
| WP_066093948.1 | WP_090762628.1 | WP_059283615.1 |
| WP_048009440.1 | WP_066189121.1 | WP_041964633.1 |
| WP_019380596.1 | WP_007087445.1 | WP_023613550.1 |
| WP_066442299.1 | WP_095301761.1 | WP_101648384.1 |

In embodiments, the engineered microorganism includes modifications that attenuates or eliminates an endogenous activity of a fructose-bisphosphate aldolase, and that introduces an exogenous fructose-bisphosphate aldolase.

In embodiments, the engineered microorganism can include a modification that introduces an exogenous activity of a triose-phosphate isomerase (tpi, such as tpiA). Exemplary triose-phosphate isomerase genes that can be introduced into the engineered microorganism are listed in Table 22 below:

TABLE 22

Exemplary tpiA homologs—Accession Number

| | | | |
|---|---|---|---|
| WP_049625147.1 | WP_048622612.1 | WP_119544996.1 | WP_061465550.1 |
| WP_057984053.1 | WP_066442636.1 | WP_098797852.1 | WP_048688041.1 |
| NP_418354.1 | WP_066258742.1 | WP_099352518.1 | WP_066290710.1 |
| WP_003352090.1 | WP_080844080.1 | WP_133312649.1 | WP_016203861.1 |
| WP_003349425.1 | WP_071460731.1 | WP_028403379.1 | WP_106027029.1 |
| WP_125927893.1 | WP_066065633.1 | WP_113969130.1 | WP_120034658.1 |
| WP_101658881.1 | WP_079532208.1 | WP_054403564.1 | WP_130156825.1 |
| WP_101664621.1 | WP_090857112.1 | WP_029284585.1 | WP_110928513.1 |
| WP_101575971.1 | WP_098530337.1 | WP_048015738.1 | WP_033021492.1 |
| WP_026582029.1 | WP_113926855.1 | WP_091704422.1 | WP_096339383.1 |
| WP_101580490.1 | WP_098930974.1 | WP_078414242.1 | WP_046131103.1 |
| WP_110064628.1 | WP_098352031.1 | WP_121663490.1 | PGZ97936.1 |
| PWW29569.1 | WP_058002855.1 | WP_010175280.1 | WP_081160821.1 |
| WP_090833149.1 | WP_040204128.1 | WP_131235750.1 | WP_088008494.1 |
| WP_125481486.1 | WP_071976496.1 | WP_019242991.1 | WP_104058107.1 |
| WP_113883700.1 | WP_126863303.1 | WP_124564487.1 | WP_003397292.1 |
| WP_044390541.1 | WP_108671576.1 | WP_089098086.1 | WP_114896973.1 |
| HAQ06002.1 | WP_075689781.1 | WP_081189305.1 | OUM91325.1 |
| WP_066230398.1 | WP_088089551.1 | WP_015865021.1 | WP_066141854.1 |
| WP_102264288.1 | WP_126405446.1 | WP_097159265.1 | WP_097961009.1 |
| WP_041967473.1 | WP_121617301.1 | WP_095480439.1 | WP_020155099.1 |
| WP_107920638.1 | WP_061809791.1 | WP_062677276.1 | WP_063233964.1 |
| WP_108069989.1 | WP_101635495.1 | WP_133376450.1 | WP_116516504.1 |
| WP_113883700.1 | WP_034764215.1 | WP_101568078.1 | WP_098864843.1 |
| WP_079506869.1 | WP_044893559.1 | WP_028396129.1 | WP_013085385.1 |
| WP_053433745.1 | WP_060672585.1 | WP_066419543.1 | WP_089361938.1 |
| WP_066366023.1 | WP_101643715.1 | WP_125907547.1 | WP_095371908.1 |
| WP_095310191.1 | WP_080860079.1 | WP_041113450.1 | WP_061141152.1 |
| WP_061791816.1 | WP_041087339.1 | WP_100332287.1 | WP_097899256.1 |
| WP_076258936.1 | WP_042353961.1 | WP_136378456.1 | WP_098060328.1 |
| WP_023613939.1 | WP_059172080.1 | WP_116353411.1 | WP_098308454.1 |
| WP_035329301.1 | WP_119709961.1 | WP_041094811.1 | WP_035430455.1 |
| WP_046524451.1 | WP_003353516.1 | WP_077619443.1 | WP_098779423.1 |
| WP_066387219.1 | WP_117306959.1 | WP_102232454.1 | WP_035066254.1 |
| WP_043930314.1 | WP_028393606.1 | WP_059283432.1 | WP_057957776.1 |
| WP_026575982.1 | WP_136832879.1 | WP_042350706.1 | WP_057215872.1 |
| WP_053597872.1 | WP_132092731.1 | GAE47365.1 | WP_026684780.1 |
| WP_009331815.1 | WP_119113030.1 | WP_063384768.1 | WP_063193279.1 |
| WP_127488577.1 | WP_100333252.1 | WP_066175408.1 | WP_013860187.1 |
| WP_053360533.1 | WP_095246679.1 | WP_085787813.1 | WP_098185504.1 |
| WP_050616384.1 | WP_048013384.1 | WP_110112470.1 | WP_113803922.1 |
| WP_009793077.1 | WP_044741433.1 | WP_026559622.1 | WP_116366259.1 |
| WP_114746353.1 | WP_101647122.1 | WP_134375855.1 | WP_001231047.1 |
| WP_118921487.1 | SHT19397.1 | WP_004892489.1 | WP_098684976.1 |
| WP_032086617.1 | WP_115451363.1 | WP_066329182.1 | WP_002174167.1 |
| WP_034674239.1 | WP_066322819.1 | WP_066249154.1 | WP_033843086.1 |
| WP_071354652.1 | WP_117322511.1 | WP_012096134.1 | WP_002144919.1 |
| WP_038537244.1 | TMU84398.1 | WP_121446321.1 | WP_001231042.1 |
| WP_095243508.1 | WP_060665410.1 | WP_053536810.1 | WP_098135924.1 |
| WP_048827021.1 | WP_048006747.1 | WP_021093689.1 | WP_070807150.1 |
| WP_019383298.1 | WP_066058820.1 | WP_025727119.1 | WP_049166282.1 |
| WP_121611084.1 | WP_101592182.1 | REJ24619.1 | WP_064467230.1 |
| WP_027409935.1 | WP_075982879.1 | WP_094245233.1 | EEL91210.1 |
| WP_133333986.1 | | | |

TABLE 22-continued

Exemplary tpiA homologs—Accession Number

| | | | |
|---|---|---|---|
| WP_132003505.1 | WP_072578458.1 | GAJ43858.1 | WP_098645443.1 |
| WP_027320678.1 | WP_123919364.1 | WP_099361576.1 | WP_098870165.1 |
| WP_126649451.1 | WP_010196828.1 | WP_076368239.1 | WP_001231046.1 |
| WP_066096909.1 | WP_098439087.1 | WP_078378974.1 | WP_128267196.1 |
| WP_090743218.1 | WP_066149736.1 | WP_003248110.1 | WP_018660881.1 |
| WP_055738838.1 | WP_047969990.1 | WP_041060902.1 | WP_060788254.1 |
| WP_019153676.1 | WP_045518085.1 | WP_128356640.1 | EEK76346.1 |
| WP_078543970.1 | WP_096156668.1 | WP_090948441.1 | WP_002112798.1 |
| WP_090632599.1 | WP_044338273.1 | WP_034309988.1 | WP_061187910.1 |
| WP_071619677.1 | WP_040375829.1 | KYD07778.1 | WP_001231036.1 |
| WP_044892996.1 | WP_095297184.1 | WP_062109228.1 | OUB37012.1 |
| WP_101352804.1 | WP_088019477.1 | SLL35741.1 | WP_003235214.1 |
| WP_066200502.1 | WP_066224972.1 | WP_064552345.1 | WP_120667089.1 |
| TCL47385.1 | WP_071393617.1 | WP_026694507.1 | WP_001231034.1 |
| WP_132949072.1 | WP_046514094.1 | WP_063386958.1 | WP_017153354.1 |
| WP_111645022.1 | WP_064093006.1 | WP_077429731.1 | WP_100062914.1 |
| WP_117327782.1 | WP_094833549.1 | WP_006322696.1 | WP_035190571.1 |
| WP_007083466.1 | WP_015595638.1 | WP_066269699.1 | WP_076541647.1 |
| WP_049683119.1 | WP_121679697.1 | WP_042410586.1 | WP_065224384.1 |
| WP_062185738.1 | WP_064098916.1 | WP_017435719.1 | WP_069150333.1 |
| WP_066314500.1 | WP_070878079.1 | WP_095258588.1 | WP_053348617.1 |
| WP_026567800.1 | WP_102273864.1 | WP_043906652.1 | WP_137016647.1 |
| WP_077215437.1 | WP_100401758.1 | WP_078431648.1 | WP_019394944.1 |
| WP_098260028.1 | WP_039230741.1 | WP_111617058.1 | WP_016079761.1 |
| WP_042462893.1 | WP_035404544.1 | WP_057776373.1 | WP_013059700.1 |
| WP_053368188.1 | WP_057763397.1 | WP_101223713.1 | WP_098836424.1 |
| WP_098572329.1 | WP_090761376.1 | WP_047943786.1 | WP_063670679.1 |
| WP_024031175.1 | WP_053477630.1 | WP_136358937.1 | WP_016718893.1 |
| WP_098312709.1 | WP_006838605.1 | WP_054398720.1 | WP_081207163.1 |
| WP_063263115.1 | WP_098492711.1 | WP_050820775.1 | WP_044743781.1 |
| WP_098906044.1 | WP_033012090.1 | WP_098874391.1 | WP_134975096.1 |
| WP_039073025.1 | WP_098563453.1 | WP_098123602.1 | WP_001231039.1 |
| WP_124051235.1 | WP_018783331.1 | WP_014478011.1 | WP_071392302.1 |
| WP_074553722.1 | WP_043977318.1 | WP_063164796.1 | WP_098758980.1 |
| WP_001231038.1 | WP_010899687.1 | AFQ59244.1 | WP_001990120.1 |
| WP_061574301.1 | WP_057239856.1 | WP_048566659.1 | WP_016937890.1 |
| WP_017561245.1 | WP_003201936.1 | WP_098437038.1 | WP_098909730.1 |
| WP_010676552.1 | WP_088113869.1 | WP_128747234.1 | WP_001231044.1 |
| WP_015375781.1 | WP_077671068.1 | WP_026580128.1 | WP_098191861.1 |
| WP_009362287.1 | WP_134378576.1 | WP_033883443.1 | WP_065410424.1 |
| WP_031407162.1 | WP_066106223.1 | WP_079288779.1 | WP_044439339.1 |
| WP_066192014.1 | WP_098163180.1 | ABK87818.1 | WP_002139168.1 |
| WP_017726328.1 | WP_016085605.1 | WP_098149639.1 | WP_105585595.1 |
| WP_098881737.1 | WP_086404129.1 | WP_098009310.1 | WP_098224919.1 |
| WP_061912389.1 | WP_001231041.1 | WP_094911130.1 | WP_098582415.1 |
| WP_014097474.1 | WP_071708738.1 | WP_043925539.1 | WP_073543968.1 |
| WP_031540679.1 | WP_002159914.1 | WP_100664262.1 | WP_124047914.1 |
| WP_057244845.1 | WP_137023276.1 | ANC33038.1 | WP_060749269.1 |
| WP_061570307.1 | WP_074601757.1 | WP_069838710.1 | WP_081133124.1 |
| WP_055441732.1 | KZM58399.1 | WP_059037336.1 | WP_025949885.1 |
| WP_098087536.1 | WP_113303501.1 | WP_071728240.1 | WP_042513393.1 |
| WP_128805263.1 | WP_098578860.1 | WP_098946395.1 | WP_033673190.1 |
| WP_053430308.1 | WP_016112483.1 | WP_001231037.1 | WP_098562107.1 |
| WP_057912038.1 | WP_025148228.1 | WP_001231043.1 | WP_071710099.1 |
| WP_118043288.1 | WP_088024791.1 | WP_020756339.1 | WP_098481312.1 |
| WP_129447198.1 | WP_071389124.1 | REJ13911.1 | WP_049664732.1 |
| WP_098053973.1 | WP_024713486.1 | WP_057998856.1 | WP_097794489.1 |
| WP_113769676.1 | WP_002124085.1 | WP_002016069.1 | AFJ63586.1 |
| WP_097895391.1 | WP_137011592.1 | WP_097840938.1 | WP_071736583.1 |
| WP_056524524.1 | WP_103185464.1 | WP_129705348.1 | WP_039075461.1 |
| WP_061686728.1 | WP_020453003.1 | WP_131887487.1 | WP_003151618.1 |
| WP_049669517.1 | WP_046218016.1 | WP_057275308.1 | WP_087991169.1 |
| WP_118498271.1 | WP_038413800.1 | WP_039810889.1 | WP_045385091.1 |
| WP_116821155.1 | WP_003243394.1 | WP_098094278.1 | REJ30438.1 |
| WP_129507564.1 | WP_019715758.1 | WP_061679291.1 | WP_098544968.1 |
| WP_016136934.1 | WP_034634933.1 | WP_020961189.1 | WP_130572861.1 |
| WP_076788798.1 | WP_075421549.1 | WP_102956614.1 | WP_098374188.1 |
| WP_070170654.1 | WP_010328643.1 | TKH99978.1 | WP_105981242.1 |
| WP_001231040.1 | WP_003219962.1 | EDR92067.1 | WP_088232033.1 |
| WP_106073398.1 | WP_103749369.1 | WP_033015090.1 | WP_017418891.1 |
| WP_061047067.1 | WP_104849558.1 | WP_010331914.1 | WP_001231045.1 |
| WP_025907462.1 | WP_063094158.1 | WP_106074644.1 | WP_070082401.1 |
| WP_082998444.1 | | | |

Methylglyoxal synthase (EC 4.2.3.3), also known as glycerone-phosphate phospho-lyase, is an enzyme that catalyzes the formation of methylglyoxal and phosphate from dihydroxyacetone phosphate. In *E. coli*, methylglyoxal synthase is encoded by mgsA (Uniprot P0A731).

Optionally, the engineered microorganism can include a modification that can attenuate or eliminate the activity of a methylglyoxal synthase, such as *E. coli* mgsA. In turn this can result in an increase in the pools of dihydroxyacetone phosphate, which in turn can be converted to G3P or sedoheptulose 1,7, which can complement the introduction and activity of the exogenous gapN expressed in the cells, and optionally the deletion or attenuation of gapA activity.

Deoxyribose phosphate aldolase (EC 4.1.2.4) catalyzes a reversible aldol reaction between acetaldehyde and D-glyceraldehyde 3-phosphate to generate 2-deoxy-D-ribose 5-phosphate. In *E. coli*, Doxyribose phosphate aldolase is encoded by deoC (Uniprot P0A6L0).

Optionally, the engineered microorganism can include a modification that can attenuate or eliminate the activity of the deoxyribose phosphate aldolase, such as *E. coli* deoC. In turn this can result in an increase in the pools of G3P, which can complement the introduction and activity of the exogenous gapN expressed in the cells, and optionally the deletion or attenuation of gapA activity.

Figure 5:
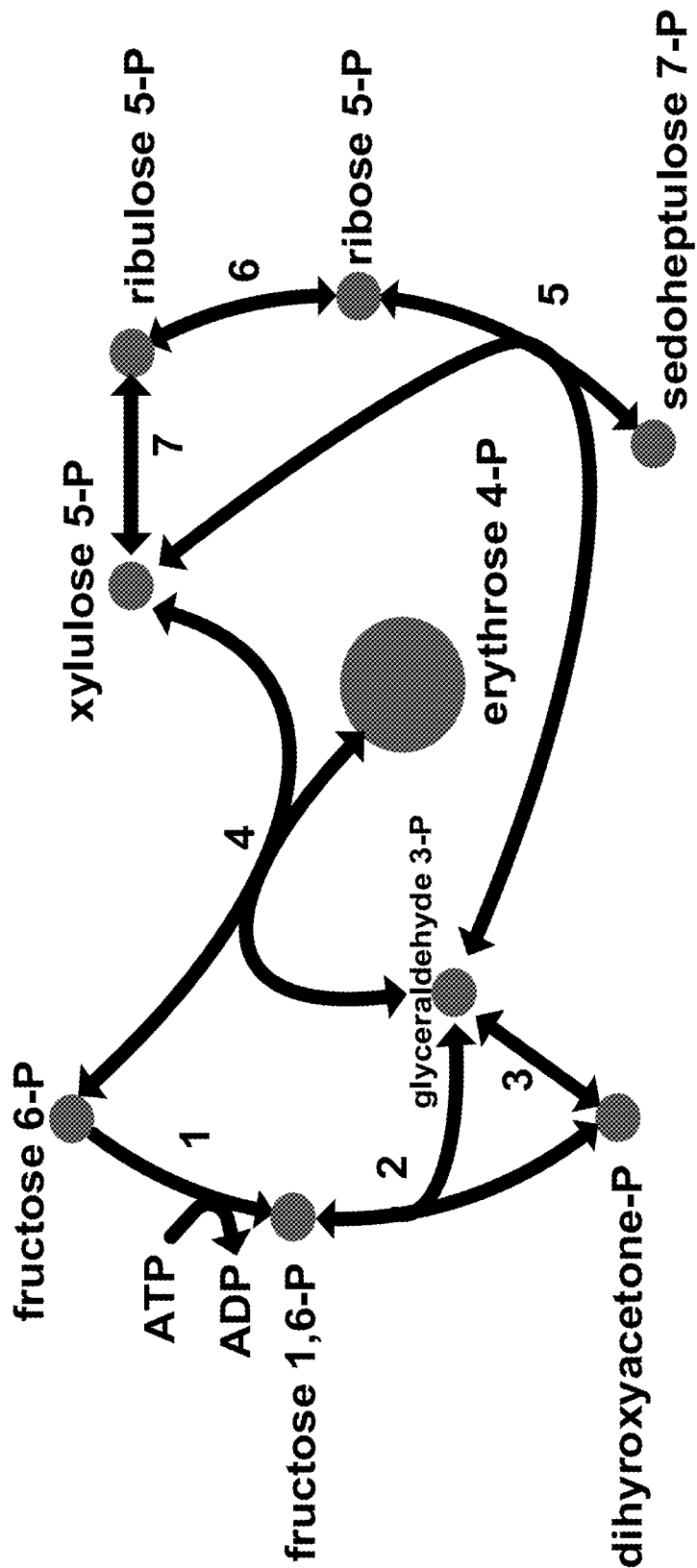
FIG. 5 illustrates metabolic pathways leading to and from various 3, 4, 5, and 6 carbon metabolites including glyceraldehyde 3-phosphate (G3P), dihydroxyacetone-phosphate, erythrose 4-phospohate, ribose 5-phosphate, ribulose 5-phosphate, xylulose 5-phosphate, fructose 6-phosphate, and fructose 1,6-biphosphate in a cell having synthetic methylotrophy. Reaction 1 is catalyzed by a 6-phosphofructokinase (pfk, preferably pfkAB); Reaction 2 by a fructose-bisphosphate aldolase (fba, preferably fbaAB); Reaction 3 by a triose-phosphate isomerase (tpi, preferably tpiA); Reaction 4 by a transketolase (tkt, preferably tktAB); Reaction 5 by a transketolase (tkt, preferably tktAB); Reaction 6 a by ribose-5-phosphate isomerase (rpi, preferably rpiAB); Reaction 7 by a ribulose-phosphate 3-epimerase (rpe).
Figure 6:
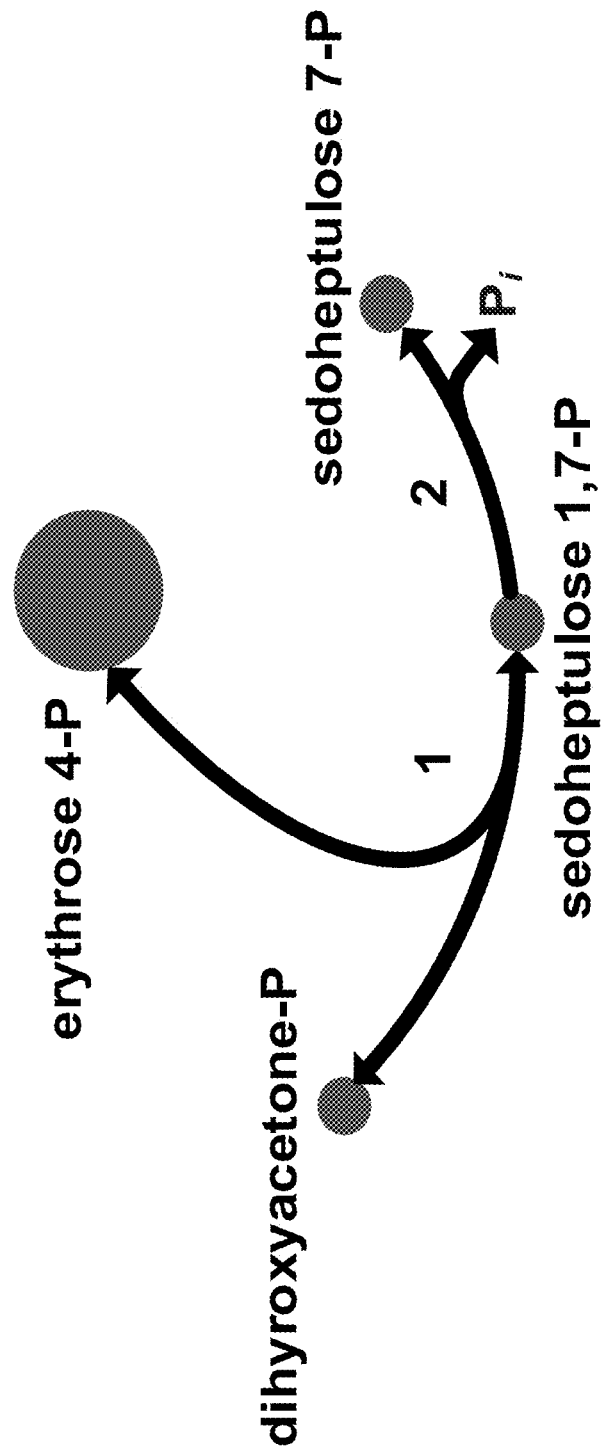
FIG. 6 illustrates metabolic pathways leading to and from, dihydroxyacetone-phosphate, erythrose 4-phospohate, sedoheptulose-1,7-biphosphate, and sedoheptulose-7-phosphate, in a cell having synthetic methylotrophy. Reaction 1 is catalyzed by a fructose-bisphosphate aldolase (fba); Reaction 2 by a fructose-1,6-bisphosphatase (glpX).

With reference to FIG. 5, in embodiments, the engineered microorganism can include a modification that attenuates or eliminates an endogenous activity of an ATP-dependent 6-phosphofructokinase. This enzyme can catalyze the phosphorylation of D-fructose 6-phosphate to fructose 1,6-bisphosphate by ATP. In *E. coli*, the ATP-dependent 6-phosphofructokinase isozyme 1 is encoded by pfkA, which can be modified to delete or attenuate phosphofructokinase enzymatic activity.

In embodiments, the engineered microorganism can include a modification that introduces an exogenous ATP-dependent 6-phosphofructokinase, such as one from *Bacillus*. For example, the ATP-dependent 6-phosphofructokinase Pfk2 from *Bacillus methanolicus* MGA3, or a homolog or variant thereof, can be introduced into the engineered microorganism. The engineered microorganism can express a pfk sequence that is related to *Bacillus methanolicus* MGA3 pfk2, such as a *Bacillus methanolicus* MGA pfk2 homolog or variant. For example, the pfk sequence can be 50% or greater, 60% or greater, 70% or greater, 80% or greater, 85% or greater, 90% or greater, or 95% or greater identity to *Bacillus methanolicus* MGA3 pfk2 (SEQ ID NO:5).

Other exemplary ATP-dependent 6-phosphofructokinase genes that can be introduced into the engineered microorganism are listed in Table 12 below.

TABLE 12

| Gene | Organism | NCBI accession number |
|---|---|---|
| pfk | *Amycolatopsis methanolica* 239 | AIJ24607.1 |
| pfk | *Geobacillus thermodenitrificans* NG80-2 | WP_008880861.1 |
| pfl2 | *Bacillus methanolicus* MGA3 | WP_003347446.1 |
| pfkB | *Escherichia coli* K-12 MG1655 | NP_416237.3 |

In embodiments, the engineered microorganism includes modifications that attenuates or eliminates an endogenous activity of an ATP-dependent 6-phosphofructokinase, and that introduces an exogenous ATP-dependent 6-phosphofructokinase. Optionally, these modifications can be combined with the overexpression of exogenous GapN and the attenuation/deletion of GapA.

With reference to FIG. 5, in embodiments, the engineered microorganism can include a modification that attenuates or eliminates an endogenous activity of a ribulose-phosphate 3-epimerase.

This enzyme can catalyze the reversible epimerization of D-ribulose 5-phosphate to D-xylulose 5-phosphate. In *E. coli.*, ribulose-phosphate 3-epimerase is encoded by rpe, which can be modified to delete or attenuate ribulose-phosphate 3-epimerase activity.

In embodiments, the engineered microorganism can include a modification that introduces an exogenous ribulose-phosphate 3-epimerase, such as one from *Bacillus*.

For example, the ribulose-phosphate 3-epimerase rpe from *Bacillus methanolicus* PB1, or a homolog or variant thereof, can be introduced into the engineered microorganism. The engineered microorganism can express a rpe sequence that is related to *Bacillus methanolicus* MGA3 rpe, such as a *Bacillus methanolicus* MGA rpe homolog or variant. For example, the rpe sequence can be 30% or greater, 40% or greater, 50% or greater, 60% or greater, 70% or greater, 80% or greater, 85% or greater, 90% or greater, or 95% or greater identity to *Bacillus methanolicus* MGA3 rpe (SEQ ID NO:6).

Exemplary ribulose-phosphate 3-epimerase genes that can be introduced into the engineered microorganism are listed in Table 13 below.

TABLE 13

| Gene | Organism | NCBI accession number |
|---|---|---|
| rpe | *Amycolatopsis methanolica* 239 | AIJ24612.1 |
| rpe | *Amycolatopsis methanolica* 239 | AIJ24222.1 |
| rpe | *Bacillus methanolicus* MGA3 plasmid pBM19 | WP_003349832.1 |
| rpe | *Bacillus methanolicus* PB1 | WP_003352245.1 |
| rpe | *Geobacillus thermodenitrificans* NG80-2 | WP_008878632.1 |
| rpe | *Methylobacillus flagellatus* | ABE50737.1 |
| rpe | *Methylophilus methylotrophus* ATCC 53528 | WP_018987244.1 |

In embodiments, the engineered microorganism includes modifications that attenuates or eliminates an endogenous activity of a ribulose-phosphate 3-epimerase, and that introduces an exogenous ribulose-phosphate 3-epimerase.

With reference to FIG. 5, in embodiments, the engineered microorganism can include a modification that attenuates or eliminates an endogenous activity of a ribose-5-phosphate isomerase.

This enzyme can catalyze the reversible conversion of ribose-5-phosphate to ribulose 5-phosphate. In *E. coli*, the ribose-5-phosphate isomerase A enzyme is encoded by rpiA, and ribose-5-phosphate isomerase B enzyme is encoded by rpiB, and either or both rpiA and/or rpiB can be modified to delete or attenuate ribose-5-phosphate isomerase activity.

In embodiments, the engineered microorganism can include a modification that introduces an exogenous ribose-5-phosphate isomerase, such as one from *Bacillus*.

For example, the ribose-5-phosphate isomerase rpiB from *Bacillus methanolicus* PB1, or a homolog or variant thereof, can be introduced into the engineered microorganism. The engineered microorganism can express a rpi sequence that is related to *Bacillus methanolicus* MGA3 rpiB, such as a *Bacillus methanolicus* MGA rpiB homolog or variant. For example, the rpi sequence can be 30% or greater, 40% or greater, 50% or greater, 60% or greater, 70% or greater, 80% or greater, 85% or greater, 90% or greater, or 95% or greater identity to *Bacillus methanolicus* MGA3 rpiB (SEQ ID NO:7). Other exemplary ribose-5-phosphate isomerase genes that can be introduced into the engineered microorganism are listed in Table 14 below.

TABLE 14

| Gene | Organism | NCBI accession number |
|---|---|---|
| rpi | *Amycolatopsis methanolica* 239 | AIJ26616.1 |
| rpi | *Geobacillus thermodenitrificans* NG80-2 | WP_008880705.1 |
| rpi | *Methylobacillus flagellatus* | ABE48400.1 |
| rpi | *Methylophilus methylotrophus* ATCC 53528 | WP_018987608.1 |
| rpiB | *Amycolatopsis methanolica* 239 | AIJ24621.1 |
| rpiB | *Bacillus methanolicus* MGA3 | WP_003346829.1 |
| rpiB | *Bacillus methanolicus* PB1 | WP_003351746.1 |
| rpiB | *Methylobacillus flagellatus* | ABE49230.1 |

In embodiments, the engineered microorganism includes modifications that attenuates or eliminates an endogenous activity of a ribose-5-phosphate isomerase, and that introduces an exogenous ribose-5-phosphate isomerase.

With reference to FIG. 5, in embodiments, the engineered microorganism can include a modification that attenuates or eliminates an endogenous activity of a transketolase. This enzyme can catalyze the reversible transfer of a two-carbon ketol group from sedoheptulose-7-phosphate to glyceraldehyde-3-phosphate, producing xylulose-5-phosphate and ribose-5-phosphate. In *E. coli*, the transketolase 1 enzyme is encoded by tktA, and the transketolase 2 enzyme is encoded by tktB, and either or both tktA and/or tktB can be modified to delete or attenuate transketolase activity.

In embodiments, the engineered microorganism can include a modification that introduces an exogenous transketolase, such as one from *Bacillus*. For example, the transketolase tkt2 from *Bacillus methanolicus* PB1, or a homolog or variant thereof, can be introduced into the engineered microorganism. The engineered microorganism can express a tkt sequence that is related to *Bacillus methanolicus* PB1 tkt2, such as a *Bacillus methanolicus* PB1 tkt2 homolog or variant. For example, the tkt sequence can be 50% or greater, 60% or greater, 70% or greater, 80% or greater, 85% or greater, 90% or greater, or 95% or greater identity to *Bacillus methanolicus* PB1 tkt2 (SEQ ID NO:8). Other exemplary transketolase genes that can be introduced into the engineered microorganism are listed in Table 15 below

TABLE 15

| Gene | Organism | NCBI accession number |
|---|---|---|
| tkt | *Amycolatopsis methanolica* 239 | AIJ24610.1 |
| tkt2 | *Bacillus methanolicus* MGA3 | WP_003349240.1 |
| tkt | *Bacillus methanolicus* MGA3 plasmid pBM19 | WP_003349838.1 |
| tkt2 | *Bacillus methanolicus* PB1 | WP_003350079.1 |
| tkt | *Bacillus methanolicus* PB1 plasmid pBM20 | WP_003352246.1 |
| tkt | *Geobacillus thermodenitrificans* NG80-2 | WP_008879527.1 |
| tkt | *Methylobacillus flagellatus* | ABE50516.1 |
| tkt | *Methylophilus methylotrophus* ATCC 53528 | WP_018987341.1 |
| tkt | *Pichia pastoris* GS115 | XP_002490261.1 |
| tktA | *Amycolatopsis methanolica* 239 | AIJ24184.1 |
| tktA1 | *Amycolatopsis methanolica* 239 | AIJ22337.1 |
| tktA2 | *Amycolatopsis methanolica* 239 | AIJ22338.1 |

In embodiments, the engineered microorganism includes modifications that attenuates or eliminates an endogenous activity of a transketolase, and that introduces an exogenous transketolase.

In one route 6-phosphofructokinase (EC 2.7.1.11) phosphorylates FMP to fructose 1,6-bisphosphate (FDP). Fructose-bisphosphate aldolase (EC 4.1.2.13) then cleaves FDP into dihydroxy acetone phosphate (DHAP) and glyceraldehyde 3-phosphate.

In another route glucose-6-phosphate isomerase (EC 5.3.1.9) isomerizes FMP to glucose 6-phosphate (GMP). Glucose-6-phosphate 1-dehydrogenase (EC 1.1.1.49) then dehydrogenates GMP to D-glucono-1,5-lactone 6-phosphate which is further dehydrogenated to 6-phospho-gluconate by 6-phosphogluconolactonase (EC 3.1.1.31). Phosphogluconate dehydratase (EC 4.2.1.12) then converts 6-phospho-gluconate to 2-keto-3-deoxy-6-phospho-D-gluconate (KDPG). Subsequently, KDPG aldolase (EC 4.1.2.14) cleaves KDPG into glyceraldehyde 3-phosphate and pyruvate. Pyruvate and DHAP formed through this pathway can be used in cellular pathways for the synthesis of biomolecules.

Optionally, the engineered microorganism can include a modification that can attenuate or eliminate the activity of a KHG/KDPG aldolase. In *E. coli* KHG/KDPG aldolase is encoded by the eda gene (Uniprot P0A955). Optionally, the engineered microorganism can include a modification that can attenuate or eliminate the activity of a glucose-6-phosphate 1-dehydrogenase. In *E. coli* glucose-6-phosphate 1-dehydrogenase is encoded by the zwf gene (Uniprot P0AC53). The glucose-6-phosphate 1-dehydrogenase reaction encoded by the zwf gene can provide a dissimilatory pathway due to the decarboxylation catalyzed by the GND reaction, and in turn result in suboptimal yield of biosynthetic pathways from methanol. However, the dissimilatory RuMP pathway via zwf may provide a route for formaldehyde detoxification to balance formaldehyde assimilation via assimilatory RuMP. In addition to formaldehyde dissimilation via pentose phosphate pathway (zwf), bacteria also possess a linear formaldehyde dissimilation pathway, where formaldehyde is oxidized to formate and then to $CO_2$. This pathway is encoded by endogenous genes frmR, frmA, frmB in *E. coli*. Additionally, some methylotrophs also possess genes such as folD, fhs, and fdhA to encode for this linear dissimilation pathway. The advantage of the formaldehyde dissimilation via pentose phosphate pathway is that it regenerates ribulose-5-phosphate for the RuMP cycle and relies on RuMP pathway (Hps and Phi activity). Synthetic methylotrophy can be facilitated by balancing formaldehyde dissimilation and assimilation via the RuMP cycle. This can be achieved by deletion or attenuation of the linear pathway of formaldehyde dissimilation encoded by the endogenous genes frmR, frmA, frmB in *E. coli* or the introduction of an exogenous formaldehyde dissimilation pathway encoded by folD, fhs, and fdhA from *B. methanolicus*.

Alternatively, modifications can include the attenuation or deletion of endogenous zwf gene in *E. coli*. The endogenous zwf in *E. coli* is inhibited by high NADH levels and high pool sizes of F6P. Inhibition can be addressed by replacing the endogenous zwf of *E. coli* with an exogenous zwf2 that is non-naturally regulated and responsive to formaldehyde concentrations. An exemplary exogenous gene candidate is the zwf2 from *B. methanolicus* PB1 and MGA3. The engineered microorganism can express a tkt sequence that is related to *Bacillus methanolicus* PB1 or MGA3 zwf2, such as a *Bacillus methanolicus* PB1 or MGA3 zwf2 homolog or variant. For example, the zwf sequence can be 50% or greater, 60% or greater, 70% or greater, 80% or greater, 85% or greater, 90% or greater, or 95% or greater identity to *Bacillus methanolicus* PB1 or MGA3 zwf2 (SEQ ID NO:10).

Optionally, the engineered microorganism can include a modification that can attenuate or eliminate the activity of an endogenous zwf and introduce the activity of an exogenous zwf2 from *B. methanolicus*. This can also be combined with the introduction of gapN and the attenuation or deletion of endogenous GapA activity.

TABLE 16

| zwf2 | *Bacillus methanolicus* MGA3 | fba2 |
| zwf2 | *Bacillus methanolicus* PB1 | WP_003350053.1 |

Candidate exogenous genes for introduction to balance formaldehyde dissimilation and assimilation include those in Table 17.

TABLE 17

| Gene | Organism | NCBI accession number |
|---|---|---|
| fdhA | *Bacillus methanolicus* MGA3 | WP_004434290.1 |
| fdhD | *Bacillus methanolicus* MGA3 | WP_004434293.1 |
| fhs | *Bacillus methanolicus* MGA3 | WP_004435057.1 |
| folD | *Bacillus methanolicus* MGA3 | WP_004435562.1 |

Acetate kinase catalyzes the formation of acetyl phosphate from acetate and ATP. The *E. coli* acetate kinase is encoded by ackA (Skarstedt and Silverstein, *J. Biol. Chem.* 251:6775-6783 (1976)), and phosphorylates propionate in addition to acetate (Hesslinger et al., *Mol. Microbiol.* 27:477-492 (1998)). Optionally, the engineered microorganism can include a modification that can attenuate or eliminate the activity of an acetate kinase. For example, the *E. coli* acetate ackA (Uniprot P0AC53) can be deleted or its activity attenuated. Deletion or attenuation of ackA can be beneficial in various strain embodiments, such as when phosphoketolase and/or and phosphotransacetylase are overexpressed. Since phosphoketolase forms acetyl_phosphate which can be converted to acetate, deletion of ackA and overexpression phosphotransacetylase can promote conversion of the resulting acetyl_phosphate to acetyl CoA.

In an embodiment, the engineered microorganism includes the following modifications: (1) exogenous enzyme A that (ai) is capable of converting glyceraldehyde 3-phosphate (G3P) to 3-phosphoglycerate (3PG), or (aii) has at least 50% sequence identity to SEQ ID NO:1 (*B. methanolicus* gapN), wherein enzyme A is capable of reducing NADP to NADPH, (2) exogenous hexulose-6-phosphate synthase (hps), (3) exogenous 6-phospho-3-hexuloisomeras (phi), (4) exogenous methanol dehydrogenase (MeDH), and (5) exogenous fructose-1,6-bisphosphatase (glpX).

In an embodiment, the engineered microorganism includes the following modifications: (1) exogenous enzyme A (e.g., gapN), (2) exogenous hps, (3) exogenous phi, (4) exogenous MeDH, (5) exogenous glpX, and (6) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, and (6) exogenous PK, and (7) endogenous methyl glyoxal synthase (mgsA) deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, and (6) endogenous NAD-dependent glyceraldehyde-3-phosphate dehydrogenase (gapA) deletion or attenuation.

In an embodiment, the engineered microorganism includes the following modifications: (1) exogenous enzyme A (e.g., gapN), (2) exogenous hps, (3) exogenous phi, (4)

exogenous MeDH, (5) exogenous glpX, (6) endogenous gapA deletion or attenuation, (7) endogenous transaldolase activity (talB, talA, and/or talC) deletion or attenuation, (8) exogenous ATP-dependent 6-phosphofructokinase (pfk2), and (9) exogenous fructose-bisphosphate aldolase (fba).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gapA deletion or attenuation, (7) endogenous talB, talA, and/or talC deletion or attenuation, (8) exogenous ribulose-phosphate 3-epimerase (rpe), (9) exogenous ribose-5-phosphate isomerase (rpi), (10) exogenous transketolase (tkt), and (11) exogenous fructose-bisphosphate aldolase (fba).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gapA deletion or attenuation, (7) exogenous ribulose-phosphate 3-epimerase (rpe), (8) endogenous rpe deletion or attenuation, (9) exogenous ribose-5-phosphate isomerase (rpi), (10) endogenous rpi deletion or attenuation, (11) endogenous transketolase (tkt) deletion or attenuation, (12) exogenous transketolase (tkt), (13) exogenous fructose-bisphosphate aldolase (fba), (14) endogenous fba deletion or attenuation, (15) exogenous glucose-6-phosphate 1-dehydrogenase (zwf), and (16) endogenous zwf deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gapA deletion or attenuation, (7) endogenous talB, talA, and/or talC deletion or attenuation, (8) exogenous ATP-dependent 6-phosphofructokinase (pfk), (9) endogenous pfk deletion or attenuation, (10) exogenous ribulose-phosphate 3-epimerase (rpe), (11) endogenous rpe deletion or attenuation, (12) exogenous ribose-5-phosphate isomerase (rpi), (13) endogenous rpi deletion or attenuation, (14) endogenous transketolase (tkt) deletion or attenuation, (15) exogenous transketolase (tkt), (16) exogenous fructose-bisphosphate aldolase (fba), (17) endogenous fba deletion or attenuation, (18) exogenous glucose-6-phosphate 1-dehydrogenase (zwf), and (19) endogenous zwf deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gapA deletion or attenuation, and (7) endogenous methyl glyoxal synthase (mgsA) deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gapA deletion or attenuation, (7) endogenous talB, talA, and/or talC deletion or attenuation, and (8) endogenous mgsA deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gapA deletion or attenuation, (7) endogenous talB, talA, and/or talC deletion or attenuation, (8) exogenous ribulose-phosphate 3-epimerase (rpe), (9) exogenous ribose-5-phosphate isomerase (rpi), (10) exogenous transketolase (tkt), (11) exogenous fructose-bisphosphate aldolase (fba), and (12) endogenous mgsA deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gapA deletion or attenuation, (7) exogenous ribulose-phosphate 3-epimerase (rpe), (8) endogenous rpe deletion or attenuation, (9) exogenous ribose-5-phosphate isomerase (rpi), (10) endogenous rpi deletion or attenuation, (11) endogenous transketolase (tkt) deletion or attenuation, (12) exogenous transketolase (tkt), (13) exogenous fructose-bisphosphate aldolase (fba), (14) endogenous fba deletion or attenuation, (15) exogenous glucose-6-phosphate 1-dehydrogenase (zwf), (16) endogenous zwf deletion or attenuation, and (17) endogenous mgsA deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gapA deletion or attenuation, (7) endogenous talB, talA, and/or talC deletion or attenuation, (8) exogenous ATP-dependent 6-phosphofructokinase (pfk), (9) endogenous pfk deletion or attenuation, (10) exogenous ribulose-phosphate 3-epimerase (rpe), (11) endogenous rpe deletion or attenuation, (12) exogenous ribose-5-phosphate isomerase (rpi), (13) endogenous rpi deletion or attenuation, (14) endogenous transketolase (tkt) deletion or attenuation, (15) exogenous transketolase (tkt), (16) exogenous fructose-bisphosphate aldolase (fba), (17) endogenous fba deletion or attenuation, (18) exogenous glucose-6-phosphate 1-dehydrogenase (zwf), and (19) endogenous zwf deletion or attenuation, and (20) endogenous mgsA deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gapA deletion or attenuation, (7) endogenous mgsA deletion or attenuation, and (8) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gapA deletion or attenuation, (7) endogenous talB, talA, and/or talC deletion or attenuation, (8) endogenous mgsA deletion or attenuation, (9) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gapA deletion or attenuation, (7) endogenous transaldolase activity (talB, talA, and/or talC) deletion or attenuation, (8) exogenous ribulose-phosphate 3-epimerase (rpe), (9) exogenous ribose-5-phosphate isomerase (rpi), (10) exogenous transketolase (tkt), (11) exogenous fructose-bisphosphate aldolase (fba), (12) endogenous mgsA deletion or attenuation, and (13) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gapA deletion or attenuation,
(7) exogenous ribulose-phosphate 3-epimerase (rpe), (8) endogenous rpe deletion or attenuation, (9) exogenous ribose-5-phosphate isomerase (rpi), (10) endogenous rpi deletion or attenuation, (11) endogenous transketolase (tkt) deletion or attenuation, (12) exogenous transketolase (tkt), (13) exogenous fructose-bisphosphate aldolase (fba), (14) endogenous fba deletion or attenuation, (15) exogenous glucose-6-phosphate 1-dehydrogenase (zwf), (16) endogenous zwf deletion or attenuation, (17) endogenous mgsA deletion or attenuation, and (18) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gapA deletion or attenuation, (7) endogenous talB, talA, and/or talC deletion or attenuation, (8) exogenous ATP-dependent 6-phosphofructokinase (pfk), (9) endogenous pfk deletion or attenuation, (10) exogenous ribulose-phosphate 3-epimerase (rpe), (11) endogenous rpe deletion or attenuation, (12) exogenous ribose-5-phosphate isomerase (rpi), (13) endogenous rpi deletion or attenuation, (14) endogenous transketolase (tkt) deletion or attenuation, (15) exogenous transketolase (tkt), (16) exogenous fructose-bisphosphate aldolase (fba), (17) endogenous fba deletion or attenuation, (18) exogenous glucose-6-phosphate 1-dehydrogenase (zwf), and (19) endogenous zwf deletion or attenuation, (20) endogenous mgsA deletion or attenuation, and (21) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous phosphoglycerate kinase (pgk) deletion or attenuation, (7) endogenous mgsA deletion or attenuation, and (8) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous pgk deletion or attenuation, (7) endogenous talB, talA, and/or talC deletion or attenuation, (7) endogenous mgsA deletion or attenuation, (8) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous pgk deletion or attenuation, (7) endogenous transaldolase activity (talB, talA, and/or talC) deletion or attenuation, (8) exogenous ribulose-phosphate 3-epimerase (rpe), (9) exogenous ribose-5-phosphate isomerase (rpi), (10) exogenous transketolase (tkt), (11) exogenous fructose-bisphosphate aldolase (fba), (12) endogenous mgsA deletion or attenuation, and (13) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous pgk deletion or attenuation, (7) exogenous ribulose-phosphate 3-epimerase (rpe), (8) endogenous rpe deletion or attenuation, (9) exogenous ribose-5-phosphate isomerase (rpi), (10) endogenous rpi deletion or attenuation, (11) endogenous transketolase (tkt) deletion or attenuation, (12) exogenous transketolase (tkt), (13) exogenous fructose-bisphosphate aldolase (fba), (14) endogenous fba deletion or attenuation, (15) exogenous glucose-6-phosphate 1-dehydrogenase (zwf), (16) endogenous zwf deletion or attenuation, (17) endogenous mgsA deletion or attenuation, and (18) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous phosphoglycerate kinase (pgk) deletion or attenuation, (7) endogenous talB, talA, and/or talC deletion or attenuation, (8) exogenous ATP-dependent 6-phosphofructokinase (pfk), (9) endogenous pfk deletion or attenuation, (10) exogenous ribulose-phosphate 3-epimerase (rpe), (11) endogenous rpe deletion or attenuation, (12) exogenous ribose-5-phosphate isomerase (rpi), (13) endogenous rpi deletion or attenuation, (14) endogenous transketolase (tkt) deletion or attenuation, (15) exogenous transketolase (tkt), (16) exogenous fructose-bisphosphate aldolase (fba), (17) endogenous fba deletion or attenuation, (18) exogenous glucose-6-phosphate 1-dehydrogenase (zwf), and (19) endogenous zwf deletion or attenuation, (20) endogenous mgsA deletion or attenuation, and (21) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous phosphoglycerate mutase (gpm) deletion or attenuation, (7) endogenous mgsA deletion or attenuation, and (8) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gpm deletion or attenuation, (7) endogenous talB, talA, and/or talC deletion or attenuation, (8) endogenous mgsA deletion or attenuation, (9) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gpm deletion or attenuation, (7) endogenous talB, talA, and/or talC deletion or attenuation, (8) exogenous ribulose-phosphate 3-epimerase (rpe), (9) exogenous ribose-5-phosphate isomerase (rpi), (10) exogenous transketolase (tkt), (11) exogenous fructose-bisphosphate aldolase (fba), (12) endogenous mgsA deletion or attenuation, and (13) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gpm deletion or attenuation, (7) exogenous ribulose-phosphate 3-epimerase (rpe), (8) endogenous rpe deletion or attenuation, (9) exogenous ribose-5-phosphate isomerase (rpi), (10) endogenous rpi deletion or attenuation, (11) endogenous transketolase (tkt) deletion or attenuation, (12) exogenous transketolase (tkt), (13) exogenous fructose-bisphosphate aldolase (fba), (14) endogenous fba deletion or attenuation, (15) exogenous glucose-6-phosphate 1-dehydrogenase (zwf), (16) endogenous zwf deletion or attenuation, (17) endogenous mgsA deletion or attenuation, and (18) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous gpm deletion or attenuation, (7) endogenous talB, talA, and/or talC deletion or attenuation, (8) exogenous ATP-dependent 6-phosphofructokinase (pfk), (9) endogenous pfk deletion or attenuation, (10) exogenous ribulose-phosphate 3-epimerase (rpe), (11) endogenous rpe deletion or attenuation, (12) exogenous ribose-5-phosphate isomerase (rpi), (13) endogenous rpi deletion or attenuation, (14) endogenous transketolase (tkt) deletion or attenuation, (15) exogenous transketolase (tkt), (16) exogenous fructose-bisphosphate aldolase (fba), (17) endogenous fba deletion or attenuation, (18) exogenous glucose-6-phosphate 1-dehydrogenase (zwf), and (19) endogenous zwf deletion or attenuation, (20) endogenous mgsA deletion or attenuation, and (21) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous enolase (eno) deletion or attenuation, (7) endogenous mgsA deletion or attenuation, and (8) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous eno deletion or attenuation, (7) endogenous talB, talA, and/or talC deletion or attenuation, (8) endogenous mgsA deletion or attenuation, (9) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous eno deletion or attenuation, (7) endogenous talB, talA, and/or talC deletion or attenuation, (8) exogenous ribulose-phosphate 3-epimerase (rpe), (9) exogenous ribose-5-phosphate isomerase (rpi), (10) exogenous transketolase (tkt), (11) exogenous fructose-bisphosphate aldolase (fba), (12) endogenous mgsA deletion or attenuation, and (13) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous eno deletion or attenuation, (7) exogenous ribulose-phosphate 3-epimerase (rpe), (8) endogenous rpe deletion or attenuation, (9) exogenous ribose-5-phosphate isomerase (rpi), (10) endogenous rpi deletion or attenuation, (11) endogenous transketolase (tkt) deletion or attenuation, (12) exogenous transketolase (tkt), (13) exogenous fructose-bisphosphate aldolase (fba), (14) endogenous fba deletion or attenuation, (15) exogenous glucose-6-phosphate 1-dehydrogenase (zwf), (16) endogenous zwf deletion or attenuation, (17) endogenous mgsA deletion or attenuation, and (18) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous eno deletion or attenuation, (7) endogenous talB, talA, and/or talC deletion or attenuation, (8) exogenous ATP-dependent 6-phosphofructokinase (pfk), (9) endogenous pfk deletion or attenuation, (10) exogenous ribulose-phosphate 3-epimerase (rpe), (11) endogenous rpe deletion or attenuation, (12) exogenous ribose-5-phosphate isomerase (rpi), (13) endogenous rpi deletion or attenuation, (14) endogenous transketolase (tkt) deletion or attenuation, (15) exogenous transketolase (tkt), (16) exogenous fructose-bisphosphate aldolase (fba), (17) endogenous fba deletion or attenuation, (18) exogenous glucose-6-phosphate 1-dehydrogenase (zwf), and (19) endogenous zwf deletion or attenuation, (20) endogenous mgsA deletion or attenuation, and (21) exogenous phosphoketolase (PK).

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoxyribose phosphate aldolase (deoC) deletion or attenuation, (7) endogenous mgsA deletion or attenuation, (8) exogenous phosphoketolase (PK), and (9) endogenous gapA deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoC deletion or attenuation, (7) endogenous talB, talA, and/or talC deletion or attenuation, (8) endogenous mgsA deletion or attenuation, (9) exogenous phosphoketolase (PK), and (10) endogenous gapA deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoC deletion or attenuation, (7) endogenous talB, talA, and/or talC deletion or attenuation, (8) exogenous ribulose-phosphate 3-epimerase (rpe), (9) exogenous ribose-5-phosphate isomerase (rpi), (10) exogenous transketolase (tkt), (11) exogenous fructose-bisphosphate aldolase (fba), (12) endogenous mgsA deletion or attenuation, (13) exogenous phosphoketolase (PK), and (14) endogenous gapA deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoC deletion or attenuation, (7) exogenous ribulose-phosphate 3-epimerase (rpe), (8) endogenous rpe deletion or attenuation, (9) exogenous ribose-5-phosphate isomerase (rpi), (10) endogenous rpi deletion or attenuation, (11) endogenous transketolase (tkt) deletion or attenuation, (12) exogenous transketolase (tkt), (13) exogenous fructose-bisphosphate aldolase (fba), (14) endogenous fba deletion or attenuation, (15) exogenous glucose-6-phosphate 1-dehydrogenase (zwf), (16) endogenous zwf deletion or attenuation, (17) endogenous mgsA deletion or attenuation, (18) exogenous phosphoketolase (PK), and (19) endogenous gapA deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoC deletion or attenuation, (7) endogenous talB, talA, and/or talC deletion or attenuation, (8) exogenous ATP-dependent 6-phosphofructokinase (pfk), (9) endogenous pfk deletion or attenuation, (10) exogenous ribulose-phosphate 3-epimerase (rpe), (11) endogenous rpe deletion or attenuation, (12) exogenous ribose-5-phosphate isomerase (rpi), (13) endogenous rpi deletion or attenuation, (14) endogenous transketolase (tkt) deletion or attenuation, (15) exogenous transketolase (tkt), (16) exogenous fructose-bisphosphate aldolase (fba), (17) endogenous fba deletion or attenuation, (18) exogenous glucose-6-phosphate 1-dehydrogenase (zwf), and (19) endogenous zwf deletion or attenuation, (20) endogenous mgsA deletion or attenuation, (21) exogenous phosphoketolase (PK), and (22) endogenous gapA deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoxyribose phosphate aldolase (deoC) deletion or attenuation, (7) endogenous mgsA deletion or attenuation, (8) exogenous phosphoketolase (PK), and (9) endogenous pgk deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoC deletion or attenuation, (7) endogenous talB, talA, and/or talC deletion or attenuation, (8) endogenous mgsA deletion or attenuation, (9) exogenous phosphoketolase (PK), and (10) endogenous pgk deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoC deletion or attenuation, (7) endogenous talB, talA, and/or talC deletion or attenuation, (8) exogenous ribulose-phosphate 3-epimerase (rpe), (9) exogenous ribose-5-phosphate isomerase (rpi), (10) exogenous transketolase (tkt), (11) exogenous fructose-bisphosphate aldolase (fba), (12) endogenous mgsA deletion or attenuation, (13) exogenous phosphoketolase (PK), and (14) endogenous pgk deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoC deletion or attenuation, (7) exogenous ribulose-phosphate 3-epimerase (rpe), (8) endogenous rpe deletion or attenuation, (9) exogenous ribose-5-phosphate isomerase (rpi), (10) endogenous rpi deletion or attenuation, (11) endogenous transketolase (tkt) deletion or attenuation, (12) exogenous transketolase (tkt), (13) exogenous fructose-bisphosphate aldolase (fba), (14) endogenous fba deletion or attenuation, (15) exogenous glucose-6-phosphate 1-dehydrogenase (zwf), (16) endogenous zwf deletion or attenuation, (17) endogenous mgsA deletion or attenuation, (18) exogenous phosphoketolase (PK), and (19) endogenous pgk deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoC deletion or attenuation, (7) endogenous talB, talA, and/or talC deletion or attenuation, (8) exogenous ATP-dependent 6-phosphofructokinase (pfk), (9) endogenous pfk deletion or attenuation, (10) exogenous ribulose-phosphate 3-epimerase (rpe), (11) endogenous rpe deletion or attenuation, (12) exogenous ribose-5-phosphate isomerase (rpi), (13) endogenous rpi deletion or attenuation, (14) endogenous transketolase (tkt) deletion or attenuation, (15) exogenous transketolase (tkt), (16) exogenous fructose-bisphosphate aldolase (fba), (17) endogenous fba deletion or attenuation, (18) exogenous glucose-6-phosphate 1-dehydrogenase (zwf), and (19) endogenous zwf deletion or attenuation, (20) endogenous mgsA deletion or attenuation, (21) exogenous phosphoketolase (PK), and (22) endogenous pgk deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoxyribose phosphate aldolase (deoC) deletion or attenuation, (7) endogenous mgsA deletion or attenuation, (8) exogenous phosphoketolase (PK), and (9) endogenous gpm deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoC deletion or attenuation, (7) endogenous talB, talA, and/or talC deletion or attenuation, (8) endogenous mgsA deletion or attenuation, (9) exogenous phosphoketolase (PK), and (10) endogenous gpm deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoC deletion or attenuation, (7) endogenous talB, talA, and/or talC deletion or attenuation, (8) exogenous ribulose-phosphate 3-epimerase (rpe), (9) exogenous ribose-5-phosphate isomerase (rpi), (10) exogenous transketolase (tkt), (11) exogenous fructose-bisphosphate aldolase (fba), (12) endogenous mgsA deletion or attenuation, (13) exogenous phosphoketolase (PK), and (14) endogenous gpm deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoC deletion or attenuation, (7) exogenous ribulose-phosphate 3-epimerase (rpe), (8) endogenous rpe deletion or attenuation, (9) exogenous ribose-5-phosphate isomerase (rpi), (10) endogenous rpi deletion or attenuation, (11) endogenous transketolase (tkt) deletion or attenuation, (12) exogenous transketolase (tkt), (13) exogenous fructose-bisphosphate aldolase (fba), (14) endogenous fba deletion or attenuation, (15) exogenous glucose-6-phosphate 1-dehydrogenase (zwf), (16) endogenous zwf deletion or attenuation, (17) endogenous mgsA deletion or attenuation, (18) exogenous phosphoketolase (PK), and (19) endogenous gpm deletion or attenuation.

In an embodiment, the engineered microorganism includes the following modifications: (1) exogenous enzyme A (e.g., gapN), (2) exogenous hps, (3) exogenous phi, (4) exogenous MeDH, (5) exogenous glpX, (6) endogenous deoC deletion or attenuation, (7) endogenous talB, talA, and/or talC deletion or attenuation, (8) exogenous ATP-dependent 6-phosphofructokinase (pfk), (9) endogenous pfk deletion or attenuation, (10) exogenous ribulose-phosphate 3-epimerase (rpe), (11) endogenous rpe deletion or attenuation, (12) exogenous ribose-5-phosphate isomerase (rpi), (13) endogenous rpi deletion or attenuation, (14) endogenous transketolase (tkt) deletion or attenuation, (15) exogenous transketolase (tkt), (16) exogenous fructose-bisphosphate aldolase (fba), (17) endogenous fba deletion or attenuation, (18) exogenous glucose-6-phosphate 1-dehydrogenase (zwf), and (19) endogenous zwf deletion or attenuation, (20) endogenous mgsA deletion or attenuation, (21) exogenous phosphoketolase (PK), and (22) endogenous gpm deletion or attenuation. In an embodiment, the engineered microorganism includes the following modifications: (1) exogenous hps, (2) exogenous phi, (3) exogenous MeDH, (4) exogenous glpX, (5) endogenous transaldolase activity (talB, talA, and/or talC) deletion or attenuation, (6) exogenous ATP-dependent 6-phosphofructokinase (pfk2), and (7) exogenous fructose-bisphosphate aldolase (fba).

In an embodiment, the engineered microorganism has the following modifications: (1) exogenous hps, (2) exogenous phi, (3) exogenous MeDH, (4) exogenous glpX, (5) endogenous talB, talA, and/or talC deletion or attenuation, (6) exogenous ribulose-phosphate 3-epimerase (rpe), (7) exogenous ribose-5-phosphate isomerase (rpi), (8) exogenous transketolase (tkt), and (9) exogenous fructose-bisphosphate aldolase (fba).

In an embodiment, the engineered microorganism includes the following modifications: (1) exogenous hps, (2) exogenous phi, (3) exogenous MeDH, (4) exogenous glpX, (5) endogenous talB, talA, and/or talC deletion or attenuation, (6) exogenous ATP-dependent 6-phosphofructokinase (pfk), (7) endogenous pfk deletion or attenuation, (8) exogenous ribulose-phosphate 3-epimerase (rpe), (9) endogenous rpe deletion or attenuation, (10) exogenous ribose-5-phosphate isomerase (rpi), (11) endogenous rpi deletion or attenuation, (12) endogenous transketolase (tkt) deletion or attenuation, (13) exogenous transketolase (tkt), (14) exogenous fructose-bisphosphate aldolase (fba), (15) endogenous fba deletion or attenuation, (16) exogenous glucose-6-phosphate 1-dehydrogenase (zwf), and (17) endogenous zwf deletion or attenuation.

In an embodiment, the engineered microorganism includes the following modifications: (1) exogenous hps, (2) exogenous phi, (3) exogenous MeDH, (4) exogenous glpX, (5) endogenous talB, talA, and/or talC deletion or attenuation, (6) exogenous ATP-dependent 6-phosphofructokinase (pfk), (7) endogenous pfk deletion or attenuation, (8) exogenous ribulose-phosphate 3-epimerase (rpe), (9) endogenous rpe deletion or attenuation, (10) exogenous ribose-5-phosphate isomerase (rpi), (11) endogenous rpi deletion or attenuation, (12) endogenous transketolase (tkt) deletion or attenuation, (13) exogenous transketolase (tkt), (14) exogenous fructose-bisphosphate aldolase (fba), (15) endogenous fba deletion or attenuation, (16) exogenous glucose-6-phosphate 1-dehydrogenase (zwf), and (17) endogenous zwf deletion or attenuation, (18) endogenous mgsA deletion or attenuation, and (19) exogenous phosphoketolase (PK).

In an embodiment, the engineered microorganism includes the following modifications: (1) exogenous hps, (2) exogenous phi, (3) exogenous MeDH, (4) exogenous glpX, (5) endogenous talB, talA, and/or talC deletion or attenuation, (6) endogenous mgsA deletion or attenuation, (7) exogenous phosphoketolase (PK).

In an embodiment, the engineered microorganism includes the following modifications: (1) exogenous hps, (2) exogenous phi, (3) exogenous MeDH, (4) exogenous glpX, (5) endogenous transaldolase activity (talB, talA, and/or talC) deletion or attenuation, (6) exogenous ribulose-phosphate 3-epimerase (rpe), (7) exogenous ribose-5-phosphate isomerase (rpi), (8) exogenous transketolase (tkt), (9) exogenous fructose-bisphosphate aldolase (fba), (10) endogenous mgsA deletion or attenuation, and (11) exogenous phosphoketolase (PK).

In an embodiment, the engineered microorganism has the following modifications: (1) exogenous enzyme A (e.g., gapN), (2) exogenous hps, (3) exogenous phi, (4) exogenous MeDH, (5) exogenous glpX, (6) endogenous talB, talA, and/or talC deletion or attenuation, (7) exogenous ATP-dependent 6-phosphofructokinase (pfkA and pfkB), (8) exogenous ribulose-phosphate 3-epimerase (rpe), (9) endogenous rpe deletion or attenuation, (10) exogenous ribose-5-phosphate isomerase (rpi), (11) endogenous rpi deletion or attenuation, (12) endogenous transketolase (tkt) deletion or attenuation, (13) exogenous transketolase (tkt), (14) exogenous fructose-bisphosphate aldolase (fba), (15) endogenous fba deletion or attenuation, (15) exogenous glucose-6-phosphate 1-dehydrogenase (zwf), and (16) endogenous zwf deletion or attenuation, (17) endogenous mgsA deletion or attenuation, (18) exogenous phosphoketolase (PK), Given the teachings and guidance provided herein, those skilled in the art also will understand that enzymatic activity or expression can be attenuated using well known methods. Reduction of the activity or amount of an enzyme can mimic complete disruption of a gene if the reduction causes activity of the enzyme to fall below a critical level that is normally required for a pathway to function. Reduction of enzymatic activity by various techniques rather than use of a gene disruption can be important for an organism's viability. Methods of reducing enzymatic activity that result in similar or identical effects of a gene disruption include, but are not limited to: reducing gene transcription or translation; destabilizing mRNA, protein or catalytic RNA; and mutating a gene that affects enzyme activity or kinetics (See, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, MD (1999). Natural or imposed regulatory controls can also accomplish enzyme attenuation including: promoter replacement (See, Wang et al., *Mol. Biotechnol.* 52(2):300-308 (2012)); loss or alteration of transcription factors (Dietrick et al., *Annu. Rev. Biochem.* 79:563-590 (2010); and Simicevic et al., *Mol. Biosyst.* 6(3):462-468 (2010)); introduction of inhibitory RNAs or peptides such as siRNA, antisense RNA, RNA or peptide/small-molecule binding aptamers, ribozymes, aptazymes and riboswitches (Wieland et al., *Methods* 56(3): 351-357 (2012); O'Sullivan, *Anal. Bioanal. Chem.* 372(1): 44-48 (2002); and Lee et al., *Curr. Opin. Biotechnol.* 14(5): 505-511 (2003)); and addition of drugs or other chemicals that reduce or disrupt enzymatic activity such as an enzyme inhibitor, an antibiotic or a target-specific drug.

One skilled in the art will also understand and recognize that attenuation of an enzyme can be done at various levels. For example, at the gene level, a mutation causing a partial or complete null phenotype, such as a gene disruption, or a mutation causing epistatic genetic effects that mask the activity of a gene product (Miko, *Nature Education* 1(1) (2008)), can be used to attenuate an enzyme. At the gene expression level, methods for attenuation include: coupling transcription to an endogenous or exogenous inducer, such as isopropylthio-β-galactoside (IPTG), then adding low amounts of inducer or no inducer during the production phase (Donovan et al., *J. Ind. Microbiol.* 16(3):145-154 (1996); and Hansen et al., *Curr. Microbiol.* 36(6):341-347 (1998)); introducing or modifying a positive or a negative regulator of a gene; modify histone acetylation/deacetylation in a eukaryotic chromosomal region where a gene is integrated (Yang et al., *Curr. Opin. Genet. Dev.* 13(2):143-153 (2003) and Kurdistani et al., *Nat. Rev. Mol. Cell Biol.* 4(4):276-284 (2003)); introducing a transposition to disrupt a promoter or a regulatory gene (Bleykasten-Brosshans et al., *C. R. Biol.* 33(8-9):679-686 (2011); and McCue et al., *PLoS Genet.* 8(2):e1002474 (2012)); flipping the orientation of a transposable element or promoter region so as to modulate gene expression of an adjacent gene (Wang et al., *Genetics* 120(4):875-885 (1988); Hayes, Annu. Rev. Genet. 37:3-29 (2003); in a diploid organism, deleting one allele resulting in loss of heterozygosity (Daigaku et al., *Mutation Research/Fundamental and Molecular Mechanisms of Mutagenesis* 600(1-2)177-183 (2006)); introducing nucleic acids that increase RNA degradation (Houseley et al., *Cell,* 136(4):763-776 (2009); or in bacteria, for example, introduction of a transfer-messenger RNA (tmRNA) tag, which can lead to RNA degradation and ribosomal stalling (Sunohara et al., *RNA* 10(3):378-386 (2004); and Sunohara et al., *J Biol. Chem.* 279:15368-15375 (2004)). At the translational level, attenuation can include: introducing rare codons to limit translation (Angov, *Biotechnol. J* 6(6):650-659 (2011)); introducing RNA interference molecules that block translation (Castel et al., *Nat. Rev. Genet.* 14(2):100-112 (2013); and Kawasaki et al., *Curr. Opin. Mol. Ther.* 7(2): 125-131 (2005); modifying regions outside the coding sequence, such as introducing secondary structure into an untranslated region (UTR) to block translation or reduce efficiency of translation (Ringner et al., *PLoS Comput. Biol.* 1(7):e72 (2005)); adding RNAase sites for rapid transcript degradation (Pasquinelli, *Nat. Rev. Genet.* 13(4):271-282 (2012); and Arraiano et al., *FEMS Microbiol. Rev.* 34(5): 883-932 (2010); introducing antisense RNA oligomers or antisense transcripts (Nashizawa et al., *Front. Biosci.* 17:938-958 (2012)); introducing RNA or peptide aptamers, ribozymes, aptazymes, riboswitches (Wieland et al., *Methods* 56(3):351-357 (2012); O'Sullivan, *Anal. Bioanal. Chem.* 372(1):44-48 (2002); and Lee et al., *Curr. Opin. Biotechnol.* 14(5):505-511 (2003)); or introducing translational regulatory elements involving RNA structure that can prevent or reduce translation that can be controlled by the presence or absence of small molecules (Araujo et al., Comparative and Functional Genomics, Article ID 475731, 8 pages (2012)). At the level of enzyme localization and/or longevity, enzyme attenuation can include: adding a degradation tag for faster protein turnover (Hochstrasser, *Annual Rev. Genet.* 30:405-439 (1996); and Yuan et al., *PLoS One* 8(4):e62529 (2013)); or adding a localization tag that results in the enzyme being secreted or localized to a subcellular compartment in a eukaryotic cell, where the enzyme would not be able to react with its normal substrate (Nakai et al. *Genomics* 14(4):897-911 (1992); and Russell et al., *J. Bact.* 189(21)7581-7585 (2007)). At the level of post-translational regulation, enzyme attenuation can include: increasing intracellular concentration of known inhibitors; or modifying post-translational modified sites (Mann et al., *Nature Biotech.* 21:255-261 (2003)). At the level of enzyme activity, enzyme attenuation can include: adding an endogenous or an exogenous inhibitor, such as an enzyme inhibitor, an antibiotic or a target-specific drug, to reduce enzyme activity; chelating a metal ion that is required for enzyme activity; or introducing a dominant negative mutation. The applicability of a technique for attenuation described above can depend upon whether a given host microbial organism is prokaryotic or eukaryotic, and it is understand that a determination of what is the appropriate technique for a given host can be readily made by one skilled in the art.

An expression vector or vectors can be constructed to include one or more exogenous protein-encoding nucleic acids as exemplified herein, operably linked to expression control sequences functional in the host organism. Expression vectors applicable for use in the microbial host organisms provided include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art.

The exogenous protein(s) can be co-expressed with one or more additional nucleic acids that may encode enzyme(s) useful for converting intermediates. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The term "exogenous" is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid can utilize either or both a heterologous or homologous encoding nucleic acid.

It is understood that when more than one exogenous nucleic acid is included in a microbial organism, the more than one exogenous nucleic acid refers to the referenced encoding nucleic acid or biosynthetic activity, as discussed above. It is further understood, as disclosed herein, that more than one exogenous nucleic acid can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein, such as an exogenous nucleic acid that expresses an exogenous protein of the disclosure, and one or more other enzymes that convert an intermediate generated from the methylotrophic pathway to a desired bioproduct.

In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

Exogenous enzyme-encoding nucleic acid sequences can be introduced stably or transiently into a host cell using techniques well known in the art including, but not limited to, conjugation, electroporation, chemical transformation, transduction, transfection, and ultrasound transformation. Optionally, for exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

The terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As discussed herein, a microbial organism can be described in terms of its inability or ability to utilize C1 compounds such as methanol as a source of energy and cellular carbon. A host cell in which exogenous enzymes are introduced to generate synthetic methylotrophy can be described as a "non-methylotrophic," that is, the host cell without engineering is unable to utilize a 1C carbon as an energy source. Microorganisms that are non-methylotrophic and that can be engineered with exogenous enzyme(s) of the disclosure include *E. coli* and other prokaryotic and eukaryotic organisms as described herein.

The term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments.

In some aspects a nucleic acid encoding an exogenous enzyme of the disclosure is introduced into a cell with a gene disruption. The term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions. The phenotypic effect of a gene disruption can be a null mutation, which can arise from many types of mutations including inactivating point mutations, entire gene deletions, and deletions of chromosomal segments or entire chromosomes. Specific antisense nucleic acid compounds and enzyme inhibitors, such as antibiotics, can also produce null mutant phenotype, therefore being equivalent to gene disruption.

A metabolic modification refers to a biochemical reaction that is altered from its naturally occurring state. Therefore, microorganisms may have genetic modifications to nucleic acids encoding metabolic polypeptides, or functional fragments thereof. Exemplary metabolic modifications are disclosed herein.

The microorganisms provided herein can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

A variety of microorganism may be suitable for incorporating one or more nucleic acid encoding protein(s) which allow the cell to have synthetic or enhanced methylotrophy. Such organisms include both prokaryotic and eukaryotic organisms including, but not limited to, bacteria, including archaea and eubacteria, and eukaryotes, including yeast, plant, insect, animal, and mammal, including human. Exemplary species are reported in U.S. Patent Pub No. 2014/

0058056 (Burgard et al.), which is incorporated herein by reference, and include, for example, *Escherichia coli, Saccharomyces cerevisiae, Saccharomyces kluyveri, Candida boidinii, Clostridium kluyveri, Clostridium acetobutylicum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pedicoccus pentosaceus, Zymomonas mobilis, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum*, marine gamma proteobacterium, butyrate-producing bacterium, *Nocardia iowensis, Nocardia farcinica, Streptomyces griseus, Schizosaccharomyces pombe, Geobacillus thermoglucosidasius, Salmonella typhimurium, Vibrio cholera, Heliobacter pylori, Nicotiana tabacum, Oryza sativa, Haloferax mediterranei, Agrobacterium tumefaciens, Achromobacter denitrificans, Fusobacterium nucleatum, Streptomyces clavuligenus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnificus, Selenomonas ruminantium, Vibrio parahaemolyticus, Archaeoglobus fulgidus, Haloarcula marismortui, Pyrobaculum aerophilum, Mycobacterium smegmatis MC2 155, Mycobacterium avium* subsp. *paratuberculosis* K-10, *Mycobacterium marinum* M, *Tsukamurella paurometabola* DSM 20162, *Cyanobium* PCC7001, *Dictyostelium discoideum* AX4, as well as other exemplary species disclosed herein or available as source organisms for corresponding genes.

In certain embodiments, suitable organisms include *Acinetobacter baumannii* Naval-82, *Acinetobacter* sp. ADP1, *Acinetobacter* sp. strain M-1, *Actinobacillus succinogenes* 130Z, *Allochromatium vinosum* DSM 180, *Amycolatopsis methanolica, Arabidopsis thaliana, Atopobium parvulum* DSM 20469, *Azotobacter vinelandii* DJ, *Bacillus alcalophilus* ATCC 27647, *Bacillus azotoformans* LMG 9581, *Bacillus coagulans* 36D1, *Bacillus megaterium, Bacillus methanolicus* MGA3, *Bacillus methanolicus* PB1, *Bacillus methanolicus* PB-1, *Bacillus selenitireducens* MLS10, *Bacillus smithii, Bacillus subtilis, Burkholderia cenocepacia, Burkholderia cepacia, Burkholderia multivorans, Burkholderia pyrrocinia, Burkholderia stabilis, Burkholderia thailandensis* E264, *Burkholderiales bacterium* Joshi_001, Butyrate-producing bacterium L2-50, *Campylobacter jejuni, Candida albicans, Candida boidinii, Candida methylica, Carboxydothermus hydrogenoformans, Carboxydothermus hydrogenoformans* Z-2901, *Caulobacter* sp. AP07, *Chloroflexus aggregans* DSM 9485, *Chloroflexus aurantiacus* J-10-fl, *Citrobacter freundii, Citrobacter koseri* ATCC BAA-895, *Citrobacter youngae, Clostridium, Clostridium acetobutylicum, Clostridium acetobutylicum* ATCC 824, *Clostridium acidurici, Clostridium aminobutyricum, Clostridium asparagiforme* DSM 15981, *Clostridium beijerinckii, Clostridium beijerinckii* NCIMB 8052, *Clostridium bolteae* ATCC BAA-613, *Clostridium carboxidivorans* P7, *Clostridium cellulovorans* 743B, *Clostridium difficile, Clostridium hiranonis* DSM 13275, *Clostridium hylemonae* DSM 15053, *Clostridium kluyveri, Clostridium kluyveri* DSM 555, *Clostridium ljungdahli, Clostridium ljungdahlii* DSM 13528, *Clostridium methylpentosum* DSM 5476, *Clostridium pasteurianum, Clostridium pasteurianum* DSM 525, *Clostridium perfringens, Clostridium perfringens* ATCC 13124, *Clostridium perfringens* str. 13, *Clostridium phytofermentans* ISDg, *Clostridium saccharobutylicum, Clostridium saccharoperbutylacetonicum, Clostridium saccharoperbutylacetonicum* N1-4, *Clostridium tetani, Corynebacterium glutamicum* ATCC 14067, *Corynebacterium glutamicum* R, *Corynebacterium* sp. U-96, *Corynebacterium variabile, Cupriavidus necator* N-1, *Cyanobium* PCC7001, *Desulfatibacillum alkenivorans* AK-01, *Desulfitobacterium hafniense, Desulfitobacterium metallireducens* DSM 15288, *Desulfotomaculum reducens* MI-1, *Desulfovibrio africanus* str. Walvis Bay, *Desulfovibrio fructosovorans* JJ, *Desulfovibrio vulgaris* str. Hildenborough, *Desulfovibrio vulgaris* str. Miyazaki F, *Dictyostelium discoideum* AX4, *Escherichia coli, Escherichia coli* K-12, *Escherichia coli* K-12 MG1655, *Eubacterium hallii* DSM 3353, *Flavobacterium frigoris, Fusobacterium nucleatum* subsp. *polymorphum* ATCC 10953, *Geobacillus* sp. Y4.1MC1, *Geobacillus themodenitrificans* NG80-2, *Geobacter bemidjiensis* Bem, *Geobacter sulfurreducens, Geobacter sulfurreducens* PCA, *Geobacillus stearothermophilus* DSM 2334, *Haemophilus influenzae, Helicobacter pylori, Hydrogenobacter thermophilus, Hydrogenobacter thermophilus* TK-6, *Hyphomicrobium denitrificans* ATCC 51888, *Hyphomicrobium zavarzinii, Klebsiella pneumoniae, Klebsiella pneumoniae* subsp. *pneumoniae* MGH 78578, *Lactobacillus brevis* ATCC 367, *Leuconostoc mesenteroides, Lysinibacillus fusiformis, Lysinibacillus sphaericus, Mesorhizobium loti* MAFF303099, *Metallosphaera sedula, Methanosarcina acetivorans, Methanosarcina acetivorans* C2A, *Methanosarcina barkeri, Methanosarcina mazei* Tuc01, *Methylobacter marinus, Methylobacterium extorquens, Methylobacterium extorquens* AM1, *Methylococcus capsulatas, Methylomonas aminofaciens, Moorella thermoacetica, Mycobacter* sp. strain JC1 DSM 3803, *Mycobacterium avium* subsp. *paratuberculosis* K-10, *Mycobacterium bovis* BCG, *Mycobacterium gastri, Mycobacterium marinum* M, *Mycobacterium smegmatis, Mycobacterium smegmatis* MC2 155, *Nitrosopumilus salaria* BD31, *Nitrososphaera gargensis* Ga9.2, *Nocardia farcinica* IFM 10152, *Nocardia iowensis* (sp. NRRL 5646), *Nostoc* sp. PCC 7120, *Ogataea angusta, Ogataea parapolymorpha* DL-1 (*Hansenula polymorpha* DL-1), *Paenibacillus peoriae* KCTC 3763, *Paracoccus denitrificans, Penicillium chrysogenum, Photobacterium*

*profundum* 3TCK, *Phytofermentans* ISDg, *Pichia pastoris*, *Picrophilus torridus* DSM9790, *Porphyromonas gingivalis*, *Porphyromonas gingivalis* W83, *Pseudomonas aeruginosa* PA01, *Pseudomonas denitrificans*, *Pseudomonas knackmussii*, *Pseudomonas putida*, *Pseudomonas* sp, *Pseudomonas syringae* pv. *syringae* B728a, *Pyrobaculum islandicum* DSM 4184, *Pyrococcus abyssi*, *Pyrococcus furiosus*, *Pyrococcus horikoshii* OT3, *Ralstonia eutropha*, *Ralstonia eutropha* H16, *Rhodobacter capsulatus*, *Rhodobacter sphaeroides*, *Rhodobacter sphaeroides* ATCC 17025, *Rhodopseudomonas palustris*, *Rhodopseudomonas palustris* CGA009, *Rhodopseudomonas palustris* DX-1, *Rhodospirillum rubrum*, *Rhodospirillum rubrum* ATCC 11170, *Ruminococcus obeum* ATCC 29174, *Saccharomyces cerevisiae*, *Saccharomyces cerevisiae* S288c, *Salmonella enterica*, *Salmonella enterica* subsp. *enterica* serovar *Typhimurium* str. LT2, *Salmonella enterica typhimurium*, *Salmonella typhimurium*, *Schizosaccharomyces pombe*, *Sebaldella termitidis* ATCC 33386, *Shewanella oneidensis* MR-4, *Sinorhizobium meliloti* 1021, *Streptomyces coelicolor*, *Streptomyces griseus* subsp. *griseus* NBRC 13350, *Sulfolobus acidocalarius*, *Sulfolobus solfataricus* P-2, *Synechocystis* str. PCC 6803, *Syntrophobacter fumaroxidans*, *Thauera aromatica*, *Thermoanaerobacter* sp. X514, *Thermococcus kodakaraensis*, *Thermococcus litoralis*, *Thermoplasma acidophilum*, *Thermoproteus neutrophilus*, *Thermotoga maritima*, *Thiocapsa roseopersicina*, *Tolumonas auensis* DSM 9187, *Trichomonas vaginalis* G3, *Tsukamurella paurometabola* DSM 20162, *Vibrio harveyi* ATCC BAA-1116, *Xanthobacter autotrophicus* Py2, and *Yersinia intermedia*.

Therefore, an engineered cell having synthetic or enhanced methylotrophy including (a) exogenous enzyme A that (ai) is capable of converting glyceraldehyde 3-phosphate (G3P) to 3-phosphoglycerate (3PG), that (aii) has at least 50% sequence identity to SEQ ID NO:1 (*B. methanolicus* gapN), wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), can include one or more further genetic alterations, such as inserted transgenes, deletions, attenuation, mutations, etc., desired to increase levels of one or more intermediates or a product thereof, and include those genetic modifications as described in U.S. Patent Pub No. 2014/0058056 (Burgard et al.), and include those genetic modifications as described in WO2009/135074 (Burk et al.), the disclosures of which are incorporated herein by reference.

Of particular interest are target products obtained using pyruvate and acetyl-CoA as entry point or precursor to its product pathway(s), in part because the methanol metabolic pathway using the novel enzymes enables fixing the carbon of methanol into pathways to pyruvate and acetyl-CoA. Target products include (a) 1,4-butanediol and intermediates thereto, such as 4-hydroxybutanoic acid (4-hydroxybutanoate, 4-hydroxybutyrate, 4-HB), (b) butadiene and intermediates thereto, such as 1,4-butanediol, 1,3-butanediol, crotyl alcohol, 3-buten-2-ol (methyl vinyl carbinol) and 3-buten-1-ol, (c) 1,3-butanediol and intermediates thereto, such as 2,4-pentadienoate, crotyl alcohol or 3-buten-1-ol, (d) adipate, 6-aminocaproic acid, caprolactam, hexamethylenediamine and levulinic acid and their intermediates, e.g. 4-aminobutyryl-CoA, (e) methacrylic acid (2-methyl-2-propenoic acid) and its esters known collectively as methacrylates, such as methyl methacrylate, methyl methacrylate, 3-hydroxyisobutyrate and/or 2-hydroxyisobutyrate and their intermediates, (f) 1,2-propanediol (propylene glycol), n-propanol, 1,3-propanediol and glycerol, and their intermediates and (g) succinic acid and intermediates thereto.

In some aspects, an engineered cell having synthetic or enhanced methylotrophy including (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), is used with a product pathway for increased levels of 1,4-butanediol (BDO) or hydroxylbutyrate (4-HB). Those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

With the complete genome sequence available for now more than 550 species (with more than half of these available on public databases such as the NCBI), including 395 microorganism genomes and a variety of yeast, fungi, plant, and mammalian genomes, the identification of genes encoding the requisite BDO or 4-HB biosynthetic pathway as well as other known biosynthetic pathways for 1,3-butanediol (13BDO), butadiene, 6-amino caproic acid (6ACA), hexamethylenediamine (HMDA), adipic acid or derivatives thereof, croytl alcohol, methyl vinyl carbinol, 3-buten-1-ol, succinic acid or derivatives thereof, n-propanol, isopropanol, propylene, methacrylic acid or derivatives thereof, methanol metabolic and/or formaldehyde assimilation activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of various target products including 1,3-butanediol (13BDO), 1, 4-butanediol (BDO), 4-HB, butadiene, 6-amino caproic acid (6ACA), hexamethyldiamine (HMDA), adipic acid or derivatives thereof, croytl alcohol, methyl vinyl carbinol, 3-buten-1-ol, succinic acid or derivatives thereof, n-propanol, isopropanol, propylene, methacrylic acid or derivatives thereof, metabolism of methanol and/or assimilation of formaldehyde described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

Exemplary alcohol metabolic pathway gene(s), such as described in U.S. Patent Pub No. 2014/0058056, encode a protein selected from the group consisting of: a formate dehydrogenase, a formaldehyde activating enzyme, a formaldehyde dehydrogenase, a S-(hydroxymethyl)glutathione synthase, a glutathione-dependent formaldehyde dehydrogenase, a S-formylglutathione hydrolase, a formate hydrogen lyase, and a hydrogenase, any or more can be coexpressed with (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), in the engineered cell.

Other exemplary alcohol metabolic pathway gene(s), such as described in U.S. Patent Pub No. 2014/0058056, encode an alcohol metabolic pathway gene(s) encoding a protein selected from the group consisting of a succinyl-CoA reductase (aldehyde forming), a 4-hydroxybutyrate (4-HB) dehydrogenase, a 4-HB kinase, a phosphotrans-4-hydroxybutyrylase, a 4-hydroxybutyryl-CoA reductase (aldehyde forming), a 1,4-butanediol dehydrogenase; a succinate reductase, a succinyl-CoA reductase (alcohol forming), 4-hydroxybutyryl-CoA transferase, a 4-hydroxybutyryl-CoA synthetase, a 4-HB reductase, and a 4-hydroxybutyryl-CoA reductase (alcohol forming), a succinyl-CoA transferase, and a succinyl-CoA synthetase, any or more can be co-expressed with (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), in the engineered cell.

1,4-butanediol and intermediates thereto, such as 4-hydroxybutanoic acid (4-hydroxybutanoate, 4-hydroxybutyrate, 4-HB), are target products that can be made by co-expressing the (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), described herein with a product pathway described herein as well as in the following documents. Suitable product pathways and enzymes, methods for screening and methods for isolating are found herein as well as in the following documents, incorporated herein by reference: WO2008115840A2 published 25 Sep. 2008 entitled "Compositions and Methods for the Biosynthesis of 1, 4-Butanediol and Its Precursors"; WO2010141780A1 published 9 Dec. 2010 entitled "Process of Separating Components of A Fermentation Broth"; WO2010141920A2 published 9 Dec. 2010 entitled "Microorganisms for the Production of 1, 4-Butanediol and Related Methods"; WO2010030711A2 published 18 Mar. 2010 entitled "Microorganisms for the Production of 1, 4-Butanediol"; WO2010071697A1 published 24 Jun. 2010 entitled "Microorganisms and Methods for Conversion of Syngas and Other Carbon Sources to Useful Products"; WO2009094485A1 published 30 Jul. 2009 entitled "Methods and Organisms for Utilizing Synthesis Gas or Other Gaseous Carbon Sources and Methanol"; WO2009023493A1 published 19 Feb. 2009 entitled "Methods and Organisms for the Growth-Coupled Production of 1,4-Butanediol"; WO2008115840A2 published 25 Sep. 2008 entitled "Compositions and Methods for the Biosynthesis of 1,4-Butanediol and Its Precursors"; and International Application No. PCT/US13/56725 filed 27 Aug. 2013 entitled "Microorganisms an Methods for Enhancing the Availability of Reducing Equivalents in the Presence of Methanol, and for Producing 1,4-Butanediol Related Thereto".

Butadiene and intermediates thereto, such as 1,4-butanediol, 1,3-butanediol, crotyl alcohol, 3-buten-2-ol (methyl vinyl carbinol) and 3-buten-1-ol, are target products that can be made by co-expressing the (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), described herein with a product pathway described in the following documents. In addition to direct fermentation to produce butadiene, 1,3-butanediol, 1,4-butanediol, crotyl alcohol, 3-buten-2-ol (methyl vinyl carbinol) and 3-buten-1-ol can be separated, purified (for any use), and then dehydrated to butadiene in a second step involving metal-based catalysis. Suitable product pathways and enzymes, methods for screening and methods for isolating are found in the following documents, incorporated herein by reference: WO2011140171A2 published 10 Nov. 2011 entitled "Microorganisms and Methods for the Biosynthesis of Butadiene"; WO2012018624A2 published 9 Feb. 2012 entitled "Microorganisms and Methods for the Biosynthesis of Aromatics, 2,4-Pentadienoate and 1,3-Butadiene"; WO2011140171A2 published 10 Nov. 2011 entitled "Microorganisms and Methods for the Biosynthesis of Butadiene"; WO2013040383A1 published 21 Mar. 2013 entitled "Microorganisms and Methods for Producing Alkenes"; WO2012177710A1 published 27 Dec. 2012 entitled "Microorganisms for Producing Butadiene and Methods Related thereto"; WO2012106516A1 published 9 Aug. 2012 entitled "Microorganisms and Methods for the Biosynthesis of Butadiene"; WO2013028519A1 published 28 Feb. 2013 entitled "Microorganisms and Methods for Producing 2,4-Pentadienoate, Butadiene, Propylene, 1,3-Butanediol and Related Alcohols"; and U.S. Patent Pub No. 2015/0050708.

1,3-butanediol and intermediates thereto, such as 2,4-pentadienoate, crotyl alcohol or 3-buten-1-ol, are target products that can be made by co-expressing the (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), described herein with a product pathway described herein as well as in the following documents. Suitable product pathways and enzymes, methods for screening and methods for isolating are found herein as well as in the following documents, incorporated herein by reference: WO2011071682A1 published 16 Jun. 2011 entitled "Methods and Organisms for Converting Synthesis Gas or Other Gaseous Carbon Sources and Methanol to 1, 3-Butanediol"; WO2011031897A published 17 Mar. 2011 entitled "Microorganisms and Methods for the Co-Production of Isopropanol with Primary Alcohols, Diols and Acids"; WO2010127319A2 published 4 Nov. 2010 entitled "Organisms for the Production of 1,3-Butanediol"; WO2013071226A1 published 16 May 2013 entitled "Eukaryotic Organisms and Methods for Increasing the Availability of Cytosolic Acetyl-CoA, and for Producing 1,3-Butanediol"; WO2013028519A1 published 28 Feb.

2013 entitled "Microorganisms and Methods for Producing 2,4-Pentadienoate, Butadiene, Propylene, 1,3-Butanediol and Related Alcohols"; WO2013036764A1 published 14 Mar. 2013 entitled "Eukaryotic Organisms and Methods for Producing 1,3-Butanediol"; WO2013012975A1 published 24 Jan. 2013 entitled "Methods for Increasing Product Yields"; WO2012177619A2 published 27 Dec. 2012 entitled "Microorganisms for Producing 1, 3-Butanediol and Methods Related Thereto"; and U.S. Patent Pub No. 2015/0050708.

Adipate, 6-aminocaproic acid, caprolactam, hexamethylenediamine and levulinic acid, and their intermediates, e.g. 4-aminobutyryl-CoA, are target products, useful for example for making nylon polymers, that can be made by co-expressing the (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), described herein with a product pathway described herein as well as in the following documents. Suitable product pathways and enzymes, methods for screening and methods for isolating are found herein as well as in the following documents, incorporated herein by reference: WO2010129936A1 published 11 Nov. 2010 entitled "Microorganisms and Methods for the Biosynthesis of Adipate, Hexamethylenediamine and 6-Aminocaproic Acid"; WO2013012975A1 published 24 Jan. 2013 entitled "Methods for Increasing Product Yields"; WO2012177721A1 published 27 Dec. 2012 entitled "Microorganisms for Producing 6-Aminocaproic Acid"; WO2012099621A1 published 26 Jul. 2012 entitled "Methods for Increasing Product Yields"; and U.S. Patent Pub No. 2014/0329916 entitled "Microorganisms an Methods for Enhancing the Availability of Reducing Equivalents in the Presence of Methanol, and for Producing Adipate, 6-Aminocaproate, Hexamethylenediamine or Caprolactam Related Thereto".

Methacrylic acid (2-methyl-2-propenoic acid; used in the preparation of its esters known collectively as methacrylates, such as methyl methacrylate, which is used most notably in the manufacture of polymers), methacrylate ester such as methyl methacrylate, 3-hydroxyisobutyrate and/or 2-hydroxyisobutyrate and their intermediates are target products, useful for example for making polymers, that can be made by co-expressing the (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), described herein with a product pathway described herein as well as in the following documents. Suitable product pathways and enzymes, methods for screening and methods for isolating are found herein as well as in the following documents, incorporated herein by reference: WO2012135789A2 published 4 Oct. 2012 entitled "Microorganisms for Producing Methacrylic Acid and Methacrylate Esters and Methods Related Thereto"; WO2009135074A2 published 5 Nov. 2009 entitled "Microorganisms for the Production of Methacrylic Acid"; and U.S. Patent Pub No. 2014/0288254 entitled "Microorganisms an Methods for Enhancing the Availability of Reducing Equivalents in the Presence of Methanol, and for Producing 3-Hydroxyisobutyate or Methacrylic Acid Related Thereto".

Figure 8:
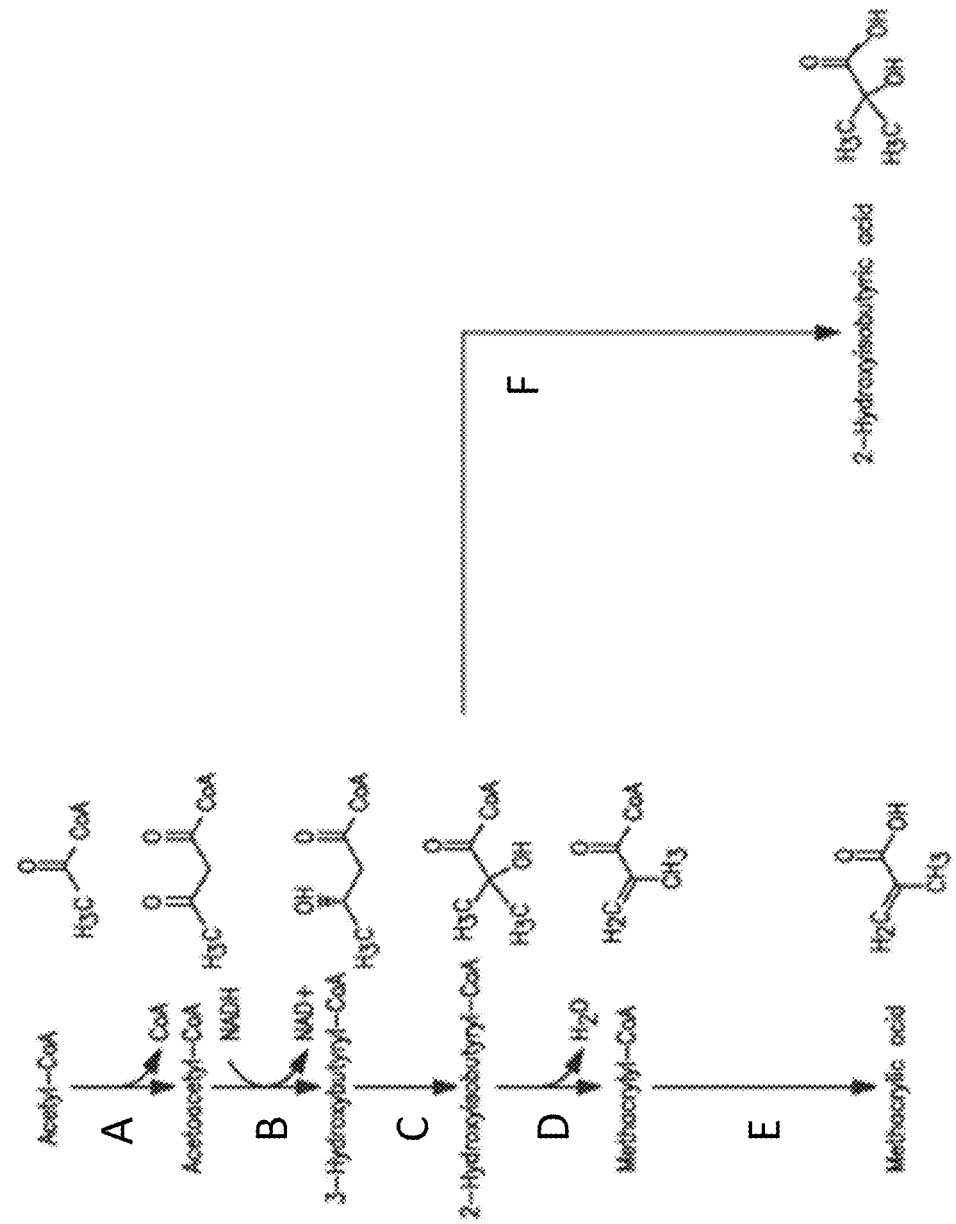
FIG. 8 illustrates exemplary target product pathways, 2-hydroxyisobutyrate and methacrylic acid from acetyl-CoA/methyl-methacrylate (MMA), which can exploit acetyl-CoA available from methanol assimilation as disclosed herein, 2-Hydroxyisobutyrate and methacrylic acid production can be carried out by the following enzymes: A) acetyl-CoA:acetyl-CoA acyltransferase, B) acetoacetyl-CoA reductase (ketone reducing), C) 3-hydroxybutyrl-CoA mutase, D) 2-hydroxyisobutyryl-CoA dehydratase, E) methacrylyl-CoA synthetase, hydrolase, or transferase, F) 2-hydroxyisobutyryl-CoA synthetase, hydrolase, or transferase.

FIG. 8 illustrates exemplary target product pathways, 2-hydroxyisobutyrate and methacrylic acid from acetyl-CoA/methyl-methacrylate (MMA), which can exploit acetyl-CoA available from methanol assimilation as disclosed herein, 2-Hydroxyisobutyrate and methacrylic acid production can be carried out by the following enzymes: A) acetyl-CoA:acetyl-CoA acyltransferase, B) acetoacetyl-CoA reductase (ketone reducing), C) 3-hydroxybutyrl-CoA mutase, D) 2-hydroxyisobutyryl-CoA dehydratase, E) methacrylyl-CoA synthetase, hydrolase, or transferase, F) 2-hydroxyisobutyryl-CoA synthetase, hydrolase, or transferase.

1,2-propanediol (propylene glycol), n-propanol, 1,3-propanediol and glycerol, and their intermediates are target products, useful for example for making polymers, that can be made by co-expressing the (a) exogenous enzyme A that (ai) is capable of converting G3P to 3PG, that (aii) has at least 50% sequence identity to SEQ ID NO: 1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), described herein with a product pathway described herein as well as in the following documents. Suitable product pathways and enzymes, methods for screening and methods for isolating are found herein as well as in the following documents, incorporated herein by reference: WO2009111672A1 published 9 Nov. 2009 entitled "Primary Alcohol Producing Organisms"; WO2011031897A1 17 Mar. 2011 entitled "Microorganisms and Methods for the Co-Production of Isopropanol with Primary Alcohols, Diols and Acids"; WO2012177599A2 published 27 Dec. 2012 entitled 'Microorganisms for Producing N-Propanol 1, 3-Propanediol, 1, 2-Propanediol or Glycerol and Methods Related Thereto"; and U.S. Patent Pub No. 2014/0302575 entitled "Microorganisms an Methods for Enhancing the Availability of Reducing Equivalents in the Presence of Methanol, and for Producing 1,2-Propanediol, n-Propanol, 1,3-Propanediol, or Glycerol Related Thereto".

Succinic acid and intermediates thereto (useful to produce products including polymers, e.g. PBS, 1,4-butanediol, tetrahydrofuran, pyrrolidone, solvents, paints, deicers, plastics, fuel additives, fabrics, carpets, pigments, and detergents) are target products that can be made by co-expressing the (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), described herein with a product pathway described herein as well as in the following documents. Suitable product pathways and enzymes, methods for screening and methods for isolating are found herein as well as in the following documents, incorporated herein by reference: EP1937821A2 published 2 Jul. 2008 entitled "Methods and Organisms for the Growth-Coupled Production of Succinate"; and U.S. Patent Pub No. 2014/0302575 entitled "Microorganisms and Methods for Enhancing the Availability of Reducing Equivalents in the Presence of Methanol, and for Producing Succinate Related Thereto".

Target products obtained from, and product pathways suitable for producing in, host cells co-expressing the (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), described herein include the following. Butadiene and intermediates thereto, such as 1,4-butanediol, 1,3-butanediol, crotyl alcohol, 3-buten-2-ol (methyl vinyl carbinol) and 3-buten-1-ol, are target products that can be made by co-expressing the expressing the (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), with a product pathway described in the following documents. In addition to direct fermentation to produce butadiene, 1,3-butanediol, 1,4-butanediol, crotyl alcohol, 3-buten-2-ol (methyl vinyl carbinol) and 3-buten-1-ol can be separated, purified (for any use), and then dehydrated to butadiene in a second step involving metal-based catalysis. Suitable product pathways and enzymes, methods for screening and methods for isolating are found in: WO2011140171A2 published 10 Nov. 2011 entitled "Microorganisms and Methods for the Biosynthesis of Butadiene"; WO2012018624A2 published 9 Feb. 2012 entitled "Microorganisms and Methods for the Biosynthesis of Aromatics, 2, 4-Pentadienoate and 1, 3-Butadiene"; WO2011140171A2 published 10 Nov. 2011 entitled "Microorganisms and Methods for the Biosynthesis of Butadiene"; WO2013040383A1 published 21 Mar. 2013 entitled "Microorganisms and Methods for Producing Alkenes"; WO2012177710A1 published 27 Dec. 2012 entitled "Microorganisms for Producing Butadiene and Methods Related thereto"; WO2012106516A1 published 9 Aug. 2012 entitled "Microorganisms and Methods for the Biosynthesis of Butadiene"; WO2013028519A1 published 28 Feb. 2013 entitled "Microorganisms and Methods for Producing 2,4-Pentadienoate, Butadiene, Propylene, 1,3-Butanediol and Related Alcohols"; and U.S. Patent Pub No. 2015/0050708.

Figure 7:
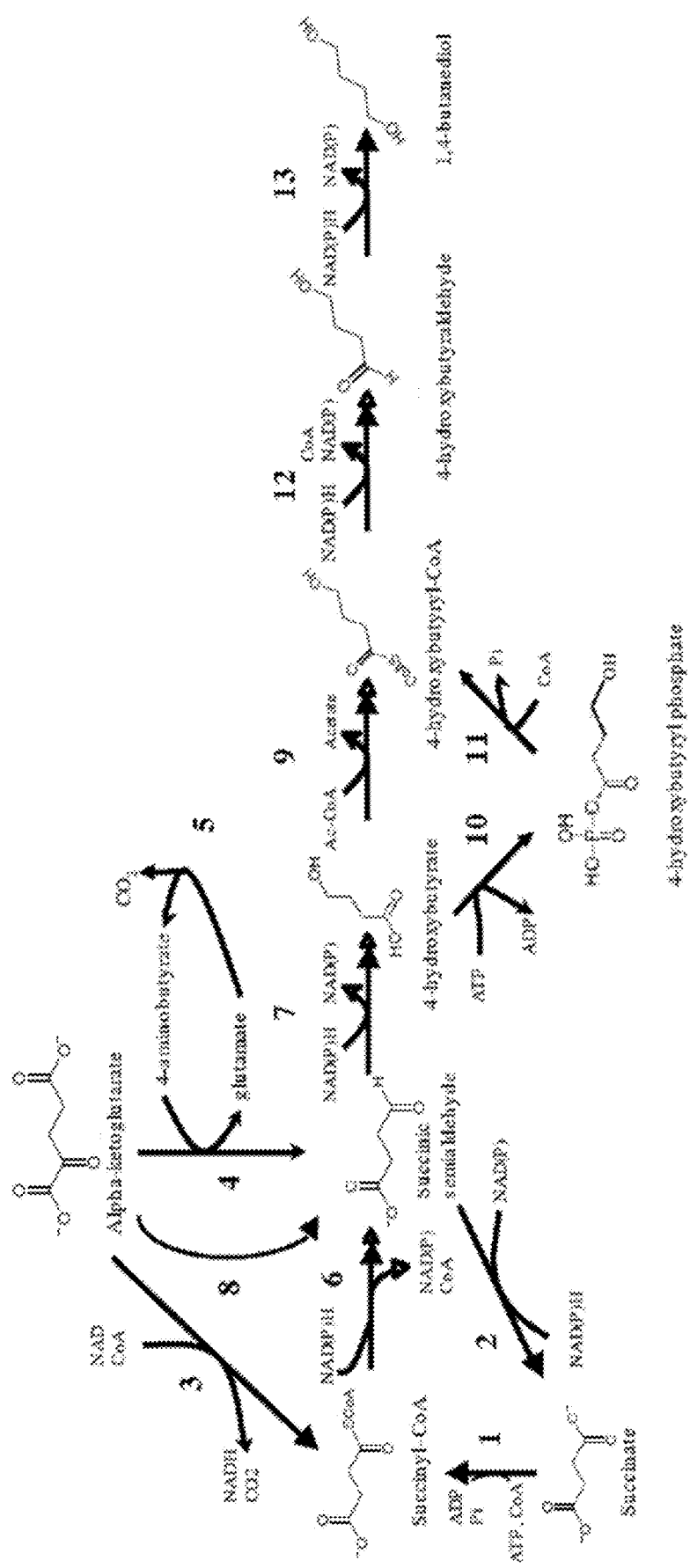
FIG. 7 illustrates an exemplary target product pathway, a 1,4-BDO product pathway, which can exploit acetyl-CoA available from methanol assimilation as disclosed herein. Enzymes catalyzing the biosynthetic reactions are: (1) succinyl-CoA synthetase; (2) CoA-independent succinic semialdehyde dehydrogenase; (3) α-ketoglutarate dehydrogenase; (4) glutamate:succinate semialdehyde transaminase; (5) glutamate decarboxylase; (6) CoA-dependent succinic semialdehyde dehydrogenase; (7) 4-hydroxybutanoate dehydrogenase; (8) α-ketoglutarate decarboxylase; (9) 4-hydroxybutyryl CoA: acetyl-CoA transferase; (10) butyrate kinase; (11) phosphotransbutyrylase; (12) aldehyde dehydrogenase; (13) alcohol dehydrogenase.

Enzymes, genes and methods for engineering pathways from acetyl-CoA, succinate and succinyl-CoA to various products, such as BDO, into a microorganism, are now known in the art (see, e.g., U.S. Publ. No. 2011/0201089). A set of BDO pathway enzymes represents a group of enzymes that can convert succinate or alpha-ketoglutarate to BDO as shown in FIG. 7. For example, BDO can be produced from succinyl-CoA via previously disclosed pathways (see for example, Burk et al., WO 2008/115840). FIG. 7 presents exemplary pathways which can use the primary metabolites, e.g. acetyl-CoA, made available by the use of methanol as a carbon source as described herein. In FIG. 7, the organism comprises at least one exogenous nucleic acid encoding a BDO pathway enzyme expressed in a sufficient amount to produce BDO. In certain embodiments, the BDO pathway enzyme is selected from the group consisting of (1) a succinyl-CoA synthetase; (2) a CoA-independent succinic semialdehyde dehydrogenase; (3) a α-ketoglutarate dehydrogenase; (4) a glutamate:succinate semialdehyde transaminase; (5) a glutamate decarboxylase; (6) a CoA-dependent succinic semialdehyde dehydrogenase; (7) a 4-hydroxybutanoate dehydrogenase; (8) a α-ketoglutarate decarboxylase; (9) a 4-hydroxybutyryl CoA:acetyl-CoA transferase; (10) a butyrate kinase; (11) a phosphotransbutyrylase; (12) an aldehyde dehydrogenase; and (13) an alcohol dehydrogenase. Preferred pathways include those from alpha-ketoglutarate, e.g. steps 8, 7, 9, 12 and 13; steps 3, 6, 7, 9, 12 and 13; and steps 1, 6, 7, 9, 12, 13. In an alternative, a single protein can comprise the activities of steps 12 and 13. Specific enzymes, classes of enzymes and sources of enzymes and their genes can be found in WO2008115840, for example.

In some embodiments, the disclosure provides organisms comprising (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), and that are engineered to improve the availability of reducing equivalents, which can be used for the production of target product molecules. It will be recognized by one skilled in the art that any product molecule that utilizes reducing equivalents in its production can exhibit enhanced production through other biosynthetic pathways.

In numerous engineered pathways, realization of maximum product yields based on carbohydrate feedstock is hampered by insufficient reducing equivalents or by loss of reducing equivalents to byproducts. Methanol is a relatively inexpensive organic feedstock that can be used to generate reducing equivalents by using the (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), and one or more metabolic enzymes. The reducing equivalents produced by the metabolism of methanol can then be used to power the glucose to BDO production pathways, for example, as shown in FIG. 7.

FIG. 7 presents exemplary pathways which can use the primary metabolites, e.g. acetyl-CoA, made available by the use of methanol as a carbon source as described herein. In FIG. 7, the organism comprises at least one exogenous nucleic acid encoding a BDO pathway enzyme expressed in a sufficient amount to produce BDO. In certain embodiments, the BDO pathway enzyme is selected from the group consisting of (1) a succinyl-CoA synthetase; (2) a CoA-independent succinic semialdehyde dehydrogenase; (3) a α-ketoglutarate dehydrogenase; (4) a glutamate:succinate semialdehyde transaminase; (5) a glutamate decarboxylase; (6) a CoA-dependent succinic semialdehyde dehydrogenase; (7) a 4-hydroxybutanoate dehydrogenase; (8) a α-ketoglutarate decarboxylase; (9) a 4-hydroxybutyryl CoA:acetyl-CoA transferase; (10) a butyrate kinase; (11) a phosphotransbutyrylase; (12) an aldehyde dehydrogenase; and (13) an alcohol dehydrogenase. Preferred pathways include those from alpha-ketoglutarate, e.g. steps 8, 7, 9, 12 and 13; steps 3, 6, 7, 9, 12 and 13; and steps 1, 6, 7, 9, 12, 13. In an alternative, a single protein can comprise the activities of steps 12 and 13. Specific enzymes, classes of enzymes and sources of enzymes and their genes can be found in WO2008115840A2, for example.

Enzymes, genes and methods for engineering pathways from succinate and succinyl-CoA to various products, such as BDO, into a microorganism, are now known in the art (see, e.g., U.S. Publ. No. 2011/0201089). A set of BDO pathway enzyme s represents a group of enzymes that can convert succinate or alpha-ketoglutarate to BDO as shown in FIG. 7. The additional reducing equivalents obtained from the MeDH pathway, as disclosed herein, improve the yields of all these products when utilizing carbohydrate-based feedstock. For example, BDO can be produced from succinyl-CoA via previously disclosed pathways (see for example, Burk et al., WO 2008/115840).

In other embodiments, the organism having (a) exogenous enzyme A that (ai) is capable of converting G3P to 3PG, that (aii) has at least 50% sequence identity to SEQ ID NO: 1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), either alone or in combination with a BDO or a methacrylic acid pathway, pathway, as provided herein, may further comprise a second formaldehyde assimilation pathway (FAP). The second FAP can also utilize formaldehyde, for example, formaldehyde that not utilized by the primary pathway, in the formation of intermediates of certain central metabolic pathways that can be used, for example, in the formation of biomass.

With reference to FIG. 4, in the second formaldehyde assimilation pathway, the organism comprises at least one exogenous nucleic acid encoding a formaldehyde assimilation pathway enzyme that is different than the gapN, hexulose-6-phosphate synthase, 6-phospho-3-hexuloisomerase, and phosphoketolase proteins. Enzymes of the second formaldehyde assimilation pathway can be expressed in a sufficient amount to produce an intermediate of glycolysis and/or a metabolic pathway that can be used in the formation of biomass. In one embodiment, the second formaldehyde assimilation pathway enzyme is expressed in a sufficient amount to produce an intermediate of glycolysis. In another embodiment, the second formaldehyde assimilation pathway enzyme is expressed in a sufficient amount to produce an intermediate of a metabolic pathway that can be used in the formation of biomass. In some of the embodiments, the second formaldehyde assimilation pathway comprises a dihydroxyacetone (DHA) synthase or a DHA kinase. The preferred DHA pathway is DHA Route 1 in FIG. 4, which is a combination of DHA (dihydroxyacetone) synthase, e.g. EC 2.2.1.3 (Step 6) and F6P (fructose-6-phosphate) aldolase (Step 7). In one embodiment, the intermediate is a DHA, a DHA phosphate, or a combination thereof. In certain embodiments, the organism comprises two exogenous nucleic acids, each encoding a second formaldehyde assimilation pathway enzyme.

In addition to engineered microbial cell having at (a) exogenous enzyme A that (ai) is capable of converting G3P to 3PG, that (aii) has at least 50% sequence identity to SEQ ID NO: 1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), the cell can also possess a pathway that proceeds through dihydroxyacetone (DHA). Both the enzyme of the RuMP pathway and the DHA pathway can be for the detoxification and assimilation of formaldehyde. As shown in FIG. 4, a transketolase first transfers a glycoaldehyde group from xylulose-5-phosphate to formaldehyde (Step 6, FIG. 4), resulting in the formation of DHA and G3P, which is an intermediate in glycolysis. The DHA obtained from DHA synthase is then further phosphorylated to form DHA phosphate (DHAP) by a DHA kinase. DHAP can be assimilated into glycolysis and several other pathways. Alternatively, DHA and G3P can be converted by fructose-6-phosphate aldolase to form fructose-6-phosphate (F6P) (FIG. 4, step 7).

In some embodiments, in addition to the cell having at least (a) exogenous enzyme A that (ai) is capable of converting G3P to 3PG, that (aii) has at least 50% sequence identity to SEQ ID NO:1, wherein enzyme A is capable of reducing NADP to NADPH, or (aiii) a fructose-1,6-bisphosphatase, or (ai) and (aiii), or or (aii) and (aiii); and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), the cell can also possess a pathway that proceeds through hexose-6-phosphate (H6P) as depicted in FIG. 4. The pathway that proceeds through hexose-6-phosphate (H6P) can optionally use MeDH. For example, an engineered cell of the disclosure can include a MeDH enzyme of the DHA pathway and a MeDH enzyme of the RuMP pathway, which can be for the detoxification and assimilation of formaldehyde.

Those skilled in the art will understand that an organism can be engineered that secretes the biosynthesized compounds when grown on a carbon source such as a methanol alone or combined with other carbohydrates. Such compounds include, for example, methacrylic acid, BDO, and any of the intermediate metabolites in the methacrylic acid or BDO pathways. All that is required is to engineer in one or more of the required enzyme or protein activities to achieve biosynthesis of the desired compound or intermediate including, for example, inclusion of some or all of the methacrylic acid or BDO biosynthetic pathways. Accordingly, provided herein is an organism that produces and/or secretes methacrylic acid or BDO when grown on a carbohydrate or other carbon source and produces and/or secretes any of the intermediate metabolites shown in the product pathways when grown on a carbohydrate or other carbon source. The methacrylic acid or BDO producing microbial organisms provided herein can initiate synthesis from an intermediate. The same holds true for intermediates in the formaldehyde assimilation.

In one embodiment, the carbon source is methanol or formate. In certain embodiments, methanol is used as a carbon source. In other embodiments, formate is used as a carbon source. In specific embodiments, methanol is used as a carbon source in the organisms provided herein, either alone or in combination with the product pathways provided herein.

In one embodiment, the carbon source comprises methanol, and sugar (e.g., glucose) or a sugar-containing biomass. In another embodiment, the carbon source comprises formate, and sugar (e.g., glucose) or a sugar-containing biomass. In one embodiment, the carbon source comprises methanol, formate, and sugar (e.g., glucose) or a sugar-containing biomass. In specific embodiments, the methanol or formate, or both, in the fermentation feed is provided as a mixture with sugar (e.g., glucose) or sugar-comprising biomass. In certain embodiments, sugar is provided for sufficient strain growth. In some embodiments, the sugar (e.g., glucose) is provided at a molar concentration ratio of methanol to sugar of from 200:1 to 1:200. In certain embodiments, the carbon source comprises formate and a sugar (e.g., glucose). In some embodiments, the sugar (e.g., glucose) is provided at a molar concentration ratio of formate to sugar of from 200:1 to 1:200. In certain embodiments, the carbon source comprises a mixture of methanol and formate, and a sugar (e.g., glucose). In certain embodiments, sugar is provided for sufficient strain growth. In some embodiments, the sugar (e.g., glucose) is provided at a molar concentration ratio of methanol and formate to sugar of from 200:1 to 1:200.

Suitable purification and/or assays to test, e.g., for the production of methacrylic acid or BDO can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme or protein activities from the exogenous DNA sequences can also be assayed using methods well known in the art.

The methacrylic acid or BDO or other target molecules may be separated from other components in the culture using a variety of methods well known in the art. Such separation methods include, for example, extraction procedures as well as methods that include continuous liquid-liquid extraction, pervaporation, evaporation, filtration, membrane filtration (including reverse osmosis, nanofiltration, ultrafiltration, and microfiltration), membrane filtration with diafiltration, membrane separation, reverse osmosis, electrodialysis, distillation, extractive distillation, reactive distillation, azeotropic distillation, crystallization and recrystallization, centrifugation, extractive filtration, ion exchange chromatography, size exclusion chromatography, adsorption chromatography, carbon adsorption, hydrogenation, and ultrafiltration. All of the above methods are well known in the art.

Examples of target molecule isolation processes include distillation for 13BDO, 14BDO, butadiene, methyl vinyl carbinol, 3-buten-1-ol, n-propanol, isopropanol, propylene, and crotyl alcohol; crystallization for 6ACA (alternatively it can be converted to caprolactam and then purified via distillation as a final step), HMDA, adipic acid or derivatives thereof, succinic acid or derivatives thereof, or any of crystallization, distillation, or extraction for methacrylic acid or derivatives thereof.

Target molecules such as 13BDO, 14BDO, butadiene, methyl vinyl carbinol n-propanol, isopropanol, propylene, crotyl alcohol; 3-buten-1-ol, 6ACA, HMDA, adipic acid or derviaties thereof, succinic acid or derivatives thereof, or methacrylic acid or derivatives thereof are chemicals used in commercial and industrial applications. In some embodiments, BDO and/or 4-HB are used in various commercial and industrial applications. Non-limiting examples of such applications include production of plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like. Moreover, BDO and/or 4-HB are also used as a raw material in the production of a wide range of products including plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like.

Accordingly, in some embodiments, provided are biobased plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, comprising one or more bioderived BDO and/or 4-HB or bioderived BDO and/or 4-HB intermediate thereof produced by an organism provided herein or produced using a method disclosed herein.

As used herein, the term "bioderived" means derived from or synthesized by a biological organism and can be considered a renewable resource since it can be generated by a biological organism. Such a biological organism, in particular the microbial organisms disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the disclosure. A biobased or bioderived product is in contrast to a petroleum derived product, wherein such a product is derived from or synthesized from petroleum or a petrochemical feedstock.

In some embodiments, provided herein is a culture medium comprising bioderived BDO. In some embodiments, the bioderived BDO is produced by culturing an organism having enzyme A is capable of reducing NADP to NADPH, and (b) an exogenous enzyme B which is (bi) a hexulose-6-phosphate synthase, (bii) a 6-phospho-3-hexuloisomerase, (biii) a phosphoketolase, or any combination of (bi), (bii) and (biii), and BDO pathway, as provided herein. In certain embodiments, the bioderived BDO has a carbon-12, carbon-13 and carbon-14 isotope ratio that reflects an atmospheric carbon dioxide uptake source. In one embodiment, the culture medium is separated from an organism having a fusion protein and BDO pathway.

In other embodiments, provided herein is a bioderived BDO. In some embodiments, the bioderived BDO is produced by culturing an organism having a fusion protein and BDO pathway, as provided herein. In some embodiments, the bioderived BDO has an Fm value of at least 80%, at least 85%, at least 90%, at least 95% or at least 98%. In certain embodiments, the bioderived BDO is a component of culture medium.

In certain embodiments, provided herein is a composition comprising a bioderived BDO provided herein, for example, a bioderived BDO produced by culturing an organism having a MeDH fusion protein and BDOP (BDO pathway), as provided herein. In some embodiments, the composition further comprises a compound other than said bioderived BDO. In certain embodiments, the compound other than said bioderived BDO is a trace amount of a cellular portion of an organism having a fusion protein and a BDO pathway, as provided herein.

In some embodiments, provided herein is a biobased product comprising a bioderived BDO provided herein. In certain embodiments, the biobased product is a plastic, elastic fiber, polyurethane, polyester, polyhydroxyalkanoate, poly-4-HB, co-polymer of poly-4-HB, poly(tetramethylene ether) glycol, polyurethane-polyurea copolymer, spandex, elastane, Lycra™, or nylon. In certain embodiments, the biobased product comprises at least 5% bioderived BDO. In certain embodiments, the biobased product is (i) a polymer, THF or a THF derivative, or GBL or a GBL derivative; (ii) a plastic, elastic fiber, polyurethane, polyester, polyhydroxyalkanoate, poly-4-HB, co-polymer of poly-4-HB, poly(tetramethylene ether) glycol, polyurethane-polyurea copolymer, spandex, elastane, Lycra™, or nylon; (iii) a polymer, a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing; and optionally where the biobased product is reinforced or filled and further where the biobased product is glass-reinforced or -filled or mineral-reinforced or -filled; (iv) a polymer, wherein the polymer comprises polybutylene terephthalate (PBT); (v) a polymer, wherein the polymer comprises PBT and the biobased product is a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing; and optionally where the biobased product is reinforced or filled and further where the biobased product is glass-reinforced or -filled or mineral-reinforced or -filled; (vi) a THF or a THF derivative, wherein the THF derivative is polytetramethylene ether glycol (PTMEG), a polyester ether (COPE) or a thermoplastic polyurethane; (viii) a THF derivative, wherein the THF derivative comprises a fiber; or (ix) a GBL or a GBL derivative, wherein the GBL derivative is a pyrrolidone. In certain embodiments, the biobased product comprises at least 10% bioderived BDO. In some embodiments, the biobased product comprises at least 20% bioderived BDO. In other embodiments, the biobased product comprises at least 30% bioderived BDO. In some embodiments, the biobased product comprises at least 40% bioderived BDO. In other embodiments, the biobased product comprises at least 50% bioderived BDO. In one embodiment, the biobased product comprises a portion of said bioderived BDO as a repeating unit. In another embodiment, provided herein is a molded product obtained by molding the biobased product provided herein. In other embodiments, provided herein is a process for producing a biobased product provided herein, comprising chemically reacting said bioderived-BDO with itself or another compound in a reaction that produces said biobased product. In certain embodiments, provided herein is a polymer comprising or obtained by converting the bioderived BDO. In other embodiments, provided herein is a method for producing a polymer, comprising chemically or enzymatically converting the bioderived BDO to the polymer. In yet other embodiments, provided herein is a composition comprising the bioderived BDO, or a cell lysate or culture supernatant thereof.

BDO is a valuable chemical for the production of high performance polymers, solvents, and fine chemicals. It is the basis for producing other high value chemicals such as tetrahydrofuran (THF) and gamma-butyrolactone (GBL). The value chain is comprised of three main segments including: (1) polymers, (2) THF derivatives, and (3) GBL derivatives. In the case of polymers, BDO is a comonomer for polybutylene terephthalate (PBT) production. PBT is a medium performance engineering thermoplastic used in automotive, electrical, water systems, and small appliance applications. Conversion to THF, and subsequently to polytetramethylene ether glycol (PTMEG), provides an intermediate used to manufacture spandex products such as LYCRA© fibers. PTMEG is also combined with BDO in the production of specialty polyester ethers (COPE). COPEs are high modulus elastomers with excellent mechanical properties and oil/environmental resistance, allowing them to operate at high and low temperature extremes. PTMEG and BDO also make thermoplastic polyurethanes processed on standard thermoplastic extrusion, calendaring, and molding equipment, and are characterized by their outstanding toughness and abrasion resistance. The GBL produced from BDO provides the feedstock for making pyrrolidones, as well as serving the agrochemical market. The pyrrolidones are used as high performance solvents for extraction processes of increasing use, including for example, in the electronics industry and in pharmaceutical production. Accordingly, provided herein is bioderived BDO produced according to the methods described herein and biobased products comprising or obtained using the bioderived BDO.

In some embodiments, the carbon feedstock and other cellular uptake sources such as phosphate, ammonia, sulfate, chloride and other halogens can be chosen to alter the isotopic distribution of the atoms present in BDO and/or 4-HB or any BDO and/or 4-HB pathway intermediate. The various carbon feedstock and other uptake sources enumerated above will be referred to herein, collectively, as "uptake sources." Uptake sources can provide isotopic enrichment for any atom present in the product BDO and/or 4-HB or BDO and/or 4-HB pathway intermediate, or for side products generated in reactions diverging away from a BDO and/or 4-HB pathway. Isotopic enrichment can be achieved for any target atom including, for example, carbon, hydrogen, oxygen, nitrogen, sulfur, phosphorus, chloride or other halogens. The same holds true for the MMPs and FAPs, as well as intermediates thereof, provided herein.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio.

In some embodiments, a target isotopic ratio of an uptake source can be obtained by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

Isotopic enrichment is readily assessed by mass spectrometry using techniques known in the art such as Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC) and/or high performance liquid chromatography (HPLC).

Accordingly, in some embodiments, provided are BDO and/or 4-HB or a BDO and/or 4-HB pathway intermediate thereof that has a carbon-12, carbon-13, and carbon-14 ratio that reflects an atmospheric carbon, also referred to as environmental carbon, uptake source.

Further, the disclosure relates, in part, to biologically produced BDO and/or 4-HB or BDO and/or 4-HB intermediate thereof as disclosed herein, and to the products derived therefrom, wherein the BDO and/or 4-HB or a BDO and/or 4-HB intermediate thereof has a carbon-12, carbon-13, and carbon-14 isotope ratio of about the same value as the $CO_2$ that occurs in the environment.

Those skilled in the art will understand that an organism can be engineered that secretes the biosynthesized compounds when grown on a carbon source such as a methanol alone or combined with other carbohydrates. Such compounds include, for example, BDO and any of the intermediate metabolites in the BDOP. All that is required is to engineer in one or more of the required enzyme or protein activities to achieve biosynthesis of the desired compound or intermediate including, for example, inclusion of some or all of the BDO biosynthetic pathways. Accordingly, provided herein is an organism that produces and/or secretes BDO when grown on a carbohydrate or other carbon source and produces and/or secretes any of the intermediate metabolites shown in the BDOP when grown on a carbohydrate or other carbon source. The BDO producing microbial organisms provided herein can initiate synthesis from an intermediate. The same holds true for intermediates in the formaldehyde assimilation.

Example 1—GapN Versus GapA Kinetic Comparison

Catalytic constants for *E. coli* GapA and *B. methanolicus* GapN were determined and are shown in Table 18.

TABLE 18

| GapN vs. GapA kinetic comparison | | | | | |
|---|---|---|---|---|---|
| cds | organism/enzyme | fixed | $k_{cat}(S^{-1})$ G3P | $K_m(mM)$ G3P | $k_{cat}/K_M$ $(S^{-1}mM^{-1})$ G3P |
| 87A | EC GapA | NAD | 19 ± 1 | 2.0 ± 0.3 | 9.5 |
| 10662A | BM PB1 GapN | NADP | 8.9 ± 0.8 | 1.1 ± 0.3 | 7.6 |
| 10663A | BM MGA3 GapN | NADP | 9.5 ± 0.8 | 1.6 ± 0.1 | 6.0 |
| | | | NADP | NADP | NADP |
| 10662A | BM PB1 GapN | G3P | 9.7 ± 0.8 | 0.32 + 0.07 | 31 |
| 10663A | BM MGA3 GapN | G3P | 8.2 ± 0.5 | 0.27 ± 0.04 | 30 |

Example 2—Intracellular Metabolite Profiles are Achieved Due to gapN Expression The intracellular metabolite profiles of a *E. coli* strain where *B. methanolicus* GapN enzyme (Accession WP_003351798; 95% ID to SEQ ID: 1) was expressed in conjunction with hexulose-6-phosphate synthase (Hps) (SEQ ID:2) and 6-phospho-3-hexuloisomerase (Phi) (SEQ ID:3) was compared with a strain having gapA expressing and expression of the same Hps and Phi enzymes. This strain also has a deletion of gapA, expresses a methanol dehydrogenase, and expresses fba, glpX, rpe and tkt from *B. methanolicus*. Expression of gapN resulted in increased metabolite levels for the relevant RuMP cycle metabolites compared to the strain with gapA expression without gapN. This indicates the benefit of gapN expression for RuMP cycle activity and methylotrophy. Table 19 shows the fold-change in increase of key RuMP cycle metabolites involved in and needed for methylotrophy.

TABLE 19

Fold change increase of RuMP cycle metabolites in gapN strain compared to gapA strain

| Metabolite | Fold change increase in gapN strain compared to gapA strain |
|---|---|
| Fructose-6-phosphate | 1.83 |
| Fructose-1,6-bisphosphate | 14.86 |
| Glyceraldehyde-3-phosphate | 1.41 |
| Dihydroxyacetone phosphate | 1.41 |
| Sedoheptulose-1,7-bisphosphate | 13.93 |
| Sedoheptulose-7-phosphate | 2.07 |
| Ribulose-5-phosphate | 1.85 |

Example 3—Synthetic Methylotrophy Demonstrated in Cultures

*E. coli* strain (overexpression of gapN (Accession WP_003351798; 95% ID to SEQ ID: 1), deletion of gapA, expression of other enzymes, methanol dehydrogenase, Hps (SEQ ID:2), Phi (SEQ ID:3), Fba, GlpX, Tkt) and its parent with gapA expressing were cultivated in a chemostat culture with glucose and methanol. The chemostat bioreactor was initiated as batch cultivation mode and operated at aerobic conditions with glucose as carbon source, the temperature controlled at 35 degrees C. and dissolved oxygen controlled above 20% while changing airflow, and agitation. pH was controlled constant at 6.95 by automatic addition of base or acid when necessary. Transition into methanol growth phase was performed operating fermenters as continuous by feeding medium containing methanol as sole carbon source targeting a dilution rate of 0.1 h-1. The methanol feed started before glucose depletion and the methanol growth kinetics were measured only after residual glucose was completely consumed. Cell growth during fermentation was monitored by measuring optical density of the culture at 600 nm using spectrophotometer.

Figure 10:
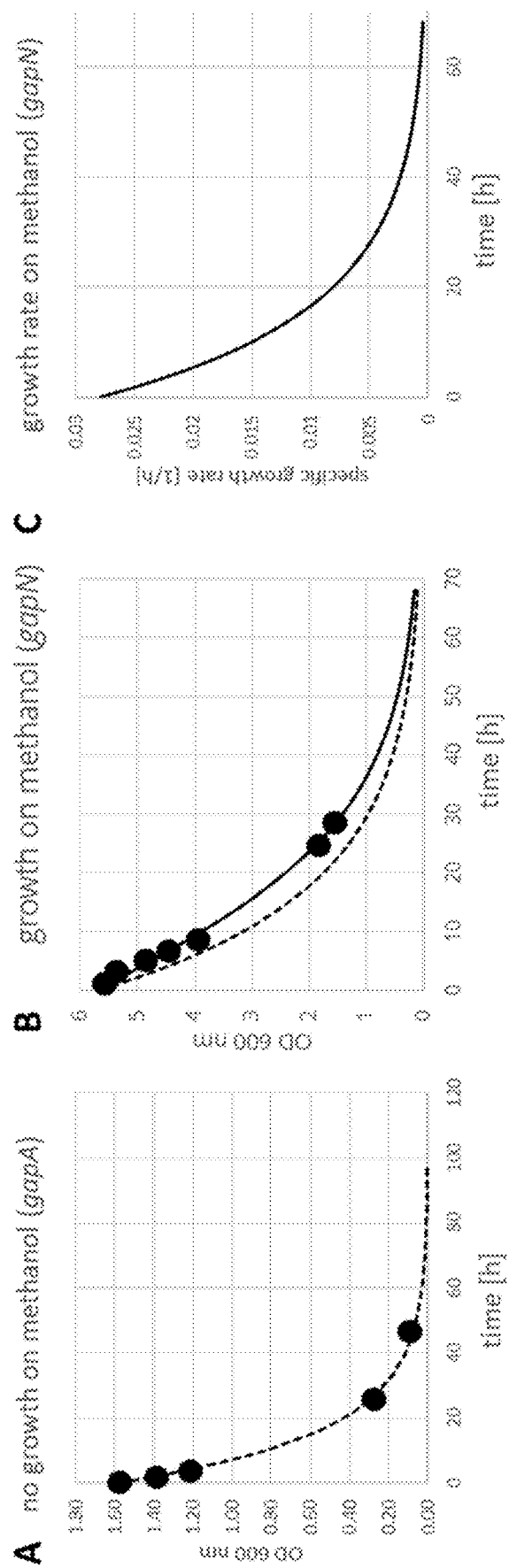
FIG. 10 demonstrates growth on methanol for a synthetic methylotroph and presents growth characteristics (optical density as OD at 600 nm; specific growth per hour). Panel A depicts growth data for control gapA expressing strain that demonstrates no growth on methanol. Panel B depicts growth data for gapN expressing strain showing growth on methanol. Panel C depicts growth rate on methanol for the gapN expressing strain. Dotted line is expected line for no growth (dilution). Solid line with black dots is the actual experimental data.

Upon transition of feed to sole carbon source of methanol, the strain with gapA but not gapN did not show growth whereas the strain with the expression of gapN exhibited growth on methanol for 30 hours. The dilution patterns for the strain with gapA fits the expectation for no growth (FIG. 10A), whereas the gapN strain exhibits synthetic methylotrophy (FIG. 10B). The observed growth rate for this strain is shown in FIG. 10C. Furthermore, the intracellular flux distribution calculated with $^{13}$C-methanol confirms the activity of a complete RuMP cycle through the presence of multiple fully $^{13}$C-labeled RuMP cycle metabolites (data not shown).

Additionally, the above GapN-expressing *E. coli* strains expressing an alternative Hps (41% ID to SEQ ID:2; Accession. WP_054009748.1) and Phi (33% ID to SEQ ID:3; Accession. WP_012298822.1) also demonstrated complete RUMP cycle activity evidenced by formaldehyde consumption as well as fully labeled RuMP cycle metabolites from $^{13}$C-methanol.

Example 4—Overexpression of Fba, Fba2, GlpX

Figure 11:
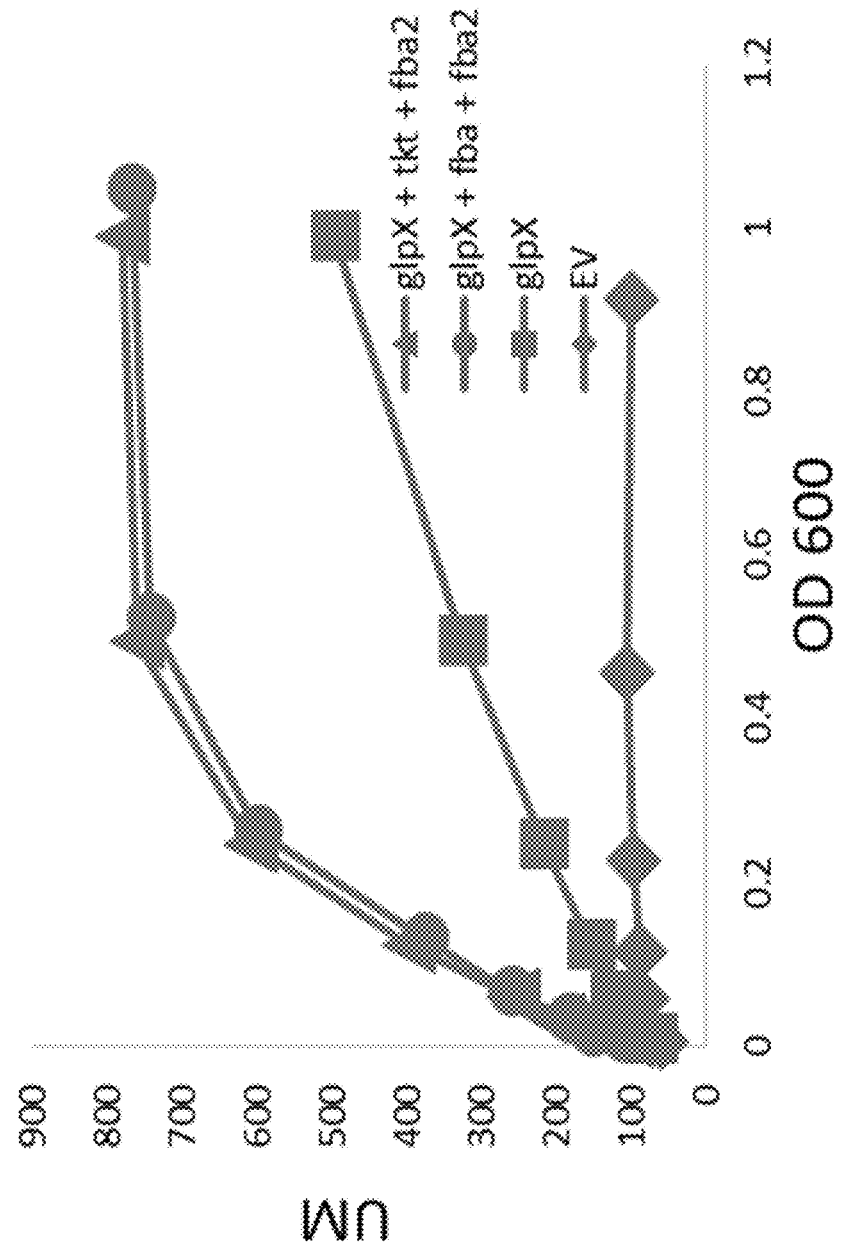
FIG. 11 demonstrates the affects of overexpression of enzymes Fba, Fba2, GlpX and Tkt on formaldehyde consumption (micromolar) at different cell densities. E. coli strains with additional GlpX expressed from a plasmid compared to the parent strain were analyzed for formaldehyde consumption in the absence of other carbon sources using a NASH assay. GlpX is Accession WP 003352248.1; Fba is Accession EIJ77616.1; Fba2 is Accession EIJ80286.1; Tkt is Accession. EIJ77615.1; and EV is control. Formaldehyde consumption, which is assimilated via the RuMP cycle enzymes is a proxy for measuring RuMP cycle activity. Optical density as OD at 600 nm is an indicator of cell density.

The effect of overexpression of GlpX (Accession. WP_003352248.1) on synthetic methylotrophy is demonstrated in FIG. 11 wherein strains with additional GlpX expressed on a plasmid compared to the parent strain exhibited increased formaldehyde consumption in the absence of other carbon sources. This formaldehyde consumption rate is further enhanced by the additional expression of Fba (Accession. EIJ77616.1), Fba2 (Accession. EIJ80286.1), and Tkt (Accession. EIJ77615.1). Formaldehyde consumption measured using NASH assay serve as a proxy for measuring RuMP cycle activity. To measure the formaldehyde consumption, the bacterial cells were grown for 5.5 hrs in Luria Broth and 2% glucose at 35 degrees C. in a 2 mL 24-deep-well plate. The cells were subsequently transferred to minimal media with 2% glucose and 4 mM MgSO4 and grown overnight in a 2 mL 48-deep-well plate. Cells were normalized to OD 0.5 and resuspended in minimal media 2% glucose, 4 mM MgSO4 and 1 mM formaldehyde in a 1.2 mL 24-deep-well plate. Samples were taken and spun down for 10 minutes at maximum rpm. Seventy-five uL of NASH B reagent was added to 75 uL of supernatant and mixed in a 96 well Costar plate and incubated at 37 degrees C. for 40 mins. Absorbance values were measured at 412 nM to obtain formaldehyde concentration.

Example 5—Deletion of talABC

There are two possible routes for carbon flux through the RuMP cycle, either through transaldolase (talABC) or SBPase encoded by fba and glpX as discussed herein. The transaldolase-using variant of the RuMP cycle creates a thermodynamic uphill for the generation of the critical sedoheptulose-7-phosphate with a standard delta G of 0.7 kJ/mol, whereas in contrast the SBPase-using variant uses a GlpX reaction that provides a very significant thermodynamic advantage for the generation of sedoheptulose-7-phosphate (standard delta G of −35.3 kJ/mol). To complete the RuMP cycle and regenerate ribulose-5-phosphate from glyceraldehyde-3-phosphate and dihydroxyacetone phosphate, this thermodynamic advantage of the SBPase variant provided by Fba (e.g. Accession. EIJ77616.1) and GlpX (e.g. Accession. WP_003352248.1) is likely crtical. The importance of this is further highlighted by the calculation of delta G' from measured intracellular metabolite levels in a natural methylotroph (*B. methanolicus*) as well as an engineered *E. coli* expressing GapN (95% ID to SEQ ID: 1; Accession WP_003351798), Hps (SEQ ID: 2), Phi (SEQ ID: 3). In the presence of transaldolase (ta/ABC), the thermodynamics are hugely unfavorable whereas the deletion of talABC and overexpression of glpX and fba shows more favorable thermodynamics (Table 20).

TABLE 20

Gibbs free energy calculated from measured intracellular metabolite levels in *B. methanolicus* as well as engineered *E. coli*.

| Delta G' (kJ/mol) | *B. methanolicus* | *E. coli* engineered with gapN |
|---|---|---|
| RuMP via transaldolase | 19 | 28 |
| RuMP via Fba & GlpX | −17 | −2 |
| | | (talABC deleted) |

Example 6—Expression of Rpi, Rpe, Tkt, Tkt2 from *B. methanolicus*

As shown in Table 21, transketolases (Tkt's) of *B. methanolicus* were determined to have significantly lower Michaelis constant $K_m$ which is the substrate concentration at which the reaction rate if half of the maximum rate. As disclosed herein, *B. methanolicus* transketolases kinetically favor the RuMP cycle flux for ribulose 5-phosphate regeneration, which is appears essential for methanol and formaldehyde assimilation. Alternatively, other transketolases can be engineered or discovered that have the desired $K_m$.

For other reversible enzymes of the RuMP cycle such as ribose 5-phosphate isomerase (RpiAB) and ribulose-phosphate 3-epimerase (Rpe), a similar consideration was discovered and applied, i.e., the corresponding *B. methanolicus* enzymes have better kinetic properties than *E. coli* homologs. *E. coli* has two isozymes of ribose 5-phosphate isomerase A (RpiA) and B (RpiB), where RpiA is the major enzyme in *E. coli*. The Michaelis constant for its substrate ribose 5-phosphate is 4.4 mM for RpiA and 0.83 mM for RpiB [1]. Therefore, deletion of rpiA and overexpression of rpiB from either *B. methanolicus* or *E. coli* should kinetically favor the product formation which is ribulose 5-phosphate. References cited in this section and Table 21 are: [1] Essenberg and Cooper, "Two Ribose-5-Phosphate Isomerases from *Escherichia coli* K12: Partial Characterisation of the Enzymes and Consideration of Their Possible Physiological Roles," European Journal of Biochemistry, vol. 55, no. 2, pp. 323-32, 1975; [2] Markert et al., "Characterization of two transketolases encoded on the chromosome and the plasmid pBM19 of the facultative ribulose monophosphate cycle methylotroph *Bacillus methanolicus*," BMC Microbiology, vol. 14, no. 7, 2014; and [3] Sprenger et al., "Transketolase A of *Escherichia coli* K12," European Journal of Biochemistry, vol. 230, no. 2, pp. 525-32, 1995.

TABLE 21

RpiB transketolase Michaelis constant $K_M$ comparison between *B. methanolicus* and *E. coli* for the reaction substrates and products.

| | $K_M$ [mM] | |
|---|---|---|
| Substrates | *B. methanolicus* [2] | *E. coli* [3] |
| fructose 6-phosphate | 0.72 | 1.1 |
| glyceraldehyde 3-phosphate | 0.92 | 2.1 |
| sedoheptulose 7-phosphate | | 4 |

| | $K_M$ [mM] | |
|---|---|---|
| Products | *B. methanolicus* [2] | *E. coli* [3] |
| erythrose 5-phosphate | | 0.09 |
| ribose 5-phosphate | 0.12 | 1.4 |
| xylulose 5-phosphate | 0.15 | 0.16 |

What is claimed is:

1. An engineered microorganism having synthetic or enhanced methylotrophy comprising:
   exogenous enzyme A that is a NADP-dependent glyceraldehyde-3-phosphate dehydrogenase having at least 85% sequence identity to SEQ ID NO:1 or SEQ ID NO:11, wherein said exogenous enzyme A is capable of converting glyceraldehyde-3-phosphate (G3P) to 3-phosphoglycerate (3PG) and capable of reducing NADP to NADPH; and
   an exogenous enzyme B which is (bi) a phosphoketolase, (bii) a hexulose-6-phosphate synthase, (biii) 6-phospho-3-hexuloisomerase, or any combination of (bi), (bii) and (biii).

2. The engineered microorganism of claim 1 comprising the exogenous enzyme A, and the (bi) exogenous phosphoketolase, and optionally the (bii) exogenous hexulose-6-phosphate synthase, and the (biii) exogenous 6-phospho-3-hexuloisomerase.

3. The engineered microorganism of claim 1 wherein the phosphoketolase is:
   (1) an exogenous fructose-6-phosphate phosphoketolase and the microorganism further comprises (a) a phosphotransacetylase, or (b) an acetyl-CoA transferase, an acetyl-CoA synthetase, or an acetyl-CoA ligase,
   (2) an exogenous xylulose-5-phosphate phosphoketolase and the engineered microorganism further comprises (a) a phosphotransacetylase, or (b1) an acetate kinase deletion and (b2) an acetyl-CoA transferase, an acetyl-CoA synthetase, or an acetyl-CoA ligase, or
   both (1) and (2).

4. The engineered microorganism of claim 1, wherein the exogenous enzyme B comprises hexulose-6-phosphate synthase having at least 85% sequence identity to SEQ ID NO: 2 (*Bacillus methanolicus* MGA HPS).

5. The engineered microorganism of claim 1 further comprising a NAD⁺-dependent methanol dehydrogenase (MDH).

6. The engineered microorganism of claim 1 which is bacteria, fungi, or yeast.

7. The engineered microorganism of claim 6 that is *Escherichia, Corynebacterium, Bacillus, Ralstonia, Staphylococcus, Pichia* or *Saccharomyces*, wherein the engineered microorganism is optionally *Escherichia coli*.

8. A method for growing a non-natural microbial organism comprising culturing the engineered microorganism of claim 1 in a medium comprising carbon-containing feedstock that comprises methanol.

9. The engineered microorganism of claim 1 wherein exogenous enzyme A has at least 90% sequence identity to SEQ ID NO:1 or SEQ ID NO:11.

10. An engineered microorganism having synthetic or enhanced methylotrophy comprising:
    exogenous enzyme A that is a NADP-dependent glyceraldehyde-3-phosphate dehydrogenase having at least 85% sequence identity to one of the following amino acid sequences: SEQ ID NO:12, SEQ ID NO: 13, SEQ ID NO:14, SEQ ID NO: 15, SEQ ID NO: 16, SEQ ID NO:17, SEQ ID NO:18, SEQ ID NO: 19, SEQ ID NO:20, SEQ ID NO:21, SEQ ID NO:22, SEQ ID NO:23, SEQ ID NO:24, SEQ ID NO:25, and SEQ ID NO:26, wherein said exogenous enzyme A is capable of converting glyceraldehyde-3-phosphate (G3P) to 3-phosphoglycerate (3PG) and capable of reducing NADP to NADPH; and
    an exogenous enzyme B which is (bi) a phosphoketolase, (bii) a hexulose-6-phosphate synthase, (biii) 6-phospho-3-hexuloisomerase, or any combination of (bi), (bii) and (biii).

11. The engineered microorganism of claim 10 wherein exogenous enzyme A has at least 90% sequence identity to one of SEQ ID NOs: 12-26.

12. The engineered microorganism of claim 1 wherein exogenous enzyme B which is (bi) the phosphoketolase comprises one of the following amino acid sequences: SEQ ID NO:27, SEQ ID NO:28, SEQ ID NO:29, SEQ ID NO:30, SEQ ID NO:31, SEQ ID NO:32, SEQ ID NO:33, or SEQ ID NO: 34.

* * * * *